(12) United States Patent
Schmidt et al.

(10) Patent No.: US 12,215,129 B2
(45) Date of Patent: Feb. 4, 2025

(54) ANTIBACTERIAL CYCLOPEPTIDES TARGETING ACINETOBACTER AND OTHER GRAM-NEGATIVE PATHOGENS

(71) Applicant: UNIVERSITY OF UTAH RESEARCH FOUNDATION, Salt Lake City, UT (US)

(72) Inventors: Eric W. Schmidt, Salt Lake City, UT (US); Margo Haygood, Portland, OR (US); Bailey Miller, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 18/034,670

(22) PCT Filed: Oct. 29, 2021

(86) PCT No.: PCT/US2021/057350
§ 371 (c)(1),
(2) Date: Apr. 28, 2023

(87) PCT Pub. No.: WO2022/094273
PCT Pub. Date: May 5, 2022

(65) Prior Publication Data
US 2023/0391827 A1    Dec. 7, 2023

Related U.S. Application Data

(60) Provisional application No. 63/187,816, filed on May 12, 2021, provisional application No. 63/107,901, filed on Oct. 30, 2020.

(51) Int. Cl.
*C07K 11/02* (2006.01)
*A61P 31/04* (2006.01)
*A61K 38/00* (2006.01)

(52) U.S. Cl.
CPC .............. *C07K 11/02* (2013.01); *A61P 31/04* (2018.01); *A61K 38/00* (2013.01)

(58) Field of Classification Search
CPC ......... C07K 11/02; A61P 31/04; A61K 38/00; A61K 45/06; Y02A 50/30
See application file for complete search history.

(56) References Cited

U.S. PATENT DOCUMENTS

| 8,481,484 B2 | 7/2013 | Uemura et al. |
| 9,605,028 B2 | 3/2017 | Ebright et al. |
| 2020/0331968 A1 | 10/2020 | Hanan et al. |

FOREIGN PATENT DOCUMENTS

| BR | 2011001414 | 6/2013 |
| BR | 2010000639 | 4/2024 |
| CN | 2021800867772 | 10/2021 |
| EP | 21887635.7 | 10/2021 |
| WO | WO 2012/126075 | 9/2012 |
| WO | WO 2014/108526 | 7/2014 |
| WO | WO 2018/142416 | 8/2018 |
| WO | WO2019/126353 | 6/2019 |
| WO | PCT/US2021/057350 | 10/2021 |

OTHER PUBLICATIONS

Lazar et al (Mol. Cell. Biol., 8:1247-1252, 1988) (Year: 1988).*
Bowie et al (Science, 1990, 247:1306-1310) (Year: 1990).*
Burgess et al (J. Cell Biol. 111:2129-2138, 1990) (Year: 1990).*
U.S. Appl. No. 63/107,901, filed Oct. 30, 2020, Eric W. Schmidt.
U.S. Appl. No. 63/187,816, filed May 12, 2021, Eric W. Schmidt.
Agner, et al. (2000), "Membrane-permeabilizing activities of cyclic lipodepsipeptides, syringopeptin 22A and syringomycin E from Pseudomonas syringae pv. syringae in human red blood cells and in bilayer lipid membranes" Bioelectrochemistry 52, pp. 161-167.
Altamia, et al. (2020), "Secondary Metabolism in the Gill Microbiota of Shipworms (Teredinidae) as Revealed by Comparison of Metagenomes and Nearly Complete Symbiont Genomes" mSystems 30;5(3):e00261-20. doi: 10.1128.
Bailey, et al. (2019), "Essential gene deletions producing gigantic bacteria". PLOS Genetics 15, e1008195.
Baaaath et al. (2019) "Structure-function analyses reveal that a glucuronoyl esterase from Teredinibacter turnerae interacts with carbohydrates and aromatic compounds" J Biological Chem 294*16): 6635-6645.
Becucci et al. (2016) "Channel-forming activity of syringopeptin 25A in mercury-supported lipid bilayers with a phosphatidylcholine distal leaflet" Bioelectrochemistry 108: 28-35.
Becucci et al. (2016) "Channel-forming activity of syringopeptin 25A in mercury-supported phospholipid monolayers and negatively charged bilayers" Bioelectrochemistry 111: 131-142.
Becucci et al. (2017) "When and how the melittin ion channel exhibits ohmic behavior" Bioelectrochemistry 113: 51-59.
Bensaci, et al. (2007) "Syringopeptin SP25A-mediated killing of Gram-positive bacteria and the role of teichoic acid D-alanylation" FEMS Microbiology 268(1): 106-111.
Benvenuto et al, "Pharmacokinetics and tolerability of daptomycin at doses up to 12 milligrams per kilogram of body weight once daily in healthy volunteers," Antimicrobial Agents and Chemotherapy, 2006, 50(10): pp. 3245-3249.
Betcher, et al. (2012), "Microbial Distribution and Abundance in the Digestive System of Five Shipworm Species (Bivalvia: Teredinidae)" PLOS One 7, e45309.
Boucher, et al. (2009), "Bad Bugs, No. Drugs: No ESKAPE! An Update from the Infectious Diseases Society of America" Clin Infect Dis 48, pp. 1-12.

(Continued)

*Primary Examiner* — Sudhakar Katakam
(74) *Attorney, Agent, or Firm* — Ballard Spahr LLP

(57) ABSTRACT

In one aspect, the invention relates to cyclopeptides and methods of using the disclosed cyclopeptides to treat bacterial infections due to, for example, Gram-negative pathogens. This abstract is intended as a scanning tool for purposes of searching in the particular art and is not intended to be limiting of the present invention.

20 Claims, 59 Drawing Sheets

(56) References Cited

OTHER PUBLICATIONS

Carpaneto et al. (2002) "The phytotoxic lipodepsipeptide syringopeptin 25A from Pseudomonas syringae pv syringae forms ion channels in sugar beet vacuoles" Journal of Membrane Biology 188(3): 237-248.

Centers for Disease Control and Prevention (U.S.), "Antibiotic resistance threats in the United States, 2019" (Centers for Disease Control and Prevention (U.S.), 2019) https:/doi.org/10.15620/cdc:82532 (Oct. 21, 2020).

Culvenor, et al. (1989), "Structure elucidation and absolute configuration of phomopsin a, a hexapeptide mycotoxin produced by phomopsis leptostromiformis" Tetrahedron 45:8, pp. 2351-2372.

Dalla Serra et al. (1999) "Conductive properties and gating of channels formed by syringopeptin 25a, a bioactive lipodepsipeptide from Pseudomonas syringae pv. syringae, in planar lipid membranes" Molecular Plant-Microbe Interactions 12(5): 401-409.

Distel, et al. (2002) "Coexistence of Multiple Proteobacterial Endosymbionts in the Gills of the Wood-Boring Bivalve Lyrodus pedicellatus (*Bivalvia: Teredinidae*)" Appl. Environ. Microbiol. 68, pp. 6292-6299.

Dixon (1986), "Leakage of periplasmic proteins from *Escherichia coli* mediated by polymyxin B nonapeptide" Antimicrob Agents Chemother 29, pp. 781-788.

Ekborg, et al. (2007) "CelAB, a Multifunctional Cellulase Encoded by Teredinibacter turnerae T7902T, a Culturable Symbiont Isolated from the Wood-Boring Marine Bivalve Lyrodus pedicellatus" Appl. Environ. Microbiol. 73, pp. 7785-7788.

Elshahawi, et al. (2013) "Boronated tartrolon antibiotic produced by symbiotic cellulose-degrading bacteria in shipworm gills" PNAS 110, E295-E304.

Fujii, et al. (1997), "A Nonempirical Method Using LC/MS for Determination of the Absolute Configuration of Constituent Amino Acids in a Peptide: Elucidation of Limitations of Marfey'sMethod and of Its Separation Mechanism". *Anal. Chem.* 69, pp. 3346-3352.

Gallagher, et al. (2020) "Ranking essential bacterial processes by speed of mutant death". PNAS 117, pp. 18010-18017.

Grgurina et al. (2002) "A new syringopeptin produced by bean strains of Pseudomonas syringae pv. Syringae" Biochimica et Biophysica Acta, Protein Structure and Molecular Enzymology 1597(1): 81-89.

Grgurina et al. (2005) "Novel cyclic lipodepsipeptide from Pseudomonas syringae pv. lachrymans strain 508 and syringopeptin antimicrobial activities" Antimicrobial Agents and Chemotherapy 49(12): 5037-5045.

Gur'nev et al. (2002) "Activity of toxins produced by Pseudomonas syringae pv. syringae in model and cell membranes" Tsitologiya 44(3): 296-304 (English Abstract).

Han, et al. (2013), "Turnerbactin, a Novel Triscatecholate Siderophore from the Shipworm Endosymbiont Teredinibacter turnerae T7901" *PLOS One* 8, e76151.

Hibi, et al. (2011), "Characterization of Bacillus thuringiensis 1-Isoleucine Dioxygenase for Production of Useful Amino Acids" *Appl. Environ. Microbiol.* 77, pp. 6926-6930.

Howard, et al. (2012), "Acinetobacter baumannii: an emerging opportunistic pathogen" *Virulence* 3, pp. 243-250.

Keating, et al. (2001), "Chain Termination Steps in Nonribosomal Peptide Synthetase Assembly Lines: Directed Acyl-S-Enzyme Breakdown in Antibiotic and Siderophore Biosynthesis" *ChemBioChem* 2, pp. 99-107.

Kozuma, et al. (2017), "Identification and biological activity of ogipeptins, novel LPS inhibitors produced by marine bacterium" *The Journal of Antibiotics* 70, pp. 79-83.

Lechene, et al. (2007), "Quantitative Imaging of Nitrogen Fixation by Individual Bacteria Within Animal Cells" *Science* 317, pp. 1563-1566.

Lee, et al. (2017), "Biology of Acinetobacter baumannii: Pathogenesis, Antibiotic Resistance Mechanisms, and Prospective Treatment Options" *Front. Cell. Infect. Microbiol.* 13;7:55.

Li, et al. (2006), "Colistin: the re-emerging antibiotic for multidrug-resistant Gram-negative bacterial infections" *Lancet Infect Dis* 6, pp. 589-601.

Li, et al. (2020), "Potashchelins, a Suite of Lipid Siderophores Bearing Both L-threo and L-erythro Beta-Hydroxyaspartic Acids, Acquired From the Potash-Salt-Ore-Derived Extremophile *Halomonas* sp. MG34" *Front Chem* 8, pp. 197.

Markolovic, et al. (2018), "The Jumonji-C oxygenase JMJD7 catalyzes (3S)-lysyl hydroxylation of TRAFAC GTPases" *Nat. Chem. Biol.* 14, pp. 688-695.

Matsui, et al. (2020), "Stalobacin: Discovery of Novel Lipopeptide Antibiotics with Potent Antibacterial Activity against Multidrug-Resistant Bacteria" *J. Med. Chem.* 63, pp. 6090-6095.

Mayer, et al. (2013) "Marine Pharmacology in 2009-2011: Marine Compounds with Antibacterial, Antidiabetic, Antifungal, Anti-Inflammatory, Antiprotozoal, Antituberculosis, and Antiviral Activiites; Affecting the Immune and Nervious Systes, and other Miscellaneous Mechanisms of Action" *Marine Drugs*, 11:7, pp. 2510-2573.

Miller, et al. (2020) Shipworm Symbiosis Ecology-Guided Discovery of Gram-Negative Selective Antibiotic with Activity Against Acinetobacter, Cell Chemical Biology 28:11 pp. 1628-1637.

Niedermeyer (2015) "Anti-Infective Natural Products from Cyanobacteria" *Planta Medica*, 81:15, pp. 1309-1325.

Nolan, et al. (2009) "How Nature Morphs Peptide Scaffolds into Antibiotics" Chembiochem 10:1, pp. 34-53.

O'Connor, et al. (2014), Gill bacteria enable a novel digestive strategy in a wood-feeding mollusk. PNAS 111, E5096-E5104.

O'Connor, et al. (2020), "A symbiotic bacterium of shipworms produces a compound with broad spectrum anti-apicomplexan activity" PLOS Pathogens 16, e1008600.

Ojima et al. (2013) "Identification and characterization of cellobiose 2-epimerases from various aerobes" Bioscience, Biotechnology, and Biochemistry 77(1): 189-193.

Pantel, et al. (2018), "Odilorhabdins, Antibacterial Agents that Cause Miscoding by Binding at a New Ribosomal Site" Molecular Cell 70, pp. 83-94.e7.

Piperaki, et al. (2019), "Carbapenem-resistant Acinetobacter baumannii: in pursuit of an effective treatment" Clinical Microbiology and Infection 25, pp. 951-957.

Raaijmakers, et al. (1995), "Utilization of heterologous siderophores and rhizosphere competence of fluorescent *Pseudomonas*" spp. *Can. J. Microbiol.* 41, pp. 126-135.

Rausch, et al. (2007) "Phylogenetic analysis of condensation domains in NRPS sheds light on their functional evolution" *BMC Evol Biol* 7, pp. 78.

Reitz, et al. (2019), "Genomic analysis of siderophore 0-hydroxylases reveals divergent stereocontrol and expands the condensation domain family" PNAS 116, pp. 19805-19814.

Rueckert, et al. (2019) "The Symbiotic Spectrum: Where Do the Gregarines Fit?" *Trends in Parasitology* 35, pp. 687-694.

Senra et al. (2010) "Genetic modification of Teredinibacter turnerae, an endosymbiont with biotechnological potential" J Molecular Microbiology and Biotechnology 18(4): 215-219.

Silver (2011) "Challenges of Antibacterial Discovery" Clinical Microbiology Reviews 24, pp. 71-109.

Tacconelli, et al. (2018), "Discovery, research, and development of new antibiotics: the WHO priority list of antibiotic-resistant bacteria and tuberculosis" The Lancet Infectious Diseases 18, pp. 318-327.

Trindade-Silva et al. (2009) "Physiological traits of the symbiotic bacterium Teredinibacter turnerae isolated from the mangrove shipworm *Neoteredo reynei*." Genetics and Molecular Biology 32(3): 572-81.

Tsukada, et al. (2006) "Histone Demethylation by a family of JmjC domain-containing proteins" *Nature* 549, pp. 811-816.

Waterbury,et al. (1983), "A Cellulolytic Nitrogen-Fixing Bacterium Cultured from the Gland of Deshayes in Shipworms (*Bivalvia: Teredinidae*)" *Science*221, pp. 1401-1403.

Wong, et al. (2017), "Clinical and Pathophysiological Overview of Acinetobacter Infections: a Century of Challenges," *Clinical Microbiology Reviews* 30, pp. 409-447.

(56) References Cited

OTHER PUBLICATIONS

Wu, et al. (2016), "Ferrous iron and a-ketoglutarate-dependent dioxygenases in the biosynthesis of microbial natural products. Biochimica et Biophysica Acta (BBA)" *Proteins and Proteomics* 1864, pp. 453-470.
Yang, et al. (2009), "The Complete Genome of Teredinibacter turnerae T7901: An Intracellular Endosymbiont of Marine Wood-Boring *Bivalves* (Shipworms)" *PLOS One* 4, e6085.
Zan, et al. (2019), "A microbial factory for defensive kahalalides in a tripartite marine symbiosis" Science 364.
Zakharova et al. (2018) "Blocking ion channels induced by antifungal lipopeptide syringomycin E with amide-linked local anesthetics" Scientific Reports 8(1): 1-10.

* cited by examiner

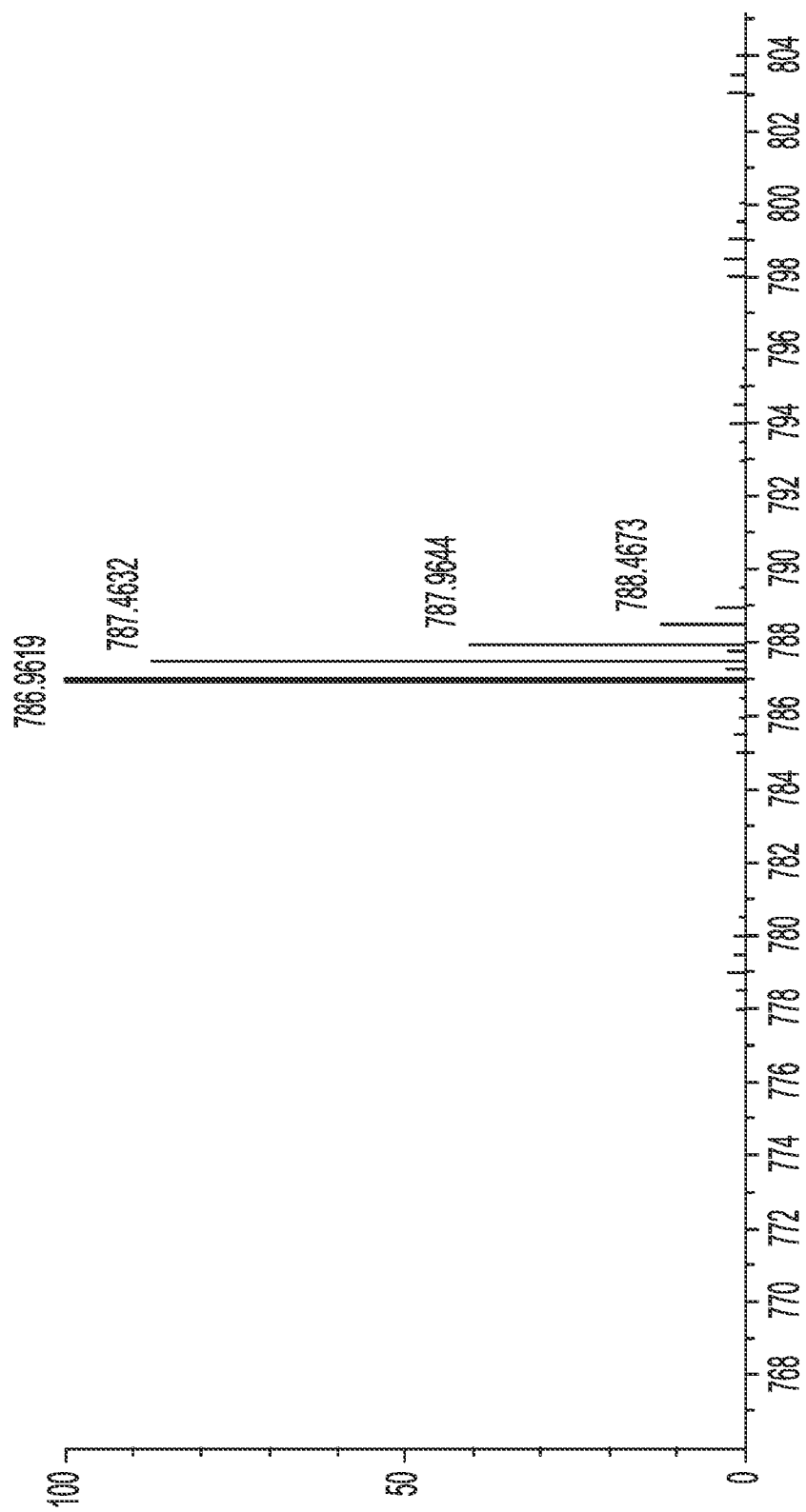

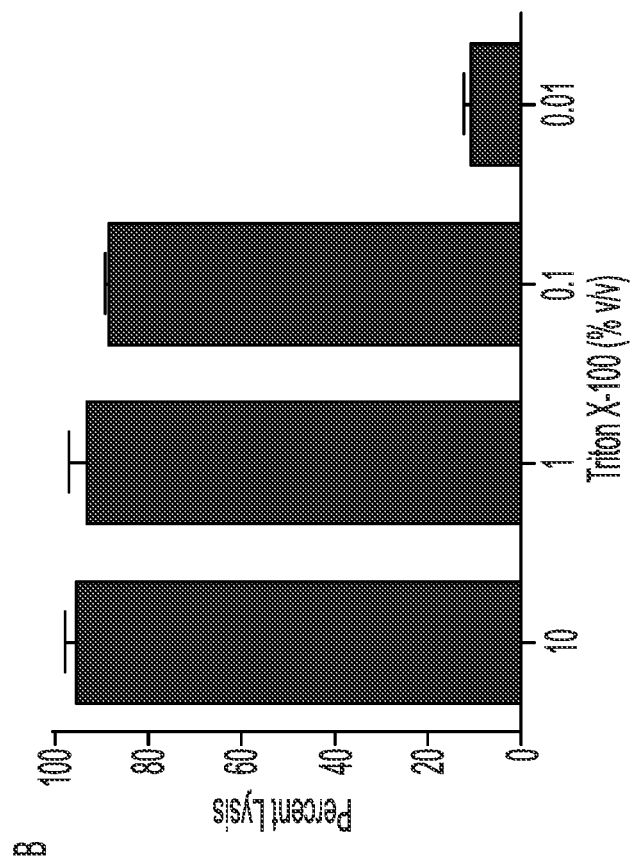
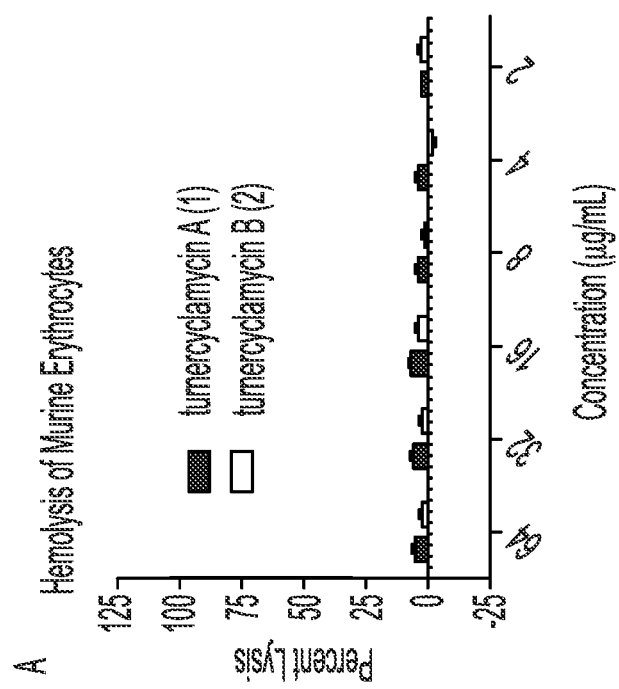
FIG. 10A
FIG. 10B

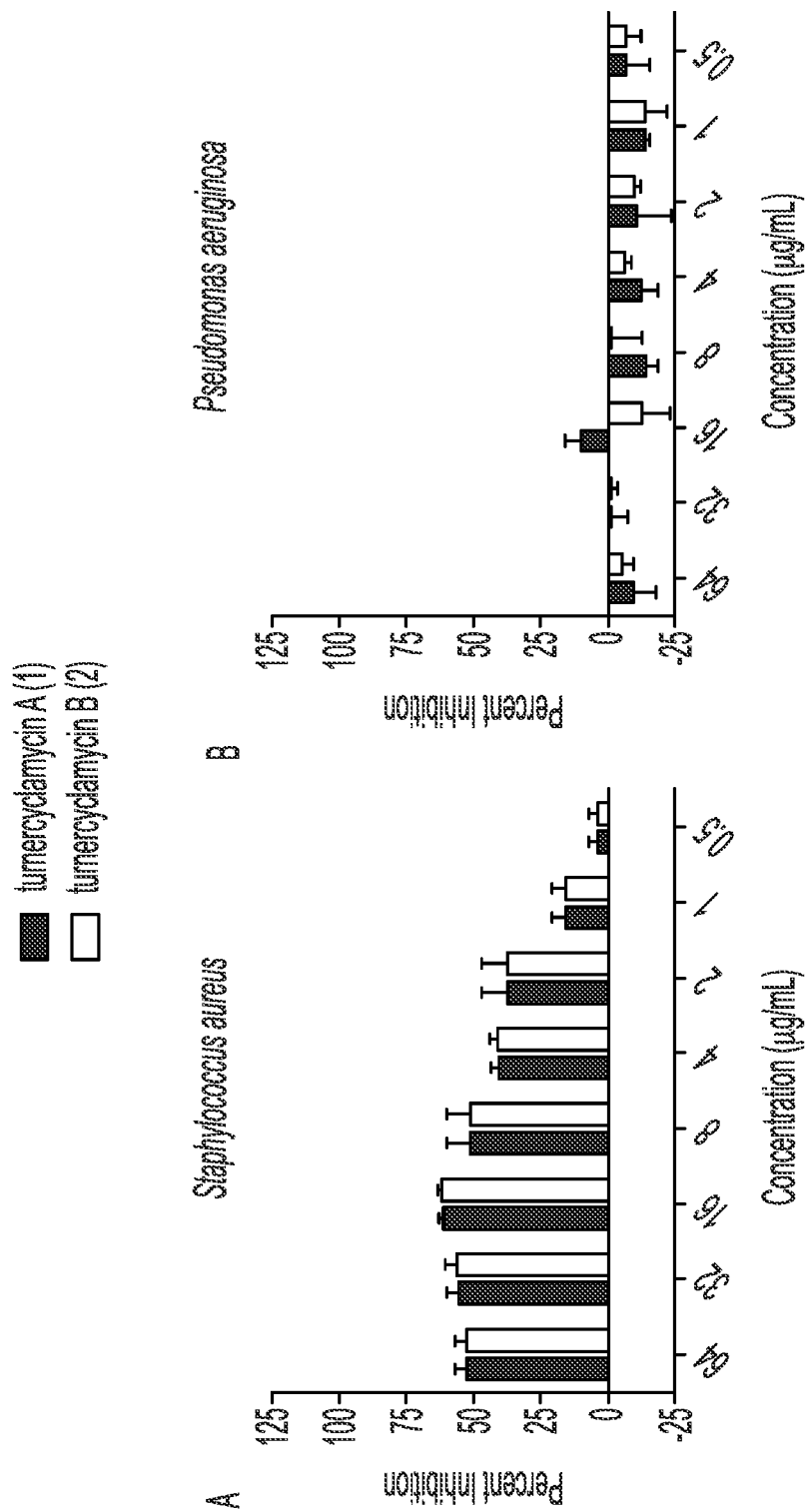

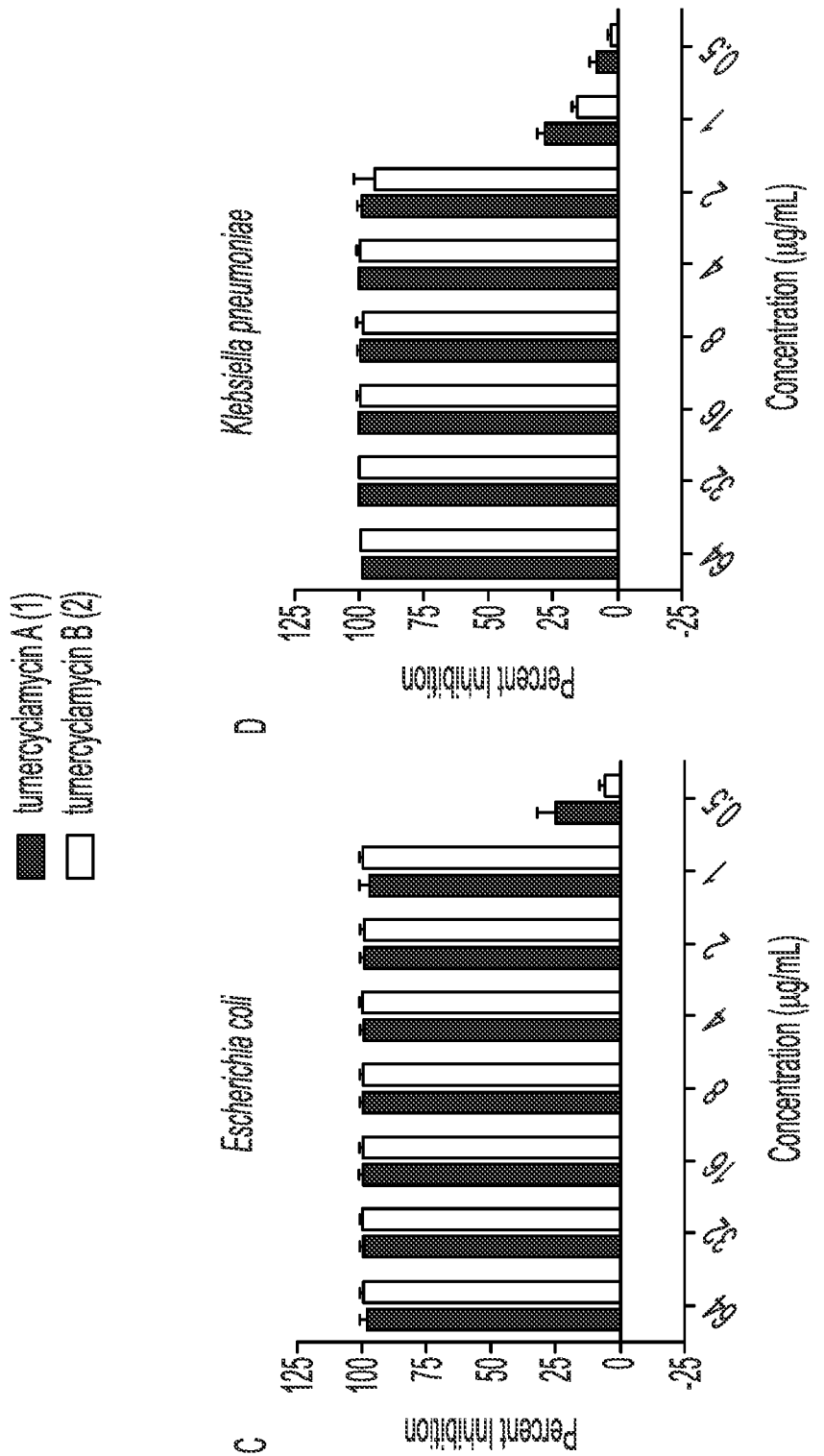

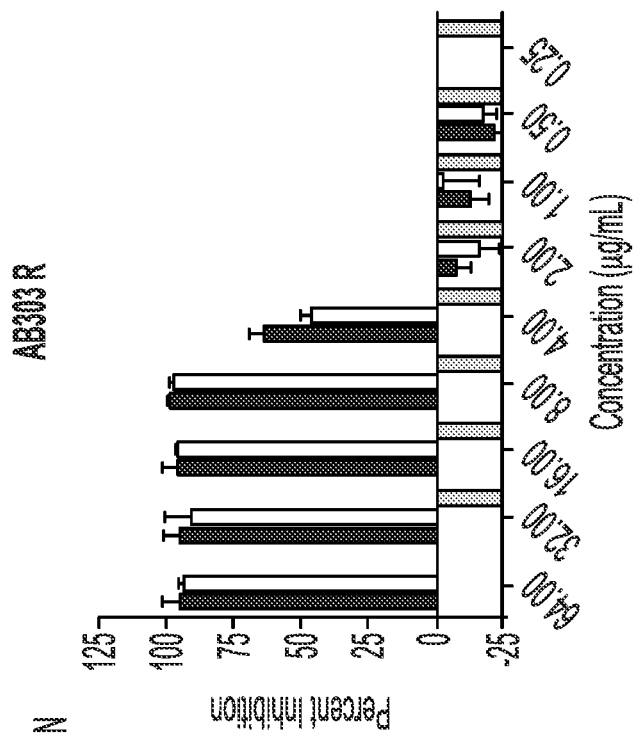
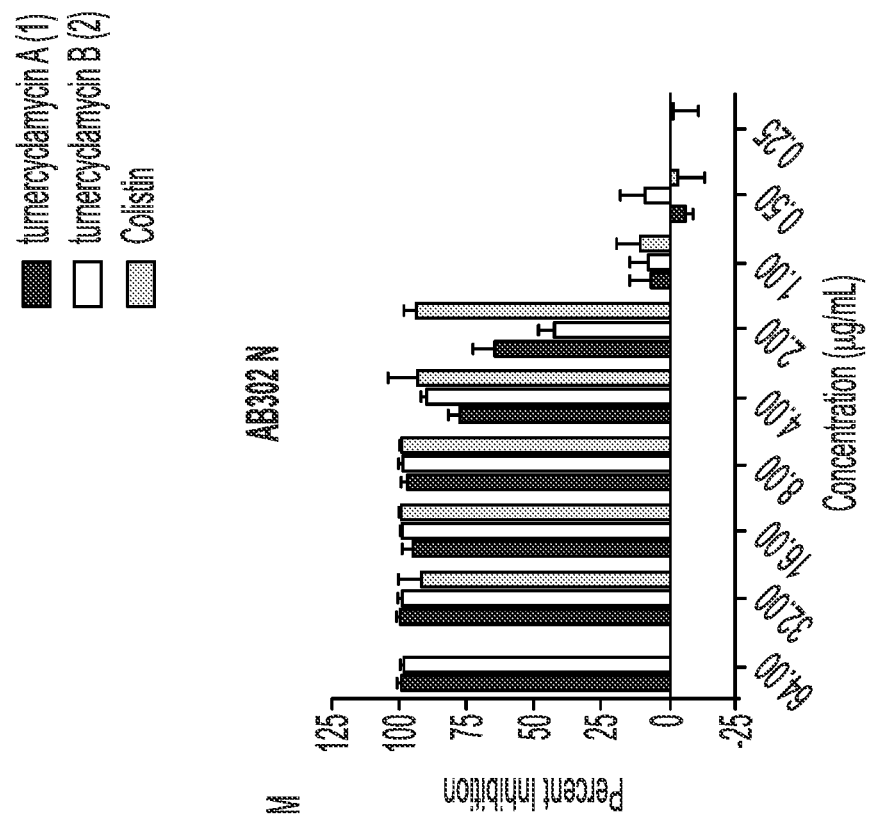
FIG. 11M
FIG. 11N

ANTIBACTERIAL CYCLOPEPTIDES TARGETING ACINETOBACTER AND OTHER GRAM-NEGATIVE PATHOGENS

CROSS-REFERENCE TO RELATED APPLICATIONS

This Application is a U.S. National Phase of International Application No. PCT/US2021/057350, filed on Oct. 29, 2021, which claims the benefit of U.S. Application No. 63/107,901, filed on Oct. 30, 2020, and U.S. Provisional Application No. 63/187,816, filed on May 12, 2021, the contents of which are incorporated herein by reference in their entireties.

STATEMENT REGARDING FEDERALLY SPONSORED RESEARCH

This invention was made with government support under GM122521 and TW008163 awarded by the National Institutes of Health and NA190AR0110303 awarded by the National Oceanic and Atmospheric Administration. The government has certain rights in the invention.

BACKGROUND

Wood eating shipworms (Teredinidae), a family of marine bivalve mollusks, have a close symbiotic relationship with the intracellular bacteria living in their gills. These bacteria, largely represented by the gammaproteobacterial genus *Teredinibacter*, support their hosts both through the fixation of atmospheric nitrogen and by contributing cellulolytic enzymes necessary for wood degradation (Distel et al., 202; Ekborg et al., 2007; Lechene et al., 2007). While these microbial communities are located in bacteriocytes within the gill filaments of the shipworm, their enzymes are transported to and can be detected in the cecum, where wood is digested (O'Connor et al., 2014). Interestingly, this organ has been shown to be nearly devoid of bacterial inhabitants, despite a presumed abundance of nutritionally accessible carbon released by digested lignocellulose (Betcher et al., 2012). Thus, in contrast to other wood-eating symbioses wherein the microbes consume energy-rich glucose and secrete lower-energy metabolites, this strategy allows the host shipworm to directly consume glucose by hosting the bacteria in the gills and not in the digestive organ. To make this remarkable lifestyle possible, it has been hypothesized that shipworm symbionts secrete potent antibiotics into the host, where they would have to be compatible with animal metabolism (Elshahawi et al., 2013; Yang et al., 2009). If so, the symbiosis might provide a ready source of new antibiotics to target the rise of multidrug resistance, a crucial problem in human health. Typically, intracellular symbiotic bacteria are difficult to cultivate, making it hard to discover the important antibiotics that result. However, a number of *Teredinibacter turnerae* strains have been successfully cultured, facilitating genome sequencing and large-scale fermentation for natural product isolation. Significantly, some of the potent compounds isolated from *Teredinibacter* in culture are also found in host shipworm animals, where they presumably help to keep out competing microbes (Han et al., 2013; Elshahawi et al, 2013). The compounds known so far include tartrolon, an exceptionally potent antiparasitic compound (Elshahawi et al., 2013; O'Connor et al., 2020), and a siderophore, tumerbactin (Han et al., 2013). However, the key antibacterial compounds, which would potentially be responsible for shaping the shipworm gill communities and the axenic cecum, have yet to be described.

One exemplary bacterial isolate, *T. turnerae* 17901, was identified as an excellent potential source of secondary metabolites based on the high content of complex polyketide synthase (PKS) and nonribosomal peptide synthetase (NRPS) biosynthetic gene clusters (Yang et al., 2009). A recent systematic analysis of additional cultivated symbiont genomes and shipworm gill metagenomes uncovered a vast pool of uncharacterized biosynthetic gene clusters (BGCs), including several that are highly conserved in the species *T. turnerae* and present in the metagenomes of all *T. turnerae* containing shipworms, implying they are important for the symbiotic relationship. (8) Furthermore, antibiotics produced by these symbionts would need to be non-toxic to the shipworm and be capable of distribution through host tissues, potentially indicating attractive toxicity and pharmacokinetic properties.

Antibiotics, particularly those with new chemical scaffolds and potentially new mechanisms of action, are urgently needed. Multidrug resistant strains of many pathogenic bacteria have been on the rise, and despite the swelling clinical need, antibiotic drug discovery has slowed or halted in recent decades (Taccolnelli et al., 2018). Most current antibiotic therapies have come from the natural product chemical space, but the rate of discovery for new scaffolds has slowed. This is largely due to the fact that the focus has largely been on soil-dwelling actinomycetes, and the low hanging fruit has already been picked (Silver, 2011).

Using a symbiosis-ecology guided rationale, shipworm gill symbionts have emerged as a potentially prolific new source of antibacterial compounds. Of the three pathways that are highly conserved throughout *T. turnerae* that have been investigated, one encodes the triscatecholate siderophore turnerbactin (Han et al., 2013). Siderophores are ecologically important compounds for both free living microbes and those in symbiotic systems. For instance, beneficial bacteria have been shown to suppress plant pathogens in the rhizosphere via iron sequestration through the production of iron chelating compounds (Raaijmakers et al., 1995). The other two conserved pathways encode antibiotic and antiparasitic compounds. The boronated polyketide macrolides tartrolon D/E have moderate antibiotic activity against (Elshahawi et al., 2013) *Pseudomonas aeruginosa* and drug-resistant *Staphylococcus aureus* (Elshahawi et al., 2013). They are much more potent, however, against apicomplexan parasites with low picomolar activity against some strains (O'Connor et al., 2020).

Despite theories that intracellular shipworm symbionts may offer antibiotic properties, and, in particular, antibiotic properties against resistant bacterial strains as detailed further herein, the identification and structure elucidation of these metabolites has yet to be determined. Further, the use of these metabolites to develop novel compounds having antibiotic properties has yet to be explored. Thus, there remains a need for antibiotics that are selective against drug-resistant pathogens and methods of making and using same. These needs and others are satisfied by the present invention.

SUMMARY

In accordance with the purpose(s) of the invention, as embodied and broadly described herein, the invention, in one aspect, relates to cyclopeptides and methods of using the disclosed cyclopeptides to treat bacterial infections due to, for example, a Gram-negative pathogen (e.g., *Acinetobacter* spp., *Aeromonas* spp., *Bordetella* spp., *Citrobacter* spp., *Enterobacter* spp., *Escherichia* spp., *Haemophilus* spp., *Klebsiella* spp., *Moraxella* spp., *Neisseria* spp., *Proteus* spp., *Pseudomonas* spp., *Salmonella* spp., *Shigella* spp., *Stenotrophomonas* spp., *Vibrio* spp., *Yersinia* spp).

Thus, disclosed are compounds having a structure represented by a formula

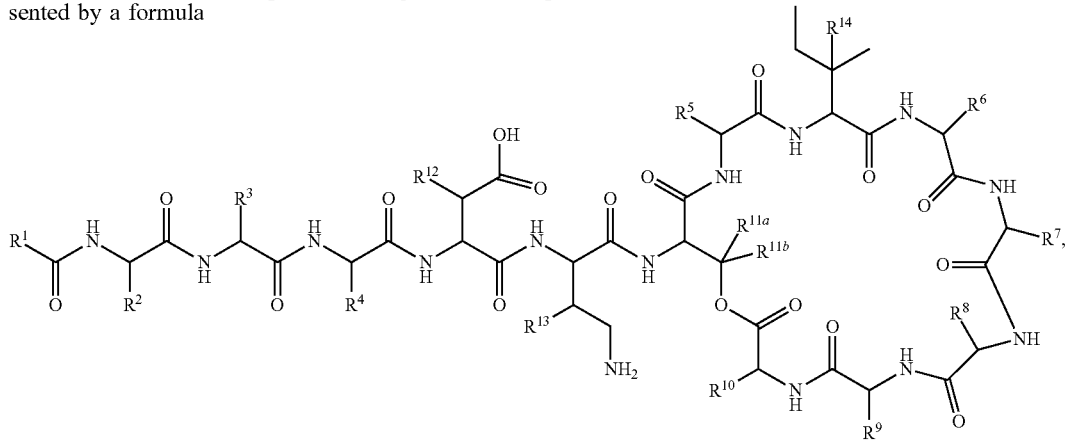

wherein $R^1$ is selected from C1-C24 alkyl, C2-C24 alkenyl, and a structure represented by a formula:

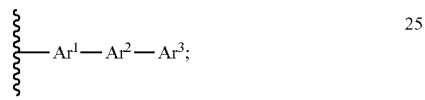

wherein each of $Ar^1$, $Ar^2$, and $Ar^3$ is independently selected from phenyl and C2-C5 heteroaryl, and is substituted with 0, 1, 2, or 3 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl; wherein each of $R^2$, $R^3$, $R^4$, $R^5$, $R^6$, $R^7$, $R^8$, $R^9$, and $R^{10}$ is independently selected from a natural amino acid residue and an unnatural amino acid residue; wherein each of $R^{11a}$ and $R^{11b}$ is independently selected from hydrogen and C1-C4 alkyl; and wherein each of $R^{12}$, $R^{13}$, and $R^{14}$ is independently selected from —OH, —SH, and —NH$_2$, or a pharmaceutically acceptable salt thereof, provided that the compound does not have a structure represented by a formula:

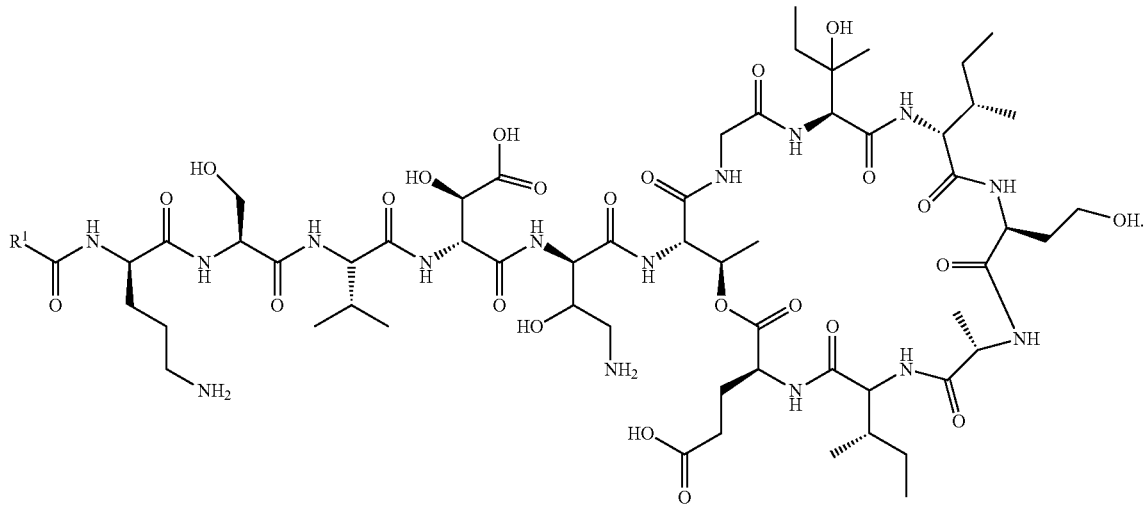

Also disclosed are compounds having a structure represented by a formula:

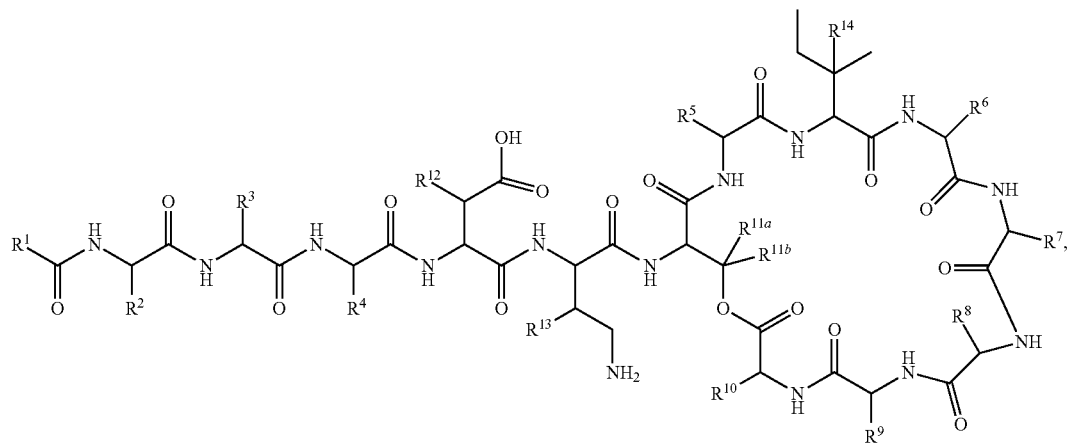

wherein $R^1$ is selected from C1-C24 alkyl and C2-C24 alkenyl; wherein each of $R^2$, $R^3$, $R^4$, $R^5$, $R^6$, $R^7$, $R^8$, $R^9$, and $R^{10}$ is independently selected from a natural amino acid residue and an unnatural amino acid residue; wherein each of $R^{11a}$ and $R^{11b}$ is independently selected from hydrogen and C1-C4 alkyl; and wherein each of $R^{12}$, $R^{13}$, and $R^{14}$ is independently selected from —OH, —SH, and —NH$_2$, or a pharmaceutically acceptable salt thereof, provided that the compound does not have a structure represented by a formula:

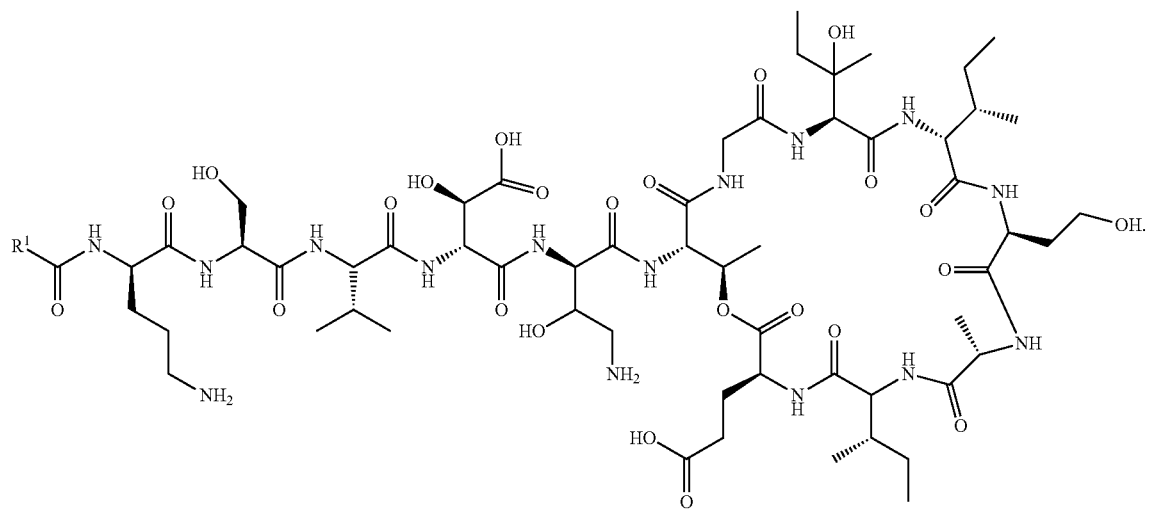

Also disclosed are compounds having a structure represented by a formula:

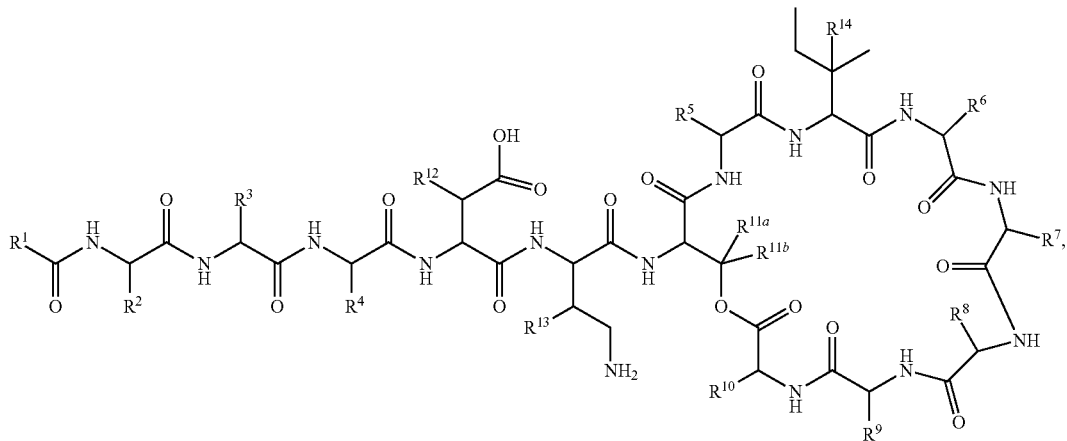

wherein $R^1$ is selected from C1-C24 alkyl and C2-C24 alkenyl; wherein each of $R^2$, $R^3$, $R^4$, $R^5$, $R^6$, $R^7$, $R^8$, $R^9$, and $R^{10}$ is independently selected from a natural amino acid residue and an unnatural amino acid residue; wherein each of $R^{11a}$ and $R^{11b}$ is independently selected from hydrogen and C1-C4 alkyl; and wherein each of $R^{12}$, $R^{13}$, and $R^{14}$ is independently selected from —OH, —SH, and —NH$_2$, or a pharmaceutically acceptable salt thereof.

Also disclosed are compounds having a structure represented by a formula:

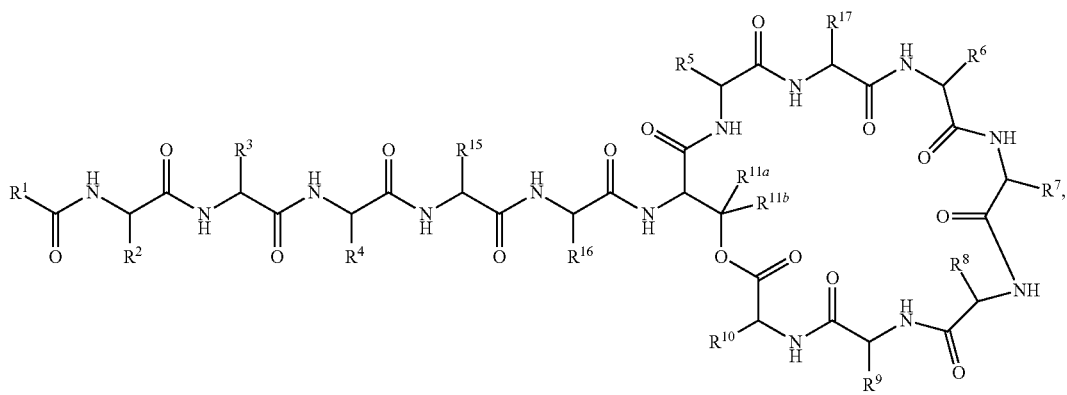

wherein $R^1$ is selected from C1-C24 alkyl, C2-C24 alkenyl, and a structure represented by a formula:

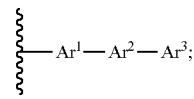

wherein each of $Ar^1$, $Ar^2$, and $Ar^3$ is independently selected from phenyl and C2-C5 heteroaryl, and is substituted with 0, 1, 2, or 3 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl; wherein each of $R^2$, $R^3$, $R^7$, $R^{10}$, $R^{15}$, and $R^{16}$ is independently selected from a natural amino acid residue and an unnatural amino acid residue, provided that each of $R^2$, $R^3$, $R^7$, $R^{10}$, $R^{15}$, and $R^{16}$ is a non-glycine residue; wherein each of $R^4$, $R^5$, $R^6$, $R^8$, $R^9$, and $R^{17}$ is independently selected from a natural amino acid residue and an unnatural amino acid residue; and wherein each of $R^{11a}$ and $R^{11b}$ is independently selected from hydrogen and C1-C4 alkyl, or a pharmaceutically acceptable salt thereof, provided that the compound does not have a structure represented by a formula:

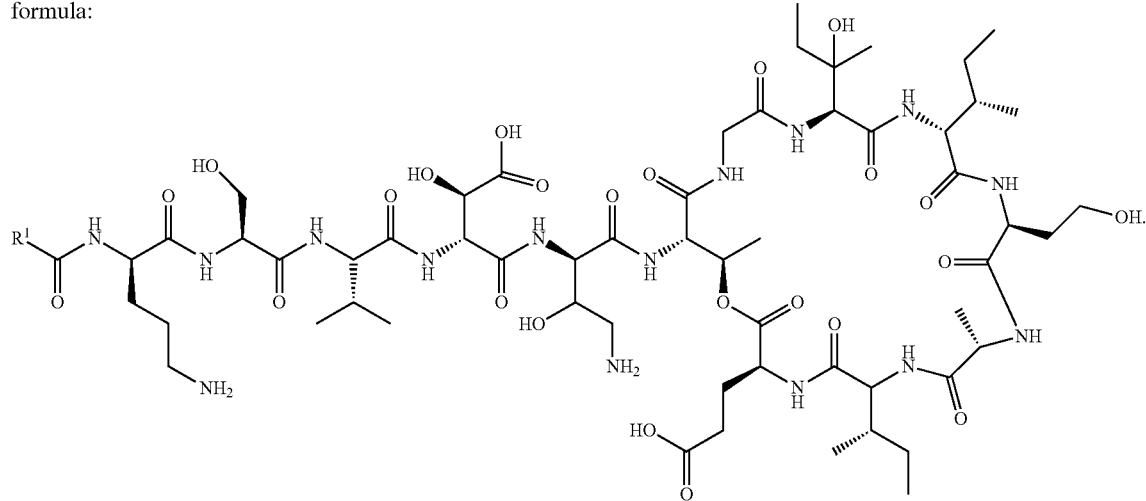

Also disclosed are compounds having a structure represented by a formula:

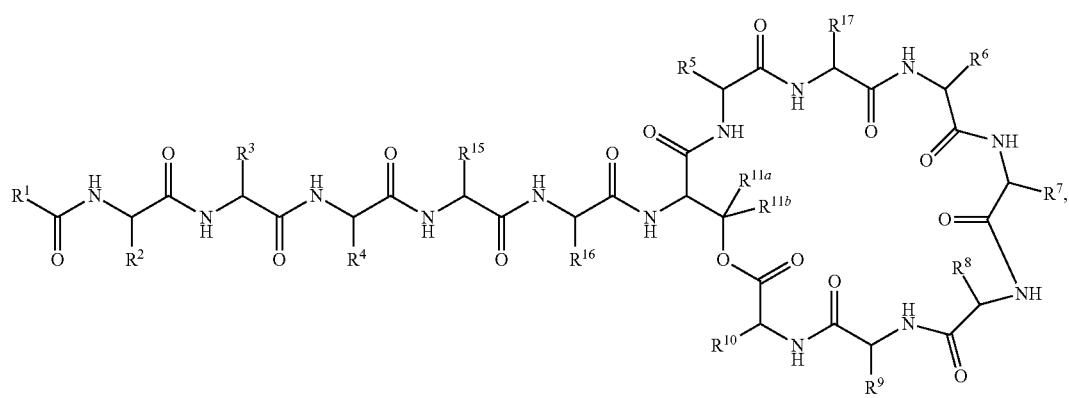

wherein R¹ is selected from C1-C24 alkyl and C2-C24 alkenyl; wherein each of $R^2$, $R^3$, $R^7$, $R^{10}$, $R^{15}$, and $R^{16}$ is independently selected from a natural amino acid residue and an unnatural amino acid residue, provided that each of $R^2$, $R^3$, $R^7$, $R^{10}$, $R^{15}$, and $R^{16}$ is a non-glycine residue; wherein each of $R^4$, $R^5$, $R^6$, $R^8$, $R^9$, and $R^{17}$ is independently selected from a natural amino acid residue and an unnatural amino acid residue; and wherein each of $R^{11a}$ and $R^{11b}$ is independently selected from hydrogen and C1-C4 alkyl, or a pharmaceutically acceptable salt thereof, provided that the compound does not have a structure represented by a formula:

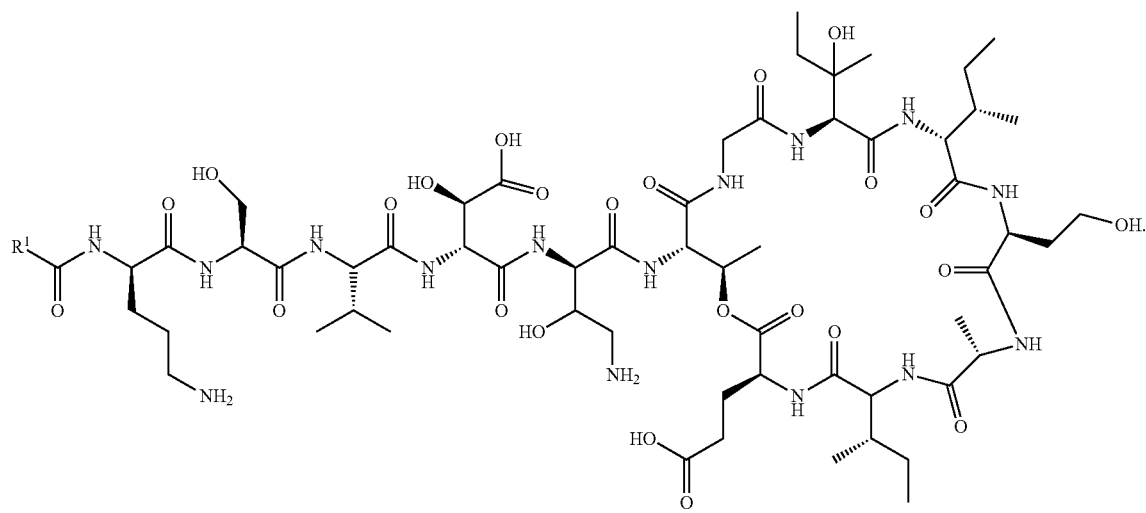

Also disclosed are compounds having a structure represented by a formula:

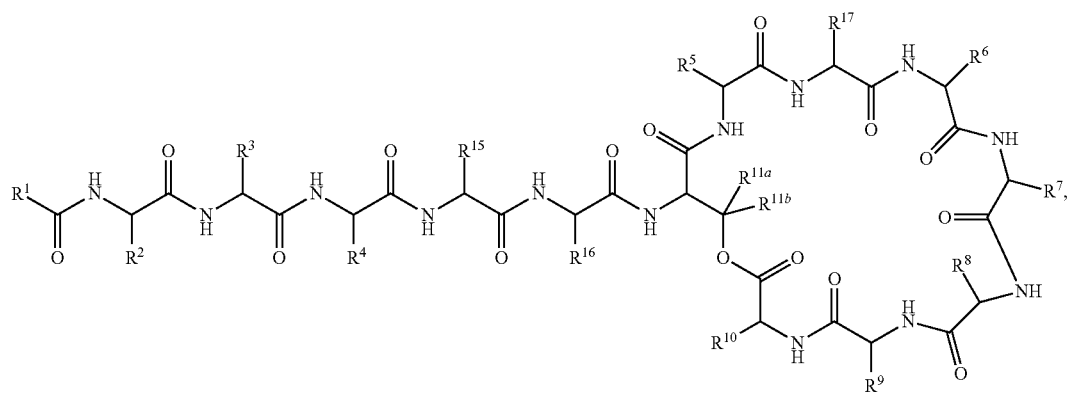

wherein R¹ is selected from C1-C24 alkyl and C2-C24 alkenyl; wherein each of $R^2$, $R^3$, $R^7$, $R^{10}$, $R^{15}$, and $R^{16}$ is independently selected from a natural amino acid residue and an unnatural amino acid residue, provided that each of $R^2$, $R^3$, $R^7$, $R^{10}$, $R^{15}$, and $R^{16}$ is a non-glycine residue; wherein each of $R^4$, $R^5$, $R^6$, $R^8$, $R^9$, and $R^{17}$ is independently selected from a natural amino acid residue and an unnatural amino acid residue; and wherein each of $R^{11a}$ and $R^{11b}$ is independently selected from hydrogen and C1-C4 alkyl, or a pharmaceutically acceptable salt thereof.

Also disclosed are pharmaceutical compositions comprising a therapeutically effective amount of a disclosed compound, and a pharmaceutically acceptable carrier.

Also disclosed are methods of treating a bacterial infection in a subject in need thereof, the method comprising administering to the subject an effective amount of a disclosed compound.

Also disclosed are methods of treating a bacterial infection in a subject in need thereof, the method comprising administering to the subject an effective amount of a compound having a structure represented by a formula:

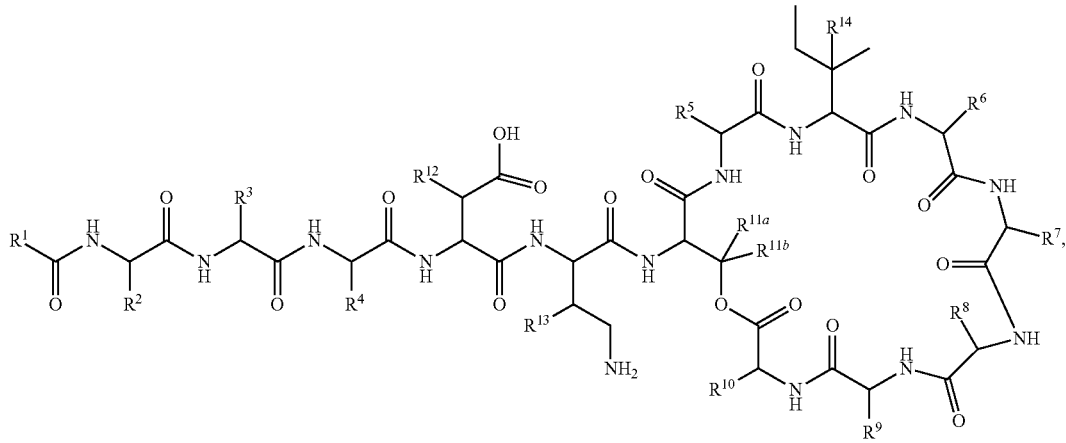

wherein $R^1$ is selected from C1-C24 alkyl, C2-C24 alkenyl, and a structure represented by a formula:

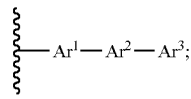

wherein each of $Ar^1$, $Ar^2$, and $Ar^3$ is independently selected from phenyl and C2-C5 heteroaryl, and is substituted with 0, 1, 2, or 3 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C4 alkylamino, (C1-C12)(C1-C12) dialkylamino, and C1-C12 aminoalkyl; wherein each of $R^2$, $R^3$, $R^4$, $R^5$, $R^6$, $R^7$, $R^8$, $R^9$, and $R^{10}$ is independently selected from a natural amino acid residue and an unnatural amino acid residue; wherein each of $R^{11a}$ and $R^{11b}$ is independently selected from hydrogen and C1-C4 alkyl; and wherein each of $R^{12}$, $R^{13}$, and $R^{14}$ is independently selected from —OH, —SH, and —NH$_2$, or a pharmaceutically acceptable salt thereof.

Also disclosed are methods of treating a bacterial infection in a subject in need thereof, the method comprising administering to the subject an effective amount of a compound having a structure represented by a formula:

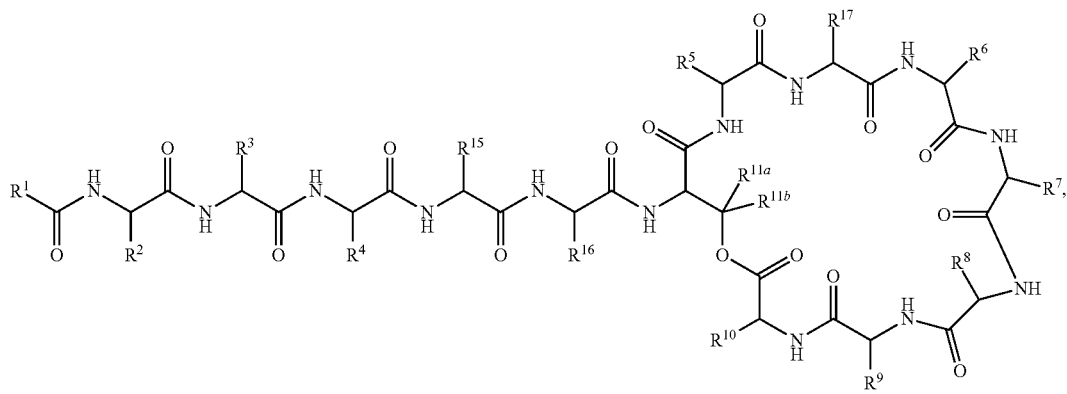

wherein R$^1$ is selected from C1-C24 alkyl, C2-C24 alkenyl, and a structure represented by a formula:

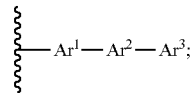

wherein each of Ar$^1$, Ar$^2$, and Ar$^3$ is independently selected from phenyl and C2-C5 heteroaryl, and is substituted with 0, 1, 2, or 3 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl; wherein each of R$^2$, R$^3$, R$^7$, R$^{10}$, R$^{15}$, and R$^{16}$ is independently selected from a natural amino acid residue and an unnatural amino acid residue, provided that each of R$^2$, R$^3$, R$^7$, R$^{10}$, R$^{15}$, and R$^{16}$ is a non-glycine residue; wherein each of R$^4$, R$^5$, R$^6$, R$^8$, R$^9$, and R$^{17}$ is independently selected from a natural amino acid residue and an unnatural amino acid residue; and wherein each of R$^{11a}$ and R$^{11b}$ is independently selected from hydrogen and C1-C4 alkyl, or a pharmaceutically acceptable salt thereof.

Also disclosed are kits comprising a disclosed compound, and one or more selected from: (a) an antibacterial agent; (b) instructions for treating a bacterial infection; and (c) instructions for administering the compound in connection with treating a bacterial infection.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE FIGURES

The accompanying figures, which are incorporated in and constitute a part of this specification, illustrate several aspects and together with the description serve to explain the principles of the invention.

Referring to FIG. 1A, COSY/TOCSY (bold bonds), key ROESY (dashed arrows), and key HMBC (solid arrows) correlations used to solve the planar structure are shown. Referring to FIG. 1B, the structure of tumercyclamycins with assigned absolute configuration are shown.

Referring to FIG. 3A, multigene BLAST identified a conserved NRPS cluster present in eight sequenced T. turnerae strains. Referring to FIG. 3B, the proteins encoded by each NRPS gene are greater than 85% identical when compared with corresponding proteins in all eight clusters.

Referring to FIG. 3C, BLASTp identity comparison of extracted adenylation domains from all identified tur gene clusters is shown. Corresponding adenylation domains retain greater than 90% identity, indicating that the peptide backbone of the product is likely highly conserved across all T. turnerae strains. Note the much higher sequence conservation of TurE and TurD adenylation domains in comparison with the rest of the TurE/TurD proteins. In addition, within single NRPS proteins, there is very little similarity between NRPS adenylation domains, even when they are activating very similar or identical amino acids (such as 2× Ile and OH-Ile).

FIG. 8A-J show representative data illustrating HRESI-MS and MSMS fragmentation of compounds 1-4, minor analogs.

FIG. 9A-I show representative data illustrating the results of advanced Marfey's for stereochemical analysis and ozonolysis for double bond placement of compound 2.

FIG. 10A-D show representative data from additional antimicrobial and cytotoxicity experiments.

FIG. 12A is a scheme depicting an in-frame, scarless deletion mutant of the turH gene which was generated through recombinant engineering.

FIG. 12B shows representative UPLC-MS data for the ΔturH strain, which did not include the peaks for tunercyclamycins A and B. Two new peaks are found with slightly altered retention times with m/z values indicating a loss of 16 amu from both major natural compounds. FIG. 12C shows representative MSMS fragments localizing the loss of 16 amu to the aspartic acid residue.

Figure 1A:
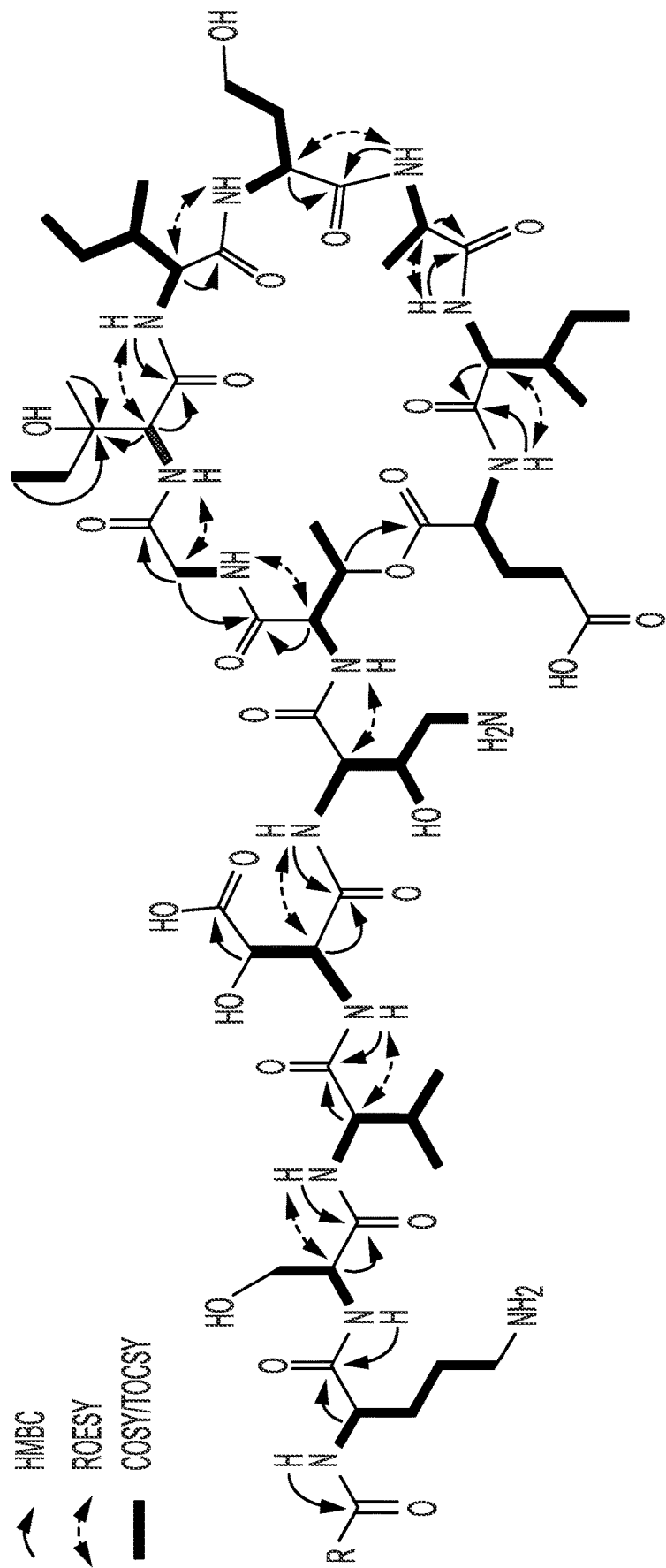
FIG. 1A and FIG. 1B show representative structure elucidation of turnercyclamycin A-D.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present disclosure can be understood more readily by reference to the following detailed description of the invention, the figures and the examples included herein.

Before the present methods and compositions are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. DEFINITIONS

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise.

"Optional" or "optionally" means that the subsequently described event, circumstance, or material may or may not occur or be present, and that the description includes instances where the event, circumstance, or material occurs or is present and instances where it does not occur or is not present.

The word "or" as used herein means any one member of a particular list and also includes any combination of members of that list.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g., a polypeptide or nucleic acid), which is assayed as described herein. A sample may also be any body fluid or excretion (for example, but not limited to, blood, urine, stool, saliva, tears, bile) that contains cells or cell components.

As used herein, the term "subject" refers to the target of administration, e.g., a human. Thus the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered.

As used herein, the term "patient" refers to a subject afflicted with a disease, disorder or condition or at risk for a disease, disorder or condition. The term "patient" includes human and veterinary subjects. In some aspects of the disclosed methods, the "patient" has been diagnosed with a need for treatment, such as, for example, prior to an administering step.

As used herein the terms "amino acid" and "amino acid identity" refers to one of the 20 naturally occurring amino acids or any non-natural analogues that may be in any of the antibodies, variants, or fragments disclosed. Thus "amino acid" as used herein means both naturally occurring and synthetic amino acids. For example, homophenylalanine, citrulline and norleucine are considered amino acids for the purposes of the invention. "Amino acid" also includes amino acid residues such as proline and hydroxyproline. The side chain may be in either the (R) or the (S) configuration. In an aspect, the amino acids are in the D- or L-configuration. If non-naturally occurring side chains are used, non-amino acid substituents may be used, for example to prevent or retard in vivo degradation.

"Inhibit," "inhibiting" and "inhibition" mean to diminish or decrease an activity, level, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in an aspect, the inhibition or reduction can be a 10, 20, 30, 40, 50, 60, 70, 80, 90, 100%, or any amount of reduction in between as compared to native or control levels. In an aspect, the inhibition or reduction is 10-20, 20-30, 30-40, 40-50, 50-60, 60-70, 70-80, 80-90, or 90-100% as compared to native or control levels. In an aspect, the inhibition or reduction is 0-25, 25-50, 50-75, or 75-100% as compared to native or control levels.

"Treatment" and "treating" refer to administration or application of a therapeutic agent (e.g., a Tat 1 analog, peptide or polypeptide described herein) to a subject or performance of a procedure or modality on a subject for the purpose of obtaining a therapeutic benefit of a disease or health-related condition. For example, a treatment may include administration of a pharmaceutically effective amount of a peptide that is capable of activating degradation by the proteasome.

As used herein, the term "treating" refers to partially or completely alleviating, ameliorating, relieving, delaying onset of, inhibiting or slowing progression of, reducing severity of, and/or reducing incidence of one or more symptoms or features of a particular disease, disorder, and/or condition. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

A "variant" can mean a difference in some way from the reference sequence other than just a simple deletion of an N- and/or C-terminal amino acid residue or residues. Where the variant includes a substitution of an amino acid residue, the substitution can be considered conservative or non-conservative. Conservative substitutions can be those within the following groups: Ser, Thr, and Cys; Leu, ILe, and Val; Glu and Asp; Lys and Arg; Phe, Tyr, and Trp; and Gln, Asn, Glu, Asp, and His. Variants can include at least one substitution and/or at least one addition, there may also be at least one deletion. Variants can also include one or more non-naturally occurring residues. For example, they may include seleno-cysteine (e.g., seleno-L-cysteine) at any position, including in the place of cysteine. Many other "unnatural" amino acid substitutes are known in the art and are available from commercial sources. Examples of non-naturally occurring amino acids include D-amino acids, amino acid residues having an acetylaminomethyl group attached to a sulfur atom of a cysteine, a pegylated amino acid, and omega amino acids of the formula $NH_2(CH_2)_nCOOH$ wherein n is 2-6 neutral, nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and ornithine is basic. Proline may be substituted with hydroxyproline and retain the conformation conferring properties of proline.

As used herein, the term "prevent" or "preventing" refers to preventing in whole or in part, or ameliorating or controlling.

The term "contacting" as used herein refers to bringing a disclosed compound and a cell, target of a disclosed peptide, or other biological entity together in such a manner that the compound can affect the activity of the target (e.g., spliceosome, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

Tis practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $—(CH_2)_a—$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $—OA^1$ where $A^1$ is alkyl or cycloalkyl as defined above. "Alkoxy" also includes polymers of alkoxy groups as just described; that is, an alkoxy can be a polyether such as $—OA^1-OA^2$ or $-OA^1-(OA^2)_n-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbomenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —$N(-alkyl)_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —$OC(O)A^1$ or —$C(O)OA^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -$(A^1O(O)C-A^2-C(O)O)$— or -$(A^1O(O)C-A^2-OC(O))$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -$(A^1O-A^2O)_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)$O-N(R^\circ)_2$; or $-(C_{1-4}$ straight or branched alkylene)$C(O)O-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^1$, or $-SSR^\bullet$ wherein each $R^\bullet$ is unsubstituted or where preceded by "halo" is substituted only with one or more halogens, and is independently selected from C14 aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, $-O(C(R^*_2))_{2-3}O-$, or $-S(C(R^*_2))_{2-3}S-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently C14 aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $-R^\bullet$, -(haloR$^\bullet$), $-OH$, $-OR^\bullet$—O(haloR$^\bullet$), $-CN$, $-C(O)OH$, $-C(O)OR^1$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, brosylate, and halides.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

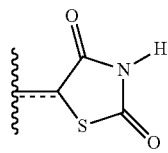

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-18%, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

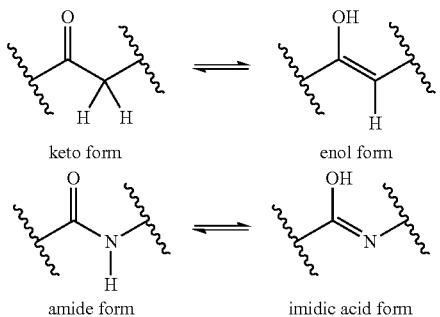

keto form      enol form amide form      imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

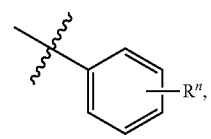

which is understood to be equivalent to a formula:

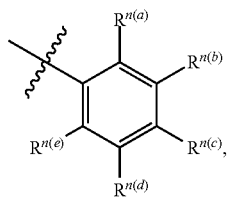

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental Volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible nonexpress basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

B. CYCLOPEPTIDES

In various aspects, the disclosed cyclopeptides can be prepared by a knockout method as disclosed elsewhere herein. Alternatively, the disclosed cyclopeptides can be the lipopeptide antibiotic products of a 13-module nonribosomal peptide synthetase (NRPS) found in *T. turnerae* strains.

In various further aspects, the disclosed cyclopeptides contain β-hydroxyisoleucine and 2,4-diamino-3-hydroxybutanoic acid.

In various further aspects, the disclosed peptides are bactericidal agents with 1, 2, and 8 μg/mL $MIC_{90}$'s against *Escherichia coli, Klebsiella pneumoniae*, and *Acinetobacter baumannii*, respectively. In various further aspects, the disclosed peptides that do not show toxicity in mammalian cells or hemolysis of mammalian erythrocytes.

Also disclosed are compositions comprising a disclosed cyclopeptide.

As used herein, the term "peptide" can also be used to include functional equivalents of the peptides described herein. As used herein, the term "functional equivalents" can refer to amino acid sequence variants having an amino acid substitution, addition, or deletion in some of the amino acid sequence of the peptide or polypeptide while simultaneously having similar or improved biological activity, compared with the peptide as described herein. In some aspects, the amino acid substitution can be a conservative substitution. Examples of the naturally occurring amino acid conservative substitution include, for example, aliphatic amino acids (Gly, Ala, and Pro), hydrophobic amino acids (Ile, Leu, and Val), aromatic amino acids (Phe, Tyr, and Trp), acidic amino acids (Asp and Glu), basic amino acids (His, Lys, Arg, Gln, and Asn), and sulfur-containing amino acids (Cys and Met). In some aspects, the amino acid deletion can be located in a region that is not directly involved in the activity of the peptide and polypeptide disclosed herein.

In some aspects, the amino acid sequence of the peptides described herein can include a peptide sequence that has substantial identity to any of the sequences of the peptides disclosed herein. As used herein, the term "substantial identity" means that two amino acid sequences, when optimally aligned and then analyzed by an algorithm normally used in the art, such as BLAST, GAP, or BESTFIT, or by visual inspection, share at least about 60%, 70%, 80%, 85%, 90%, or 95% sequence identity. Methods of alignment for sequence comparison are known in the art.

In some aspects, the amino acid sequence of the peptides described herein can include a peptide sequence that has some degree of identity or homology to any of sequences of the peptides disclosed herein. The degree of identity can vary and be determined by methods known to one of ordinary skill in the art. The terms "homology" and "identity" each refer to sequence similarity between two polypeptide sequences. Homology and identity can each be determined by comparing a position in each sequence which can be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position. A percentage of homology or identity between sequences is a function of the number of matching or homologous positions shared by the sequences. The peptides described herein can have at least or about 25%, 50%, 65%, 75%, 80%, 85%, 90%, 95%, 96%, 97%, 98%, or 99% identity or homology to the peptide or polypeptide.

In various aspects, disclosed are compounds having a structure as shown in FIG. 1A.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compound having a structure represented by a formula:

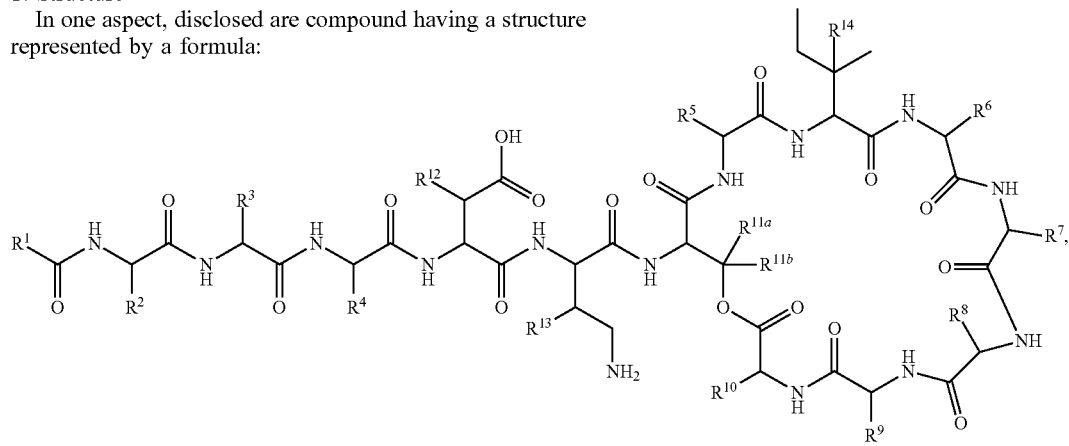

wherein $R^1$ is selected from C1-C24 alkyl, C2-C24 alkenyl, and a structure represented by a formula:

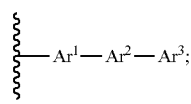

wherein each of $Ar^1$, $Ar^2$, and $Ar^3$ is independently selected from phenyl and C2-C5 heteroaryl, and is substituted with 0, 1, 2, or 3 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl; wherein each of $R^2$, $R^3$, $R^4$, $R^5$, $R^6$, $R^7$, $R^8$, $R^9$, and $R^{10}$ is independently selected from a natural amino acid residue and an unnatural amino acid residue; wherein each of $R^{11a}$ and $R^{11b}$ is independently selected from hydrogen and C1-C4 alkyl; and wherein each of $R^{12}$, $R^{13}$, and $R^{14}$ is independently selected from —OH, —SH, and —NH$_2$, or a pharmaceutically acceptable salt thereof, provided that the compound does not have a structure represented by a formula:

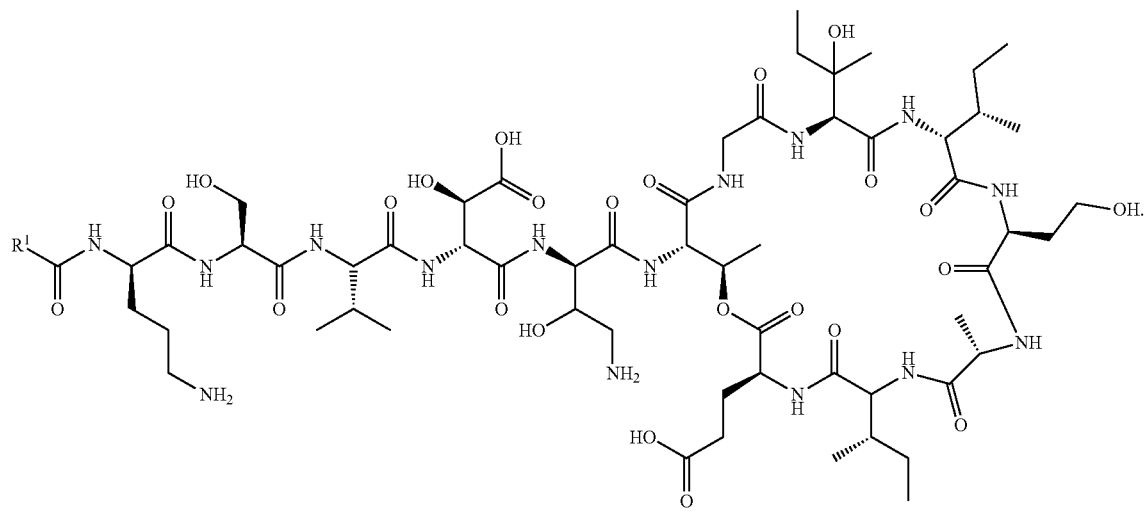

In one aspect, disclosed are compounds having a structure represented by a formula:

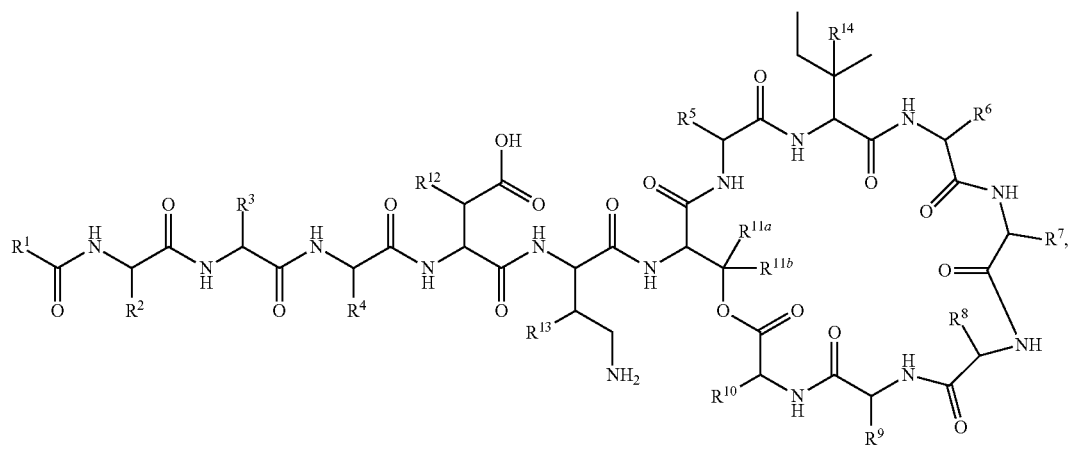

wherein $R^1$ is selected from C1-C24 alkyl and C2-C24 alkenyl; wherein each of $R^2$, $R^3$, $R^4$, $R^5$, $R^6$, $R^7$, $R^8$, $R^9$, and $R^{10}$ is independently selected from a natural amino acid residue and an unnatural amino acid residue; wherein each of $R^{11a}$ and $R^{11b}$ is independently selected from hydrogen and C1-C4 alkyl; and wherein each of $R^{12}$, $R^{13}$, and $R^{14}$ is independently selected from —OH, —SH, and —NH$_2$, or a pharmaceutically acceptable salt thereof. In a further aspect, the compound has a neutral charge.

In one aspect, disclosed are compounds having a structure represented by a formula:

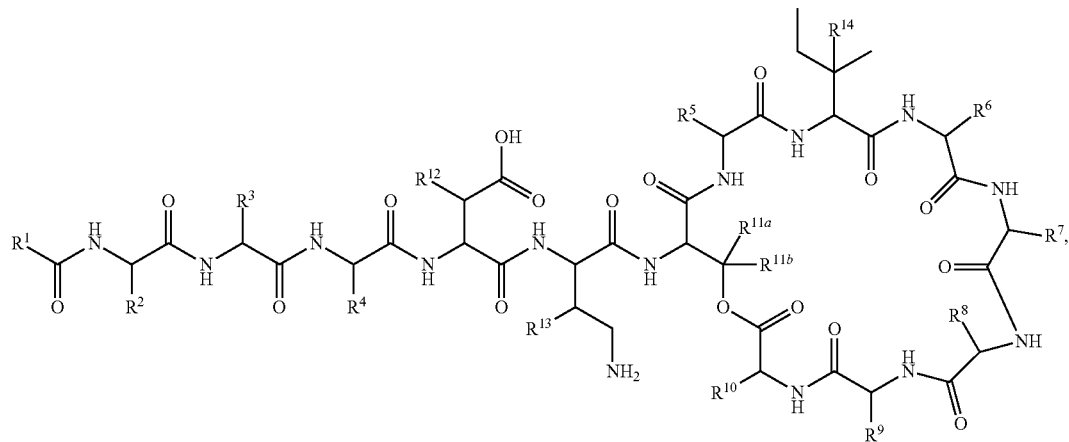

wherein $R^1$ is selected from C1-C24 alkyl and C2-C24 alkenyl; wherein each of $R^2$, $R^3$, $R^4$, $R^5$, $R^6$, $R^7$, $R^8$, $R^9$, and $R^{10}$ is independently selected from a natural amino acid residue and an unnatural amino acid residue; wherein each of $R^{11a}$ and $R^{11b}$ is independently selected from hydrogen and C1-C4 alkyl; and wherein each of $R^{12}$, $R^{13}$, and $R^{14}$ is independently selected from —OH, —SH, and —NH$_2$, or a pharmaceutically acceptable salt thereof, provided that the compound does not have a structure represented by a formula:

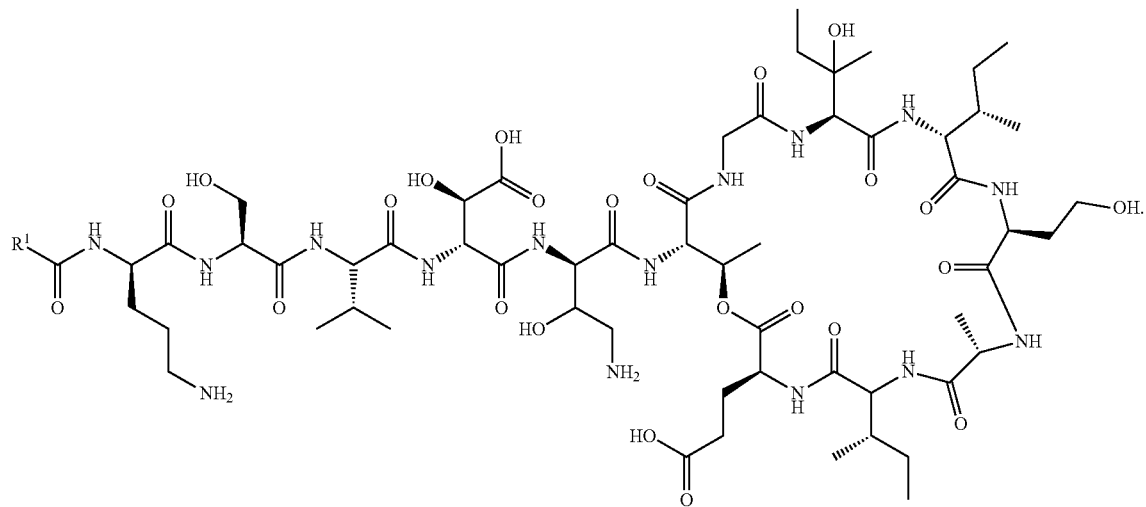

In one aspect, disclosed are compounds having a structure represented by a formula:

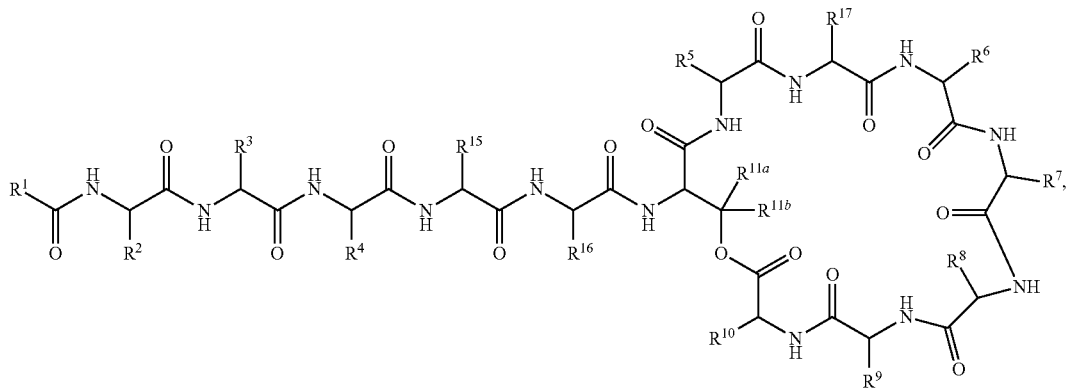

wherein $R^1$ is selected from C1-C24 alkyl, C2-C24 alkenyl, and a structure represented by a formula:

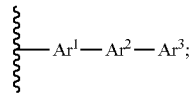

wherein each of $Ar^1$, $Ar^2$, and $Ar^3$ is independently selected from phenyl and C2-C5 heteroaryl, and is substituted with 0, 1, 2, or 3 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl; wherein each of $R^2$, $R^3$, $R^7$, $R^{10}$, $R^{15}$, and $R^{16}$ is independently selected from a natural amino acid residue and an unnatural amino acid residue, provided that each of $R^2$, $R^3$, $R^7$, $R^{10}$, $R^{15}$, and $R^{16}$ is a non-glycine residue; wherein each of $R^4$, $R^5$, $R^6$, $R^8$, $R^9$, and $R^{17}$ is independently selected from a natural amino acid residue and an unnatural amino acid residue; and wherein each of $R^{11a}$ and $R^{11b}$ is independently selected from hydrogen and C1-C4 alkyl, or a pharmaceutically acceptable salt thereof, provided that the compound does not have a structure represented by a formula:

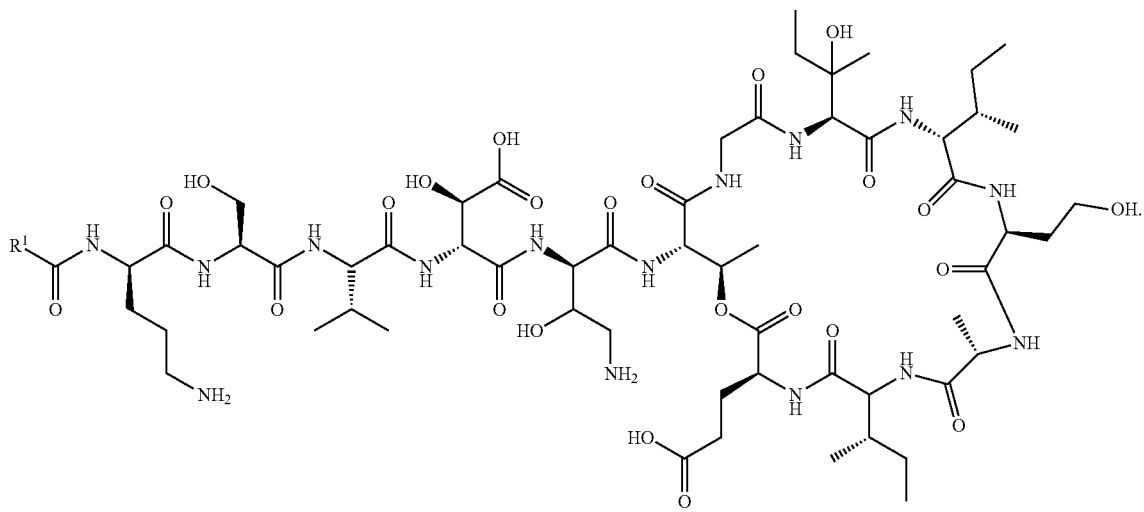

In one aspect, disclosed are compounds having a structure represented by a formula:

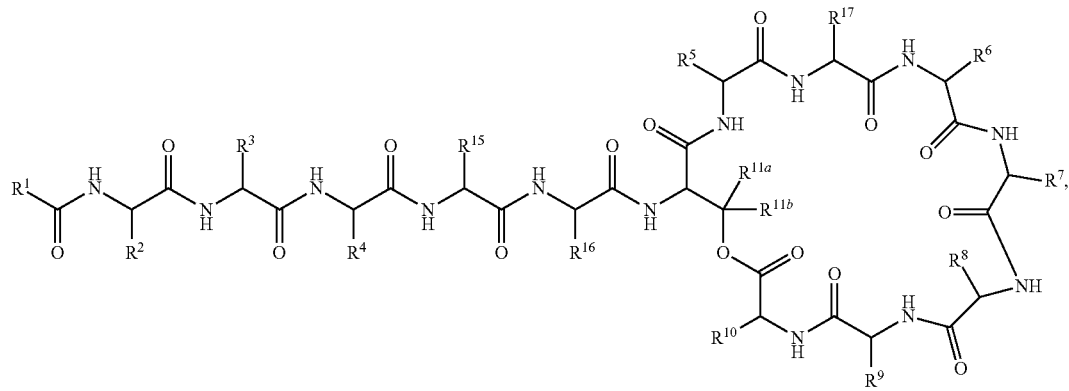

wherein $R^1$ is selected from C1-C24 alkyl and C2-C24 alkenyl; wherein each of $R^2$, $R^3$, $R^7$, $R^{10}$, $R^{15}$, and $R^{16}$ is independently selected from a natural amino acid residue and an unnatural amino acid residue, provided that each of $R^2$, $R^3$, $R^7$, $R^{10}$, $R^{15}$, and $R^{16}$ is a non-glycine residue; wherein each of $R^4$, $R^5$, $R^6$, $R^8$, $R^9$, and $R^7$ is independently selected from a natural amino acid residue and an unnatural amino acid residue; and wherein each of $R^{11a}$ and $R^{11b}$ is independently selected from hydrogen and C1-C4 alkyl, or a pharmaceutically acceptable salt thereof. In a further aspect, the compound has a neutral charge.

In one aspect, disclosed are compounds having a structure represented by a formula:

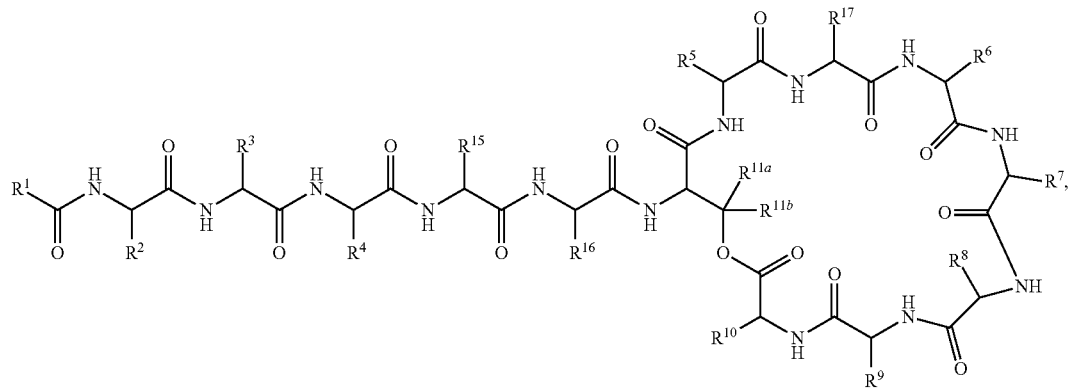

wherein $R^1$ is selected from C1-C24 alkyl and C2-C24 alkenyl; wherein each of $R^2$, $R^3$, $R^7$, $R^{10}$, $R^{15}$, and $R^{16}$ is independently selected from a natural amino acid residue and an unnatural amino acid residue, provided that each of $R^2$, $R^3$, $R^7$, $R^{10}$, $R^{15}$, and $R^{16}$ is a non-glycine residue; wherein each of $R^4$, $R^5$, $R^6$, $R^8$, $R^9$, and $R^{17}$ is independently selected from a natural amino acid residue and an unnatural amino acid residue; and wherein each of $R^{11a}$ and $R^{11b}$ is independently selected from hydrogen and C1-C4 alkyl, or a pharmaceutically acceptable salt thereof, provided that the compound does not have a structure represented by a formula:

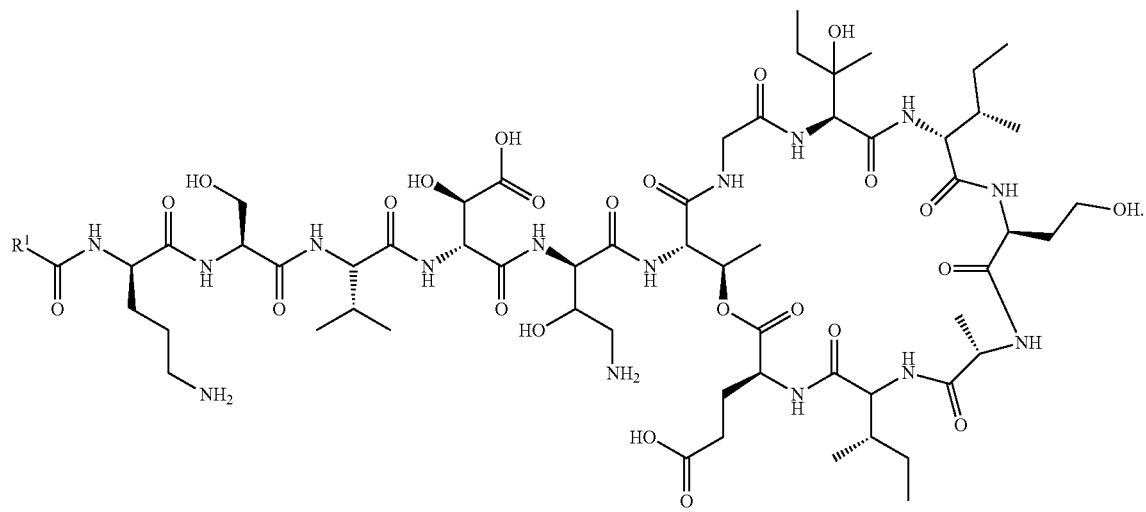
In various aspects, the compound has a structure represented by a formula:
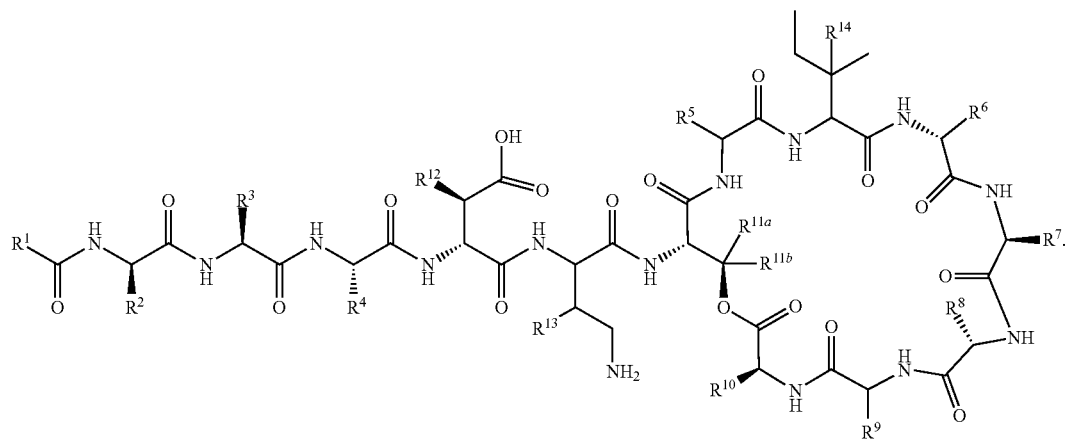
In various aspects, the compound has a structure represented by a formula:
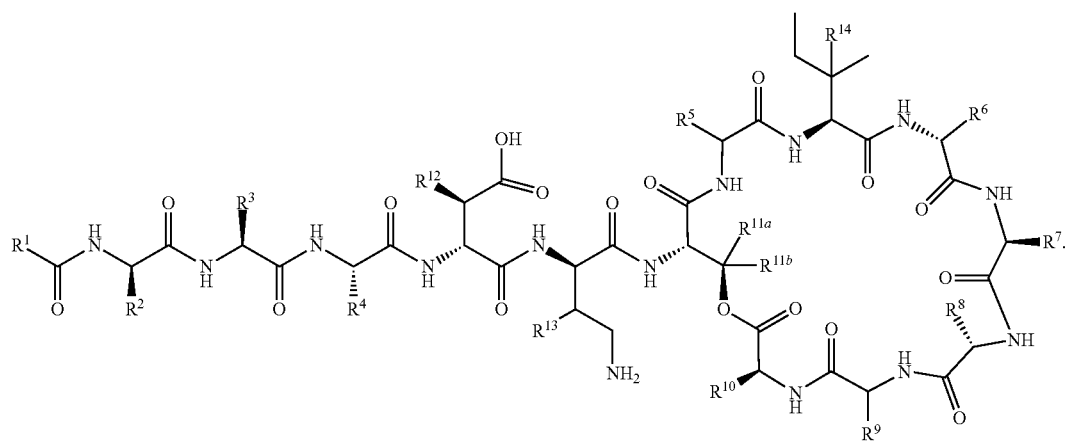

In various aspects, the compound has a structure represented by a formula:
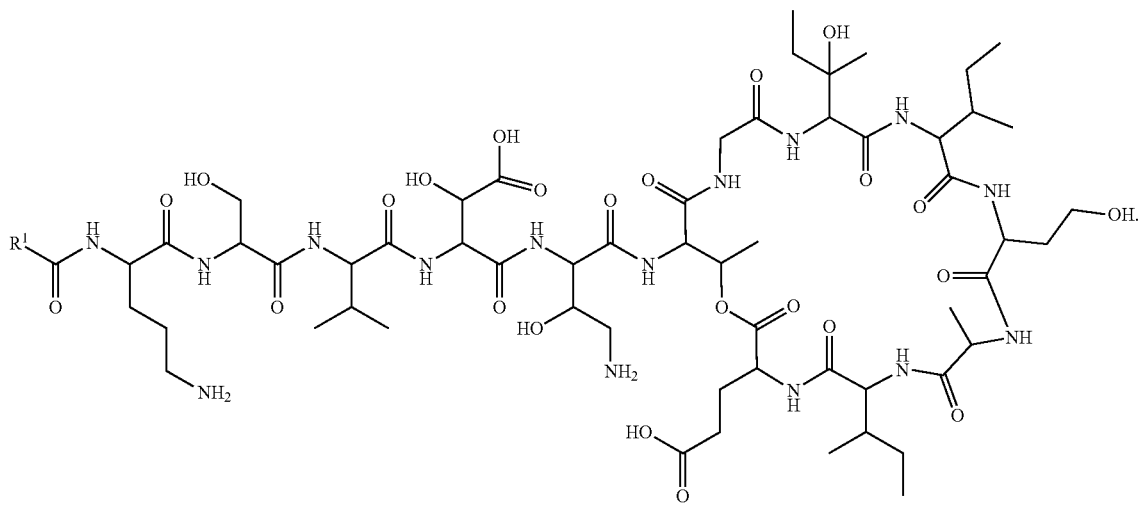
In further aspect, $R^1$ is selected from:
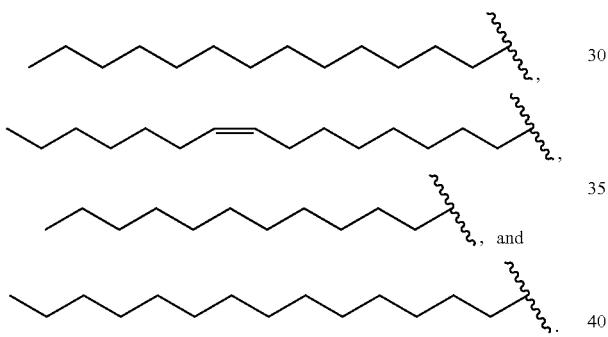
In various aspects, the compound has a structure represented by a formula:
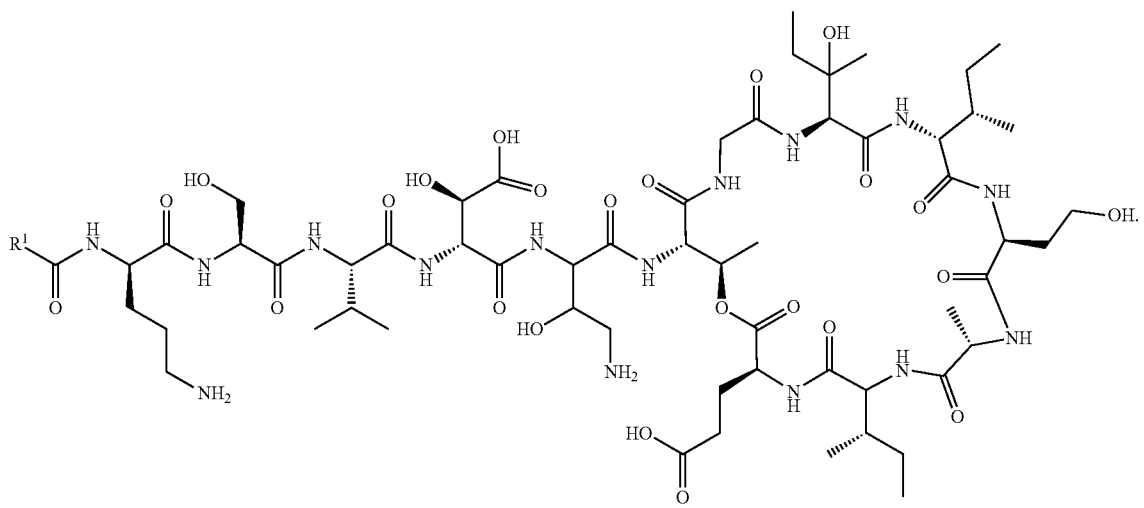

In a further aspect, R¹ is selected from:
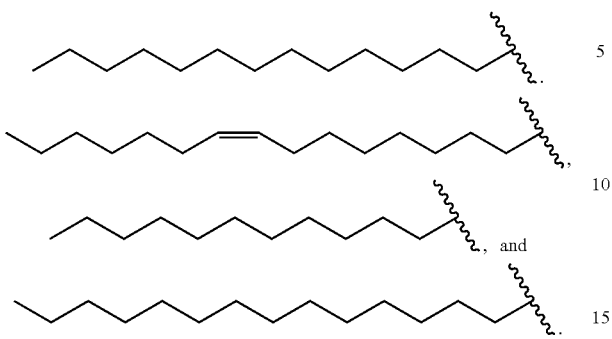
In various aspects, the compound is:
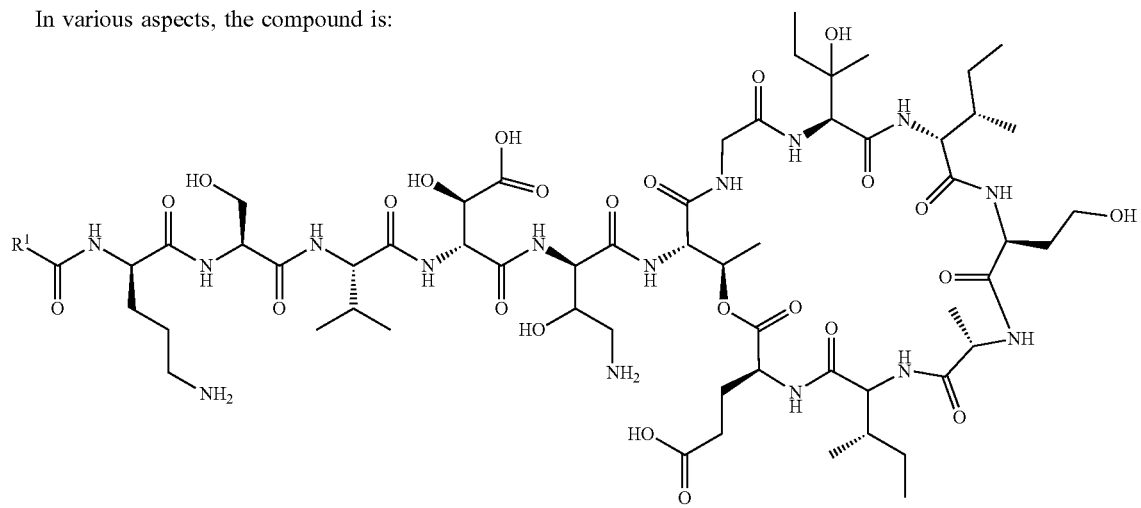
In a further aspect, R¹ is selected from:
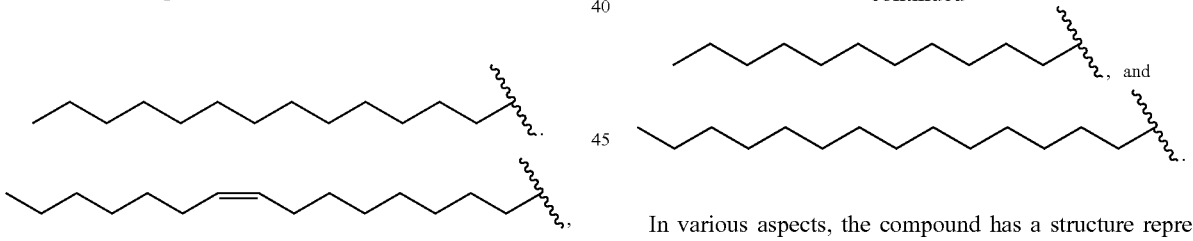
In various aspects, the compound has a structure represented by a formula:
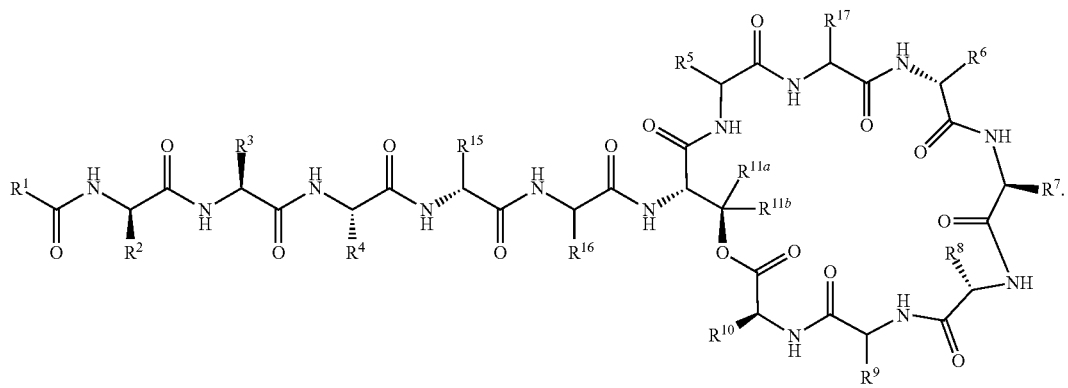

In various aspects, the compound has a structure represented by a formula:
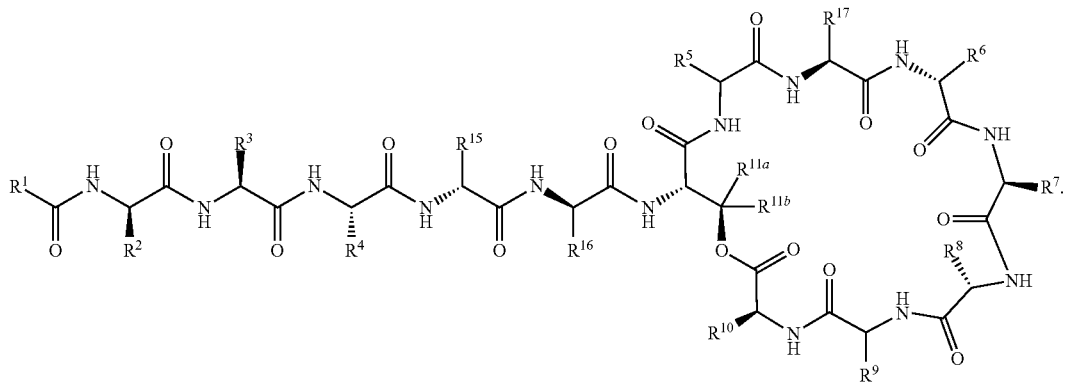
In various aspects, the compound has a structure represented by a formula:
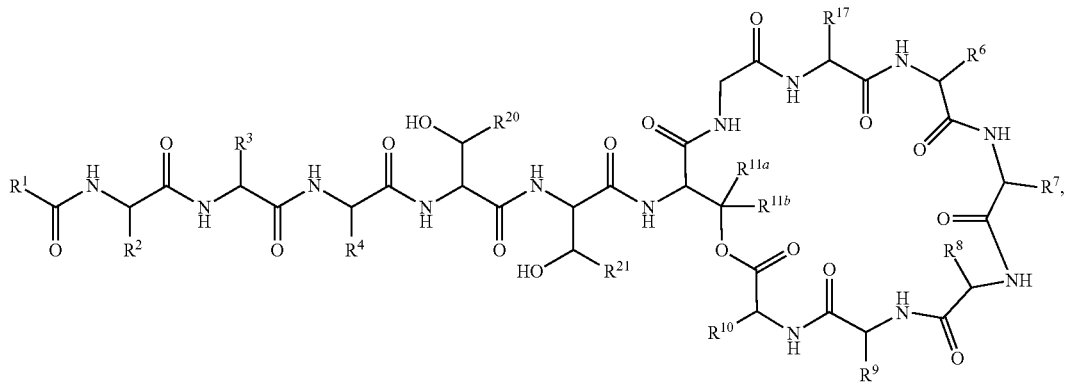
wherein each of $R^{20}$ and $R^{21}$ is independently selected from selected from —$CH_2CH_2CH_2NH_3^+$, —$C(O)NH_2$, —$C(O)O^-$, —$CH(CH_3)CH_2CH_3$, —$CH_2NH_2$, and a structure:
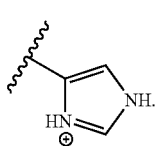

In various aspects, the compound has a structure represented by a formula selected from:
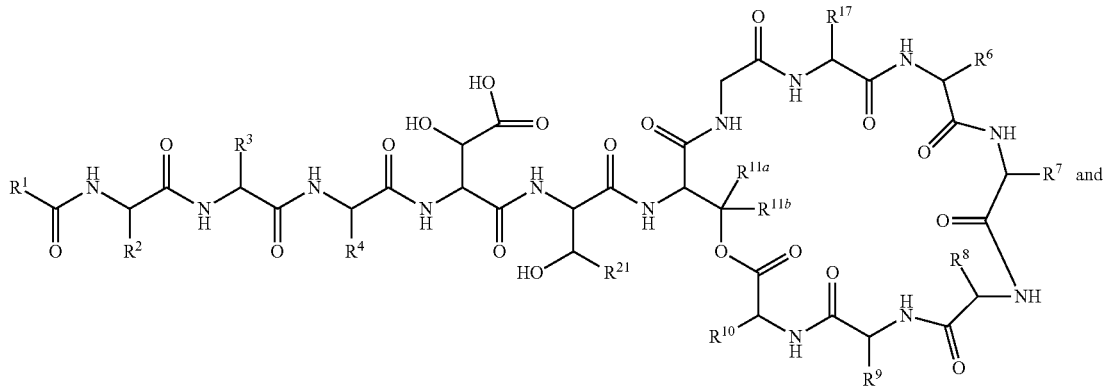
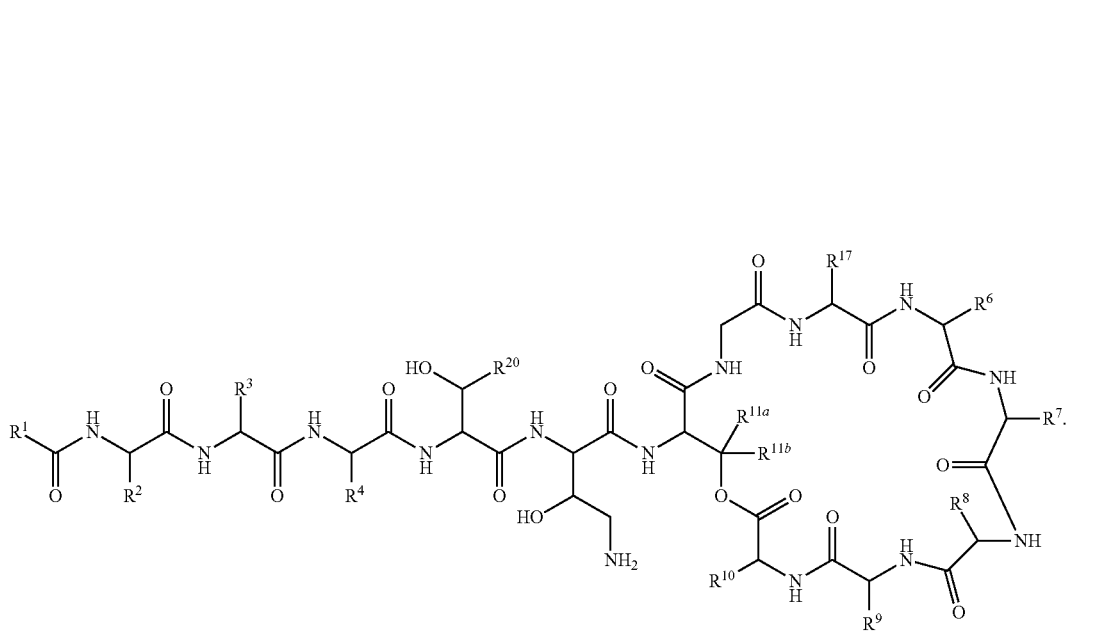
In various aspects, the compound has a structure represented by a formula:
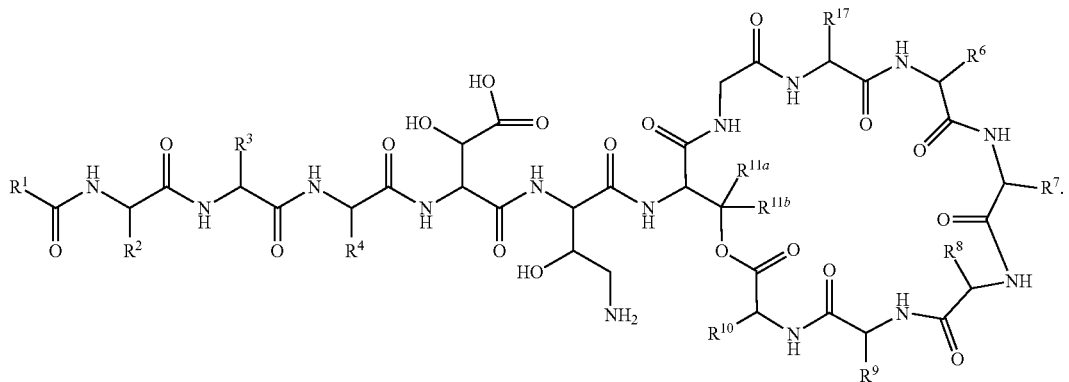

In various aspects, the compound has a structure represented by a formula:
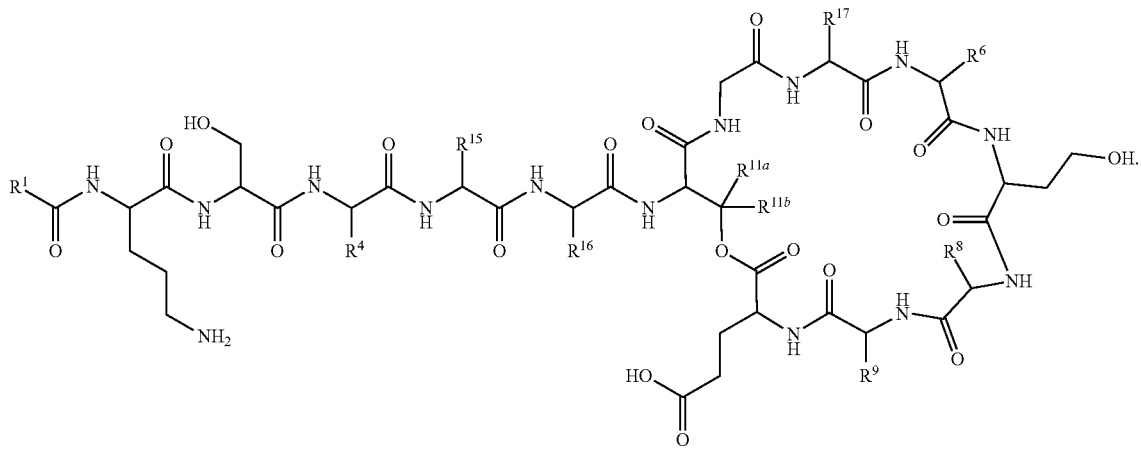
In various aspects, the compound has a structure represented by a formula:
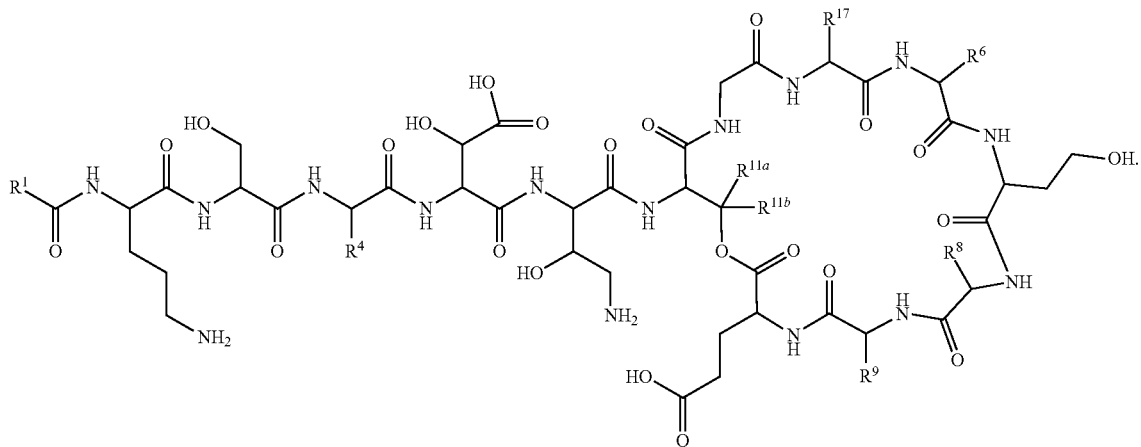
In various aspects, the compound has a structure represented by a formula selected from:
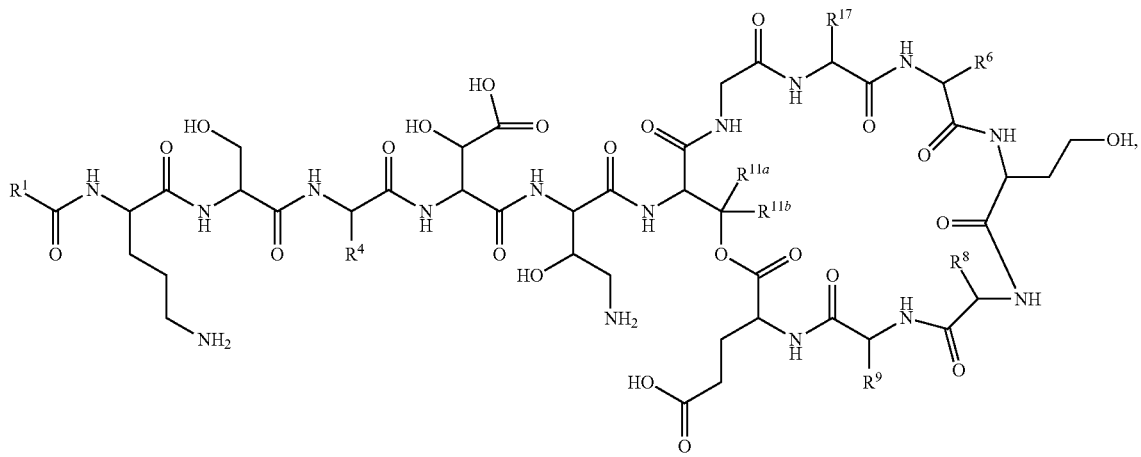

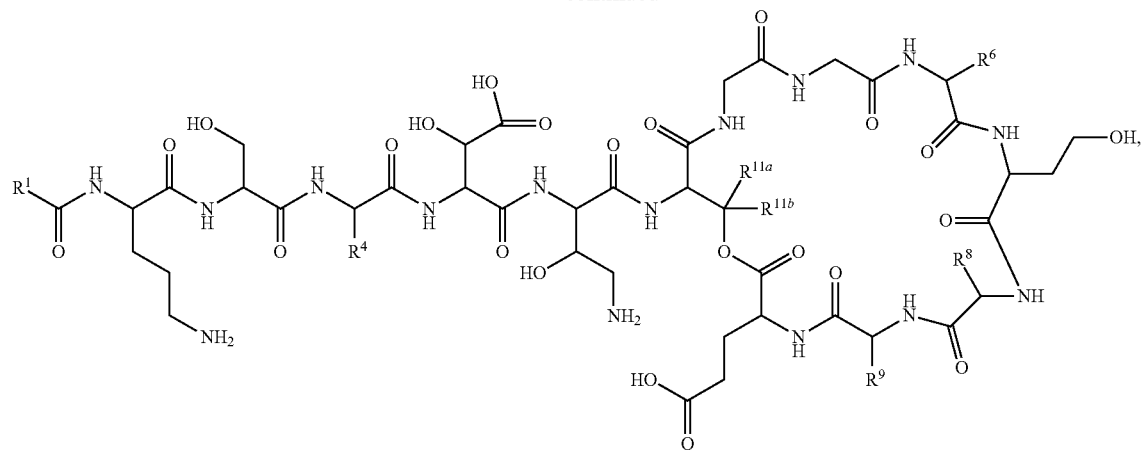
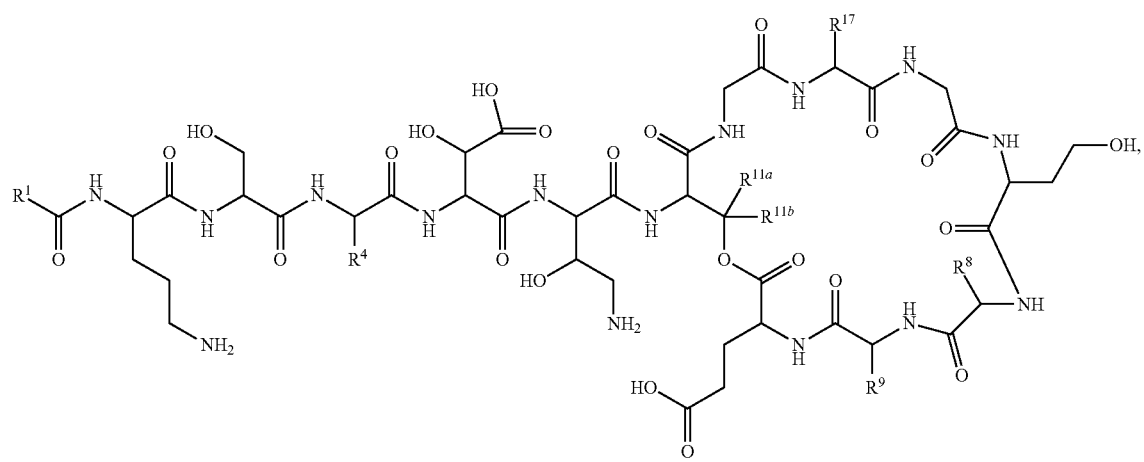
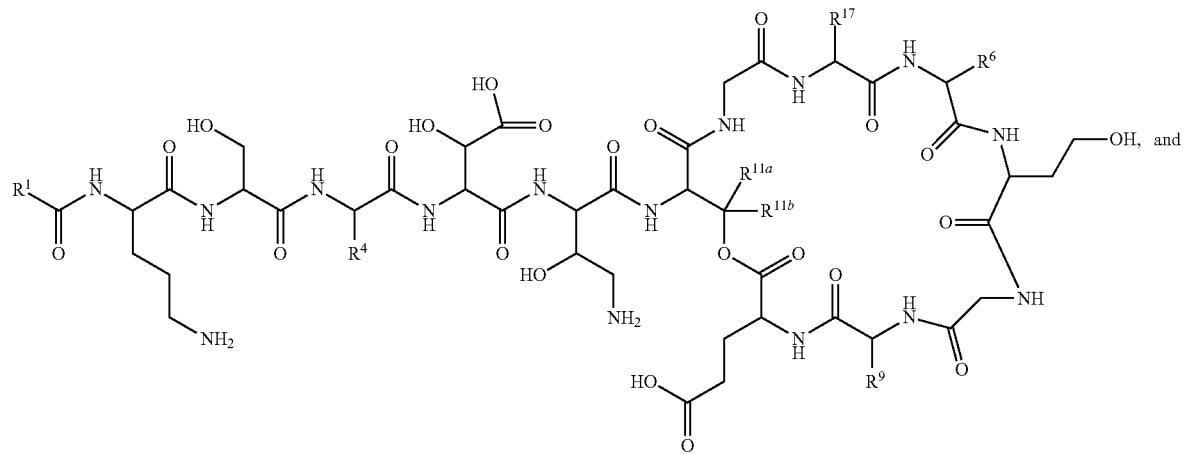

-continued
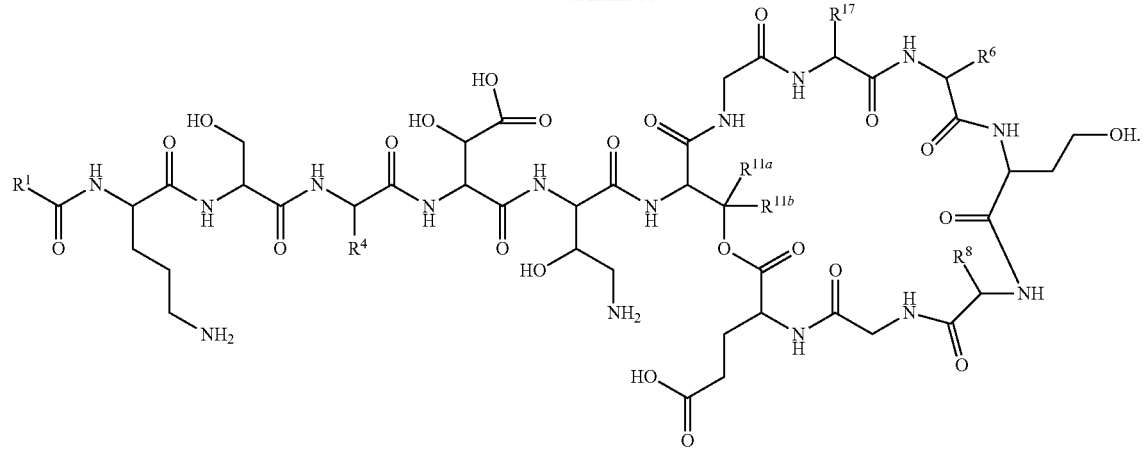
In a further aspect, $R^1$ is selected from:
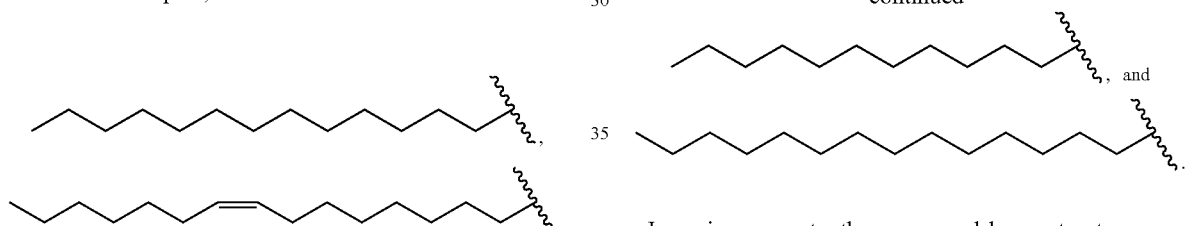
In various aspects, the compound has a structure represented by a formula selected from:
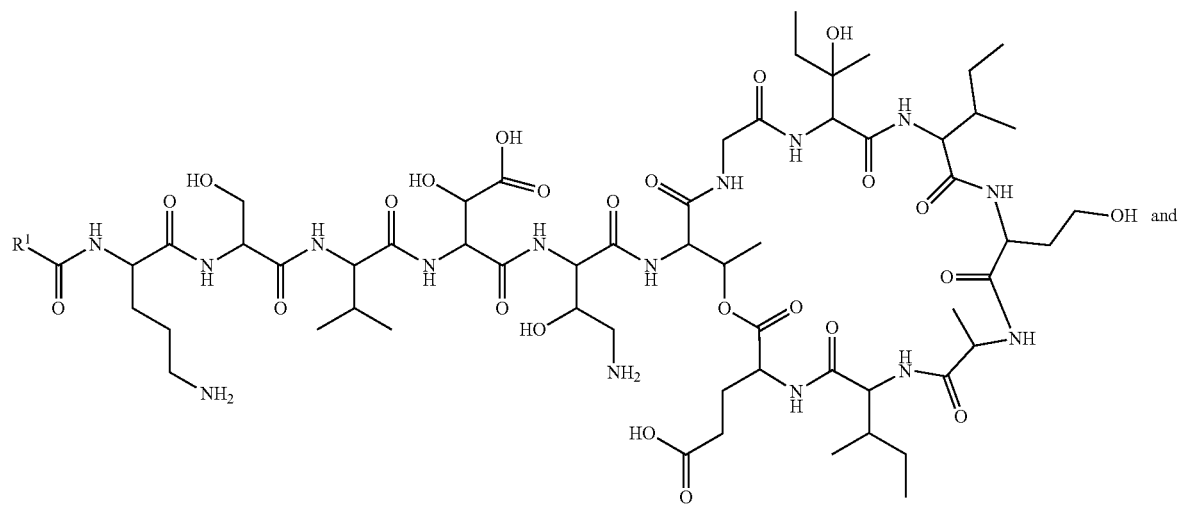

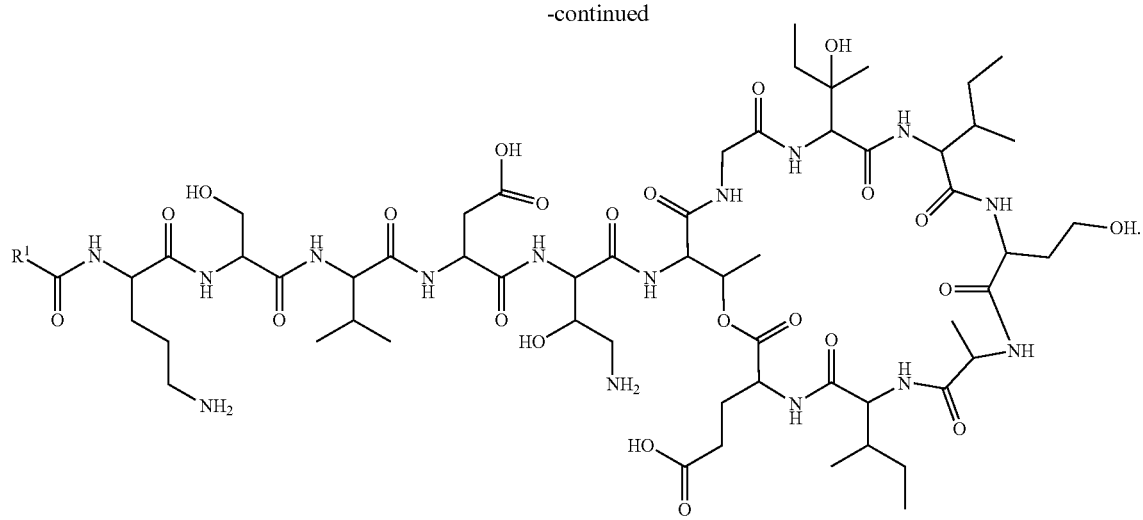
In a further aspect, R¹ is selected from:
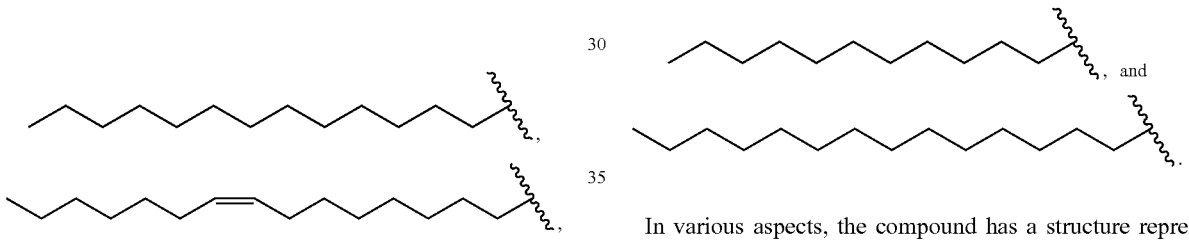
In various aspects, the compound has a structure represented by a formula:
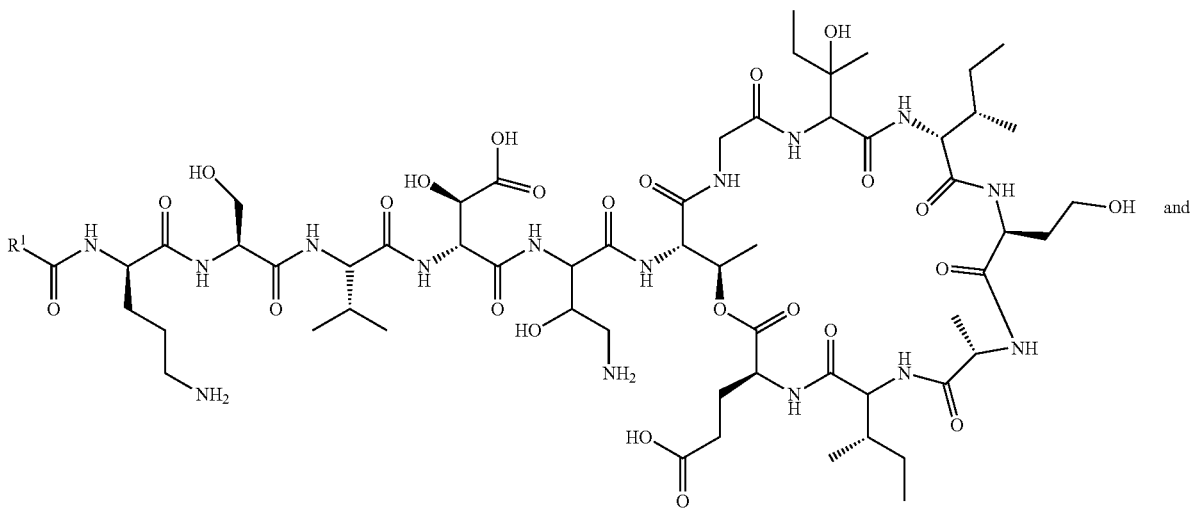

-continued
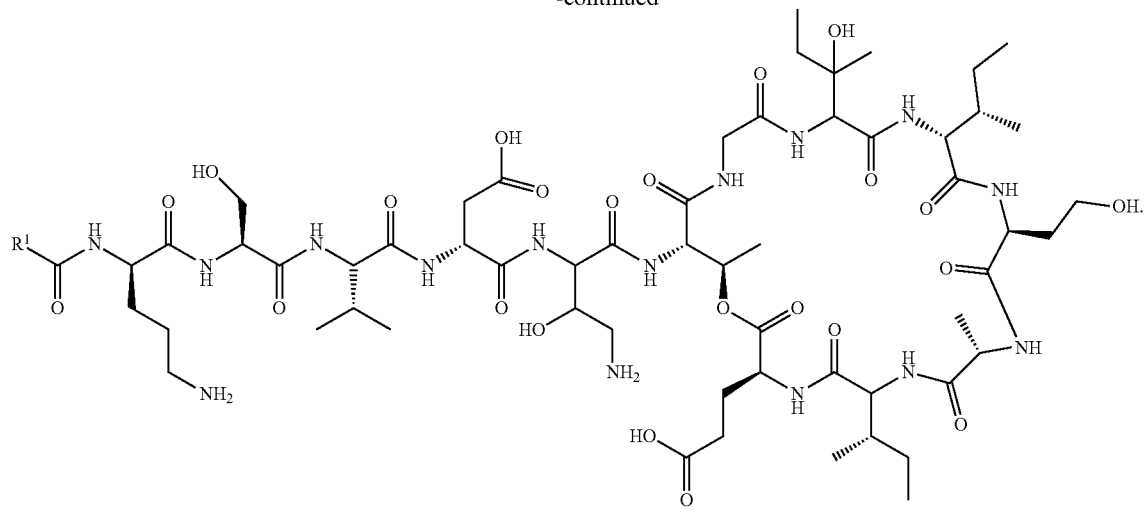
In a further aspect, $R^1$ is selected from:
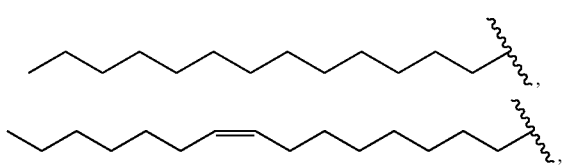
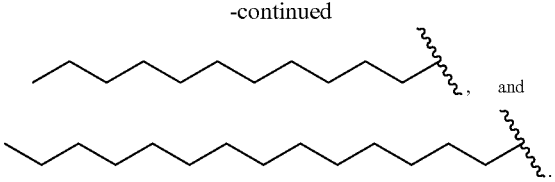
In various aspect, the compound is:
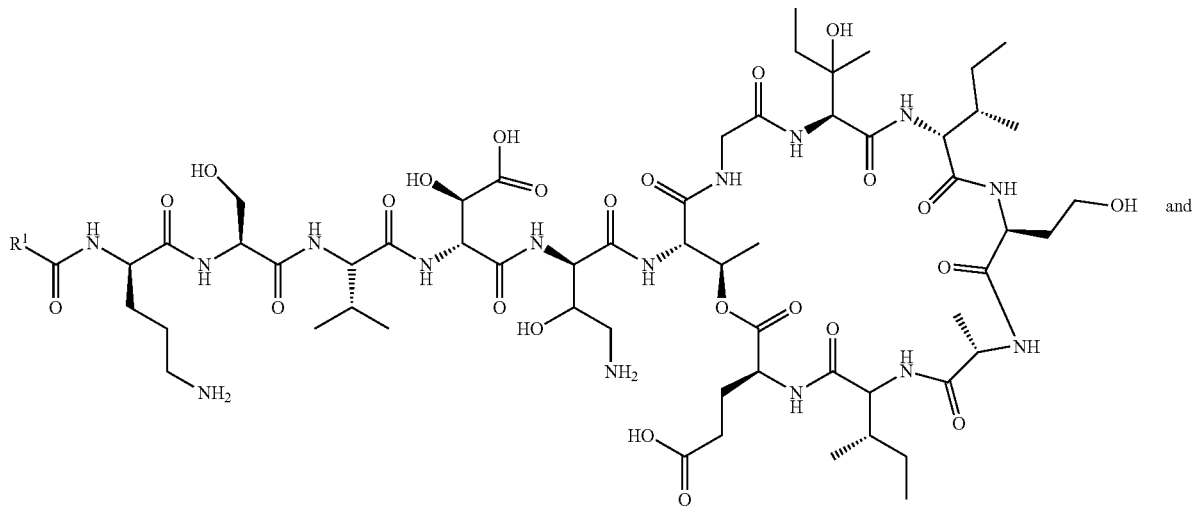

-continued
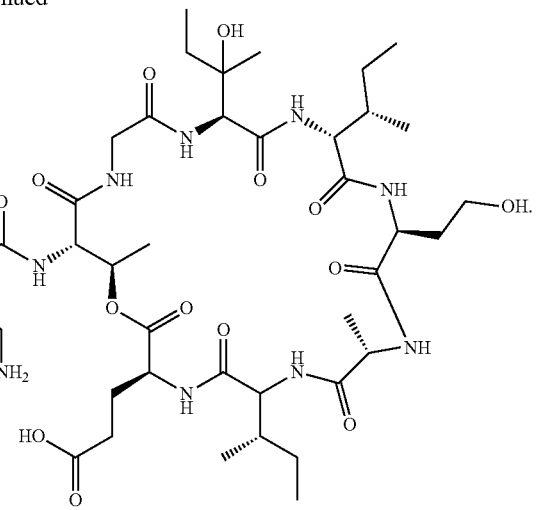
In a further aspect, $R^1$ is selected from:
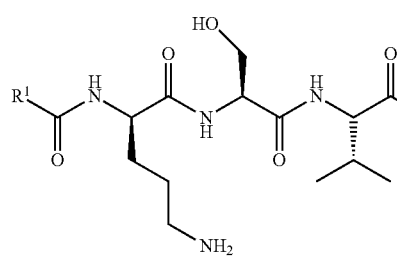
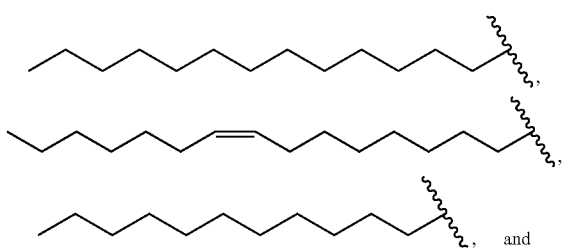
In various aspects, the compound has a structure represented by a formula:
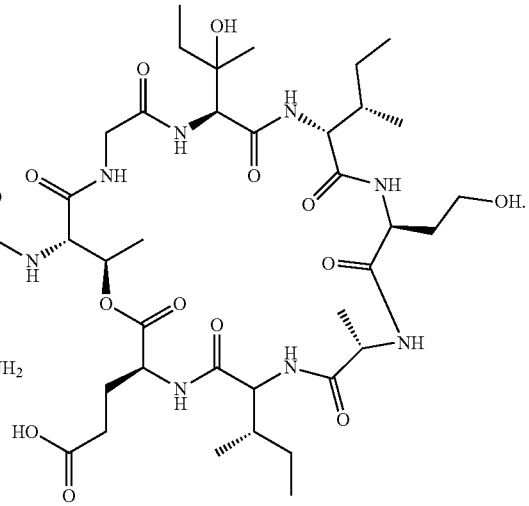

In various aspects, the compound does not have a structure represented by a formula:
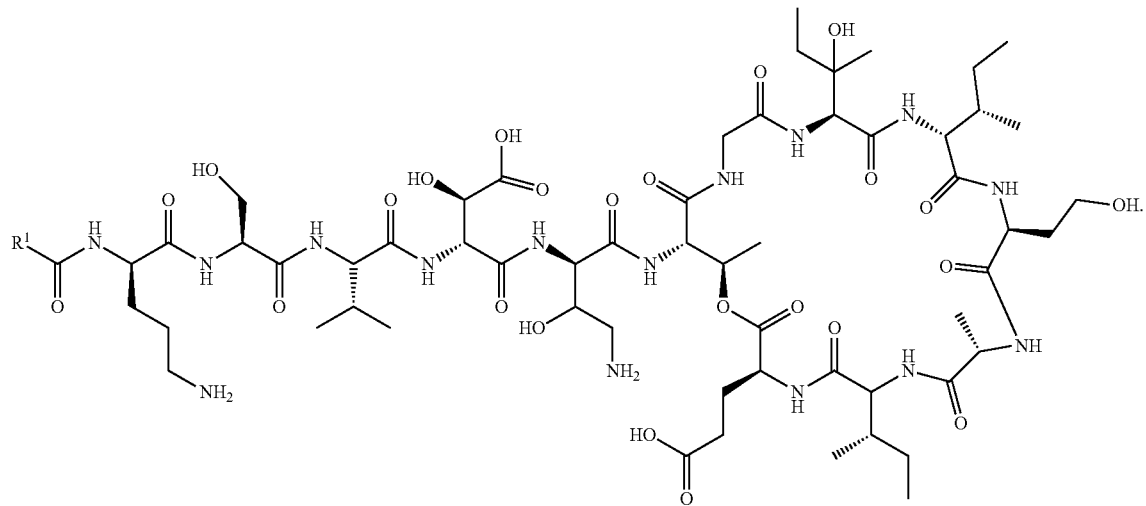
In various aspects, the compound is:
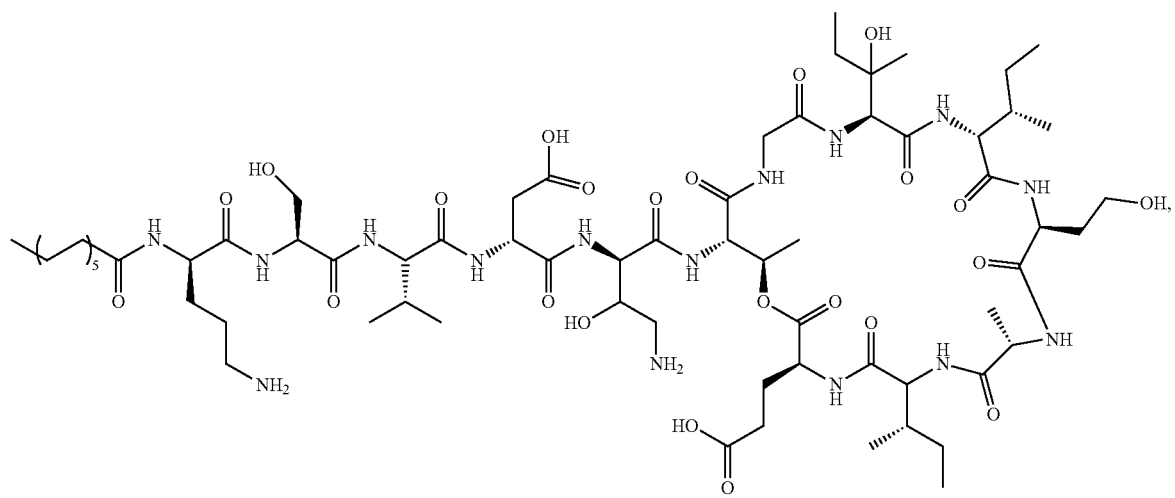
or a pharmaceutically acceptable salt thereof.

In various aspects, the compound is:
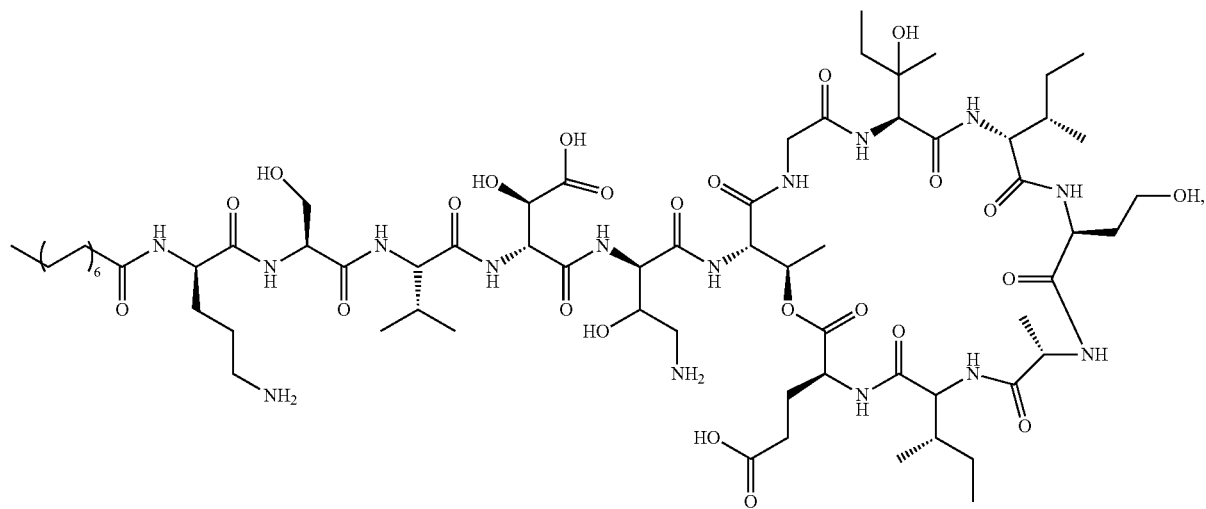
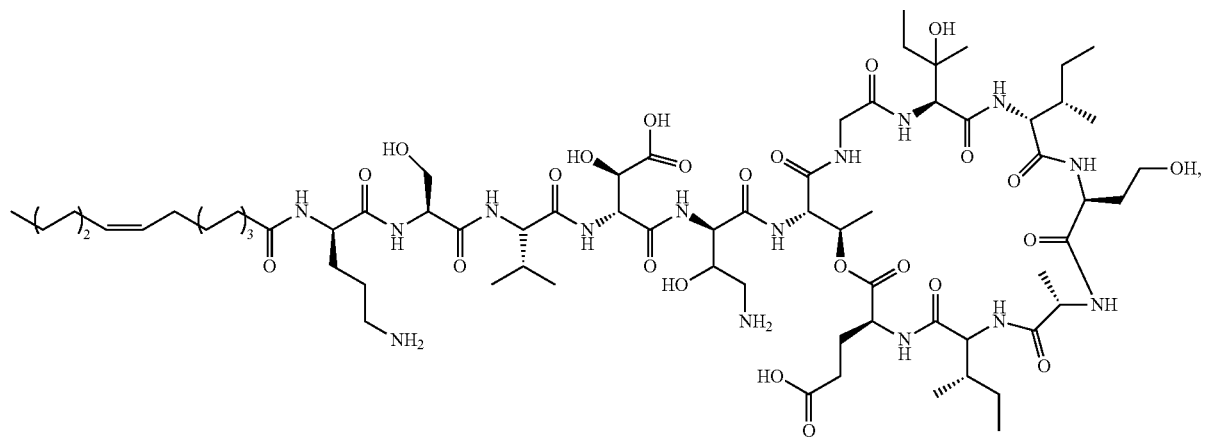
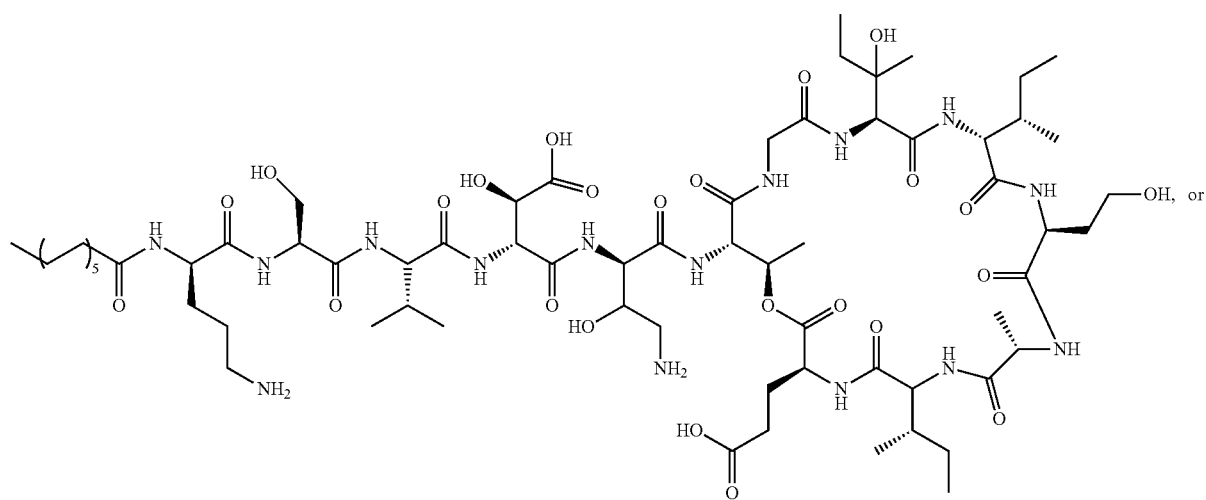

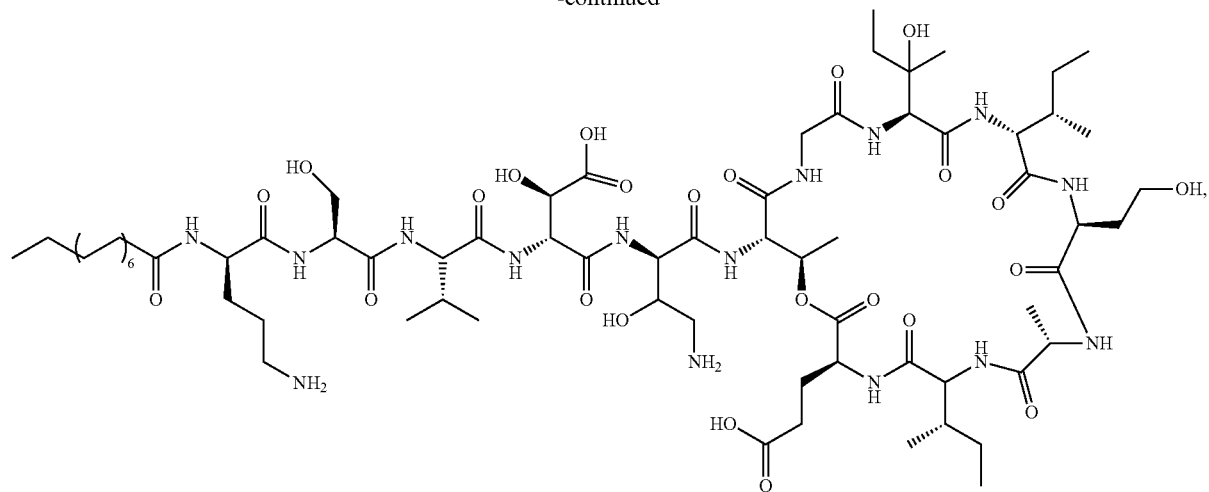
or a pharmaceutically acceptable salt thereof.
In various aspects, the compound is not:
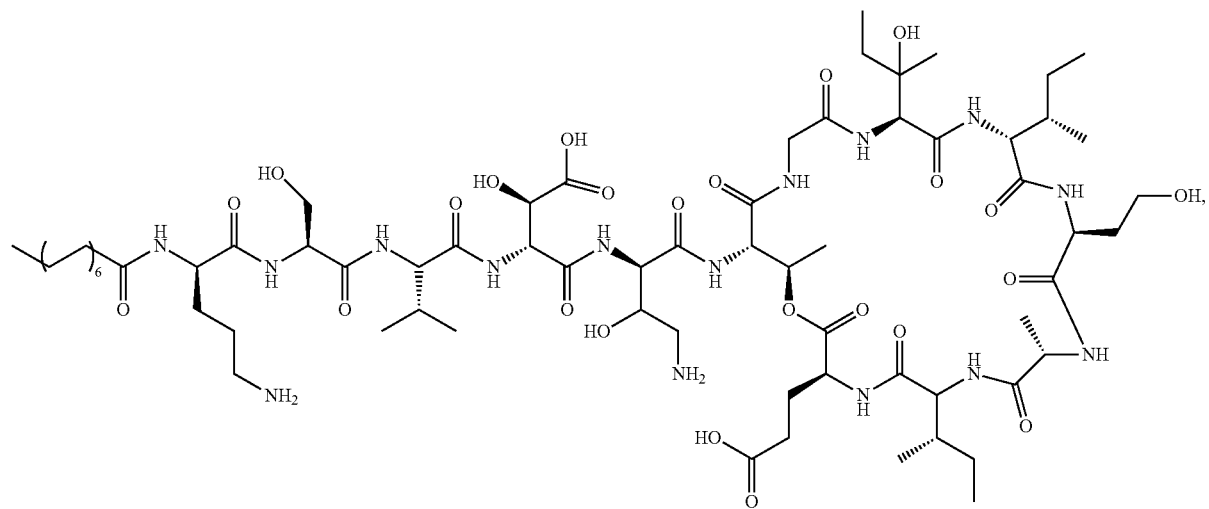
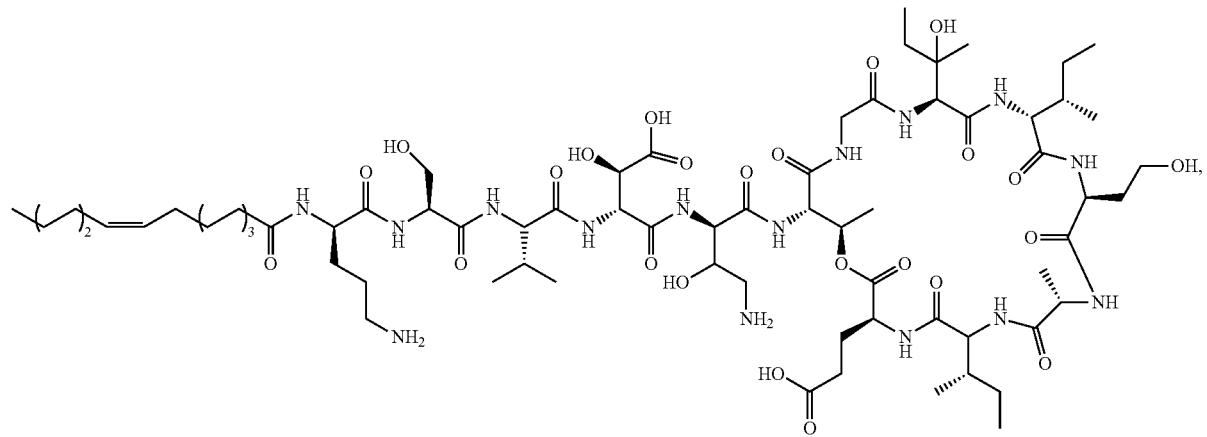

-continued

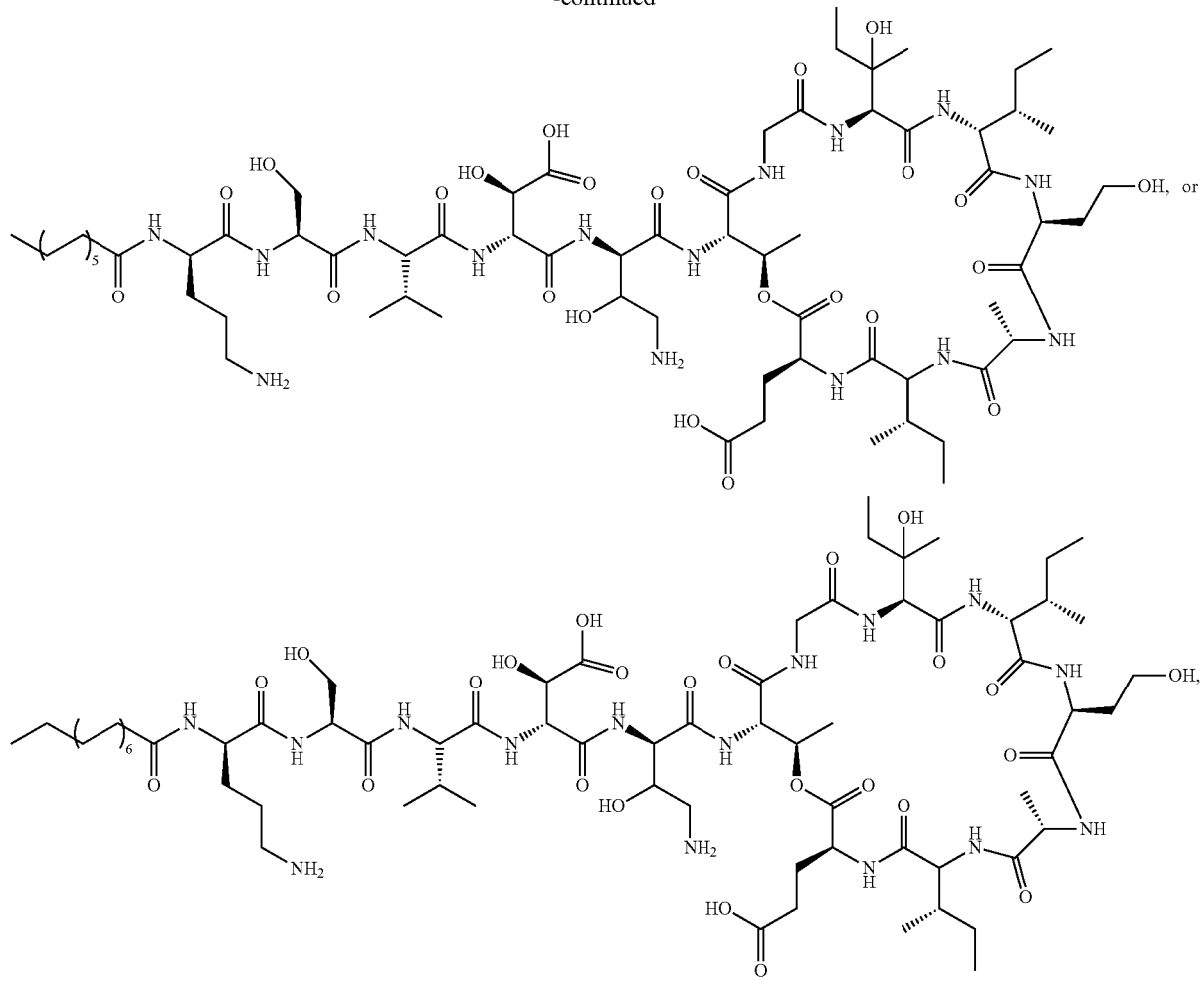

or a pharmaceutically acceptable salt thereof.

a. $R^1$ Groups

In one aspect, $R^1$ is selected from C1-C24 alkyl and C2-C24 alkenyl. In a further aspect, $R^1$ is selected from C1-C20 alkyl and C2-C20 alkenyl. In a still further aspect, $R^1$ is selected from C1-C18 alkyl and C2-C18 alkenyl. In yet a further aspect, $R^1$ is selected from C1-C16 alkyl and C2-C16 alkenyl. In an even further aspect, $R^1$ is selected from C1-C12 alkyl and C2-C12 alkenyl. In a still further aspect, $R^1$ is selected from C1-C8 alkyl and C2-C8 alkenyl. In yet a further aspect, $R^1$ is selected from C1-C4 alkyl and C2-C4 alkenyl. In an even further aspect, $R^1$ is selected from C4-C24 alkyl and C4-C24 alkenyl. In a still further aspect, $R^1$ is selected from C8-C24 alkyl and C8-C24 alkenyl. In yet a further aspect, $R^1$ is selected from C12-C24 alkyl and C12-C24 alkenyl. In an even further aspect, $R^1$ is selected from C16-C24 alkyl and C16-C24 alkenyl. In a still further aspect, $R^1$ is selected from C18-C24 alkyl and C18-C24 alkenyl. In yet a further aspect, $R^1$ is selected from C20-C24 alkyl and C20-C24 alkenyl. In an even further aspect, $R^1$ is selected from C4-C20 alkyl and C4-C20 alkenyl. In a still further aspect, $R^1$ is selected from C8-C18 alkyl and C8-C18 alkenyl. In yet a further aspect, $R^1$ is selected from C10-C18 alkyl and C10-C18 alkenyl. In an even further aspect, $R^1$ is selected from C12-C16 alkyl and C12-C16 alkenyl.

In various aspects, $R^1$ is selected from:

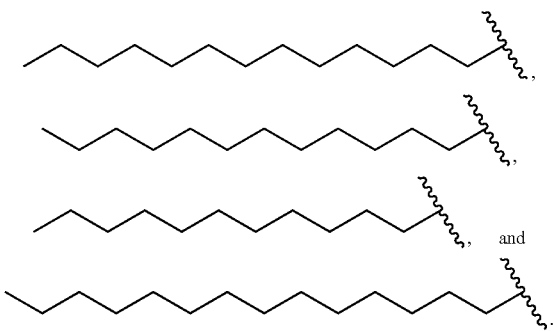

In various aspects, $R^1$ is selected from:

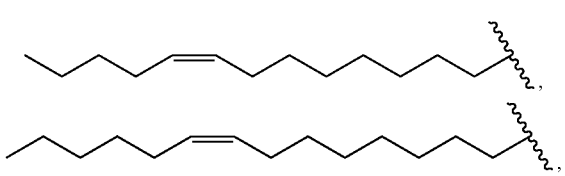

-continued

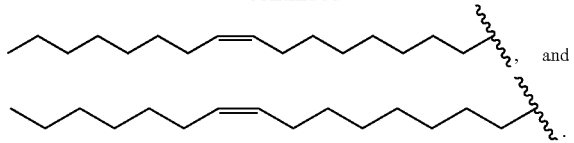
, and

In various aspects, $R^1$ is selected from:

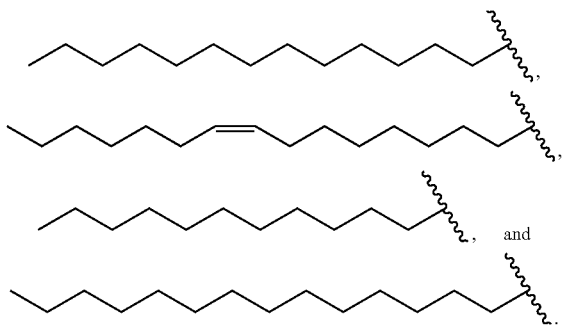
, and

In various aspects, $R^1$ is:

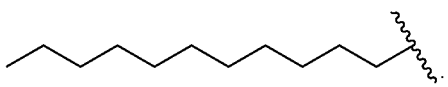 [SMILES: *CCCCCCCCCCC]

b. $R^2$, $R^3$, $R^4$, $R^5$, $R^6$, $R^7$, $R^8$, $R^9$, $R^{10}$, $R^{15}$, $R^{16}$, and $R^{17}$ Groups In one aspect, each of $R^2$, $R^3$, $R^4$, $R^5$, $R^6$, $R^7$, $R^8$, $R^9$, and $R^{10}$ is independently selected from a natural amino acid residue and an unnatural amino acid residue.

In one aspect, each of $R^2$, $R^3$, $R^7$, $R^{10}$, $R^{15}$, and $R^{16}$ is independently selected from a natural amino acid residue and an unnatural amino acid residue, provided that each of $R^2$, $R^3$, $R^7$, $R^{10}$, $R^{15}$, and $R^{16}$ is a non-glycine residue, and each of $R^4$, $R^5$, $R^6$, $R^8$, $R^9$, and $R^{17}$ is independently selected from a natural amino acid residue and an unnatural amino acid residue.

In various aspects, one or more of $R^2$, $R^3$, $R^4$, $R^5$, $R^6$, $R^7$, $R^8$, $R^9$, and $R^{10}$ is a natural amino acid residue. Examples of natural amino acid residues include, but are not limited to, valine, isoleucine, leucine, lysine, threonine, phenylalanine, methionine, histidine, tryptophan, glutamine, aspartate, glutamate, arginine, alanine, proline, cysteine, asparagine, serine, tyrosine, and glycine.

In various aspects, one or more of $R^2$, $R^3$, $R^4$, $R^5$, $R^6$, $R^7$, $R^8$, $R^9$, and $R^{10}$ is an unnatural amino acid residue. Examples of unnatural amino acid residues include, but are not limited to, non-proteinogenic amino acid residues (e.g., β-alanine, alloisoleucine, 4-aminobenzoic acid, gamma-aminobutyric acid, aminoethyl-cysteine, 2-aminoisobutyric acid, aminolevulinic acid, azetidine-2-carboxylic acid, canaline, canavanine, carboxyglutamic acid, chloroalanine, citrulline, cystine, dehydroalanine, diaminopimelic acid, dihydroxyphenylglycine, enduracididine, homocysteine, homoserine, 4-hydroxyphenylglycine, α,γ-diamino-β-hydroxybutanoic acid, hydroxyproline, hypusine, lanthionine, β-leucine, norleucine, norvaline, NV-5138, ornithine, penicillamine, plakohypaphorine, pyroglutamic acid, quisqualic acid, sarcosine, theanine, tranexamic acid, tricholomic acid), homo-amino acid residues (e.g., homolysine, homothreonine, homophenylalanine, homo-methionine, homohistidine, homotryptophan, homoglutamine, homoaspartate, homoglutamate, homoarginine, -homoalanine, homoproline, homocysteine, homoasparagine, homoserine, homovaline, homoleucine, homoisoleucine, homotyrosine), modified side group amino acid residues (e.g., p-benzoyl-phenylalanine, p-bromophenyl, p-chlorophenyl, p-trifluoromethylphenyl), alpha-methyl amino acid residues (e.g., alpha-methyl-lysine, alpha-methyl-threonine, alpha-methyl-phenylalanine, alpha-methyl-methionine, alpha-methyl-histidine, alpha-methyl-tryptophan, alpha-methyl-glutamine, alpha-methyl-aspartate, alpha-methyl-glutamate, alpha-methyl-arginine, alpha-methyl-alanine, alpha-methyl-proline, alpha-methyl-cysteine, alpha-methyl-asparagine, alpha-methyl-serine, alpha-methyl-valine, alpha-methyl-leucine, alpha-methyl-isoleucine, alpha-methyl-tyrosine), and D-amino acid residues (e.g., D-amino acid residue is selected from D-lysine, D-threonine, D-phenylalanine, D-methionine, D-histidine, D-tryptophan, D-glutamine, D-aspartate, D-glutamate, D-arginine, D-alanine, D-proline, D-cysteine, D-asparagine, D-serine, D-tyrosine, D-ornithine, D-hydroxybutanoic acid, D-alloisoleucine).

In various aspects, each of $R^3$, $R^4$, $R^5$, $R^8$, and $R^{10}$ is independently a natural amino acid residue. In a further aspect, each of $R^3$, $R^4$, $R^5$, $R^8$, and $R^{10}$ is independently selected from valine, isoleucine, leucine, lysine, threonine, phenylalanine, methionine, histidine, tryptophan, glutamine, aspartate, glutamate, arginine, alanine, proline, cysteine, asparagine, serine, tyrosine, and glycine. In a still further aspect, each of $R^3$, $R^4$, $R^5$, $R^8$, and $R^{10}$ is independently selected from serine, valine, glycine, and alanine.

In various aspects, each of $R^3$, $R^4$, $R^5$, $R^8$, and $R^{10}$ is independently an unnatural amino acid residue.

In various aspects, each of $R^2$, $R^6$, $R^7$, and $R^9$ is independently an unnatural amino acid residue. In a further aspect, each of $R^2$, $R^6$, $R^7$, and $R^9$ is independently selected from a non-proteinogenic amino acid residue, a homo-amino acid residue, a modified side group amino acid residue, an alpha-methyl amino acid residue, and a D-amino acid residue.

In various aspects, each of $R^2$, $R^6$, and $R^9$ is independently an unnatural amino acid residue such as, for example, a non-proteinogenic amino acid residue, a homo-amino acid residue, a modified side group amino acid residue, an alpha-methyl amino acid residue, or a D-amino acid residue. In a further aspect, each of $R^2$, $R^6$, and $R^9$ is a D-amino acid residue. In a still further aspect, each of $R^2$, $R^6$, and $R^9$ is independently selected from D-lysine, D-threonine, D-phenylalanine, D-methionine, D-histidine, D-tryptophan, D-glutamine, D-aspartate, D-glutamate, D-arginine, D-alanine, D-proline, D-cysteine, D-asparagine, D-serine, D-tyrosine, D-ornithine, D-hydroxybutanoic acid, and D-alloisoleucine. In yet a further aspect, each of $R^2$, $R^6$, and $R^9$ is independently selected from D-ornithine and D-alloisoleucine.

In various aspects, each of $R^2$, $R^6$, $R^7$, and $R^9$ is independently a natural amino acid residue. In various further aspects, each of $R^2$, $R^6$, and $R^9$ is independently a natural amino acid residue.

In various aspects, each of $R^2$, $R^3$, $R^4$, $R^6$, $R^7$, $R^8$, $R^9$, and $R^{10}$ is independently selected from a natural amino acid residue and an unnatural amino acid residue, provided that each of $R^2$, $R^3$, $R^4$, $R^6$, $R^7$, $R^8$, $R^9$, and $R^{10}$ is a non-glycine amino acid residue. In various further aspects, each of $R^2$, $R^3$, $R^4$, $R^6$, $R^7$, $R^8$, $R^9$, and $R^{10}$ is independently selected from a natural amino acid residue and an unnatural amino acid residue, provided that each of $R^3$, $R^6$, $R^8$, and $R^9$ is a non-glycine amino acid residue.

In various aspects, each of $R^2$, $R^3$, $R^7$, $R^{10}$, $R^{15}$, and $R^{16}$ is independently selected from a natural amino acid residue and an unnatural amino acid residue, provided that each of $R^2$, $R^3$, $R^7$, $R^{10}$, $R^{15}$, and $R^{16}$ is a non-glycine residue. In a further aspect, at least one of $R^2$, $R^3$, $R^7$, $R^{10}$, $R^{15}$, and $R^{16}$ is a natural amino acid residue. In a still further aspect, at least two of $R^2$, $R^3$, $R^7$, $R^{10}$, $R^{15}$, and $R^{16}$ are a natural amino acid residue. In yet a further aspect, at least three of $R^2$, $R^3$, $R^7$, $R^{10}$, $R^{15}$, and $R^{16}$ are a natural amino acid residue. In an even further aspect, at least four of $R^2$, $R^3$, $R^7$, $R^{10}$, $R^{15}$, and $R^{16}$ are a natural amino acid residue. In a still further aspect, at least one of $R^2$, $R^3$, $R^7$, $R^{10}$, $R^{15}$, and $R^{16}$ is an unnatural amino acid residue. In yet a further aspect, at least two of $R^2$, $R^3$, $R^7$, $R^{10}$, $R^{15}$, and $R^{16}$ are an unnatural amino acid residue. In an even further aspect, at least three of $R^2$, $R^3$, $R^7$, $R^{10}$, $R^{15}$, and $R^{16}$ are an unnatural amino acid residue. In a still further aspect, at least four of $R^2$, $R^3$, $R^7$, $R^{10}$, $R^{15}$, and $R^{16}$ are an unnatural amino acid residue.

In various aspects, each of $R^4$, $R^5$, $R^6$, $R^8$, $R^9$, and $R^{17}$ is independently selected from a natural amino acid residue and an unnatural amino acid residue. In a further aspect, at least one of $R^4$, $R^5$, $R^6$, $R^8$, $R^9$, and $R^{17}$ is a natural amino acid residue. In a still further aspect, at least two of $R^4$, $R^5$, $R^6$, $R^8$, $R^9$, and $R^{17}$ are a natural amino acid residue. In yet a further aspect, at least three of $R^4$, $R^5$, $R^6$, $R^8$, $R^9$, and $R^{17}$ are a natural amino acid residue. In an even further aspect, at least four of $R^4$, $R^5$, $R^6$, $R^8$, $R^9$, and $R^{17}$ are a natural amino acid residue. In a still further aspect, at least one of $R^4$, $R^5$, $R^6$, $R^8$, $R^9$, and $R^{17}$ is an unnatural amino acid residue. In yet a further aspect, at least two of $R^4$, $R^5$, $R^6$, $R^8$, $R^9$, and $R^{17}$ are an unnatural amino acid residue. In an even further aspect, at least three of $R^4$, $R^5$, $R^6$, $R^8$, $R^9$, and $R^{17}$ are an unnatural amino acid residue. In a still further aspect, at least four of $R^4$, $R^5$, $R^6$, $R^8$, $R^9$, and $R^{17}$ are an unnatural amino acid residue.

In various aspects, each of $R^3$, $R^{10}$, and $R^{15}$ is independently a natural amino acid residue. In a further aspect, each of $R^3$, $R^{10}$, and $R^{15}$ is independently selected from valine, isoleucine, leucine, lysine, threonine, phenylalanine, methionine, histidine, tryptophan, glutamine, aspartate, glutamate, arginine, alanine, proline, cysteine, asparagine, serine, tyrosine, and glycine.

In various aspects, at least one of $R^3$, $R^{10}$, and $R^{15}$ is an unnatural amino acid residue such as, for example, a β-hydroxyamino acid residue. In a further aspect, $R^{15}$ is a β-hydroxyamino acid residue. In yet a further aspect, at least one of $R^3$, $R^{10}$, and $R^{15}$ is selected from β-hydroxy-α-lysine, β-hydroxy-α-asparagine, β-hydroxy-α-aspartate, β-hydroxy-α-aspartic acid, β-hydroxy-α-histidine, β-hydroxy-α-isoleucine, and β-hydroxy-α-proline. In an even further aspect, $R^{15}$ is selected from β-hydroxy-α-lysine, 1-hydroxy-α-asparagine, β-hydroxy-α-aspartate, β-hydroxy-α-aspartic acid, β-hydroxy-α-histidine, β-hydroxy-α-isoleucine, and β-hydroxy-α-proline. In a still further aspect, at least one of $R^3$, $R^{10}$, and $R^{15}$ is β-hydroxy-α-aspartic acid. In yet a further aspect, $R^{15}$ is β-hydroxy-α-aspartic acid.

In various aspects, each of $R^2$, $R^7$, and $R^{16}$ is independently an unnatural amino acid residue. In a further aspect, at least one of $R^2$, $R^7$, and $R^{16}$ is a β-hydroxyamino acid residue. In a still further aspect, $R^{16}$ is a β-hydroxyamino acid residue.

In various aspects, at least one of $R^2$, $R^3$, $R^7$, $R^{10}$, $R^{15}$, and $R^{16}$ is a β-hydroxyamino acid residue. In a further aspect, the β-hydroxyamino acid residue is selected from β-hydroxy-α-lysine, β-hydroxy-α-asparagine, β-hydroxy-α-aspartate, β-hydroxy-α-aspartic acid, β-hydroxy-α-histidine, β-hydroxy-α-isoleucine, β-hydroxy-α-proline, and α,γ-diamino-β-hydroxybutanoic acid. In a still further aspect, at least two of $R^2$, $R^3$, $R^7$, $R^{10}$, $R^{15}$, and $R^{16}$ is a β-hydroxy-α-amino acid residue.

In various aspects, each of $R^4$, $R^5$, $R^8$, $R^9$, and $R^{17}$ is independently a natural amino acid residue. In a further aspect, each of $R^4$, $R^5$, $R^8$, $R^9$, and $R^{17}$ is independently selected from valine, isoleucine, leucine, lysine, threonine, phenylalanine, methionine, histidine, tryptophan, glutamine, aspartate, glutamate, arginine, alanine, proline, cysteine, asparagine, serine, tyrosine, and glycine.

In various aspect, $R^2$ is an unnatural amino acid residue such as, for example, a D-amino acid residue. In a further aspect, $R^2$ is selected from selected from D-lysine, D-threonine, D-phenylalanine, D-methionine, D-histidine, D-tryptophan, D-glutamine, D-aspartate, D-glutamate, D-arginine, D-alanine, D-proline, D-cysteine, D-asparagine, D-serine, D-tyrosine, D-ornithine, D-hydroxybutanoic acid, and D-alloisoleucine. In a still further aspect, $R^2$ is D-ornithine.

In various aspects, $R^2$ is a natural amino acid residue.

In various aspects, $R^3$ is a natural amino acid residue. In a further aspect, $R^3$ is a natural amino acid residue having a polar uncharged side chain. In a still further aspect, $R^3$ is selected from serine, threonine, asparagine, and glutamine. In yet a further aspect, $R^3$ is serine.

In various aspects, $R^3$ is an unnatural amino acid residue.

In various aspects, $R^4$ is a natural amino acid residue. In a further aspect, $R^4$ is a natural amino acid residue having a hydrophobic side chain. In a still further aspect, $R^4$ is selected from alanine, isoleucine, leucine, methionine, phenylalanine, tryptophan, tyrosine, and valine. In yet a further aspect, $R^4$ is valine.

In various aspects, $R^4$ is an unnatural amino acid residue.

In various aspects, $R^5$ is a natural amino acid residue. In a further aspect, $R^5$ is a natural amino acid residue selected from cysteine, selenocysteine, glycine, and proline. In a still further aspect, $R^5$ is glycine.

In various aspects, $R^5$ is an unnatural amino acid residue.

In various aspects, $R^6$ is an unnatural amino acid residue such as, for example, a D-amino acid residue. In a further aspect, $R^6$ is selected from D-lysine, D-threonine, D-phenylalanine, D-methionine, D-histidine, D-tryptophan, D-glutamine, D-aspartate, D-glutamate, D-arginine, D-alanine, D-proline, D-cysteine, D-asparagine, D-serine, D-tyrosine, D-ornithine, D-hydroxybutanoic acid, and D-alloisoleucine. In a still further aspect, $R^6$ is selected from D-alanine, D-isoleucine, D-alloisoleucine, D-leucine, D-methionine, D-phenylalanine, D-tryptophan, D-tyrosine, and D-valine. In yet a further aspect, $R^6$ is D-alloisoleucine.

In various aspects, $R^7$ is an unnatural amino acid residue such as, for example, a homo-amino acid residue. In a further aspect, $R^7$ is selected from homolysine, homothreonine, homophenylalanine, homo-methionine, homohistidine, homotryptophan, homoglutamine, homoaspartate, homoglutamate, homoarginine, -homoalanine, homoproline, homocysteine, homoasparagine, homoserine, homovaline, homoleucine, homoisoleucine, and homotyrosine. In a still further aspect, $R^7$ is selected from homoserine, homothreonine, homoasparagine, and homoglutamine. In yet a further aspect, $R^7$ is homoserine.

In various aspects, $R^7$ is a natural amino acid residue.

In various aspects, $R^8$ is a natural amino acid residue. In a further aspect, $R^8$ is a natural amino acid residue having a hydrophobic side chain. In a still further aspect, $R^8$ is selected from alanine, isoleucine, leucine, methionine, phenylalanine, tryptophan, tyrosine, and valine. In yet a further aspect, $R^8$ is alanine.

In various aspects, $R^8$ is an unnatural amino acid residue.

In various aspects, $R^9$ is an unnatural amino acid residue such as, for example, a D-amino acid residue. In a further aspect, $R^8$ is selected from D-lysine, D-threonine, D-phenylalanine, D-methionine, D-histidine, D-tryptophan, D-glutamine, D-aspartate, D-glutamate, D-arginine, D-alanine, D-proline, D-cysteine, D-asparagine, D-serine, D-tyrosine, D-ornithine, D-hydroxybutanoic acid, and D-alloisoleucine. In a still further aspect, $R^9$ is selected from D-alanine, D-isoleucine, D-alloisoleucine, D-leucine, D-methionine, D-phenylalanine, D-tryptophan, D-tyrosine, and D-valine. In yet a further aspect, $R^9$ is D-alloisoleucine.

In various aspects, $R^9$ is a natural amino acid residue.

In various aspects, $R^{10}$ is a natural amino acid residue. In a further aspect, $R^{10}$ is a natural amino acid residue having an electrically charged side chain. In a still further aspect, $R^{10}$ is selected from arginine, histidine, lysine, aspartic acid, and glutamic acid. In yet a further aspect, $R^{10}$ is a natural amino acid residue having a negatively charged side chain. In an even further aspect, $R^{10}$ is selected from aspartic acid and glutamic acid. In yet a further aspect, $R^{10}$ is glutamic acid.

In various aspects, $R^{10}$ is an unnatural amino acid residue.

In various aspects, each of $R^{15}$ and $R^{16}$ is independently an unnatural amino acid residue such as, for example, a β-hydroxyamino acid residue. In a further aspect, each of $R^{15}$ and $R^{16}$ is independently a β-hydroxyamino acid residue selected from β-hydroxy-α-aspartic acid and α,γ-diamino-β-hydroxybutanoic acid. In a still further aspect, $R^{15}$ is β-hydroxy-α-aspartic acid. In yet a further aspect, $R^{16}$ is α,γ-diamino-β-hydroxybutanoic acid.

In various aspects, at least one of $R^4$, $R^5$, $R^8$, $R^9$, and $R^{17}$ is glycine. In a further aspect, at least two of $R^4$, $R^5$, $R^8$, $R^9$, and $R^{17}$ is glycine. In a still further aspect, at least three of $R^4$, $R^5$, $R^8$, $R^9$, and $R^{17}$ is glycine. In yet a further aspect, $R^4$ is glycine. In an even further aspect, $R^5$ is glycine. In a still further aspect, $R^8$ is glycine. In yet a further aspect, $R^9$ is glycine. In an even further aspect, $R^{17}$ is glycine.

In various aspects, c. $R^{11a}$ and $R^{11b}$ Groups

In one aspect, each of $R^{11a}$ and $R^{11b}$ is independently selected from hydrogen and C1-C4 alkyl. In a further aspect, each of $R^{11a}$ and $R^{11b}$ is independently selected from hydrogen, methyl, ethyl, n-propyl, and isopropyl. In a still further aspect, each of $R^{11a}$ and $R^{11b}$ is independently selected from hydrogen, methyl, and ethyl. In yet a further aspect, each of $R^{11a}$ and $R^{11b}$ is independently selected from hydrogen and ethyl. In an even further aspect, each of $R^{11a}$ and $R^{11b}$ is independently selected from hydrogen and methyl.

In various aspects, each of $R^{11a}$ and $R^{11b}$ is independently C1-C4 alkyl. In a further aspect, each of $R^{11a}$ and $R^{11b}$ is independently selected from methyl, ethyl, n-propyl, and isopropyl. In a still further aspect, each of $R^{11a}$ and $R^{11b}$ is independently selected from methyl and ethyl. In yet a further aspect, each of $R^{11a}$ and $R^{11b}$ is ethyl. In an even further aspect, each of $R^{11a}$ and $R^{11b}$ is methyl.

In various aspects, $R^{11a}$ is C1-C4 alkyl, and $R^{11b}$ is hydrogen. In a further aspect, $R^{11a}$ is selected from methyl, ethyl, n-propyl, and isopropyl, and $R^{11b}$ is hydrogen. In a still further aspect, $R^{11a}$ is selected from methyl and ethyl, and $R^{11b}$ is hydrogen. In yet a further aspect, $R^{11a}$ is ethyl, and $R^{11b}$ is hydrogen. In an even further aspect, $R^{11a}$ is methyl, and $R^{11b}$ is hydrogen.

In various aspects, each of $R^{11a}$ and $R^{11b}$ is hydrogen.

d. $R^{12}$, $R^{13}$, and $R^{14}$ Groups

In one aspect, each of $R^{12}$, $R^{13}$, and $R^{14}$ is independently selected from —OH, —SH, and —NH$_2$. In a further aspect, each of $R^{12}$, $R^{13}$, and $R^{14}$ is independently selected from —OH and —SH. In a still further aspect, each of $R^{12}$, $R^{13}$, and $R^{14}$ is independently selected from —OH and —NH$_2$. In yet a further aspect, each of $R^{12}$, $R^{13}$, and $R^{14}$ is independently selected from —SH and —NH$_2$. In an even further aspect, each of $R^{12}$, $R^{13}$, and $R^{14}$ is —NH$_2$. In a still further aspect, each of $R^{12}$, $R^{13}$, and $R^{14}$ is —SH. In yet a further aspect, each of $R^{12}$, $R^{13}$, and $R^{14}$ is —OH.

In various aspects, each of $R^{12}$, $R^{13}$, and $R^{14}$ is the same. In various further aspect, each of $R^{12}$, $R^{13}$, and $R^{14}$ is different.

In various aspects, one of $R^{12}$, $R^{13}$, and $R^{14}$ is —OH. In a further aspect, two of $R^2$, $R^{13}$, and $R^{14}$ is —OH.

In various aspects, one of $R^{12}$, $R^{13}$, and $R^{14}$ is —SH. In a further aspect, two of $R^2$, $R^{13}$, and $R^{14}$ is —SH.

In various aspects, one of $R^{12}$, $R^{13}$, and $R^{14}$ is —NH$_2$. In a further aspect, two of $R^2$, $R^{13}$, and $R^{14}$ is —NH$_2$.

e. $Ar^1$, $Ar^2$, and $Ar^3$ Groups

In one aspect, each of $Ar^1$, $Ar^2$, and $Ar^3$ is independently selected from phenyl and C2-C5 heteroaryl, and is substituted with 0, 1, 2, or 3 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In a further aspect, each of $Ar^1$, $Ar^2$, and $Ar^3$ is independently selected from phenyl and C2-C5 heteroaryl, and is substituted with 0, 1, or 2 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In a still further aspect, each of $Ar^1$, $Ar^2$, and $Ar^3$ is independently selected from phenyl and C2-C5 heteroaryl, and is substituted with 0 or 1 group selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In yet a further aspect, each of $Ar^1$, $Ar^2$, and $Ar^3$ is independently selected from phenyl and C2-C5 heteroaryl, and is monosubstituted with a group selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In an even further aspect, each of $Ar^1$, $Ar^2$, and $Ar^3$ is independently selected from phenyl and C2-C5 heteroaryl, and is unsubstituted.

In various aspect, each of $Ar^1$, $Ar^2$, and $Ar^3$ is independently selected from phenyl and C2-C5 heteroaryl, and is substituted with 0, 1, 2, or 3 groups independently selected from halogen, —CN, —NH$_2$, —OH, —NO$_2$, C1-C8 alkyl, C2-C8 alkenyl, C1-C8 haloalkyl, C1-C8 cyanoalkyl, C1-C8 hydroxyalkyl, C1-C8 haloalkoxy, C1-C8 alkoxy, C1-C8 alkylamino, (C1-C8)(C1-C8) dialkylamino, and C1-C8 aminoalkyl. In a further aspect, each of $Ar^1$, $Ar^2$, and $Ar^3$ is independently selected from phenyl and C2-C5 heteroaryl, and is substituted with 0, 1, or 2 groups independently selected from halogen, —CN, —NH$_2$, —OH, —NO$_2$, C1-C8 alkyl, C2-C8 alkenyl, C1-C8 haloalkyl, C1-C8 cyanoalkyl, C1-C8 hydroxyalkyl, C1-C8 haloalkoxy, C1-C8 alkoxy, C1-C8 alkylamino, (C1-C8)(C1-C8) dialkylamino, and C1-C8 aminoalkyl. In a still further aspect, each of $Ar^1$, $Ar^2$, and $Ar^3$ is independently selected from phenyl and C2-C5 heteroaryl, and is substituted with 0 or 1 group selected from halogen, —CN, —NH$_2$, —OH, —NO$_2$, C1-C8 alkyl, C2-C8 alkenyl, C1-C8 haloalkyl, C1-C8 cyanoalkyl, C1-C8 hydroxyalkyl, C1-C8 haloalkoxy, C1-C8 alkoxy, C1-C8 alkylamino, (C1-C8)(C1-C8) dialkylamino, and C1-C8 aminoalkyl. In yet a further aspect, each of $Ar^1$, $Ar^2$, and $Ar^3$ is independently selected from phenyl and C2-C5 heteroaryl, and is monosubstituted with a group selected from halogen, —CN, —NH$_2$, —OH, —NO$_2$, C1-C8 alkyl, C2-C8 alkenyl, C1-C8 haloalkyl, C1-C8 cyanoalkyl, C1-C8 hydroxyalkyl, C1-C8 haloalkoxy, C1-C8 alkoxy, C1-C8 alkylamino, (C1-C8)(C1-C8) dialkylamino, and C1-C8 aminoalkyl. In an even further aspect, each of $Ar^1$, $Ar^2$, and $Ar^3$ is independently selected from phenyl and C2-C5 heteroaryl, and is unsubstituted.

In various aspects, $Ar^1$ is selected from phenyl and C2-C5 heteroaryl, and is substituted with 0, 1, 2, or 3 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In a further aspect, $Ar^1$ is selected from phenyl and C2-C5 heteroaryl, and is substituted with 0, 1, or 2 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In a still further aspect, $Ar^1$ is selected from phenyl and C2-C5 heteroaryl, and is substituted with 0 or 1 group selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In yet a further aspect, $Ar^1$ is selected from phenyl and C2-C5 heteroaryl, and is monosubstituted with a group selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In an even further aspect, $Ar^1$ is selected from phenyl and C2-C5 heteroaryl, and is unsubstituted.

In various aspects, $Ar^1$ is phenyl substituted with 0, 1, 2, or 3 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In a further aspect, $Ar^1$ is phenyl substituted with 0, 1, or 2 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In a still further aspect, $Ar^1$ is phenyl substituted with 0 or 1 group selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In yet a further aspect, $Ar^1$ is phenyl monosubstituted with a group selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In an even further aspect, $Ar^1$ is unsubstituted phenyl.

In various aspects, $Ar^1$ is C2-C5 heteroaryl substituted with 0, 1, 2, or 3 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. Examples of C2-C5 heteroaryls include, but are not limited to, thiophene, furan, pyrrole, oxazole, isoxazole, isothiazole, pyridine, pyrimidine, pyridazine, pyrazine, triazine, and purine. In a further aspect, $Ar^1$ is C2-C5 heteroaryl substituted with 0, 1, or 2 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In a still further aspect, $Ar^1$ is C2-C5 heteroaryl substituted with 0 or 1 group selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In yet a further aspect, $Ar^1$ is C2-C5 heteroaryl monosubstituted with a group selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In an even further aspect, $Ar^1$ is unsubstituted C2-C5 heteroaryl.

In various aspects, $Ar^2$ is selected from phenyl and C2-C5 heteroaryl, and is substituted with 0, 1, 2, or 3 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In a further aspect, $Ar^2$ is selected from phenyl and C2-C5 heteroaryl, and is substituted with 0, 1, or 2 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In a still further aspect, $Ar^2$ is selected from phenyl and C2-C5 heteroaryl, and is substituted with 0 or 1 group selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In yet a further aspect, $Ar^2$ is selected from phenyl and C2-C5 heteroaryl, and is monosubstituted with a group selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In an even further aspect, $Ar^2$ is selected from phenyl and C2-C5 heteroaryl, and is unsubstituted.

In various aspects, $Ar^2$ is phenyl substituted with 0, 1, 2, or 3 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In a further aspect, $Ar^2$ is phenyl substituted with 0, 1, or 2 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In a still further aspect, $Ar^2$ is phenyl substituted with 0 or 1 group selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In yet a further aspect, $Ar^2$ is phenyl monosubstituted with a group selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In an even further aspect, $Ar^2$ is unsubstituted phenyl.

In various aspects, $Ar^2$ is C2-C5 heteroaryl substituted with 0, 1, 2, or 3 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. Examples of C2-C5 heteroaryls include, but are not limited to, thiophene, furan, pyrrole, oxazole, isoxazole, isothiazole, pyridine, pyrimidine, pyridazine, pyrazine, triazine, and purine. In a further aspect, $Ar^2$ is C2-C5 heteroaryl substituted with 0, 1, or 2 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In a still further aspect, $Ar^2$ is C2-C5 heteroaryl substituted with 0 or 1 group selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In yet a further aspect, $Ar^2$ is C2-C5 heteroaryl monosubstituted with a group selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In an even further aspect, $Ar^2$ is unsubstituted C2-C5 heteroaryl.

In various aspects, $Ar^2$ is isoxazolyl substituted with 0, 1, 2, or 3 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In a further aspect, $Ar^2$ is isoxazolyl substituted with 0, 1, or 2 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In a still further aspect, $Ar^2$ is isoxazolyl substituted with 0 or 1 group selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In yet a further aspect, $Ar^2$ is isoxazolyl monosubstituted with a group selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In an even further aspect, $Ar^2$ is unsubstituted isoxazolyl.

In various aspects, $Ar^3$ is selected from phenyl and C2-C5 heteroaryl, and is substituted with 0, 1, 2, or 3 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In a further aspect, $Ar^3$ is selected from phenyl and C2-C5 heteroaryl, and is substituted with 0, 1, or 2 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In a still further aspect, $Ar^3$ is selected from phenyl and C2-C5 heteroaryl, and is substituted with 0 or 1 group selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In yet a further aspect, $Ar^3$ is selected from phenyl and C2-C5 heteroaryl, and is monosubstituted with a group selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In an even further aspect, $Ar^3$ is selected from phenyl and C2-C5 heteroaryl, and is unsubstituted.

In various aspects, $Ar^3$ is phenyl substituted with 0, 1, 2, or 3 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In a further aspect, $Ar^3$ is phenyl substituted with 0, 1, or 2 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In a still further aspect, $Ar^3$ is phenyl substituted with 0 or 1 group selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In yet a further aspect, $Ar^3$ is phenyl monosubstituted with a group selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In an even further aspect, $Ar^3$ is unsubstituted phenyl.

In various aspects, $Ar^3$ is C2-C5 heteroaryl substituted with 0, 1, 2, or 3 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. Examples of C2-C5 heteroaryls include, but are not limited to, thiophene, furan, pyrrole, oxazole, isoxazole, isothiazole, pyridine, pyrimidine, pyridazine, pyrazine, triazine, and purine. In a further aspect, $Ar^3$ is C2-C5 heteroaryl substituted with 0, 1, or 2 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In a still further aspect, $Ar^3$ is C2-C5 heteroaryl substituted with 0 or 1 group selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In yet a further aspect, $Ar^3$ is C2-C5 heteroaryl monosubstituted with a group selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl. In an even further aspect, $Ar^3$ is unsubstituted C2-C5 heteroaryl.

In various aspects, $Ar^3$ is monosubstituted with a C1-C12 alkoxy group. In a further aspect, $A^3$ is monosubstituted with a C1-C8 alkoxy group. In a still further aspect, $Ar^3$ is monosubstituted with a C5 alkoxy group.

In various aspects, $Ar^3$ is para-substituted with a C1-C12 alkoxy group. In a further aspect, $A^3$ is para-substituted with a C1-C8 alkoxy group. In a still further aspect, $Ar^3$ is para-substituted with a C5 alkoxy group.

In various aspects, each of $Ar^1$, $Ar^2$, and $A^3$ is a structure represented by a formula:

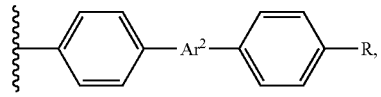

wherein R is selected from hydrogen, halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl.

In various aspects, each of $Ar^1$, $Ar^2$, and $A^3$ is a structure represented by a formula:

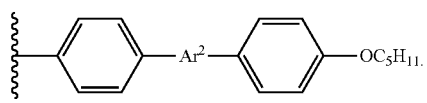

In various aspects, each of $Ar^1$, $Ar^2$, and $Ar^3$ is a structure represented by a formula:

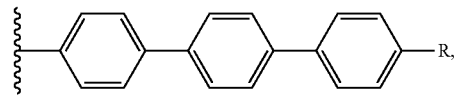

wherein R is selected from hydrogen, halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl.

In various aspects, each of $Ar^1$, $Ar^2$, and $Ar^3$ is a structure represented by a formula:

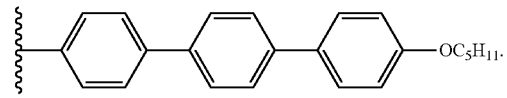

In various aspects, each of $Ar^1$, $Ar^2$, and $Ar^3$ is a structure represented by a formula:

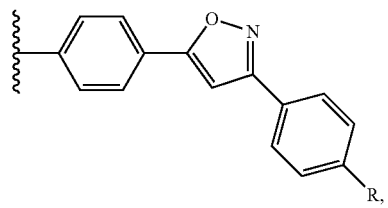

wherein R is selected from hydrogen, halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl.

In various aspects, each of $Ar^1$, $Ar^2$, and $Ar^3$ is a structure represented by a formula:

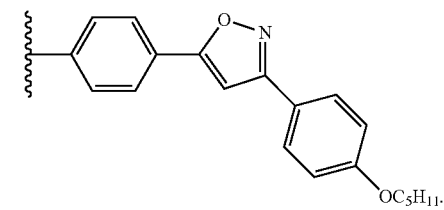

2. Example Compounds
  In one aspect, a compound can be present as:
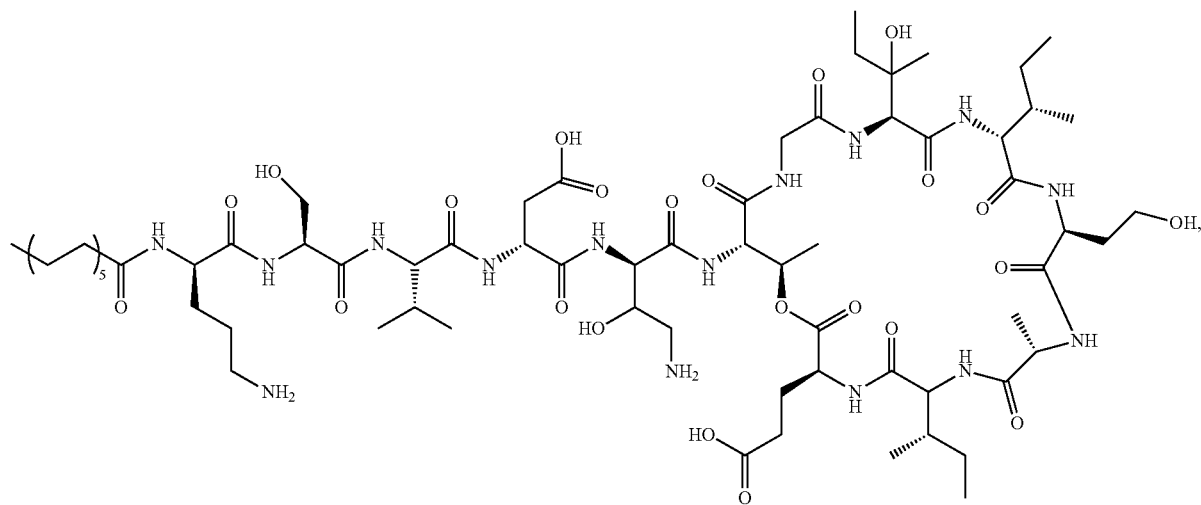
or a pharmaceutically acceptable salt thereof.
  In one aspect, a compound can be present as:
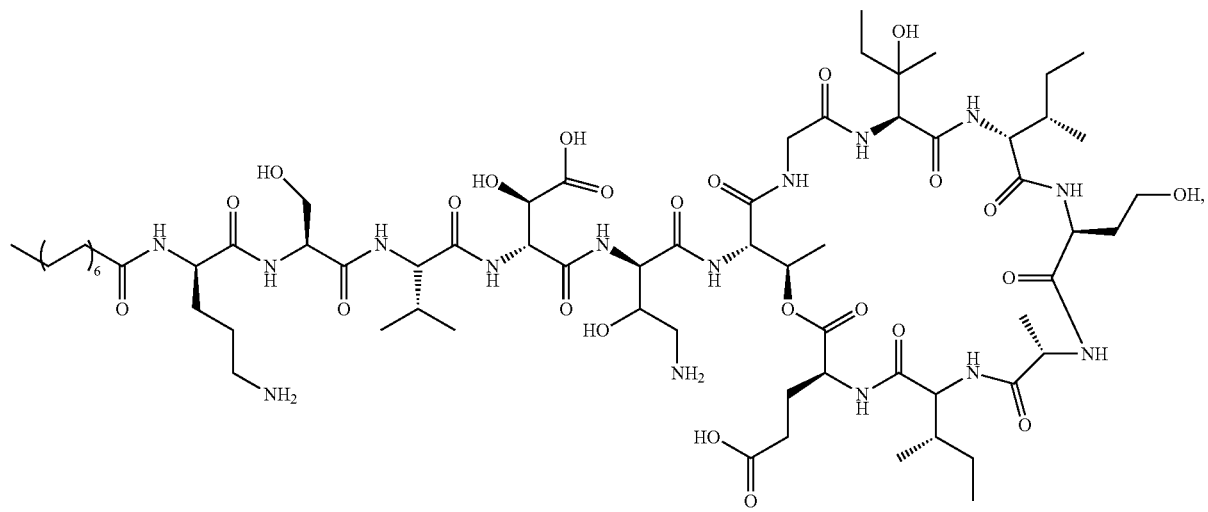
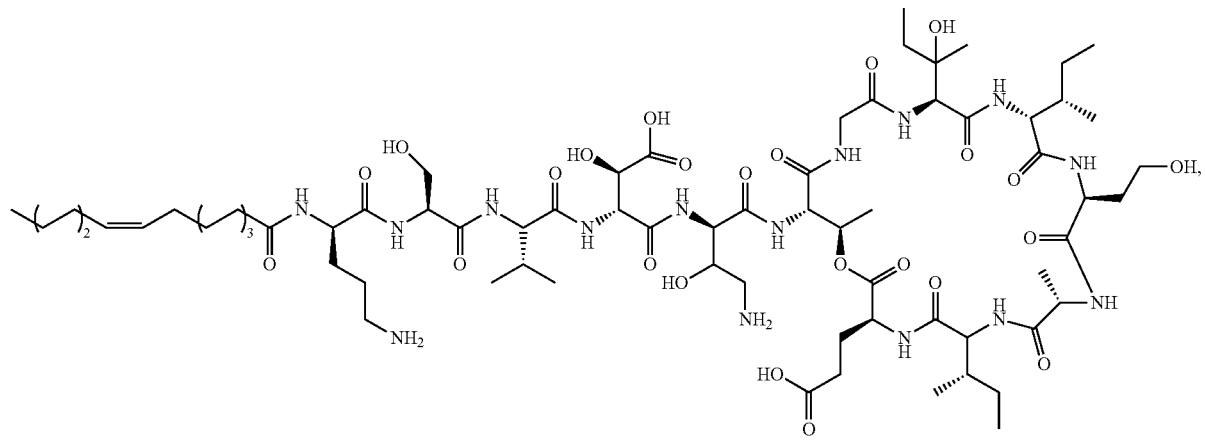

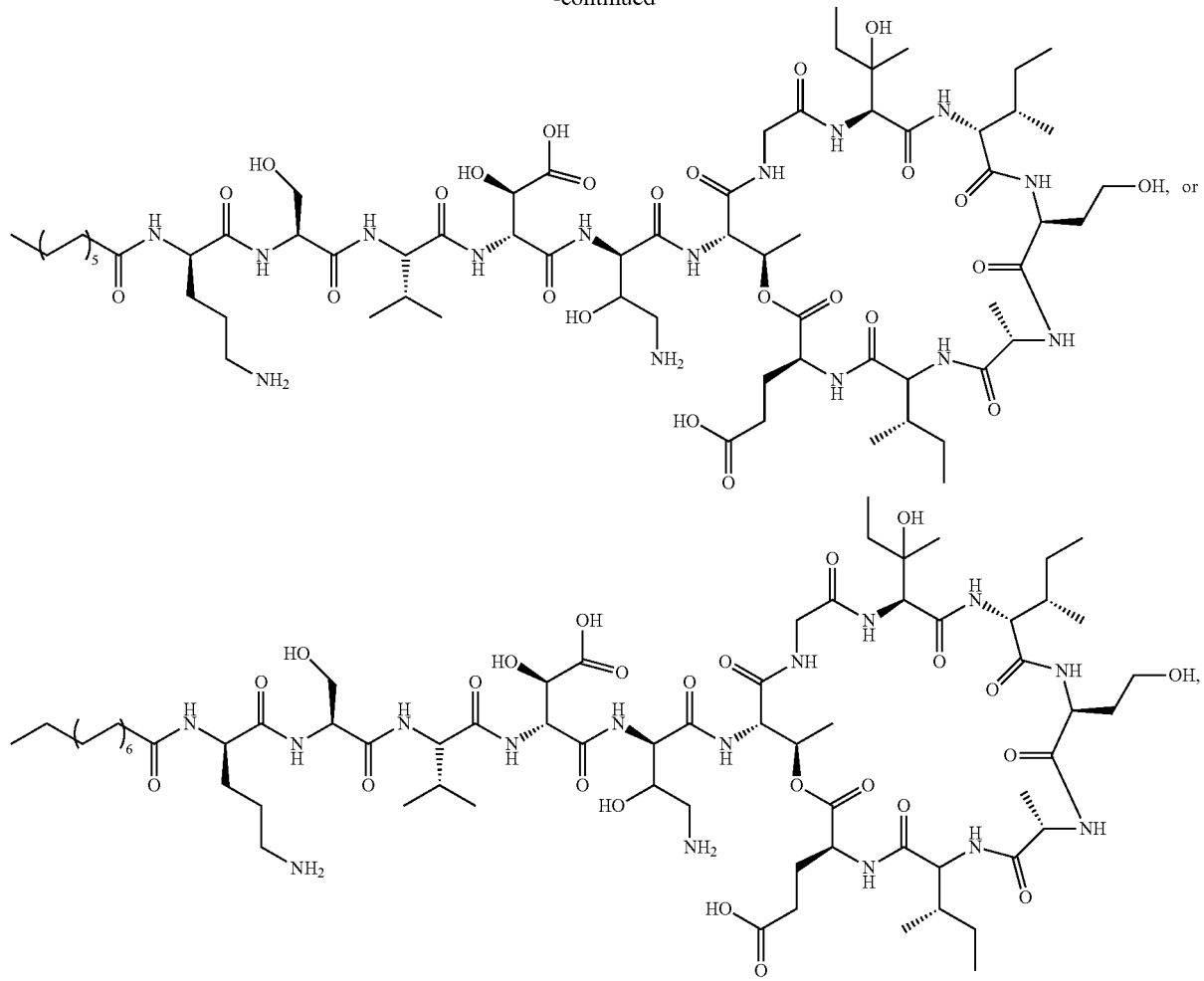
or a pharmaceutically acceptable salt thereof.
C. METHODS OF MAKING A CYCLOPEPTIDE
In one aspect, a disclosed cyclopeptide can be prepared as disclosed elsewhere herein. Thus, in various aspects, disclosed are methods of making a compound having a structure represented by a formula:
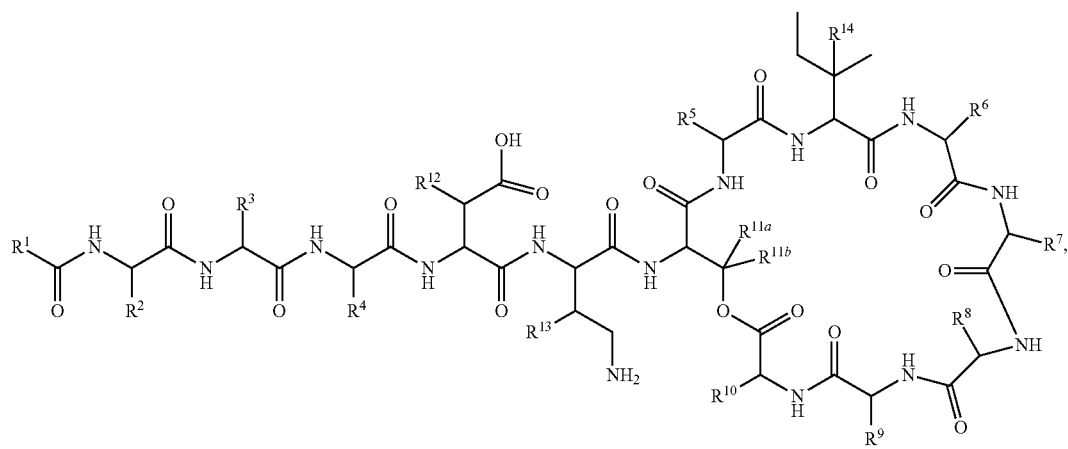

wherein Ru is selected from C1-C24 alkyl, C2-C24 alkenyl, an a structure represented by a formula:

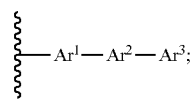

wherein each of $Ar^1$, $Ar^2$, and $Ar^3$ is independently selected from phenyl and C2-C5 heteroaryl, and is substituted with 0, 1, 2, or 3 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl; wherein each of $R^2$, $R^3$, $R^4$, $R^5$, $R^6$, $R^7$, $R^8$, $R^9$, and $R^{10}$ is independently selected from a natural amino acid residue and an unnatural amino acid residue; wherein each of $R^{11a}$ and $R^{11b}$ is independently selected from hydrogen and C1-C4 alkyl; and wherein each of $R^{12}$, $R^{13}$, and $R^{14}$ is independently selected from —OH, —SH, and —NH$_2$, or a pharmaceutically acceptable salt thereof.

Also disclosed are methods of making a compound having a structure represented by a formula:

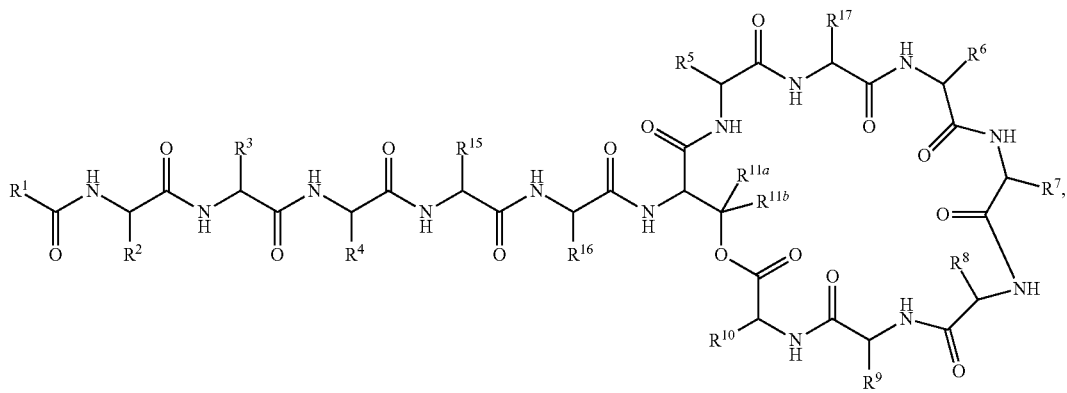

wherein $R^1$ is selected from C1-C24 alkyl, C2-C24 alkenyl, and a structure represented by a formula:

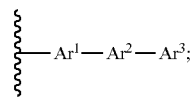

wherein each of $Ar^1$, $Ar^2$, and $Ar^3$ is independently selected from phenyl and C2-C5 heteroaryl, and is substituted with 0, 1, 2, or 3 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl; wherein each of $R^2$, $R^3$, $R^7$, $R^{10}$, $R^{15}$, and $R^{16}$ is independently selected from a natural amino acid residue and an unnatural amino acid residue, provided that each of $R^2$, $R^3$, $R^7$, $R^{10}$, $R^{15}$, and $R^{16}$ is a non-glycine residue; wherein each of $R^4$, $R^5$, $R^6$, $R^8$, $R^9$, and $R^{17}$ is independently selected from a natural amino acid residue and an unnatural amino acid residue; and wherein each of $R^{11a}$ and $R^{11b}$ is independently selected from hydrogen and C1-C4 alkyl, or a pharmaceutically acceptable salt thereof.

Also disclosed are methods of making a compound having a structure represented by a formula:

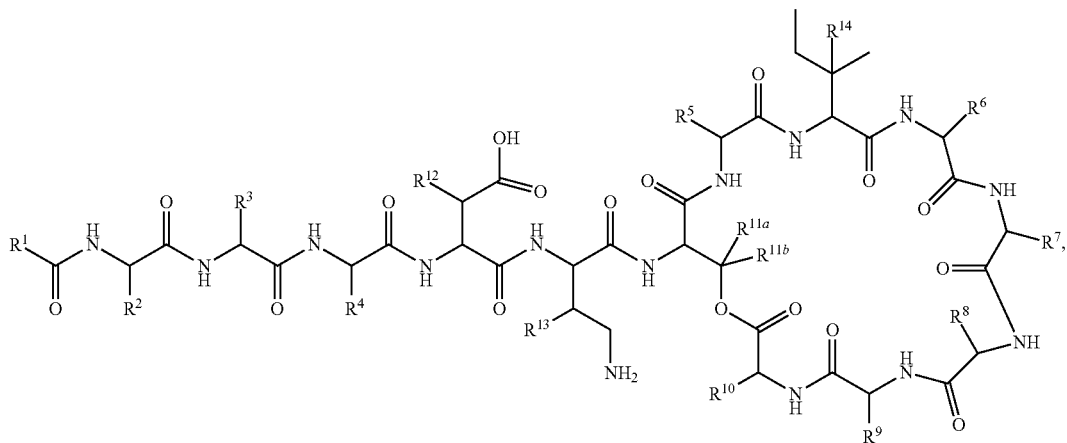

wherein $R^1$ is selected from C1-C24 alkyl and C2-C24 alkenyl; wherein each of $R^2$, $R^3$, $R^4$, $R^5$, $R^6$, $R^7$, $R^8$, $R^9$, and $R^{10}$ is independently selected from a natural amino acid residue and an unnatural amino acid residue; wherein each of $R^{11a}$ and $R^{11b}$ is independently selected from hydrogen and C1-C4 alkyl; and wherein each of $R^{12}$, $R^{13}$, and $R^{14}$ is independently selected from —OH, —SH, and —NH$_2$, or a pharmaceutically acceptable salt thereof, wherein the method comprises applying a knockout method as disclosed herein. In various aspects, the method comprises knocking out one or more target sequences, target genes or a gene cluster of interest.

Also disclosed are methods of making a compound having a structure represented by a formula:

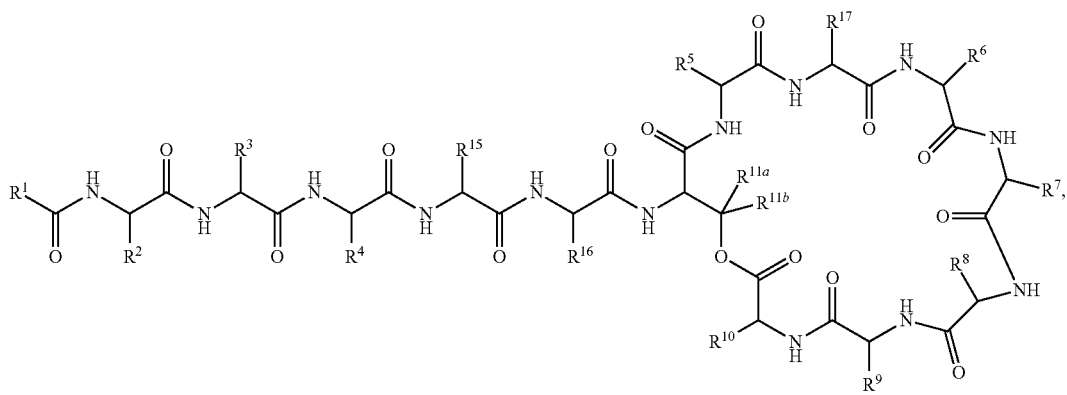

wherein $R^1$ is selected from C1-C24 alkyl and C2-C24 alkenyl; wherein each of $R^2$, $R^3$, $R^7$, $R^{10}$, $R^{15}$, and $R^{16}$ is independently selected from a natural amino acid residue and an unnatural amino acid residue, provided that each of $R^2$, $R^3$, $R^7$, $R^{10}$, $R^{15}$, and $R^{16}$ is a non-glycine residue; wherein each of $R^4$, $R^5$, $R^6$, $R^8$, $R^9$, and $R^{17}$ is independently selected from a natural amino acid residue and an unnatural amino acid residue; and wherein each of $R^{11a}$ and $R^{11b}$ is independently selected from hydrogen and C1-C4 alkyl, or a pharmaceutically acceptable salt thereof, wherein the method comprises applying a knockout method as disclosed herein. In various aspects, the method comprises knocking out one or more target sequences, target genes or a gene cluster of interest.

In various aspects, the compound has a structure represented by a formula:

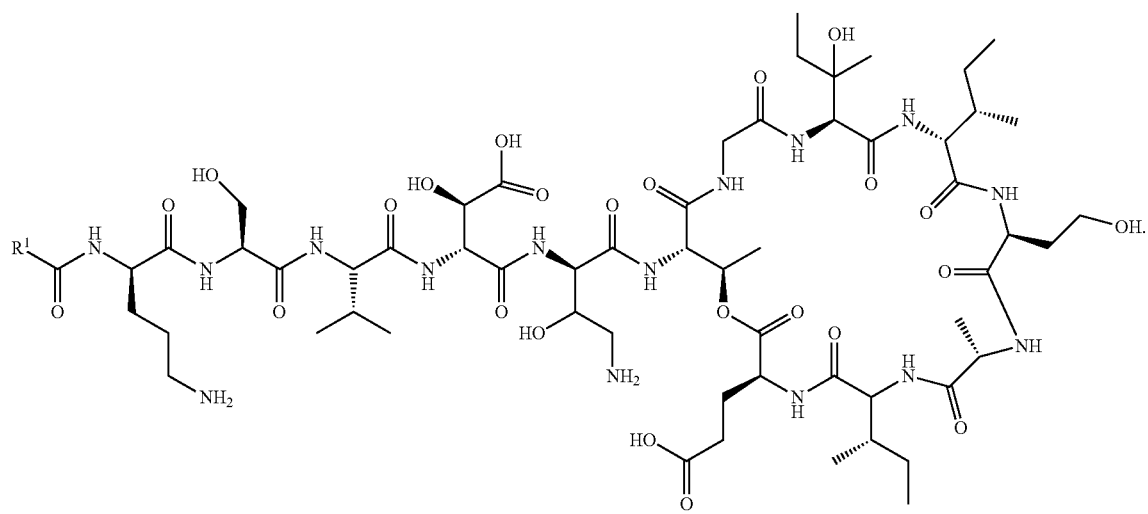

In various aspects, the compound does not have a structure represented by a formula:

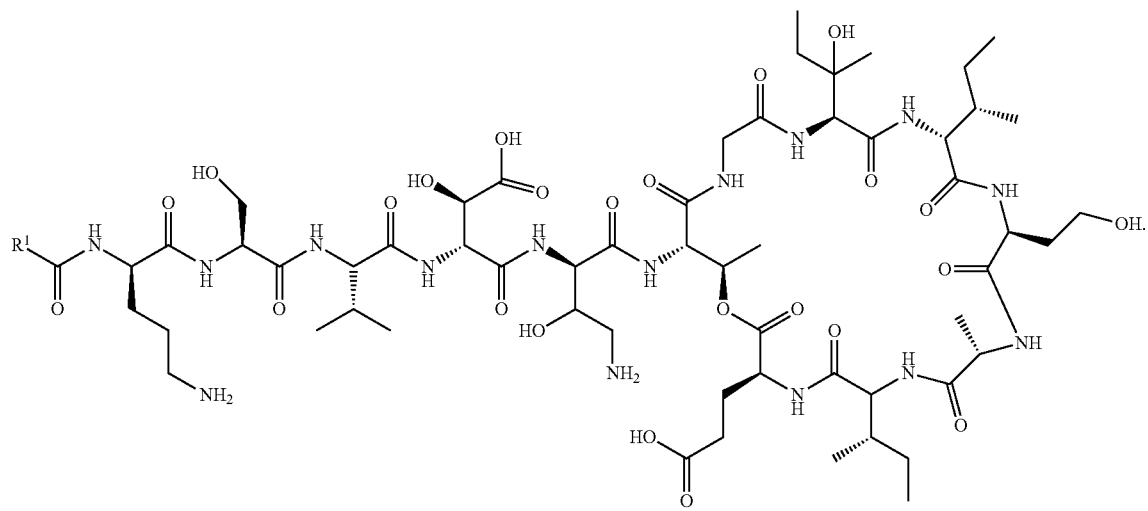

Thus, in various aspects, disclosed herein are methods of knocking out one or more target sequences, target genes or agene cluster of interest. In some aspects, in vitro techniques can be used to modify gene(s) on plasmids or Bacterial Artificial Chromosomes (BACs) and then this modified construct can be moved to the organism of interest by cell culture techniques. In some aspects, the target sequence, target gene (e.g., turH gene) or gene cluster of interest can be identified (e.g., using a set of primers to generate a DNA fragment or replicon), and be part of a replicon (e.g., BAC, PAC, plasmid, bacteriophage, chromosome) that can replicate in *E. coli* or any other recombineering-proficient organism. In some aspects, a drug-resistance cassette can be used in the knock-out method. In some aspects, the drug-resistance cassette can be of a different size than the replaced gene. In some aspects, the sequence of the drug-resistant cassette can include promoter and transcriptional terminators can then be inserted into the gene/region of interest to form the final construct. In some aspects, the drug-resistant cassette can comprise an antibiotic resistant gene. In some aspects, the antibiotic resistant gene can be a kanamycin resistance or sacB gene. In some aspects, the insertion step can generate two new DNA junctions.

In some aspects, primers can be designed to recognize the DNA junctions. In some aspects, the 5' end of the primers can be homologous to the sequence just outside the DNA junction. In some aspects, the 3' end of the primers can be designed to prime synthesis of the chosen drug cassette. In some aspects, the primers can further include additional short sequences such as His tags, frt or lox sites, or restriction sites. In some aspects, Gibson assembly reaction can be carried out to clone two more fragments in a plasmid. In some aspects, pCM488_kanT plasmid can be used as a vector backbone. In some aspects, overlapping ends can be incorporated into the fragments to allow seamless joining of adjacent fragments thereby generating an assembly product. The assembly product can be transformed into *E. coli* and verified using Sanger sequencing. The resulting plasmid can be transformed into *E. coli* donor strain for conjugation. Next, the cells can be prepared for recombineering. In some aspects, the single colony of *E. coli* can then be inoculated into LB medium that includes the appropriate drug (e.g., kanamycin). Cells are cultured, and transformed with the final construct to make the knockout. Colonies showing growth on plates that lack the drug (e.g., kanamycin) can be identified to contain the gene deletion mutants, and can be further confirmed using PCR. In some aspects, the knockout mutant can be purified and cultivated, and new compounds lacking the gene of interest can be obtained and isolated.

Also disclosed herein are transgenic bacteria, transgenic bacterial cells and vectors comprising a disrupted turH gene. Further provided are cells, comprising the disclosed vectors, bacteria comprising the disclosed cells, and bacteria comprising the disclosed vectors.

The disrupted turH gene can be any turH gene that has a different function than an unaltered turH function. Optionally, the disrupted turH gene can be a gene that encodes a non-functional turH protein.

Optionally, the disrupted turH gene can comprise a deleted sequence, a point mutation, or a missense mutation. As such, the disrupted turH gene can comprise a deleted sequence wherein the sequence exon can be any portion of the turH gene sequence. The DNA sequence of turH (*Teredinibacter* tumerae 17901 complete genome NCBI accession: NC_012997.1; T7901 complete genome assembly accession: GCF_000023025.1; Gene Location: NC_012997 REGION: 2573316..2574284; Gene Locus tag: locus_tag="TERTU_RS10345"

Protein accession number: WP_015816888.1) are known as is the cDNA sequence of turH, and the protein sequences of turH which is provided as Accession Number WP_015816888.1. One of skill in the art would be able to surmise what sequences comprise the exons.

The disrupted turH gene can also comprise other embodiments. For example, the disrupted turH gene can also comprise a marker gene. Suitable marker genes are described below and include a kanamycin resistance gene, sacB gene, the *E. coli* lacZ gene, G418 resistance gene, HPRT, thymidine kinase, the green fluorescent protein (GFP), and the red fluorescent protein (RFP). The disrupted turH gene can also comprise one or more loxP sites and one or more recombinase sites. The recombinase sites can flank some or all of the turH exons. The recombinase can be a Cre or Flp recombinase.

The disruption of TurH function or turH expression can lead to impaired an impaired ability to oxidize aspartic acid in turnercyclamycins.

Also provided herein are vectors comprising a portion of the turH gene, wherein the portion of the turH gene produces a disrupted turH gene, and wherein the vector can homologously recombine with the turH gene. Optionally, the vectors can comprise a selectable marker. Examples of suitable selectable markers include, but are not limited to, a kanamycin resistance gene, sacB gene, dihydrofolate reductase (DHFR), thymidine kinase, neomycin, neomycin analog G418, hydromycin, and puromycin. The selectable marker can be a positive or negative selection marker.

Also provided are nucleic acid molecules produced by a process, the process comprising linking in an operative way a nucleic acid comprising the sequence of a turH exon and sequence recognized by a recombinase enzyme. Further provided are cells produced by the process of transforming a cell with the nucleic acids produced by such a process.

The disclosed compositions and methods can be used for targeted gene disruption and modification in any bacteria or bacterial cell that can undergo these events.

Gene modification and gene disruption refer to the methods, techniques, and compositions that surround the selective removal or alteration of a gene or stretch of chromosome in a bacterial cell or bacteria, in a way that propagates the modification through the germ line of the bacterial cell or bacteria. In general, a cell is transformed with a vector which is designed to homologously recombine with a region of a particular chromosome contained within the cell, as for example, described herein. This homologous recombination event can produce a chromosome which has exogenous DNA introduced, for example in frame, with the surrounding DNA. This type of protocol allows for very specific mutations, such as point mutations, to be introduced into the genome contained within the cell. Methods for performing this type of homologous recombination are disclosed herein.

One of the characteristics of performing homologous recombination in bacterial cells is that the cells should be able to be cultured, because the desired recombination event occurs at a low frequency.

Bacterial cells or bacteria that are turH knockouts can be generated as discussed in the Examples.

D. PHARMACEUTICAL COMPOSITIONS

In one aspect, the invention relates to pharmaceutical compositions comprising the disclosed compounds. That is, a pharmaceutical composition can be provided comprising a therapeutically effective amount of at least one disclosed compound, or at least one product of a disclosed method, and a pharmaceutically acceptable carrier.

In one aspect, disclosed are pharmaceutical compositions comprising a therapeutically effective amount of a compound having a structure represented by a formula:

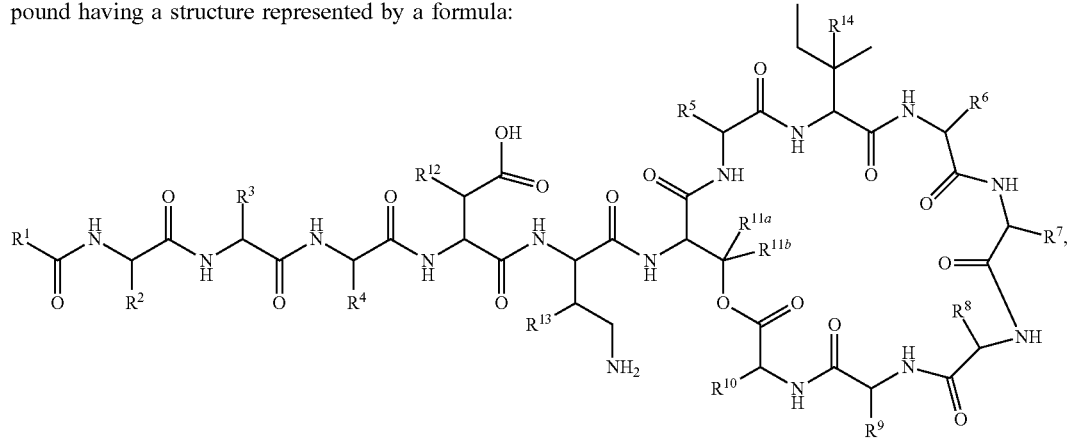

wherein $R^1$ is selected from C1-C24 alkyl, C2-C24 alkenyl, and a structure represented by a formula:

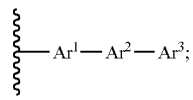

wherein each of $Ar^1$, $Ar^2$, and $Ar^3$ is independently selected from phenyl and C2-C5 heteroaryl, and is substituted with 0, 1, 2, or 3 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl; wherein each of $R^2$, $R^3$, $R^4$, $R^5$, $R^6$, $R^7$, $R^8$, $R^9$, and $R^{10}$ is independently selected from a natural amino acid residue and an unnatural amino acid residue; wherein each of $R^{11a}$ and $R^{11b}$ is independently selected from hydrogen and C1-C4 alkyl; and wherein each of $R^{12}$, $R^{13}$, and $R^{14}$ is independently selected from —OH, —SH, and —NH$_2$, or a pharmaceutically acceptable salt thereof, provided that the compound does not have a structure represented by a formula:

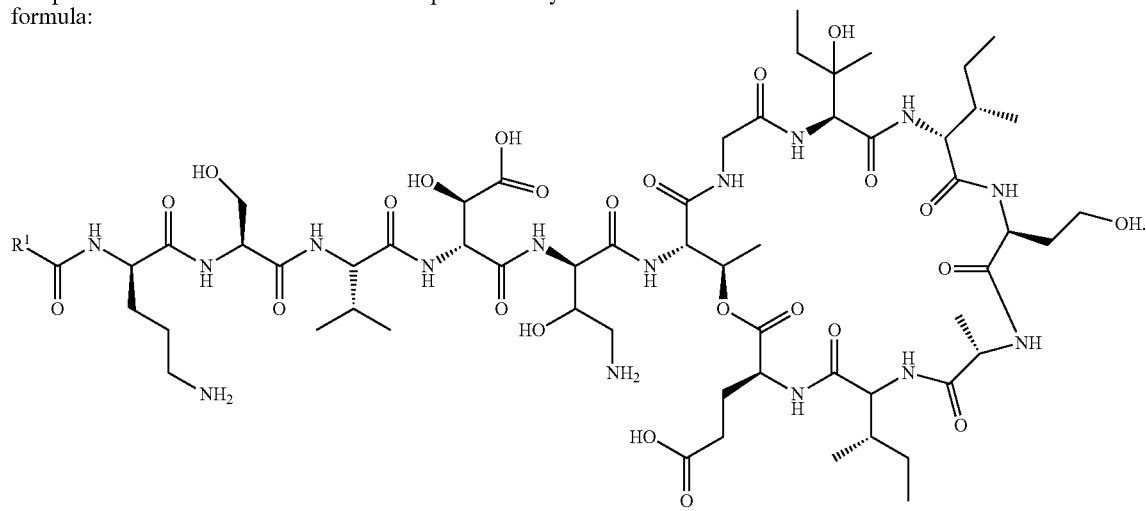

and a pharmaceutically acceptable carrier.

In one aspect, disclosed are pharmaceutical compositions comprising a therapeutically effective amount of a compound having a structure represented by a formula:

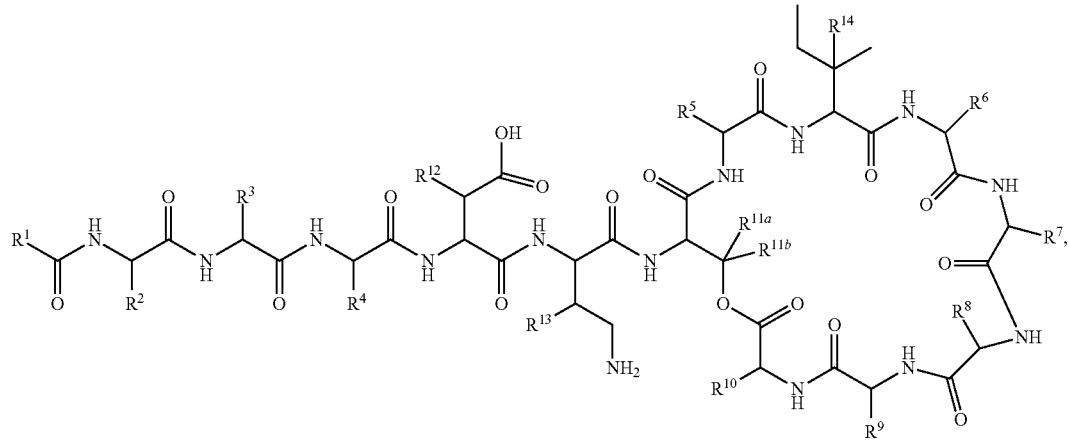

wherein $R^1$ is selected from C1-C24 alkyl and C2-C24 alkenyl; wherein each of $R^2$, $R^3$, $R^4$, $R^5$, $R^6$, $R^7$, $R^e$, $R^9$, and $R^{10}$ is independently selected from a natural amino acid residue and an unnatural amino acid residue; wherein each of $R^{11a}$ and $R^{11b}$ is independently selected from hydrogen and C1-C4 alkyl; and wherein each of $R^{12}$, $R^{13}$, and $R^{14}$ is independently selected from —OH, —SH, and —NH$_2$, or a pharmaceutically acceptable salt thereof, and a pharmaceutically acceptable carrier. In a further aspect, the compound has a neutral charge.

In one aspect, disclosed are compounds having a structure represented by a formula:

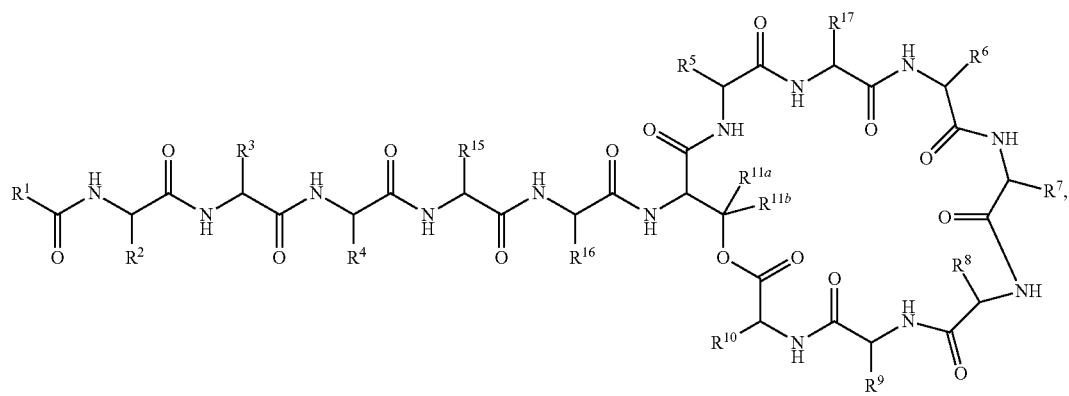

wherein R¹ is selected from C1-C24 alkyl, C2-C24 alkenyl, and a structure represented by a formula:

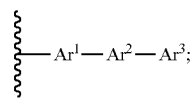

wherein each of Ar¹, Ar², and Ar³ is independently selected from phenyl and C2-C5 heteroaryl, and is substituted with 0, 1, 2, or 3 groups independently selected from halogen, —CN, —NH₂, —OH, —NO₂, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl; wherein each of R², R³, R⁷, R¹⁰, R¹⁵, and R¹⁶ is independently selected from a natural amino acid residue and an unnatural amino acid residue, provided that each of R², R³, R⁷, R¹⁰, R¹⁵, and R¹⁶ is a non-glycine residue; wherein each of R⁴, R⁵, R⁶, R⁸, R⁹, and R¹⁷ is independently selected from a natural amino acid residue and an unnatural amino acid residue; and wherein each of R¹¹ᵃ and R¹¹ᵇ is independently selected from hydrogen and C1-C4 alkyl, or a pharmaceutically acceptable salt thereof, provided that the compound does not have a structure represented by a formula:

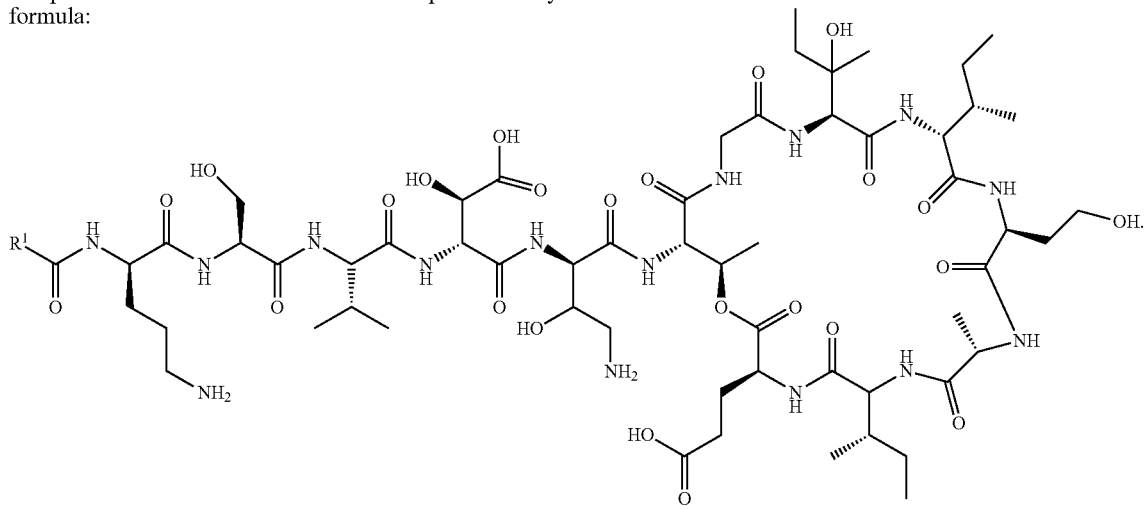

In one aspect, disclosed are pharmaceutical compositions comprising a therapeutically effective amount of a compound having a structure represented by a formula:

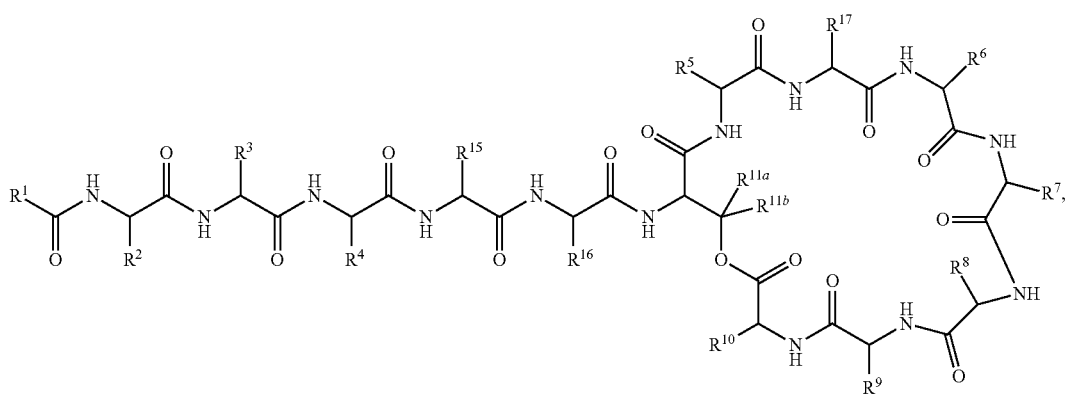

wherein $R^1$ is selected from C1-C24 alkyl and C2-C24 alkenyl; wherein each of $R^2$, $R^3$, $R^7$, $R^{10}$, $R^{15}$, and $R^{16}$ is independently selected from a natural amino acid residue and an unnatural amino acid residue, provided that each of $R^2$, $R^3$, $R^7$, $R^{10}$, $R^{15}$, and $R^{16}$ is a non-glycine residue; wherein each of $R^4$, $R^5$, $R^6$, $R^8$, $R^9$, and $R^{17}$ is independently selected from a natural amino acid residue and an unnatural amino acid residue; and wherein each of $R^{11a}$ and $R^{11b}$ is independently selected from hydrogen and C1-C4 alkyl, or a pharmaceutically acceptable salt thereof, and a pharmaceutically acceptable carrier. In a further aspect, the compound has a neutral charge.

In various aspects, the compound has a structure represented by a formula:

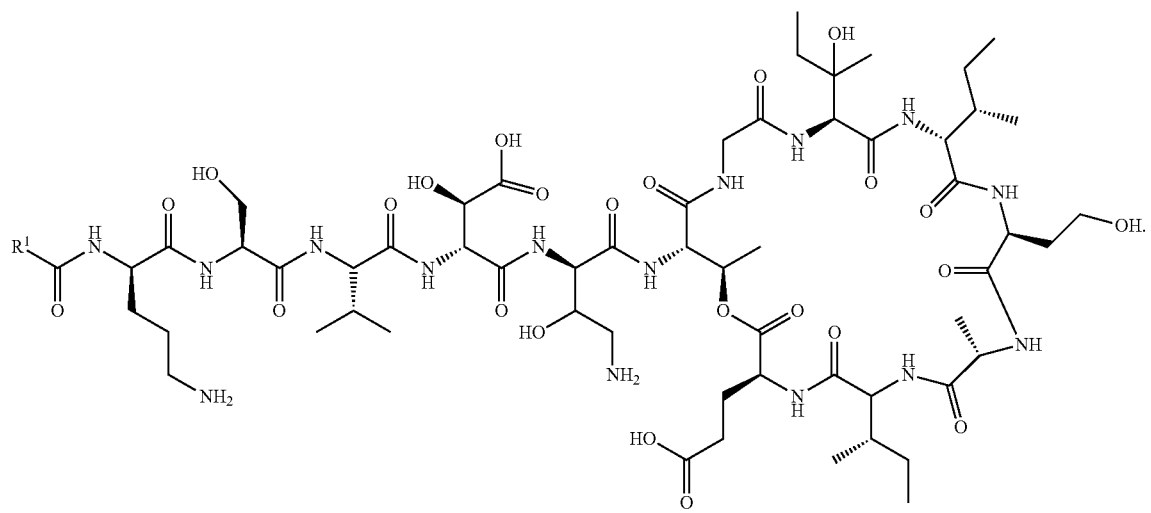

In various aspects, the compound does not have a structure represented by a formula:

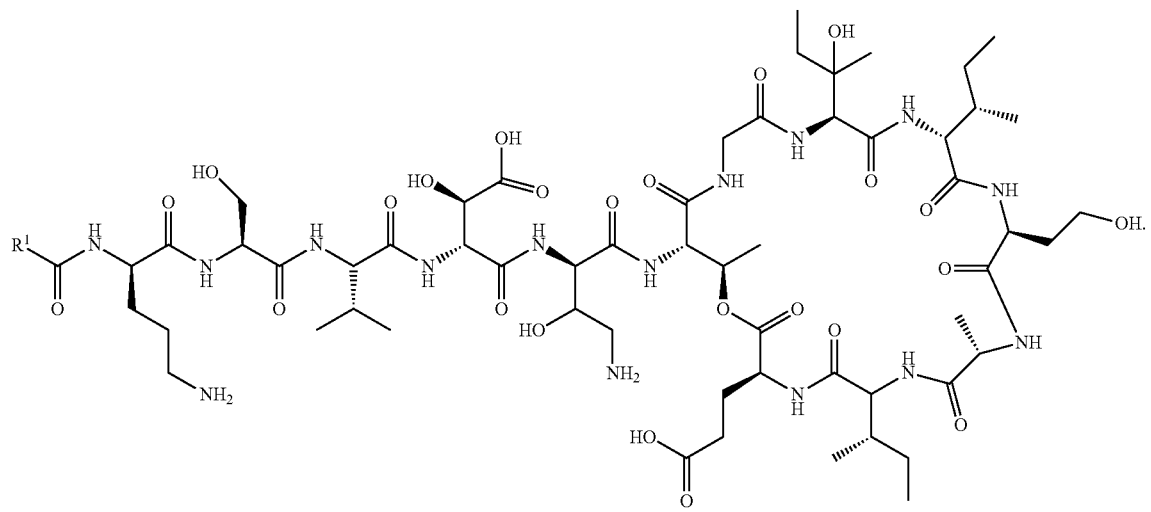

The pharmaceutical compositions described above can be formulated to include a therapeutically effective amount of a composition disclosed herein. Therapeutic administration encompasses prophylactic applications. Based on genetic testing and other prognostic methods, a physician in consultation with their patient can choose a prophylactic administration where the patient has a clinically determined predisposition or increased susceptibility (in some cases, a greatly increased susceptibility) to a bacterial infection.

The pharmaceutical compositions described herein can be administered to the subject (e.g., a human patient) in an amount sufficient to delay, reduce, or preferably prevent the onset of clinical disease. Accordingly, in some aspects, the patient can be a human patient. In therapeutic applications, compositions can be administered to a subject (e.g., a human patient) already with or diagnosed with a bacterial infection in an amount sufficient to at least partially improve a sign or symptom or to inhibit the progression of (and preferably arrest) the symptoms of the condition, its complications, and consequences. An amount adequate to accomplish this is defined as a "therapeutically effective amount." A therapeutically effective amount of a pharmaceutical composition can be an amount that achieves a cure, but that outcome is only one among several that can be achieved.

In some aspects, the pharmaceutical composition can be formulated for intravenous administration. In some aspects, the pharmaceutical composition can be formulated for subcutaneous, intranasal, oropharyngeal or oral administration. The compositions can be formulated for administration by any of a variety of routes of administration, and can include one or more physiologically acceptable excipients, which can vary depending on the route of administration. As used herein, the term "excipient" means any compound or substance, including those that can also be referred to as "carriers" or "diluents." Preparing pharmaceutical and physiologically acceptable compositions is considered routine in the art, and thus, one of ordinary skill in the art can consult numerous authorities for guidance if needed.

The pharmaceutical compositions as disclosed herein can be prepared for oral or parenteral administration. Pharmaceutical compositions prepared for parenteral administration include those prepared for intravenous (or intra-arterial), intramuscular, subcutaneous, intraperitoneal, transmucosal (e.g., intranasal, intravaginal, or rectal), or transdermal (e.g., topical) administration. Aerosol inhalation can also be used to deliver the peptides disclosed herein. Thus, compositions can be prepared for parenteral administration that include the peptides dissolved or suspended in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like). Where the compositions are formulated for application to the skin or to a mucosal surface, one or more of the excipients can be a solvent or emulsifier for the formulation of a cream, an ointment, and the like.

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

The total effective amount of the peptides disclosed herein in the pharmaceutical compositions disclosed herein can be administered to a mammal as a single dose, either as a bolus or by infusion over a relatively short period of time, or can be administered using a fractionated treatment protocol in which multiple doses are administered over a more prolonged period of time (e.g., a dose every 4-6, 8-12, 14-16, or 18-24 hours, or every 2-4 days, 1-2 weeks, or once a month). Alternatively, continuous intravenous infusions sufficient to maintain therapeutically effective concentrations in the blood are also within the scope of the present disclosure.

The therapeutically effective amount of the peptides present within the compositions described herein and used in the methods as disclosed herein applied to mammals (e.g., humans) can be determined by one of ordinary skill in the art with consideration of individual differences in age, weight, and other general conditions (as mentioned above).

In various aspects, the pharmaceutical composition further comprises an antibacterial agent. Examples of antibacterial agents include, but are not limited to, amoxicillin, ampicillin, azithromycin, aztreonam, azlocillin, bacitracin, carbenicillin, cefaclor, cefadroxil, cefamandole, cefazolin, cephalexin, cefdinir, cefditorin, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clavulanic acid, clinafloxacin, clindamycin, clofazimine, cloxacillin, colistin, dalbavancin, dalfopristin, demeclocycline, dicloxacillin, dirithromycin, doxycycline, erythromycin, enrofloxacin, enoxacin, enviomycin, ertepenem, ethambutol, flucloxacillin, fosfomycin, furazolidone, gatifloxacin, gentamicin, imipenem, isoniazid, kanamycin, linezolid, lomefloxacin, loracarbef, mafenide, moxifloxacin, meropenem, metronidazole, mezlocillin, minocycline, mupirocin, nafcillin, nalidixic acid, neomycin, netilmicin, nitrofurantoin, norfloxacin, ofloxacin, oritavancin, oxytetracycline, penicillin, piperacillin, platensimycin, polymixin B, quinupristin, retapamulin, rifabutin, rifampin, rifapentine, roxithromycin, sparfloxacin, spectinomycin, sulbactam, sulfacetamide, sulfamethizole, sulfamethoxazole, teicoplanin, telithromycin, telavancin, temafloxacin, tetracycline, thioacetazone, thioridazine, ticarcillin, tinidazole, tobramycin, torezolid, tosufloxacin, trimethoprim, troleandomycin, trovafloxacin, and vancomycin.

E. METHODS OF TREATING A BACTERIAL INFECTION

In one aspect, disclosed are methods of treating a bacterial infection in a subject in need thereof, the method comprising administering to the subject an effective amount of a disclosed compound. Thus, in various aspects, disclosed are methods of treating a bacterial infection in a subject in need thereof, the method comprising administering to the subject an effective amount of a compound having a structure represented by a formula:

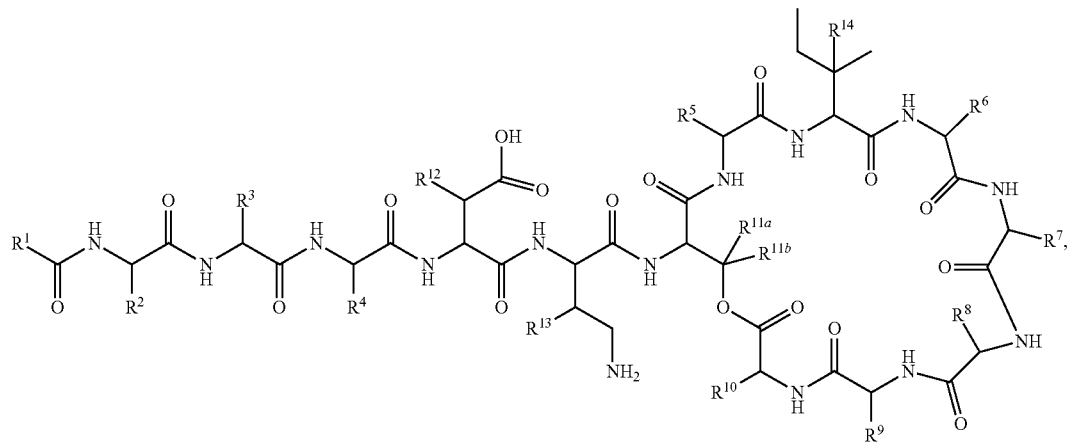

wherein R¹ is selected from C1-C24 alkyl, C2-C24 alkenyl, and a structure represented by a formula:

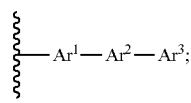

wherein each of Ar¹, Ar², and Ar³ is independently selected from phenyl and C2-C5 heteroaryl, and is substituted with 0, 1, 2, or 3 groups independently selected from halogen, —CN, —NH₂, —OH, —NO₂, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl; wherein each of R², R³, R⁴, R⁵, R⁶, R⁷, R⁸, R⁹, and R¹⁰ is independently selected from a natural amino acid residue and an unnatural amino acid residue; wherein each of R¹¹ᵃ and R¹¹ᵇ is independently selected from hydrogen and C1-C4 alkyl; and wherein each of R¹², R¹³, and R¹⁴ is independently selected from —OH, —SH, and —NH₂, or a pharmaceutically acceptable salt thereof.

In various aspects, disclosed are methods of treating a bacterial infection in a subject in need thereof, the method comprising administering to the subject an effective amount of a compound having a structure represented by a formula:

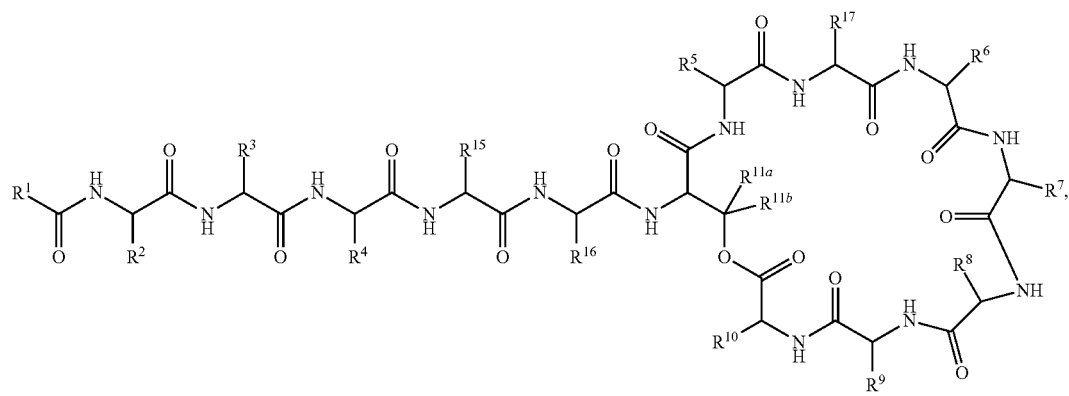

wherein $R^1$ is selected from C1-C24 alkyl, C2-C24 alkenyl, and a structure represented by a formula:

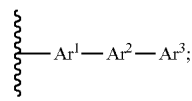

wherein each of $Ar^1$, $Ar^2$, and $Ar^3$ is independently selected from phenyl and C2-C5 heteroaryl, and is substituted with 0, 1, 2, or 3 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl; wherein each of $R^2$, $R^3$, $R^7$, $R^{10}$, $R^{15}$, and $R^{16}$ is independently selected from a natural amino acid residue and an unnatural amino acid residue, provided that each of $R^2$, $R^3$, $R^7$, $R^{10}$, $R^{15}$, and $R^{16}$ is a non-glycine residue; wherein each of $R^4$, $R^5$, $R^6$, $R^8$, $R^9$, and $R^{17}$ is independently selected from a natural amino acid residue and an unnatural amino acid residue; and wherein each of $R^{11a}$ and $R^{11b}$ is independently selected from hydrogen and C1-C4 alkyl, or a pharmaceutically acceptable salt thereof.

In various aspects, disclosed are methods of treating a bacterial infection in a subject in need thereof, the method comprising administering to the subject an effective amount of a compound having a structure represented by a formula:

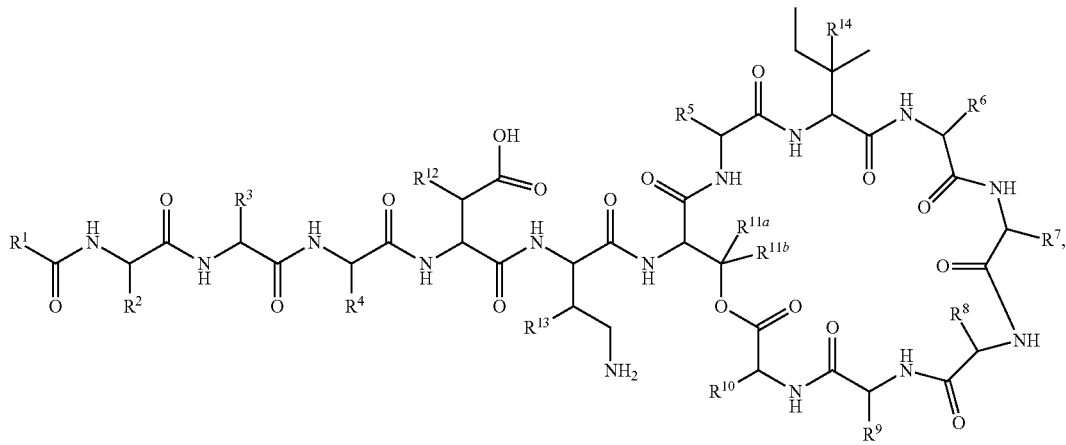

wherein $R^1$ is selected from C1-C24 alkyl and C2-C24 alkenyl; wherein each of $R^2$, $R^3$, $R^4$, $R^1$, $R^6$, $R^7$, Re, $R^9$, and $R^{10}$ is independently selected from a natural amino acid residue and an unnatural amino acid residue; wherein each of $R^{11a}$ and $R^{11b}$ is independently selected from hydrogen and C1-C4 alkyl; and wherein each of $R^{12}$, $R^{13}$, and $R^{14}$ is independently selected from —OH, —SH, and —NH$_2$, or a pharmaceutically acceptable salt thereof.

In various aspects, disclosed are methods of treating a bacterial infection in a subject in need thereof, the method comprising administering to the subject an effective amount of a compound having a structure represented by a formula:

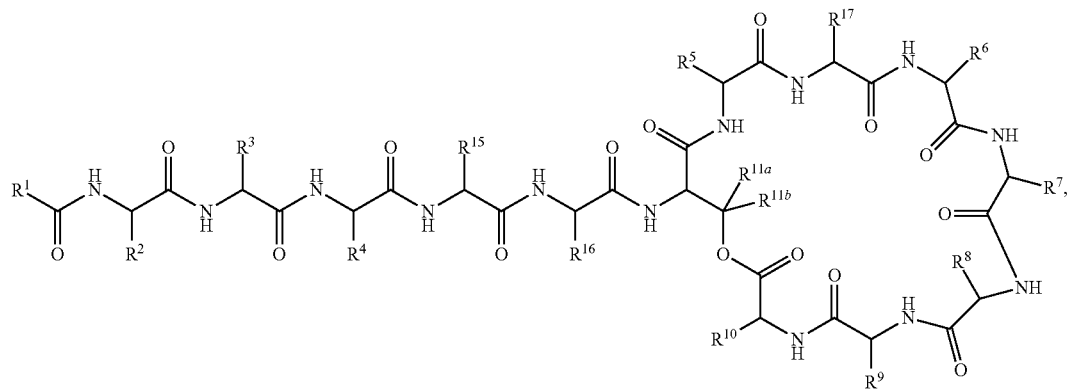

wherein $R^1$ is selected from C1-C24 alkyl and C2-C24 alkenyl; wherein each of $R^2$, $R^3$, $R^7$, $R^{10}$, $R^{15}$, and $R^{16}$ is independently selected from a natural amino acid residue and an unnatural amino acid residue, provided that each of $R^2$, $R^3$, $R^7$, $R^{10}$, $R^{15}$, and $R^{16}$ is a non-glycine residue; wherein each of $R^4$, $R^5$, $R^6$, Re, $R^9$, and $R^{17}$ is independently selected from a natural amino acid residue and an unnatural amino acid residue; and wherein each of $R^{11a}$ and $R^{11b}$ is independently selected from hydrogen and C1-C4 alkyl, or a pharmaceutically acceptable salt thereof, and a pharmaceutically acceptable carrier. In a further aspect, the compound has a neutral charge.

In various aspects, the compound has a structure represented by a formula:

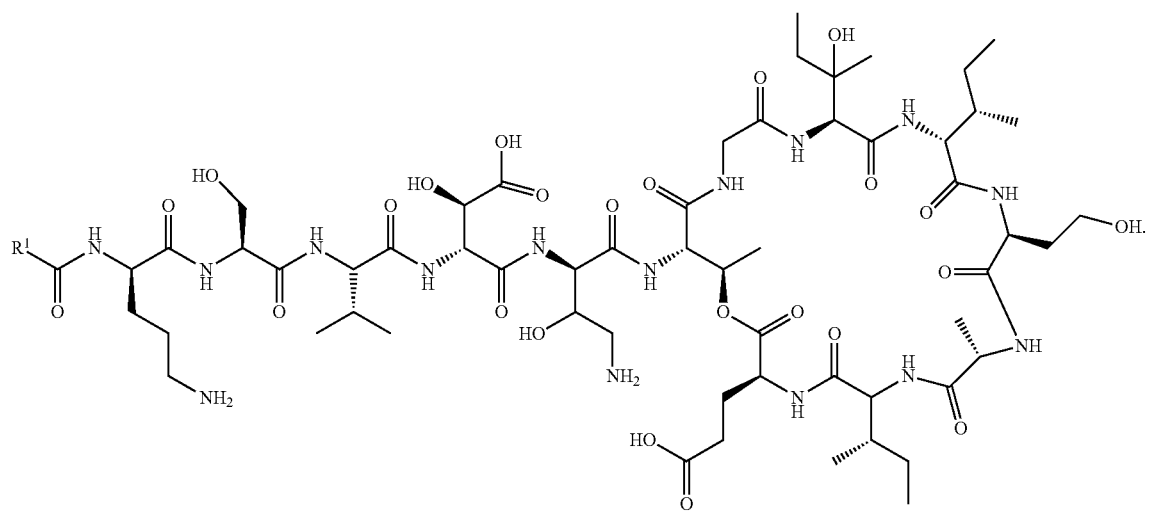

In various aspects, the compound does not have a structure represented by a formula:
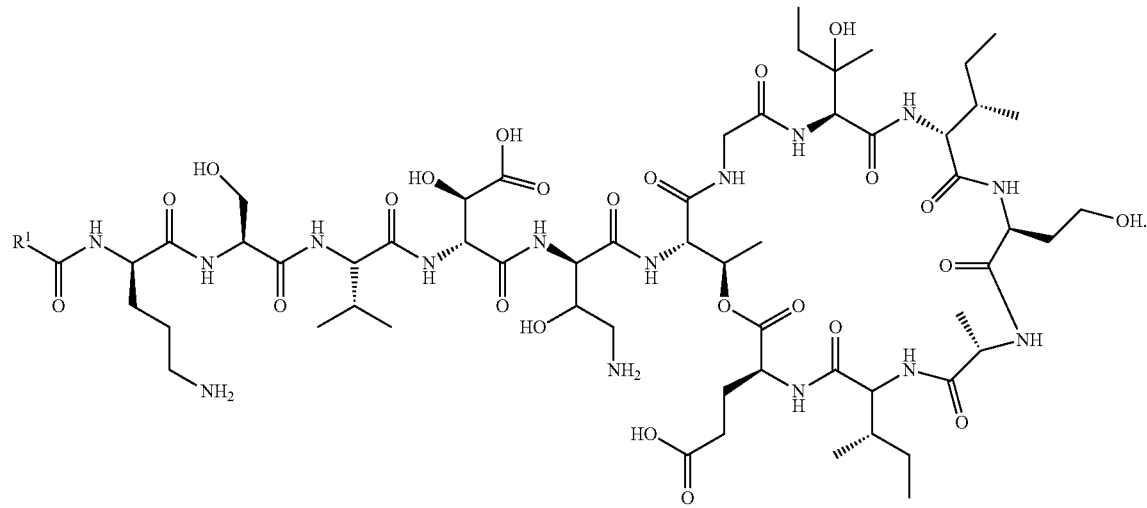
In various aspects, the compound is:
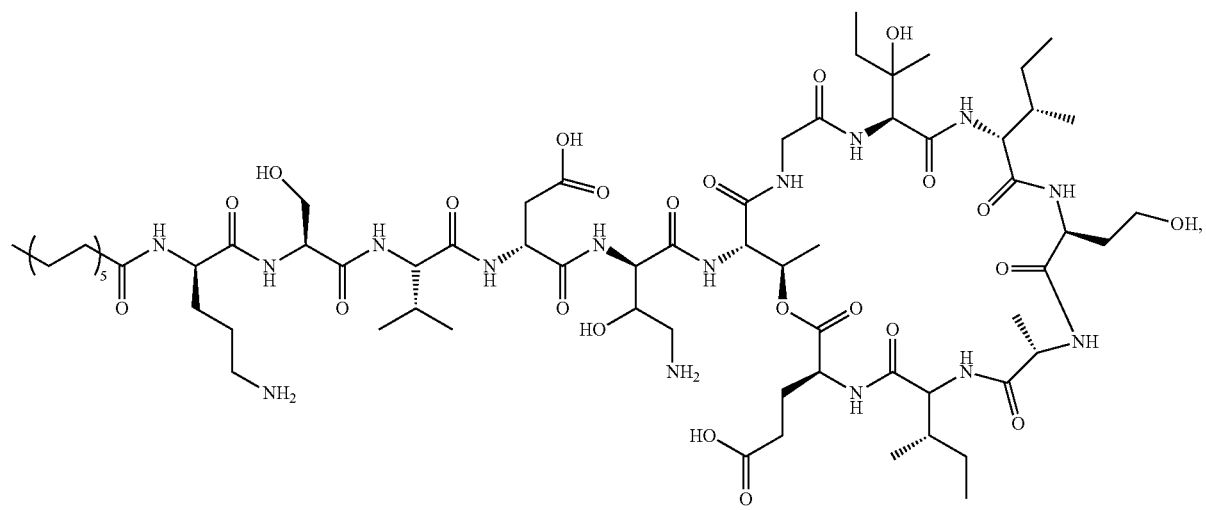
or a pharmaceutically acceptable salt thereof.

In various aspects, the compound is:
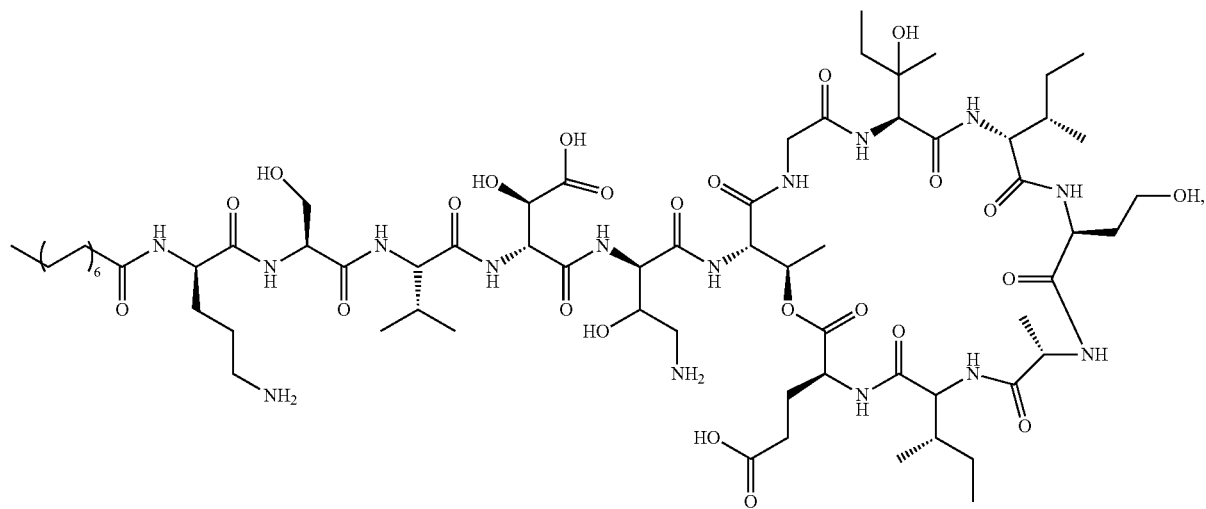
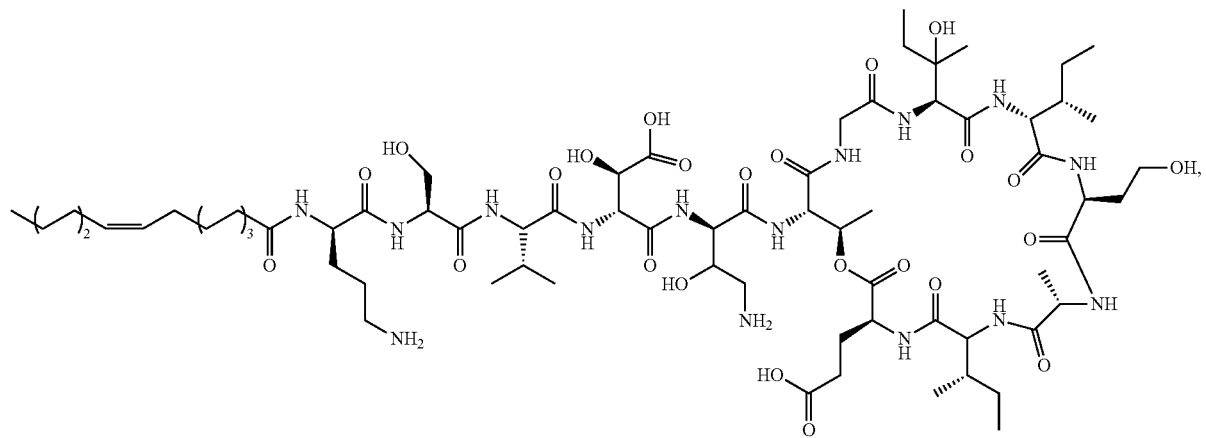
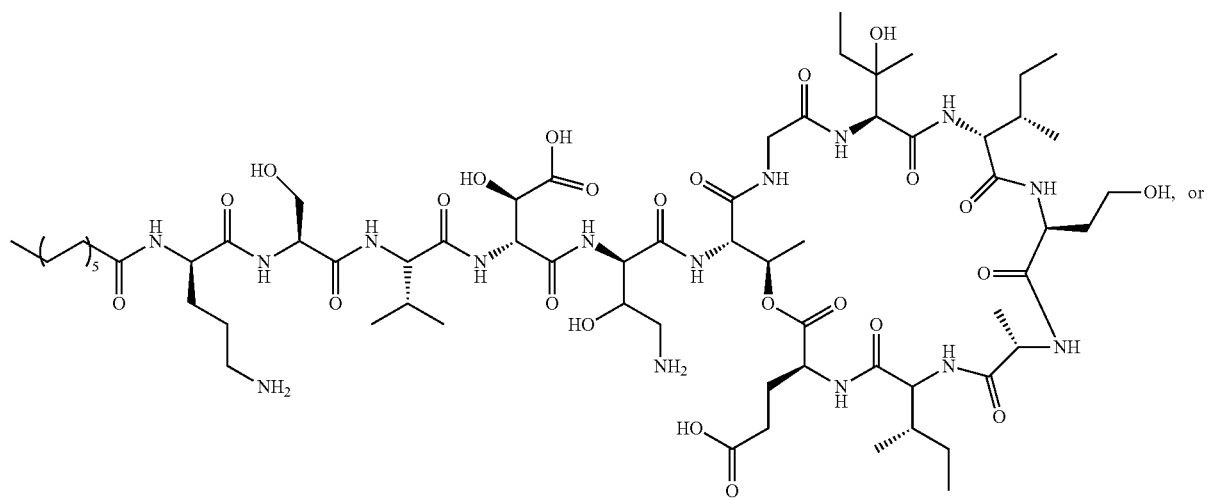

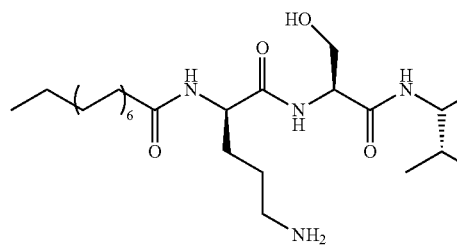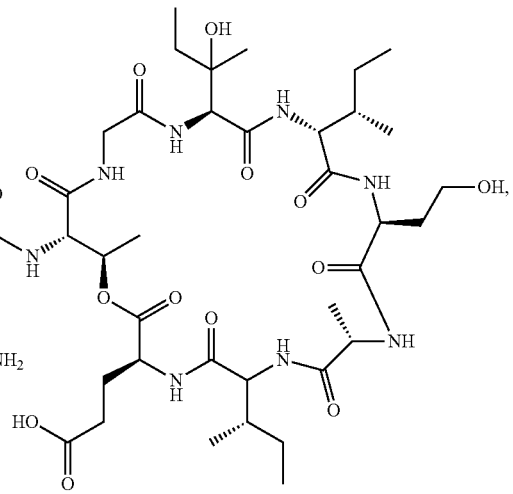

or a pharmaceutically acceptable salt thereof.

In various aspects, disclosed are methods of killing *Escherichia coli, Klebsiella pneumoniae*, and *Acinetobacter baumannii* comprising administering one or more of the compounds disclosed herein.

In various aspects, the bacterial infection is due to a bacteria that is resistant to colistin.

In various aspects, the bacterial infection is due to a Gram-negative bacteria. Examples of Gram-negative bacteria include, but are not limited to, *Acinetobacter* spp. *Aeromonas* spp., *Bordetella* spp., *Citrobacter* spp., *Enterobacter* spp., *Escherichia* spp., *Haemophilus* spp., *Klebsiella* spp., *Moraxella* spp., *Neisseria* spp., *Proteus* spp., *Pseudomonas* spp., *Salmonella* spp., *Shigella* spp., *Stenotrophomonas* spp., *Vibrio* spp., and *Yersinia* spp. Further examples of Gram-negative bacteria include, but are not limited to, *Acinetobacter baumanni, Aeromonas hydrophila, Bordetella pertussis, Bordetella parapertussis, Bordetella bronchiseptica, Citrobacter freundii, Enterobacter aerogenes, Enterobacter cloacae, Enterobacter sakazakii, Escherichia coli, Haemophilus influenzae, Haemophilus aegypticus, Haemophilus ducreyi, Klebsiella edwardsii, Klebsiella pneumoniae, Moraxella catarrhalis, Neisseria meningitidis, Neisseria gonorrhoeae, Proteus mirabilis, Salmonella enterica, Shigella boydii, Shigella dysenteriae, Shigella flexneri, Shigella sonnei, Stenotrophomonas maltophilia, Vibrio cholerae, Vibrio parahaemolyticus, Vibrio vulnificus, Vibrio fluvialis, Yersinia pestis, Yersinia enterocolitica*, and *Yersinia pseudotuberculosis*. Still further examples of Gram-negative bacteria include, but are not limited to, *Acinetobacter baumanni, Aeromonas hydrophila, Citrobacter freundii, Escherichia coli, Klebsiella edwardsii, Moraxella catarrhalis, Proteus mirabilis, Salmonella enterica, Shigella flexneri, Stenotrophomonas maltophilia, Vibrio cholerae, Yersinia pestis*, and *Yersinia enterocolitica*. In a further aspect, the Gram-negative bacteria is *Acinetobacter*. In a still further aspect, the Gram-negative bacteria is *Yersinia*. In yet a further aspect, the Gram-negative bacteria is resistant to colistin.

In various aspects, the bacterial infection is due to a Gram-positive bacteria. Examples of Gram-positive bacteria include, but are not limited to, *Streptococcus* spp., *Staphylococcus* spp., *Enterococcus* spp., *Clostridium* spp., and *Corynebacterium* spp. Further examples of Gram-positive bacteria include, but are not limited to, *Bacillus anthracis, Bacillus cereus, Bacillus subtilis, Clostridium dificile, Clostridium tetani, Clostridium botulinum, Clostridium perfringens, Corynebacterium diphtheria. Enterococcus faecalis. Enterococcus faecium. Listeria monocytogenes, Listeria ivanovii, Micrococcus luteus, Staphylococcus aureus, Staphylococcus epidermidis. Staphylococcus saprophyticus, Staphylococcus hyicus, Staphylococcus intermedius, Streptococcus pneumoniae*, and *Streptococcus pyogenes*. Still further examples of Gram-positive bacteria include, but are not limited to, *Clostridium difficile, Corynebacterium diphtheria. Enterococcus faecalis, Enterococcus faecium. Staphylococcus aureus, Staphylococcus epidermidis*, and *Streptococcus pneumoniae, Streptococcus pyogenes*. Still further examples of Gram-positive bacteria include, but are not limited to, methicillin resistant *Staphylococcus aureus* (MRSA), methicillin resistant *Staphylococcus epidermidis* (MRSE), and penicillin resistant *Streptococcus pneumoniae* (PRSP). In a further aspect, the Gram-positive bacteria is vancomycin resistant *Enterococcus* spp. (VRE).

In various aspects, the bacterial infection is selected from urinary tract infection, skin infection, intestinal infection, lung infection, ocular infection, otitis, sinusitis, pharyngitis, osteo-articular infection, genital infection, dental infection, oral infection, septicemia, nocosomial infection, bacterial meningitis, gastroenteritis, gastritis, diarrhea, ulcer, endocarditis, sexually transmitted disease, tetanus, diphtheria, leprosy, cholera, listeriosis, tuberculosis, salmonellosis, dysentery, and soft tissue. In various further aspects, the bacterial infection is selected from endocardititis, osteomyelitis, skin and soft tissue infection (SSTI), and infection associated with an indwelling device. In a still further aspect, the SSTI is a complicated SSTI (cSSTI). In yet a further aspect, the bacterial infection is a chronic bacterial infection.

In various aspects, the method further comprises administering to the subject a therapeutically effective amount of an antibacterial agent.

In various aspects, the compound and the antibacterial agent are administered simultaneously. In various further aspects, the compound and the antibacterial agent are administered sequentially.

In various aspects, the compound and the antibacterial agent are administered as a single dosage form. In various further aspects, the single dosage form is a capsule or a tablet. In a still further aspect, the single dosage form is an ampule for a single intravenous administration.

In various aspects, the subject is a mammal. In various further aspects, the subject is a human.

In various aspects the subject has been diagnosed with a need for treatment of the bacterial infection prior to the administering step.

In various aspects, the method further comprises the step of identifying a subject in need of treatment of the bacterial infection.

In various aspects, the effective amount is a therapeutically effective amount. In various further aspects, the effective amount is a prophylactically effective amount.

F. KITS

In one aspect, disclosed are kits comprising a disclosed compound, and one or more selected from: (a) an antibacterial agent; (b) instructions for treating a bacterial infection; and (c) instructions for administering the compound in connection with treating a bacterial infection.

In a further aspect, the compound has a structure represented by a formula

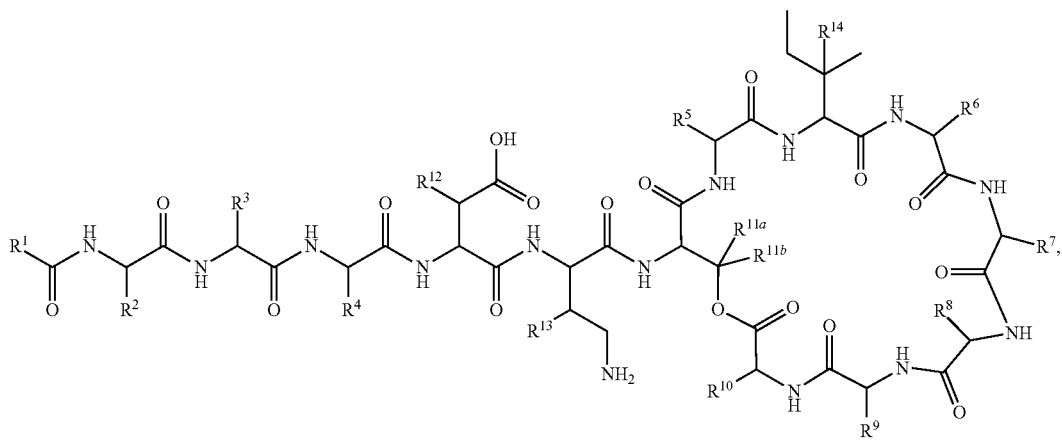

wherein $R^1$ is selected from C1-C24 alkyl, C2-C24 alkenyl, and a structure represented by a formula:

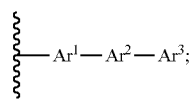

wherein each of $Ar^1$, $Ar^2$, and $Ar^3$ is independently selected from phenyl and C2-C5 heteroaryl, and is substituted with 0, 1, 2, or 3 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl; wherein each of $R^2$, $R^3$, $R^4$, $R^5$, $R^6$, $R^7$, $R^8$, $R^9$, and $R^{10}$ is independently selected from a natural amino acid residue and an unnatural amino acid residue; wherein each of $R^{11a}$ and $R^{11b}$ is independently selected from hydrogen and C1-C4 alkyl; and wherein each of $R^{12}$, $R^{13}$, and $R^{14}$ is independently selected from —OH, —SH, and —NH$_2$, or a pharmaceutically acceptable salt thereof.

In a further aspect, the compound has a structure represented by a formula

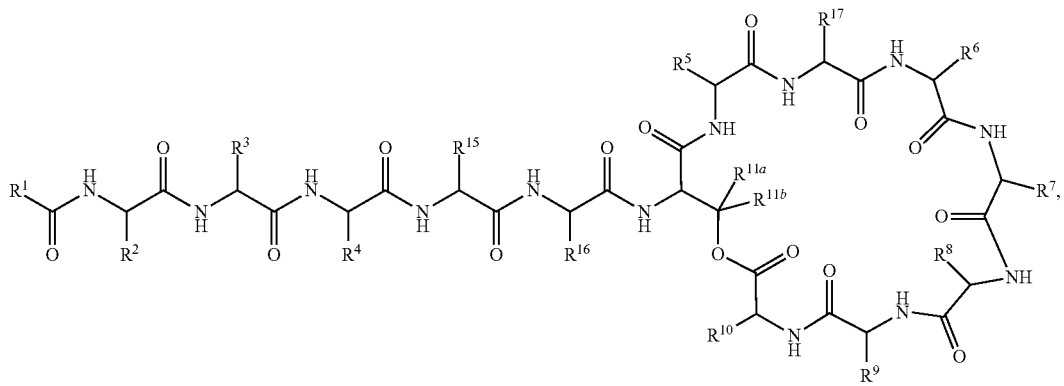

wherein $R^1$ is selected from C1-C24 alkyl, C2-C24 alkenyl, and a structure represented by a formula:

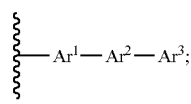

wherein each of $Ar^1$, $Ar^2$, and $Ar^3$ is independently selected from phenyl and C2-C5 heteroaryl, and is substituted with 0, 1, 2, or 3 groups independently selected from halogen, —CN, —NH$_2$, —OH, —NO$_2$, C1-C12 alkyl, C2-C12 alkenyl, C1-C12 haloalkyl, C1-C12 cyanoalkyl, C1-C12 hydroxyalkyl, C1-C12 haloalkoxy, C1-C12 alkoxy, C1-C12 alkylamino, (C1-C12)(C1-C12) dialkylamino, and C1-C12 aminoalkyl; wherein each of $R^2$, $R^3$, $R^7$, $R^{10}$, $R^{15}$, and $R^{16}$ is independently selected from a natural amino acid residue and an unnatural amino acid residue, provided that each of $R^2$, $R^3$, $R^7$, $R^{10}$, $R^{15}$, and $R^{16}$ is a non-glycine residue; wherein each of $R^4$, $R^5$, $R^6$, $R^8$, $R^9$, and $R^{17}$ is independently selected from a natural amino acid residue and an unnatural amino acid residue; and wherein each of $R^{11a}$ and $R^{11b}$ is independently selected from hydrogen and C1-C4 alkyl, or a pharmaceutically acceptable salt thereof.

In a further aspect, the compound has a structure represented by a formula

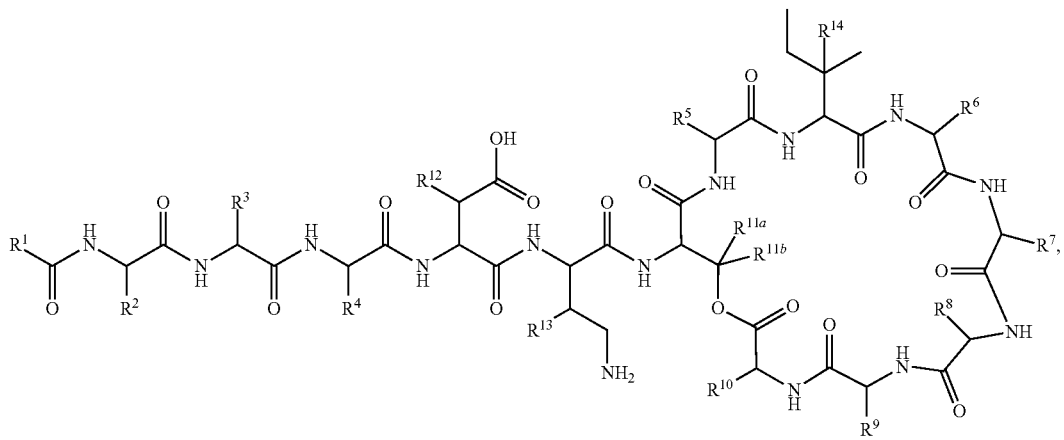

wherein $R^1$ is selected from C1-C24 alkyl and C2-C24 alkenyl; wherein each of $R^2$, $R^3$, $R^4$, $R^5$, $R^6$, $R^7$, $R^8$, $R^9$, and $R^{10}$ is independently selected from a natural amino acid residue and an unnatural amino acid residue; wherein each of $R^{11a}$ and $R^{11b}$ is independently selected from hydrogen and C1-C4 alkyl; and wherein each of $R^{12}$, $R^{13}$, and $R^{14}$ is independently selected from —OH, —SH, and —NH$_2$, or a pharmaceutically acceptable salt thereof. In a further aspect, the compound has a neutral charge.

In a further aspect, the compound has a structure represented by a formula

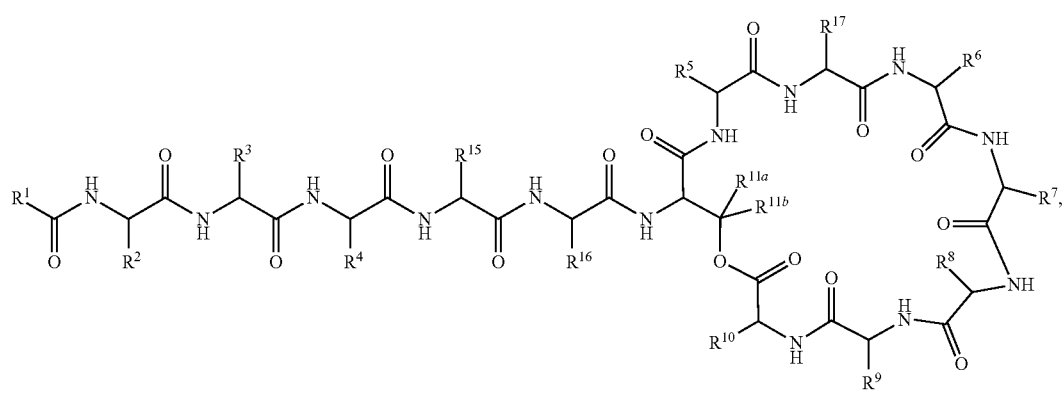

wherein $R^1$ is selected from C1-C24 alkyl and C2-C24 alkenyl; wherein each of $R^2$, $R^3$, $R^7$, $R^{10}$, $R^{15}$, and $R^{16}$ is independently selected from a natural amino acid residue and an unnatural amino acid residue, provided that each of $R^2$, $R^3$, $R^7$, $R^{10}$, $R^{15}$, and $R^{16}$ is a non-glycine residue; wherein each of $R^4$, $R^5$, $R^6$, $R^8$, $R^9$, and $R^{17}$ is independently selected from a natural amino acid residue and an unnatural amino acid residue; and wherein each of $R^{11a}$ and $R^{11b}$ is independently selected from hydrogen and C1-C4 alkyl, or a pharmaceutically acceptable salt thereof. In a further aspect, the compound has a neutral charge.

In various aspects, the compound has a structure represented by a formula:

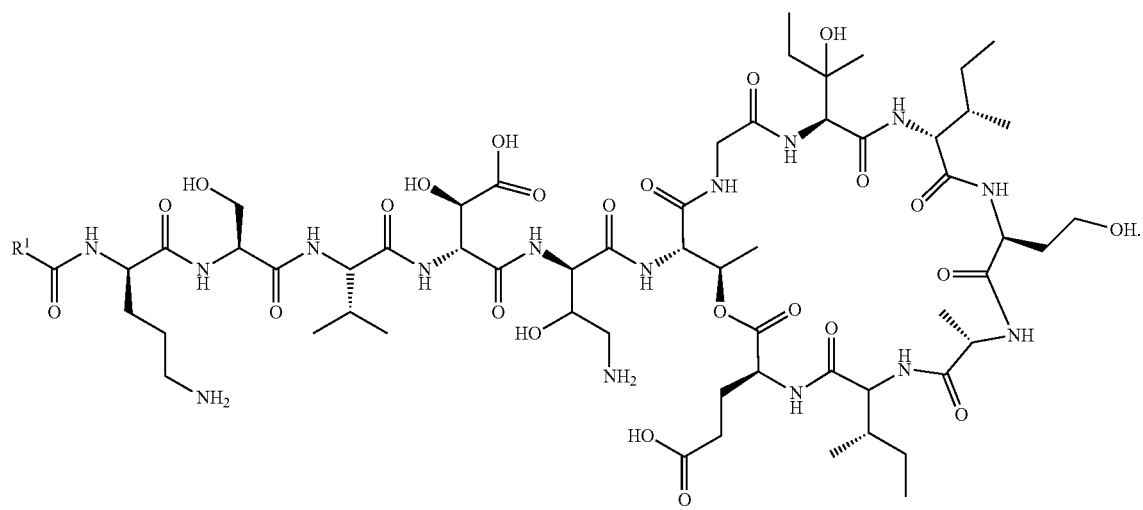

In various aspects, the compound does not have a structure represented by a formula:

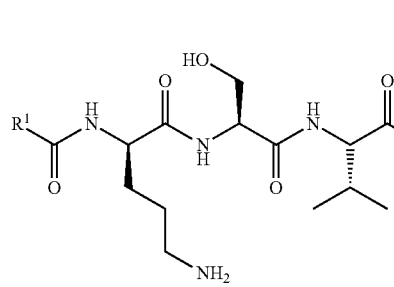 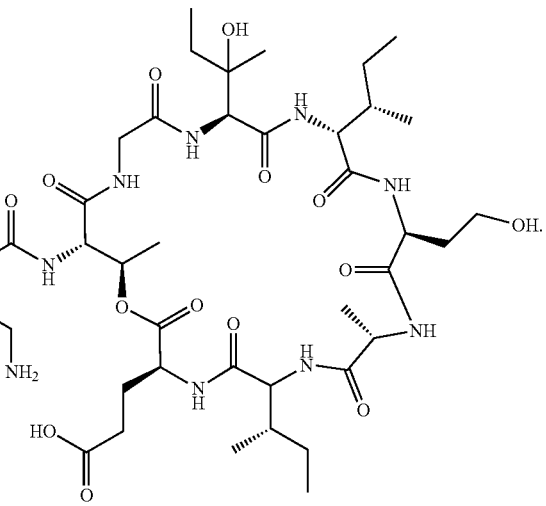

The kits can comprise one or more of the peptides or pharmaceutical compositions disclosed herein. The peptides or compositions described herein can be packaged in a suitable container labeled, for example, for use to treat a bacterial infection. Accordingly, packaged products (e.g., sterile containers containing the composition described herein and packaged for storage, shipment, or sale at concentrated or ready-to-use concentrations) and kits, including at least one or more of the peptides as described herein and instructions for use, are also within the scope of the disclosure. A product can include a container (e.g., a vial, jar, bottle, bag, or the like) containing the peptides or compositions described herein. In addition, the kits further may include, for example, packaging materials, instructions for use, syringes, buffers or other control reagents for treating or monitoring the condition for which prophylaxis or treatment is required. The product may also include a legend (e.g., a printed label or insert or other medium describing the product's use (e.g., an audio- or videotape)). The legend can be associated with the container (e.g., affixed to the container) and can describe the manner in which the compound therein should be administered (e.g., the frequency and route of administration), indications therefor, and other uses. The peptides or compositions can be ready for administration (e.g., present in dose-appropriate units), and may include a pharmaceutically acceptable adjuvant, carrier or other diluent. Alternatively, the compounds can be provided in a concentrated form with a diluent and instructions for dilution.

In various aspects, the compound and the antibacterial agent are co-formulated. In various further aspects, the compound and the antibacterial agent are co-packaged. Examples of antibacterial agents include, but are not limited to, amoxicillin, ampicillin, azithromycin, aztreonam, azlocillin, bacitracin, carbenicillin, cefaclor, cefadroxil, cefamandole, cefazolin, cephalexin, cefdinir, cefditoren, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clavulanic acid, clinafloxacin, clindamycin, clofazimine, cloxacillin, colistin, dalbavancin, dalfopristin, demeclocycline, dicloxacillin, dirithromycin, doxycycline, erythromycin, enrofloxacin, enoxacin, enviomycin, ertepenem, ethambutol, flucloxacillin, fosfomycin, furazolidone, gatifloxacin, gentamicin, imipenem, isoniazid, kanamycin, linezolid, lomefloxacin, loracarbef, mafenide, moxifloxacin, meropenem, metronidazole, mezlocillin, minocycline, mupirocin, nafcillin, nalidixic acid, neomycin, netilmicin, nitrofurantoin, norfloxacin, ofloxacin, oritavancin, oxytetracycline, penicillin, piperacillin, platensimycin, polymixin B, quinupristin, retapamulin, rifabutin, rifampin, rifapentine, roxithromycin, sparfloxacin, spectinomycin, sulbactam, sulfacetamide, sulfamethizole, sulfamethoxazole, teicoplanin, telithromycin, telavancin, temafloxacin, tetracycline, thioacetazone, thioridazine, ticarcillin, tinidazole, tobramycin, torezolid, tosufloxacin, trimethoprim, troleandomycin, trovafloxacin, and vancomycin.

In various aspects, the method further comprises a plurality of dosage forms, the plurality comprising one or more doses, wherein each dose comprises an effective amount of the compound and the antibacterial agent. In a further aspect, each dose of the compound and the antibacterial agent are co-formulated. In a still further aspect, each dose of the compound and the antibacterial agent are co-packaged. In yet a further aspect, the dosage forms are formulated for oral administration, intravenous administration, or a combination thereof.

G. EXAMPLES

To more rapidly hone in on ecologically important antibacterial compounds, the genomes of cultivated symbiont strains and the metagenomes of shipworm gills were analyzed, focusing on antibiotic-like biosynthetic gene clusters (BCGs) (Altamia et al., 2020). These symbionts and hosts were collected from around the world, including tropical and temperate waters, implying that highly conserved compounds are important for the symbiotic relationship. Supporting this idea, BCGs encoding the important antiparasitic tartrolon and siderophore tumerbactin were found in the metagenomes of all *Teredinibacter turnerae*-containing specimens (Altamia et al., 2020). In addition, a small number of uncharacterizable BCGs were observed, which may encode antibacterial compounds. One of these, BCG_1, was extremely widespread in shipworms, encoding a nonribosomal peptide synthetase (NRPS) that had features such that may encode an antibiotic lipopeptide.

Here, the identification of the chemical products of BGC_1 as potent antibacterial agents is described. The tumercyclamycins represent a new family of lipopeptides that kill several challenging Gram-negative bacterial species, including Acinetobacter baumannii, which has been designated by the World Health Organization as one of the most successful and serious of the ESKAPE pathogens (Boucher et al., 2009), and yet are not toxic to mammalian cells. Colistin (polymyxin E) is the last-line therapy for otherwise lethal A. baumannli infections, but increasing instances of resistance threaten to leave the disease without viable treatment options. Here, it is demonstrated that tumercyclamycins target the outer membrane like colistin, but they retain efficacy against colistin-resistant Acinetobacter, making them promising leads for antimicrobial development. For example, tumercyclamycins A and B kill several Gram-negative bacteria, but did not kill the Gram-positive Staphylococcus aureus. The compounds lack cytotoxicity against mammalian cells or hemolytic activity against red blood cells at concentrations relevant to their antibiotic doses.

The tumercyclamycins were not previously observed in T. turnerae cultures in part because the crude mixture of turnercyclamycins is nearly insoluble in common solvents used in natural products purification methods, although they are well behaved when purified. Bioinformatics analysis of the tur pathway to tumercyclamycins reveals that the pathway is very highly conserved across shipworm isolates and gills, so that the same or a very similar suite of compounds should be found in T. turnerae-containing shipworms globally. Without wishing to be bound by theory, these results reinforce the utility of symbiosis and chemical ecology in providing new solutions to multidrug-resistant infections.

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein.

Figures 3A, 3B:
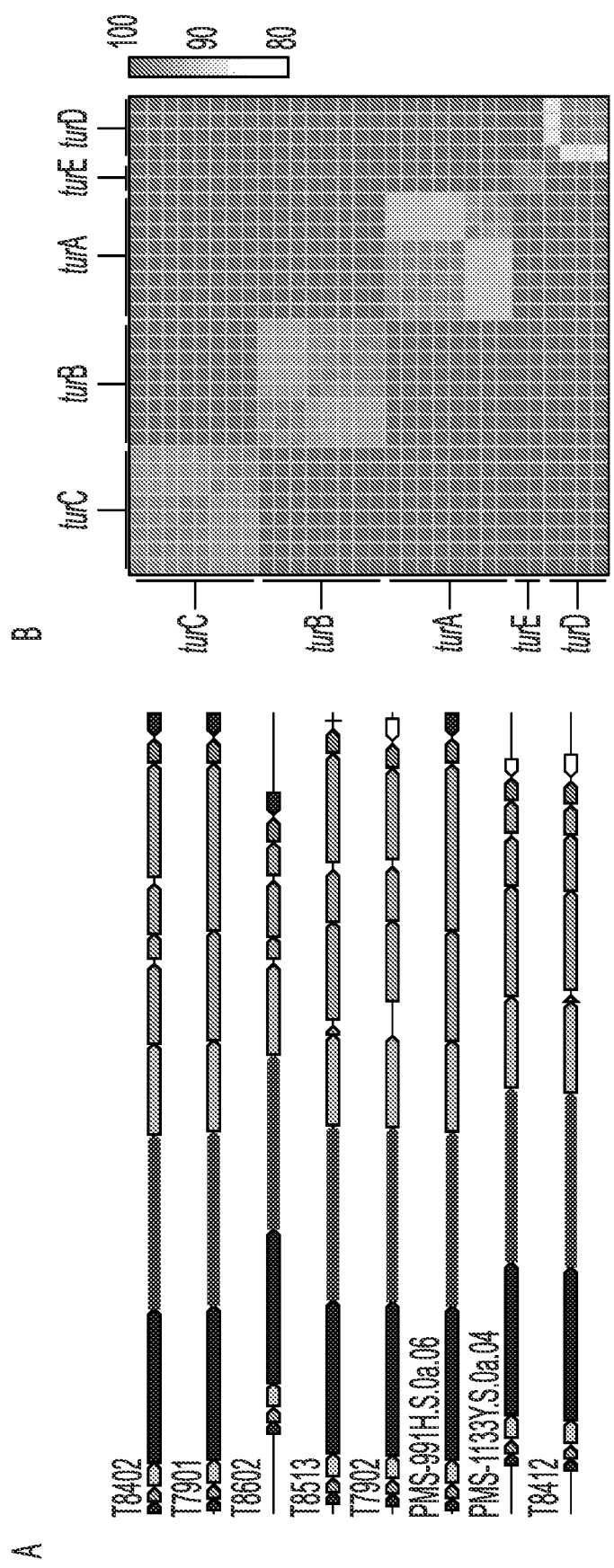
FIG. 3A-C shows representative data illustrating the conservation of the tumercyclamycin biosynthetic gene cluster.
Figure 3C:
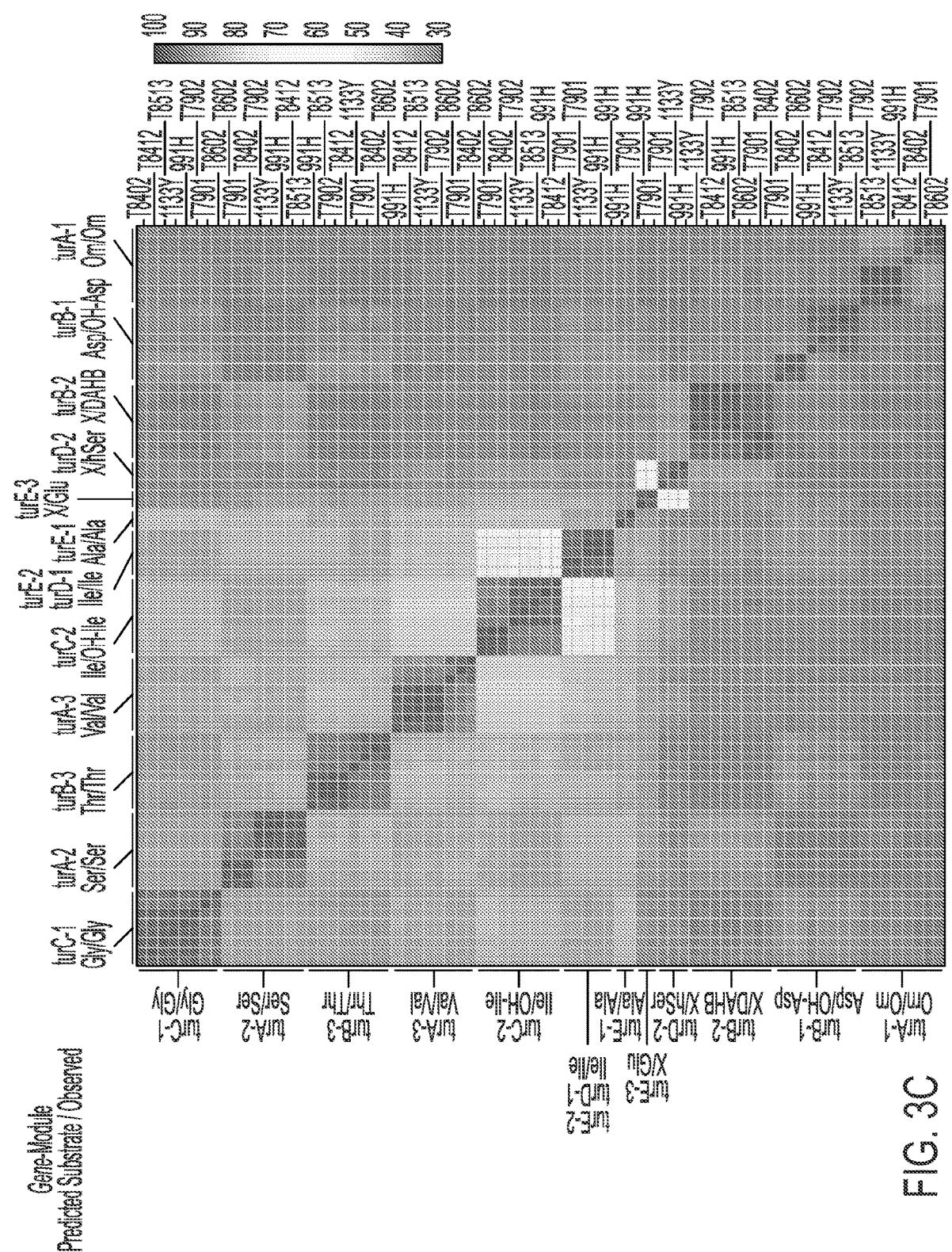

1. Results and Discussion a. Conservation of NRPS Gene Cluster Across T. Turnerae A previous systematic analysis of shipworm symbiont isolate genomes and animal gill metagenomes identified an NRPS BGC, where it was defined as "GCF_1," as being highly conserved in T. turnerae, and portions of the cluster were detected in all T. turnerae-containing shipworms (Altamia et al., 2020). Here, multigene BLAST analysis of eight sequenced T. turnerae strains found this cluster to be ubiquitous (FIG. 3A); however, the region including turD and turE appeared to be disrupted in six of these strains. In correctly assembled sequences, this region contained two repeats of 6k bp in length that were 98% identical, while in the misassembled sequences this region was scrambled. Therefore, it is likely that this is a result of bioinformatic assembly error, and that the gene cluster is intact and functional in all strains. All of the intact NRPSs were further compared by BLASTp, and it was found that each megasynthetase was greater than 85% similar to all of the other corresponding proteins from the homologous clusters, demonstrating a very high degree of conservation (FIG. 3B).

In the T. turnerae T7901 genome, the five genes within this cluster include turA (three modules, 11.2 kbp), turB (three modules, 12.8 kbp), turC (two modules, 6.6 kbp), turD (two modules, 8.1 kbp), and turE (three modules, 12.1 kbp). Each module contains a condensation (C), adenylation (A), and thiolation (T) domain, and five of the modules also contain epimerization domains. The first domain begins with a so-called C-starter domain, which is known to acylate the initial amino acid in a process known as lipoinitiation (Rausch et al., 2007). The final module terminates in a thioesterase domain, which is responsible for product release, often by means of macrocyclization (Keating et al., 2001). This domain architecture indicates that the product of the tur cluster is a cyclic lipopeptide, a known class of antibacterial scaffolds.

Often, NRPS genes are naturally combinatorialized to create families of compounds that consist of structural analogs distributed throughout related producing organisms (Zan et al., 2019). To look for the potential of variants with divergent peptide backbones, the adenylation domains for the cluster in each of the eight sequenced strains were compared by BLASTp. In some of the misassembled sequences, the A domains in turD and turE were not intact and were thus not included in the analysis. The results show that tur is an exceptionally well-conserved cluster, with each A domain retaining greater than 90% identity to all of the analogous domains across all eight strains (FIG. 4C). The substrate prediction, as determined by antiSmash 5.0, was also consistent for each domain (Blin et al., 2019). Importantly, the strains included in this analysis were isolated from a variety of shipworm genera and species collected in disparate locations around the world, indicating that this gene cluster, and thus its biosynthetic product, are well conserved, and thus likely important to the association between host and symbiont. See Table 1.

TABLE 1

| Symbiont | Host | | |
|---|---|---|---|
| Isolate | Genus | Species | Location |
| T7901 | Bankia | gouldi | Beaufort, NC, USA |
| T8602 | Dicyathifer | manni | Townsville, QLD, Aus. |
| T7902 | Lyrodus | pedicellatus | Long Beach, CA, USA |
| T8513 | Teredo | navalis | Sao Paulo, Brazil |
| T8412 | Lyrodus | bipartitus | Jim Isl., Fort Pierce, FL |
| T8402 | Teredora | malleolus | Floating wood |
| PMS-1133Y.S.0a.04 | N/A | N/A | Bil-isan, Panglao, Bohol, Philippines |
| PMS-991H.S.0a.06 | Lyrodus | pedicellatus | Danao, Iloilo City, Iloilo, Philippines |

Based upon the ubiquitous nature of this potential antibiotic, which is proposed to function in the symbiosis to defend the host and symbiont from other bacteria, discovering the products of the tur pathway was prioritized, seeking a lipopeptide containing 13 amino acids in the cultures of T. turnerae 17901.

b. Isolation and Planar Structure Elucidation

The cell pellet from a liquid culture of T. turnerae 17901 (6.6L) was extracted and subjected to a series of partitions. A particularly robust boundary layer formed between the water and ethyl acetate fractions, which was enriched in a series of lipopeptides. Semi-preparative HPLC yielded two major compounds 1 and 2, along with minor analogs 3 and 4.

Turnercyclamycin A (1) had a molecular formula of $C_{71}H_{125}N_{15}O_{24}$ based upon high resolution mass spectrometry ($[M+2H]^{2+}$ m/z=786.9618), inherent in which are 17 degrees of unsaturation. The $^1H$ and $^{13}C$ spectra were consistent with a lipopeptide based on numerous amide NH resonances between δH 7.6-8.5, alpha proton signals from δH 4.03-5.05, and the presence of a large methylene envelope centered at δH 1.23 (FIGS. 5A-G). The gradient heteronuclear single quantum coherence (gHSQC) experiment revealed the presence of 11 methyl groups, 17 distinct methylene proton pairs outside of the lipid envelope, and 19 methine protons. See Table 2.

TABLE 2

| Residue | Position | $\delta_C$ | $\delta_H$ (J in Hz) | $\delta_C$ | $\delta_H$ (J in Hz) |
|---|---|---|---|---|---|
| | | 1 | | 2 | |
| Ornithine | NH | | 8.03ᵃ | | 8.03ᵃ |
| | C=O | 171.6 | | 171.6 | |
| | α-C | 51.6 | 4.37 m | 51.5 | 4.37 m |
| | β-C | 29.0 | 1.53 m, 1.69 m | 29.0 | 1.53 m, 1.69 m |
| | γ-C | 23.6 | 1.53ᵃ | 23.6 | 1.53ᵃ |
| | δ-C | 38.5 | 2.77 br | 38.5 | 2.77 br |
| | NH₃ | | 7.72 | | 7.72 |
| Serine | NH | | 8.06ᵃ | | 8.06ᵃ |
| | C=O | 170.2 | | 170.2 | |
| | α-C | 54.5 | 4.39ᵃ | 54.5 | 4.39ᵃ |
| | β-C | 61.4 | 3.58 d (5.8) | 61.4 | 3.59 d (5.8) |
| | β-OH | | N/A | | N/A |
| Valine | NH | | 7.82ᵃ | | 7.82ᵃ |
| | C=O | 171.1 | | 171.1 | |
| | α-C | 57.7 | 4.28 | 57.7 | 4.28 |
| | β-C | 30.5 | 2.02 m | 30.6 | 2.02 m |
| | γ₁-C | 17.6 | 0.80ᵃ | 17.6 | 0.80ᵃ |
| | γ₂-C | 19.3 | 0.82ᵃ | 19.3 | 0.82ᵃ |
| β-OH-Aspartic acid | NH | | 8.12 d (9.4) | | 8.13 d (9.0) |
| | C=O | 169.2 | | 169.2 | |
| | α-C | 55.3 | 4.80 dd (8.9, 2.6) | 55.3 | 4.82 dd (8.8, 2.6) |
| | β-C | 70.3 | 4.55ᵃ | 70.3 | 4.55ᵃ |
| | β-OH | | N/A | | N/A |
| | γ-C=O | 168.5 | | 168.5 | |
| 2,4-Diamino-3-hydroxy-butyric acid | NH | | 7.84ᵃ | | 7.85ᵃ |
| | C=O | 172.8 | | 172.8 | |
| | α-C | 55.1 | 4.55ᵃ | 55.1 | 4.55ᵃ |
| | β-C | 68.0 | 4.09 m | 68.0 | 4.08 m |
| | β-OH | | 5.54 br | | 5.52 br |
| | γ-C | 41.7 | 2.68, m 2.85 | 41.7 | 2.67, m 2.86 |
| | γ-NH₃ | | 7.79 t (br) | | 7.79 t (br) |
| Threonine | NH | | 8.07ᵃ | | 8.07ᵃ |
| | C=O | 168.7 | | 168.7 | |
| | α-C | 56.6 | 4.32 m | 56.6 | 4.32 m |
| | β-C | 70.2 | 5.05 p (6.7) | 70.2 | 5.06 p (6.7) |
| | γ-C | 16.8 | 1.05 d (6.5) | 16.8 | 1.05 d (6.5) |
| Glycine | NH | | 8.21 t (6.0) | | 8.19 t (6.1) |
| | C=O | 169.4 | | 169.4 | |
| | α-C | 41.3 | 3.6 m, 4.05 dd (16.2, 5.3) | 41.3 | 3.6 m, 4.04 dd (16, 5.4) |
| 3-OH-isoleucine | NH | | 8.03ᵃ | | 8.03ᵃ |
| | C=O | 171.8 | | 171.8 | |
| | α-C | 59.5 | 4.42 d (7.0) | 59.5 | 4.42 d (7.3) |
| | β-C | 72.1 | | 72.1 | |
| | γ₁-C | 23.0 | 1.08 s | 23.0 | 1.08 s |
| | γ₂-C | 31.1 | 1.45 m | 31.1 | 1.45 m |
| | δ-C | 7.8 | 0.83ᵃ | 7.8 | 0.83ᵃ |

TABLE 2-continued

| Residue | Position | $\delta_C$ | $\delta_H$ (J in Hz) | $\delta_C$ | $\delta_H$ (J in Hz) |
|---|---|---|---|---|---|
| | | 1 | | 2 | |
| Isoleucine (1) | NH | | 8.35 d (7.7) | | 8.36 d (7.8) |
| | C=O | 170.7 | | 170.7 | |
| | α-C | 56.7 | 4.14 dd (7.6, 4.5) | 56.7 | 4.14 dd (7.6, 4.6) |
| | β-C | 35.4 | 1.93 m | 35.4 | 1.93 m |
| | γ₁-C | 14.8 | 0.86 d (6.8) | 14.8 | 0.87 d (6.8) |
| | γ₂-C | 25.7 | 1.16 m, 1.29 m | 25.7 | 1.16 m, 1.29 m |
| | δ-C | 11.6 | 0.81ᵃ | 11.6 | 0.81ᵃ |
| Homoserine | NH | | 7.60 d (br) | | 7.61 d (br) |
| | C=O | 171.1 | | 171.1 | |
| | α-C | 49.6 | 4.32ᵃ | 49.6 | 4.32ᵃ |
| | β-C | 34.5 | 1.89 m | 34.5 | 1.89 m |
| | γ-C | 58.1 | 3.31 m | 58.1 | 3.31 m |
| | γ-OH | | | | |
| Alanine | NH | | 7.94 d (8.6) | | 7.94 d (8.6) |
| | C=O | 172.4 | | 172.4 | |
| | α-C | 47.4 | 4.52 m | 47.4 | 4.52 m |
| | β-C | 19.0 | 1.20 d (7.1) | 19.0 | 1.2 d (7.1) |
| Isoleucine (2) | NH | | 8.01 d (8.8) | | 8.01ᵃ |
| | C=O | 171.5 | | 171.5 | |
| | α-C | 55.0 | 4.41ᵃ | 55.0 | 4.41ᵃ |
| | β-C | 37.0 | 1.71 m | 37.0 | 1.71 m |
| | γ₁-C | 25.6 | 1.06ᵃ, 1.25ᵃ | 25.6 | 1.06ᵃ, 1.25ᵃ |
| | γ₂-C | 14.7 | 0.78 d (7.0) | 14.6 | 0.78 d (7.8) |
| | δ-C | 11.1 | 0.83ᵃ | 11.1 | 0.83ᵃ |
| Glutamic acid | NH | | 8.54 d (6.7) | | 8.54 d (6.7) |
| | C=O | 170.7 | | 170.7 | |
| | α-C | 52.5 | 4.18 m | 52.5 | 4.17 m |
| | β-C | 25.1 | 1.77 m, 1.99 m | 25.1 | 1.76 m, 1.99 m |
| | γ-C | 29.8 | 2.32 t (7.4) | 29.8 | 2.32 t (7.4) |
| | δ-C=O | 174.1 | | 174.1 | |
| Fatty Acid | 1 | 172.6 | | 172.4 | |
| | 2 | 35.1 | 2.12 t (7.1) | 35.1 | 2.12 t (7.1) |
| | 3 | 25.3 | 1.48 m | 25.3 | 1.47 m |
| | 4 | 28.7-29.1 | 1.21-1.30 | 28.7-29.1 | 1.21-1.30 |
| | 5 | 28.7-29.1 | 1.21-1.30 | 28.7-29.1 | 1.21-1.30 |
| | 6 | 28.7-29.1 | 1.21-1.30 | 28.7-29.1 | 1.21-1.30 |
| | 7 | 28.7-29.1 | 1.21-1.30 | 29.2 | 1.29 |
| | 8 | 28.7-29.1 | 1.21-1.30 | 26.7 | 1.98 |
| | 9 | 28.7-29.1 | 1.21-1.30 | 129.6 | 5.32 |
| | 10 | 28.7-29.1 | 1.21-1.30 | 129.6 | 5.32 |
| | 11 | 28.7-29.1 | 1.21-1.30 | 26.7 | 1.98 |
| | 12 | 28.7-29.1 | 1.21-1.30 | 29.2 | 1.29 |
| | 13 | 28.7-29.1 | 1.21-1.30 | 28.7-29.1 | 1.21-1.30 |
| | 14 | 13.9 | 0.86 | 31.1 | 1.24 |
| | 15 | | | 22.1 | 1.26 |
| | 16 | | | 13.9 | 0.85 |

ᵃmultiplicity and coupling undetermined due to signal overlap

Figure 1B:
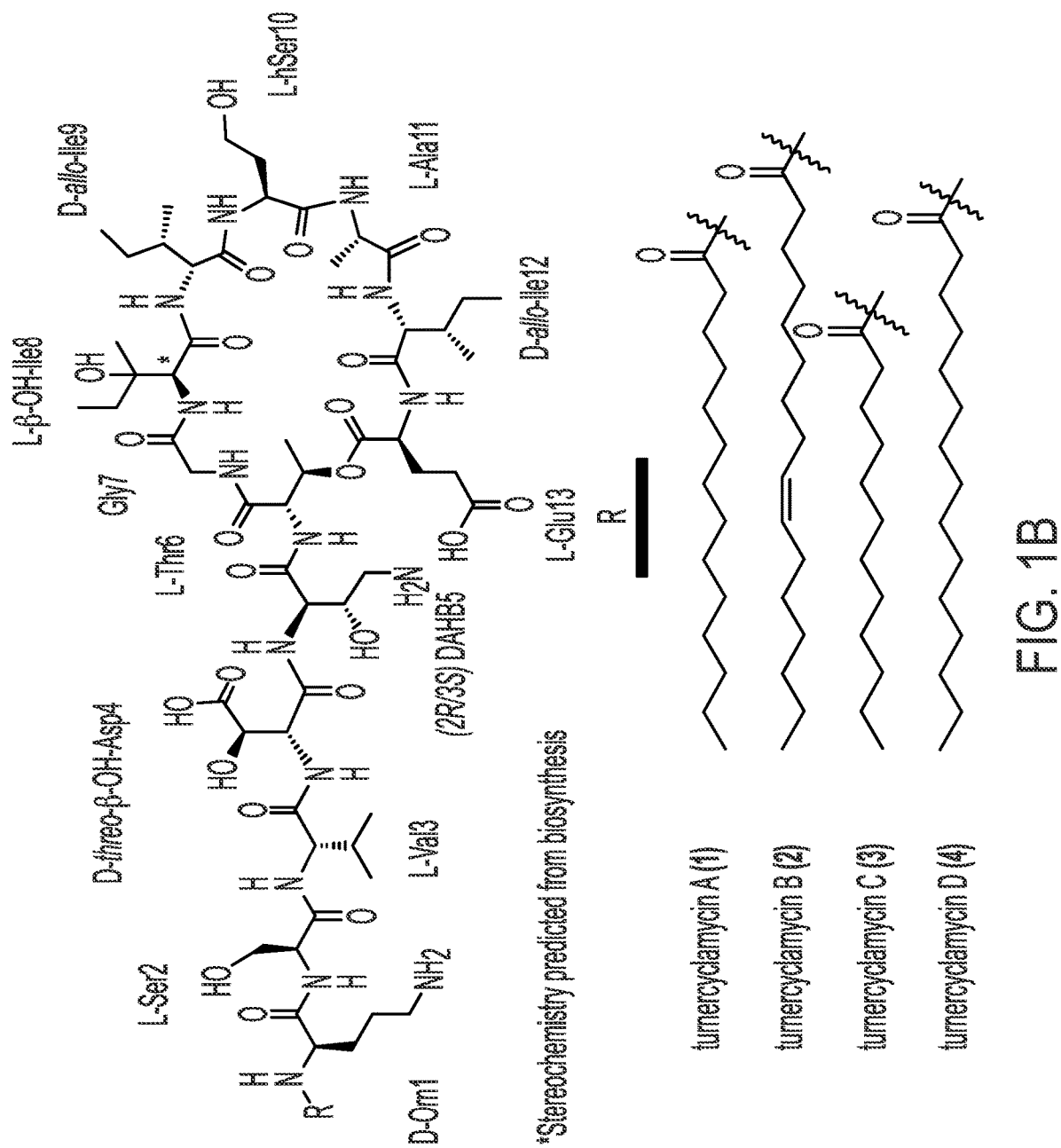

The amide NH and alpha methine protons for eight amino acids could clearly be correlated through well separated gCOSY cross peaks, and verified by gHMBC experiments. A zTOCSY experiment further confirmed these eight correlations and identified an additional five residues. A combination of gCOSY, zTOCSY, and gHMBC experiments were used to elucidate the side chain from each alpha methine proton (FIG. 1A and FIG. 1B), revealing the presence of one ornithine, one serine, one valine, one threonine, one glycine, two isoleucines, one glutamine, one alanine, one homoserine, one β-hydroxyaspartic acid, one β-hydroxyisoleucine, and an intriguing 2,4-diamino-3-hydroxybutanoic acid (DAHB) moiety. The presence of all amino acids was confirmed through subsequent Marfey's analysis, which also revealed masses consistent with the FDLA-derivatized β-hydroxyisoleucine and DAHB moieties, despite the lack of standards for retention time comparison.

gHMBC correlations from amide NH protons to carbonyls, alpha methine protons to carbonyls, and ROESY correlations from amide NH protons to alpha methine protons were used to determine the sequence of residues in the peptide portion of the molecule. These data converged on the linear sequence of Orn-Ser-Val-β-OH-Asp-DAHB-Thr-Gly-β-OH-Ile-Ile-hSer-Ala-Ile-Glu, which was consistent with the order of substrate predictions for the adenylation domains of each NRPS module in the proposed biosynthetic pathway.

The formula of the peptide backbone left a remainder of $C_{14}H_{21}O$, indicating a tetradecanoic acid, and two degrees of unsaturation. TOCSY and gHMBC correlations verified the fatty acid moiety, and gHMBC and ROESY correlations confirmed it was linked through the terminal ornithine residue. The final remaining degree of unsaturation indicated macrocyclization, a common feature of lipodesipeptides. A key HMBC correlation from the β-H of the threonine residue ($\delta_H$ 5.06) to the carbonyl of the glutamic acid moiety ($\delta_C$ 170.7) indicated that macrocyclization is via ester linkage through the threonine oxygen. This was further supported by the downfield shifted β-oxymethine carbon at $\delta_C$ 70.2.

Turnercyclamycin B (2) was obtained as the second major compound. Based on the observed $[M+2H]^{2+}$ ion at m/z=799.9693, its molecular formula was $C_{73}H_{127}N_{15}O_{24}$, differing from that of 1 by $C_2H_2$ and an additional degree of unsaturation. Comparison of the proton and HSQC spectra showed that all of the chemical shifts and correlations associated with the peptide portion of the molecule were identical to those of 1 (FIGS. 6A-G; see also Table 2, which shows $^1H$ and $^{13}C$ NMR data for compounds 1 and 2). However, an HSQC correlation between $\delta_H$5.32 (t, J=4.9 Hz, 2H) and $\delta_C$ 129.6, as well as a distinct TOCSY spin system including a methylene envelop and the olefinic protons, indicated the presence of a cis-double bond within the fatty acid side chain. The $^1H$ and $^{13}C$ chemical shifts of both olefinic protons were coincident. Both allylic carbons were observed at $\delta_C$26.7, a value that is consistent with a cis configuration. Typically, trans olefins in fatty acids result in a chemical shift approximately 5 ppm downfield of this value (Gunstone et al., 1977).

Figure 9A:
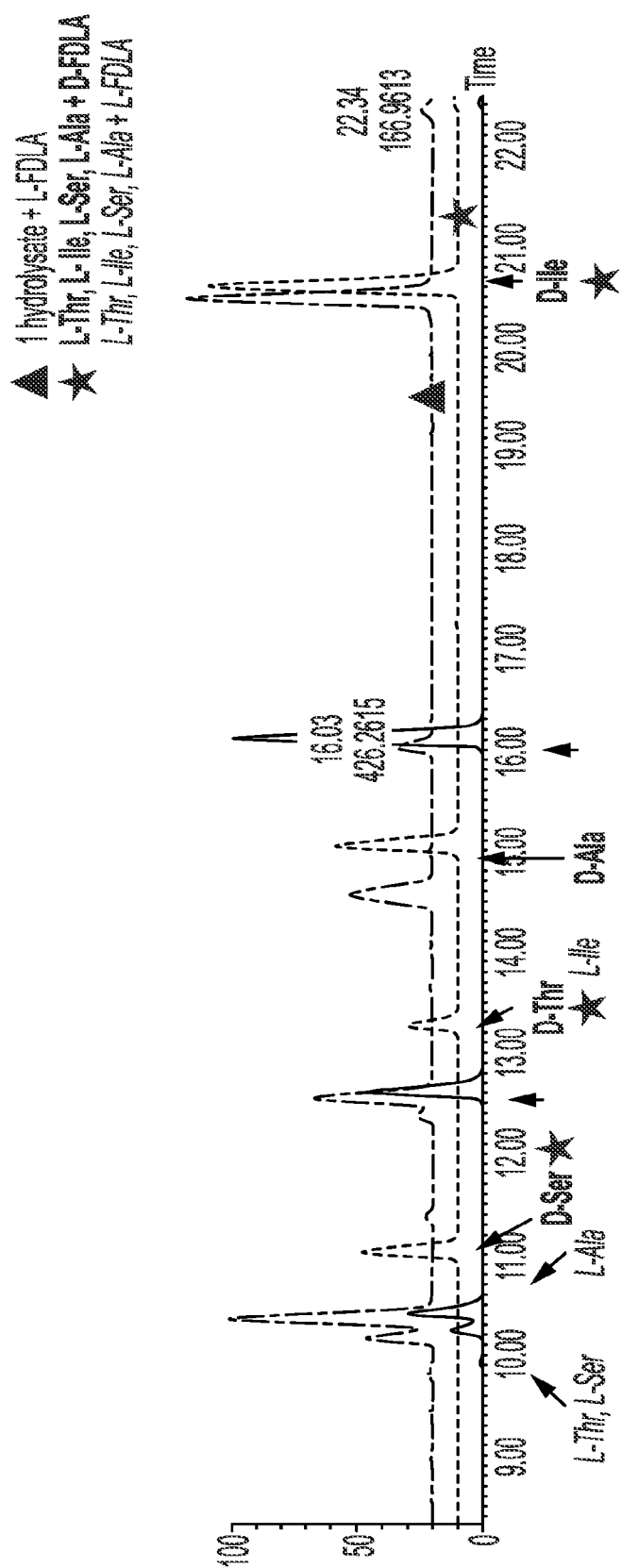
Figure 9B:
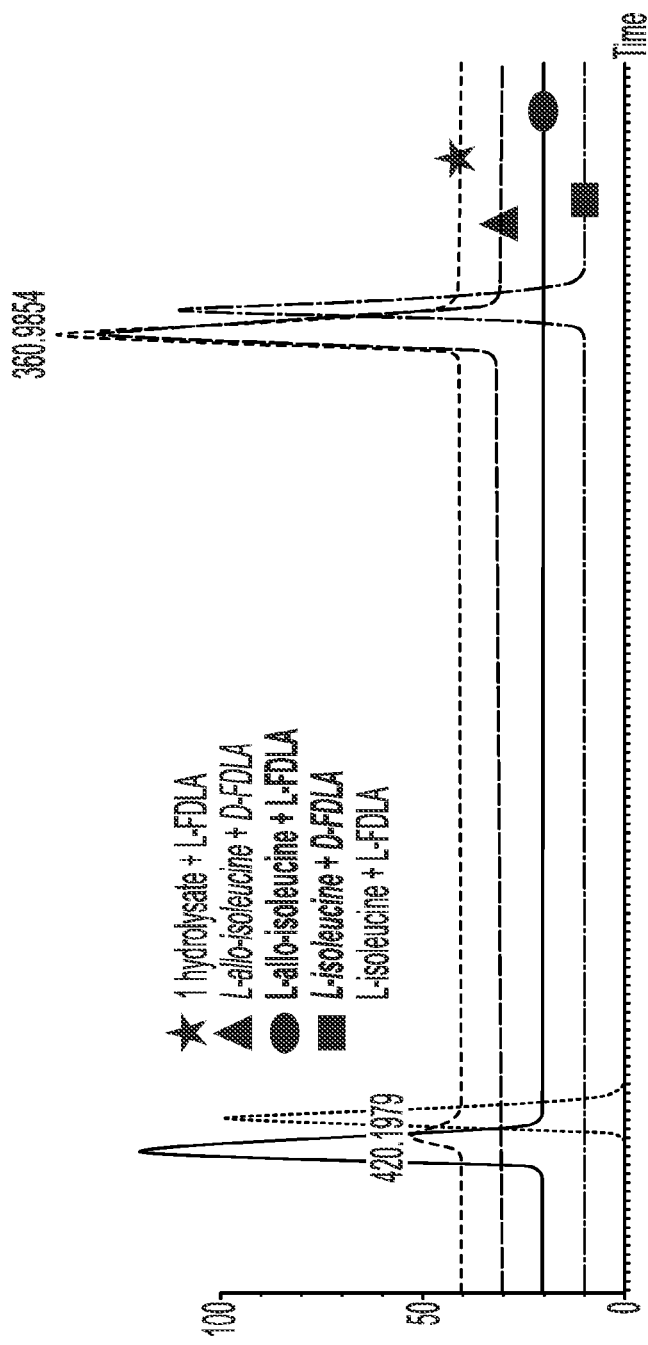
Figure 9C:
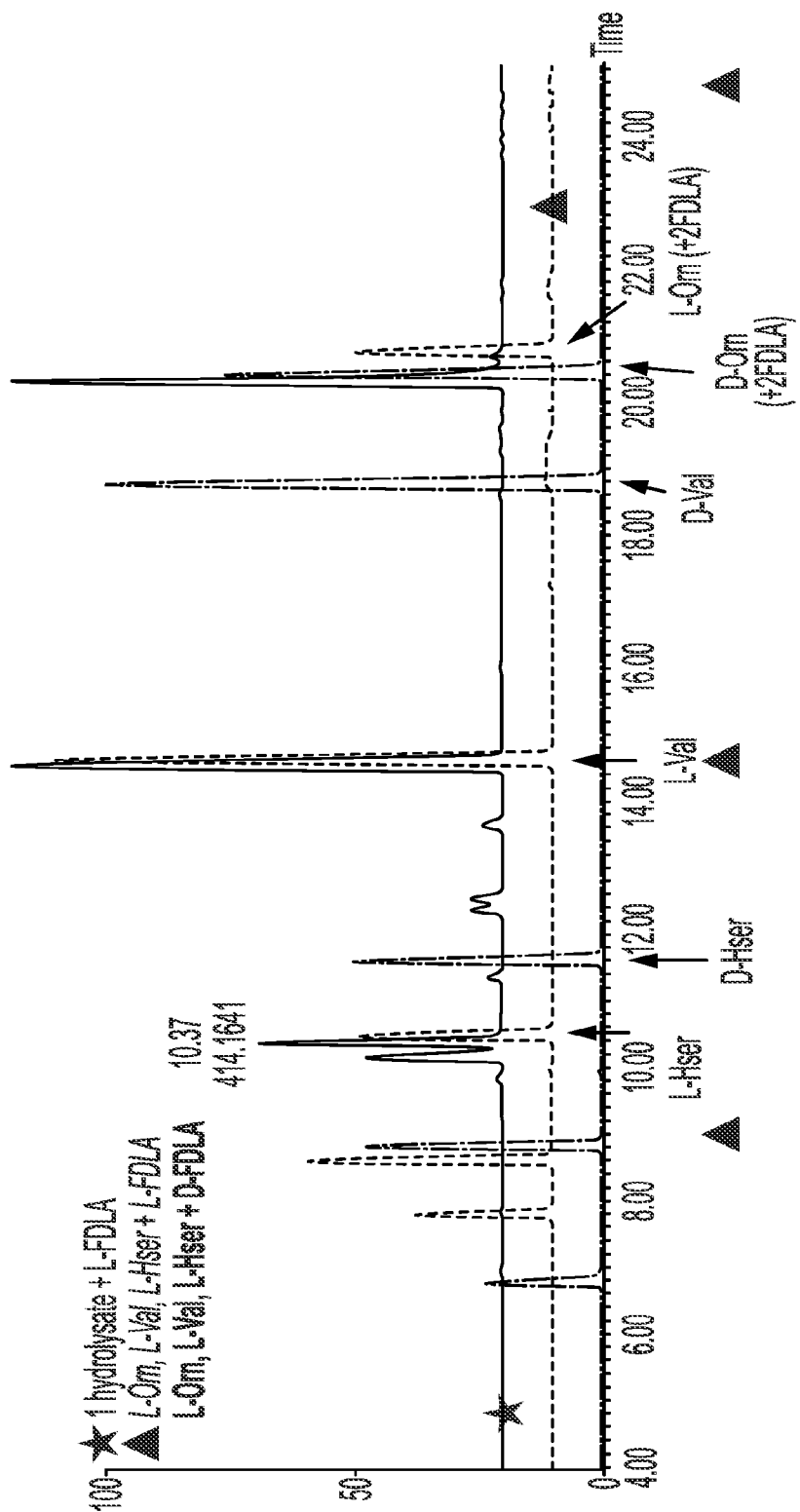
Figure 9D:
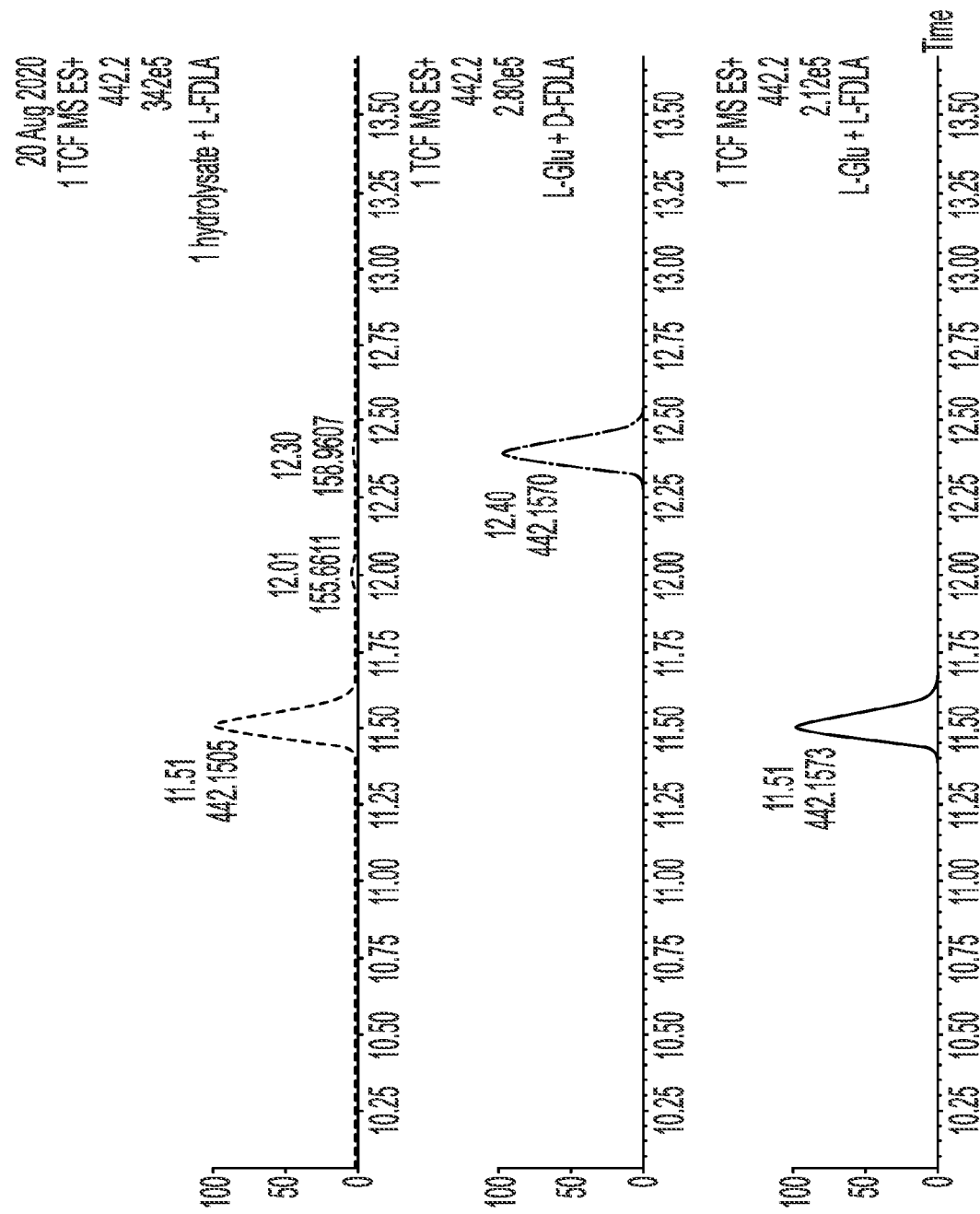
Figure 9F:
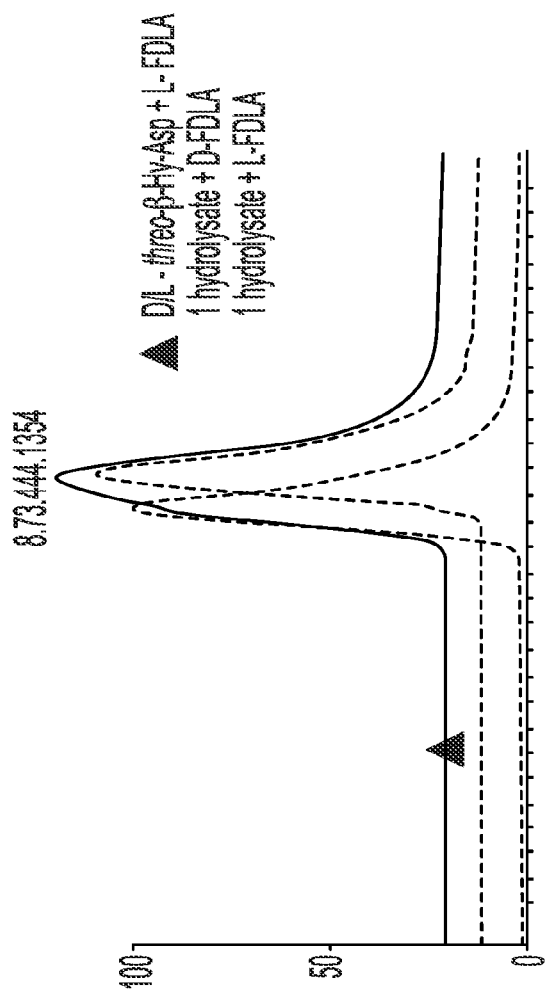
Figure 9G:
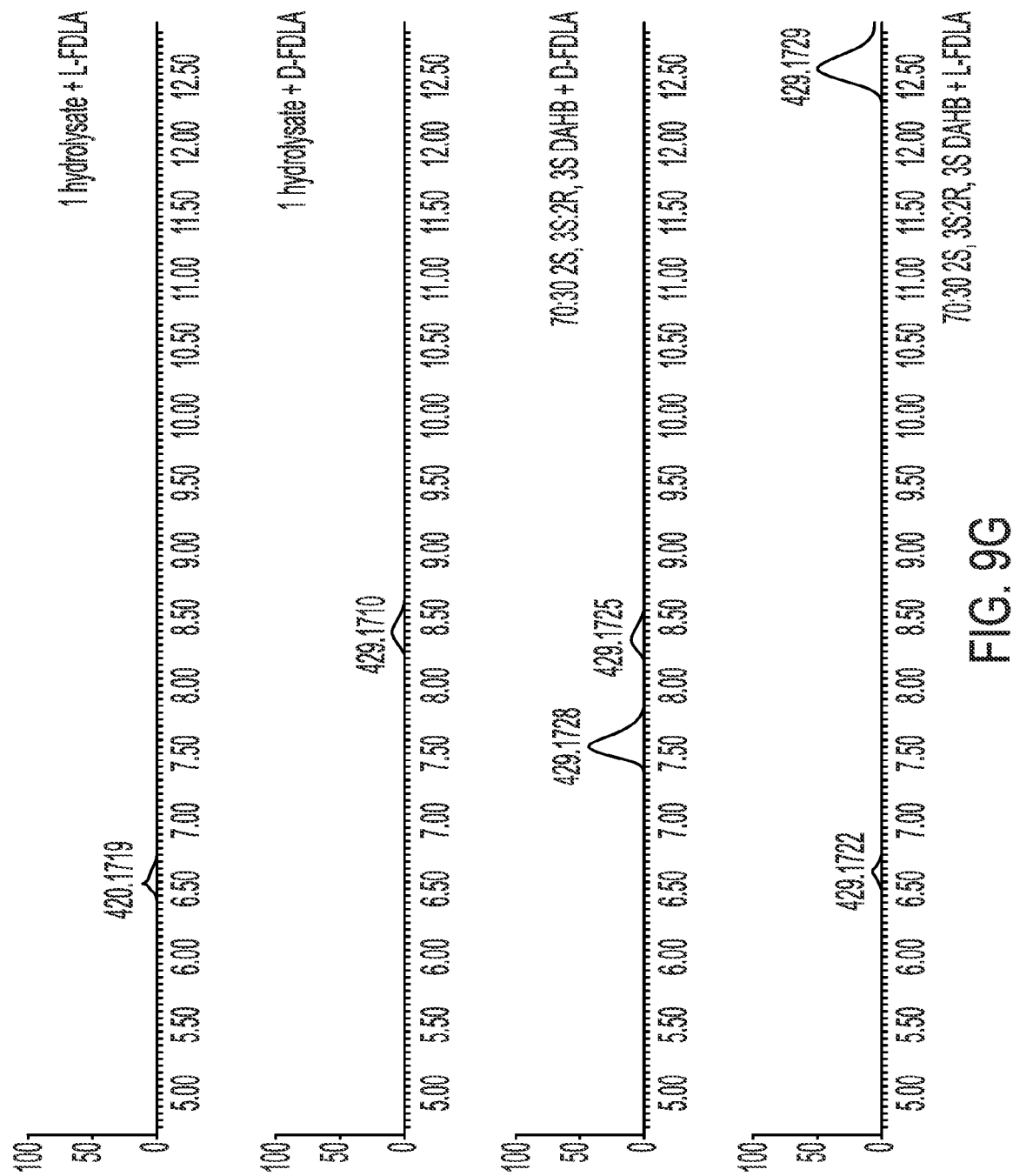
Figure 9H:
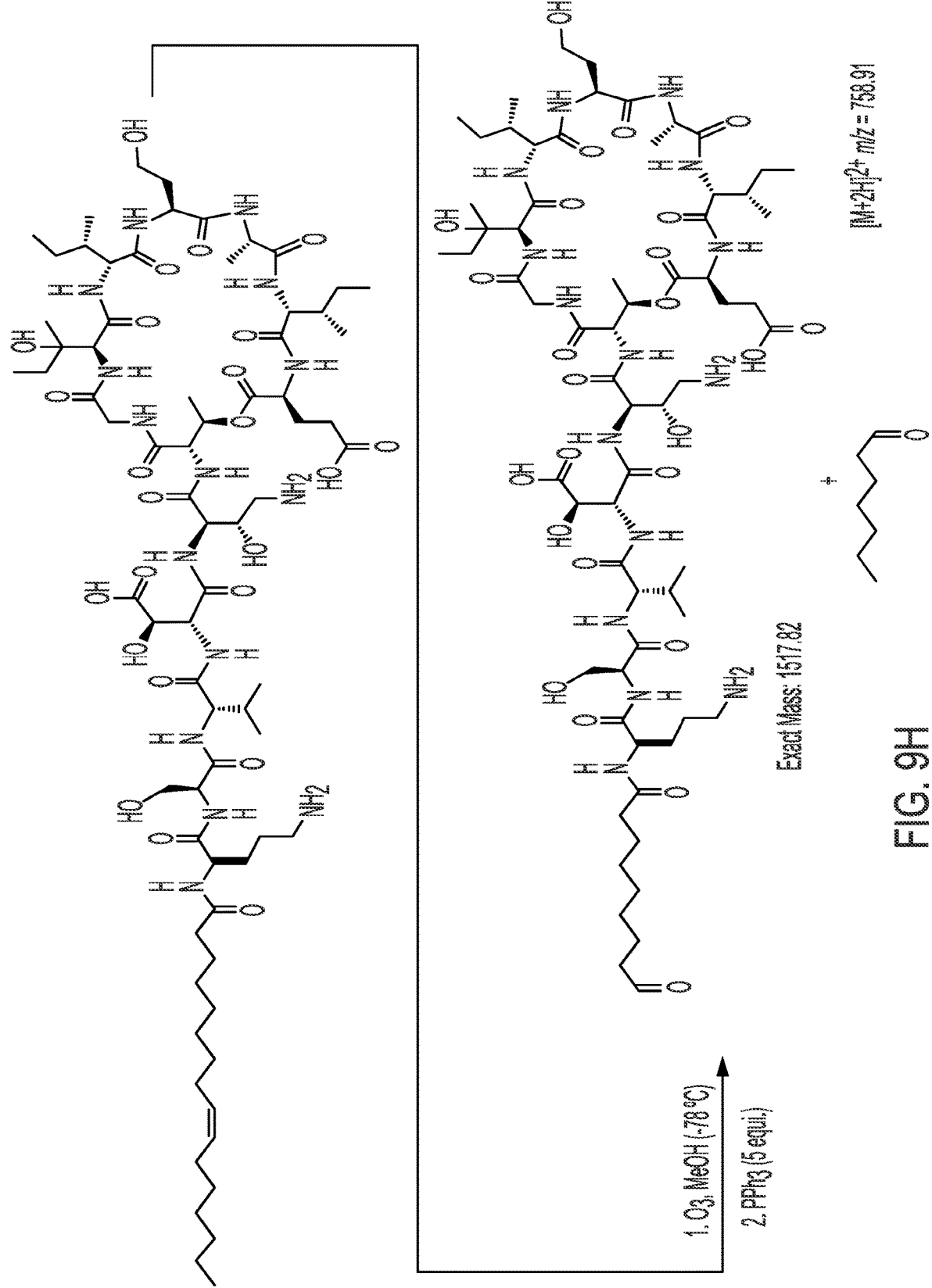
Figure 9I:
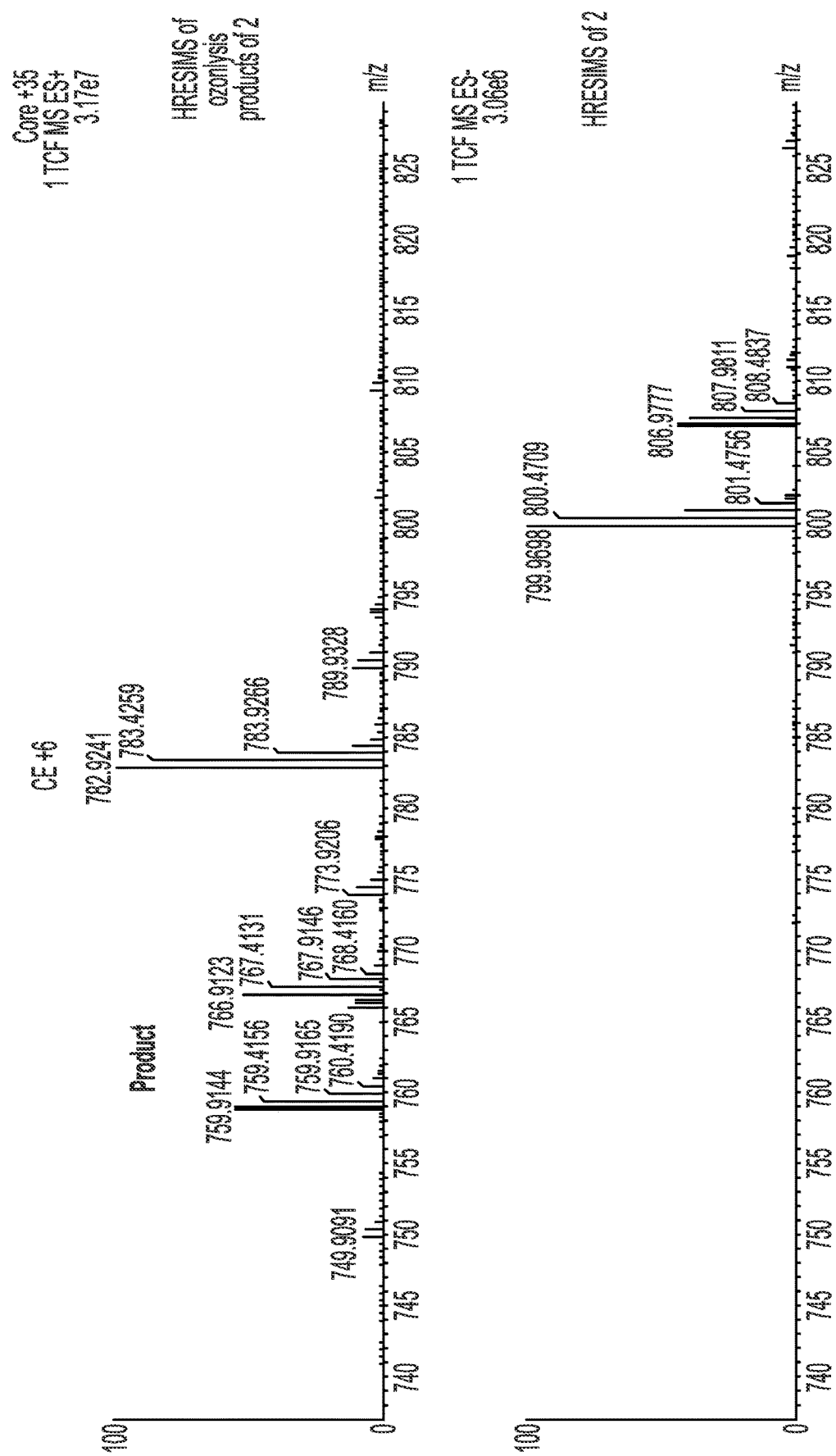
Figures 10C, 10D:
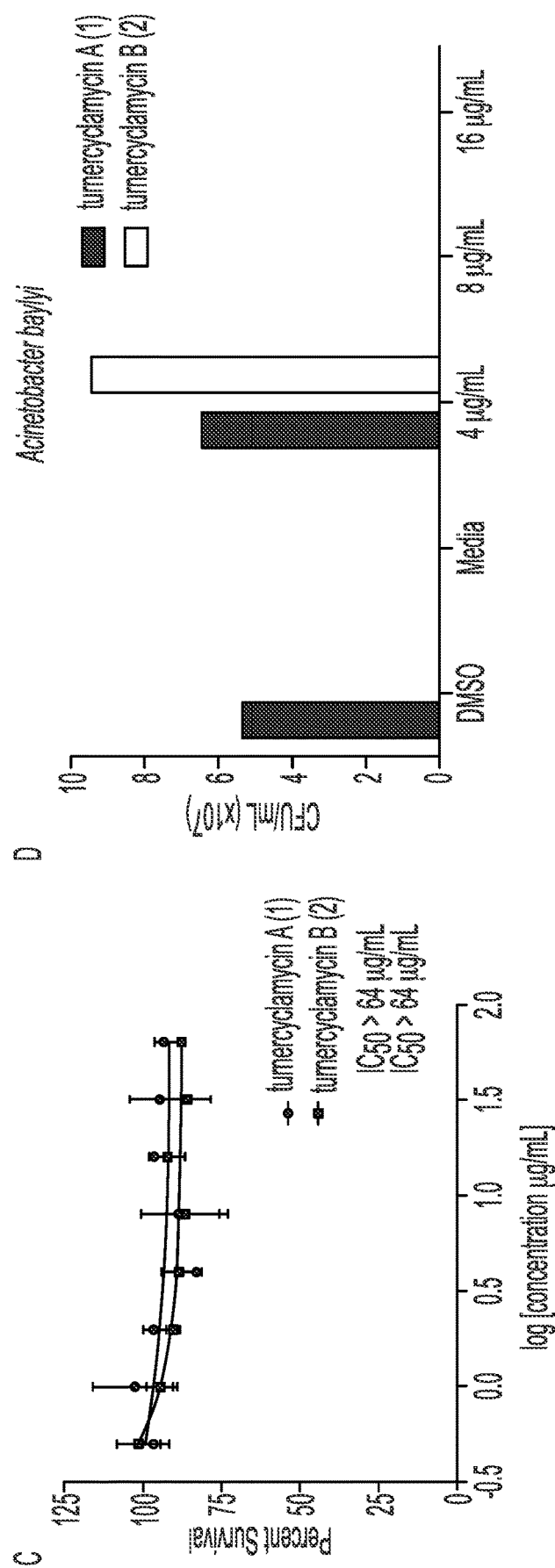

To determine the location of the double bond in the lipid side chain of 2, ozonolysis was performed on intact 2 followed by a reductive workup and LCMS. A major detected $[M+2H]^{2+}$ ion of m/z=758.91, corresponding to a monoisotopic mass of 1515.80, matches the mass of the intact peptide with a 9-formyl-nonoic acid moiety (FIG. 9H and FIG. 9I). Therefore, 2 was determined to contain a cis-9-hexadecanoic fatty acid tail.

Figure 8B:
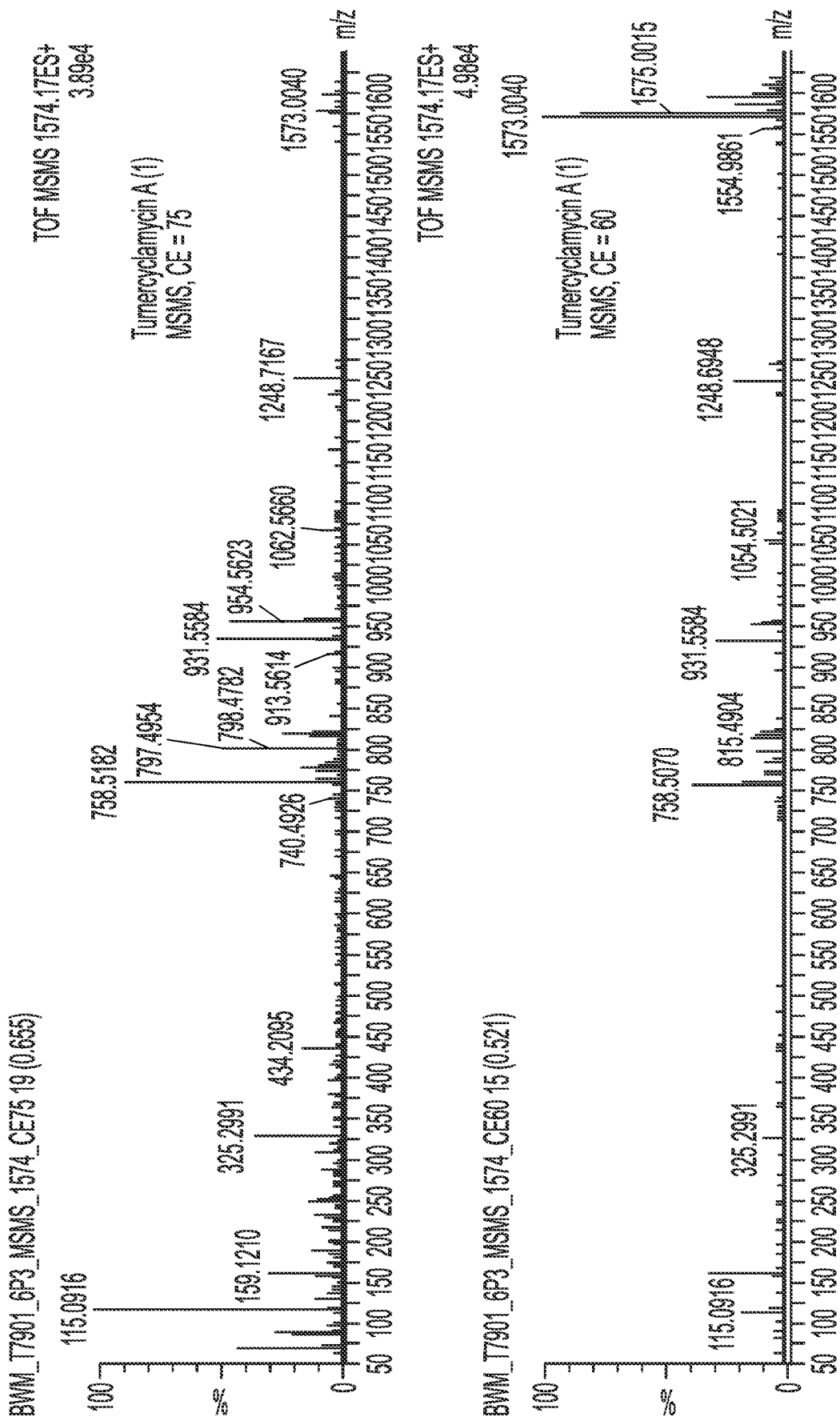
Figure 8C:
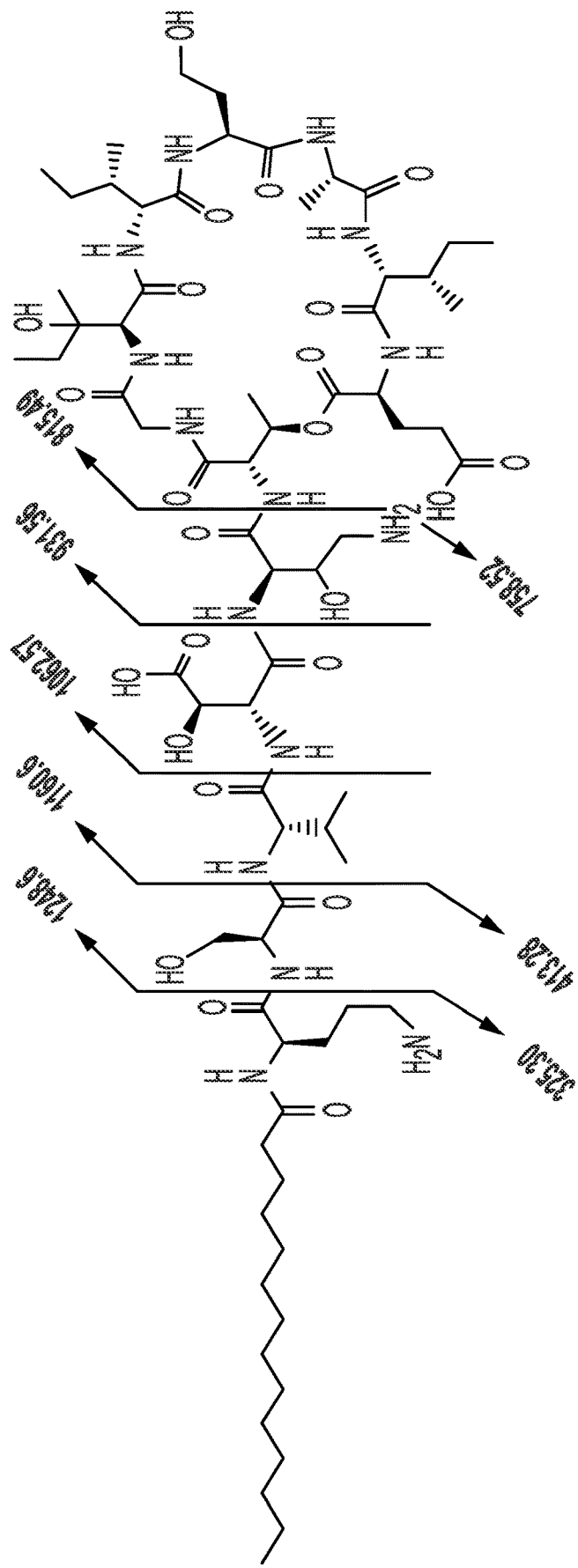

The minor analogs turnercyclamycin C (3) and D (4) were obtained as pure compounds, but in insufficient yield for complete structural characterization. However, the observed $[M+2H]^{2+}$ ions at m/z=772.9473 for 3 and m/z=793.9621 for 4 indicated formulas of $C_{69}H_{121}N_{15}O_{24}$ and $C_{72}H_{127}N_{15}O_{24}$, respectively. The $^1H$ NMR and COSY spectra for both compounds are superimposable with those of 2 (FIGS. 7A-D). MSMS fragmentation localized the differences in mass to the lipid tail (FIG. 8A and FIG. 8B), indicating that 3 and 4 are identical to 1 and 2, except that they contain unbranched C12:0 and C15:0 fatty acid tails, respectively.

Figure 8D:
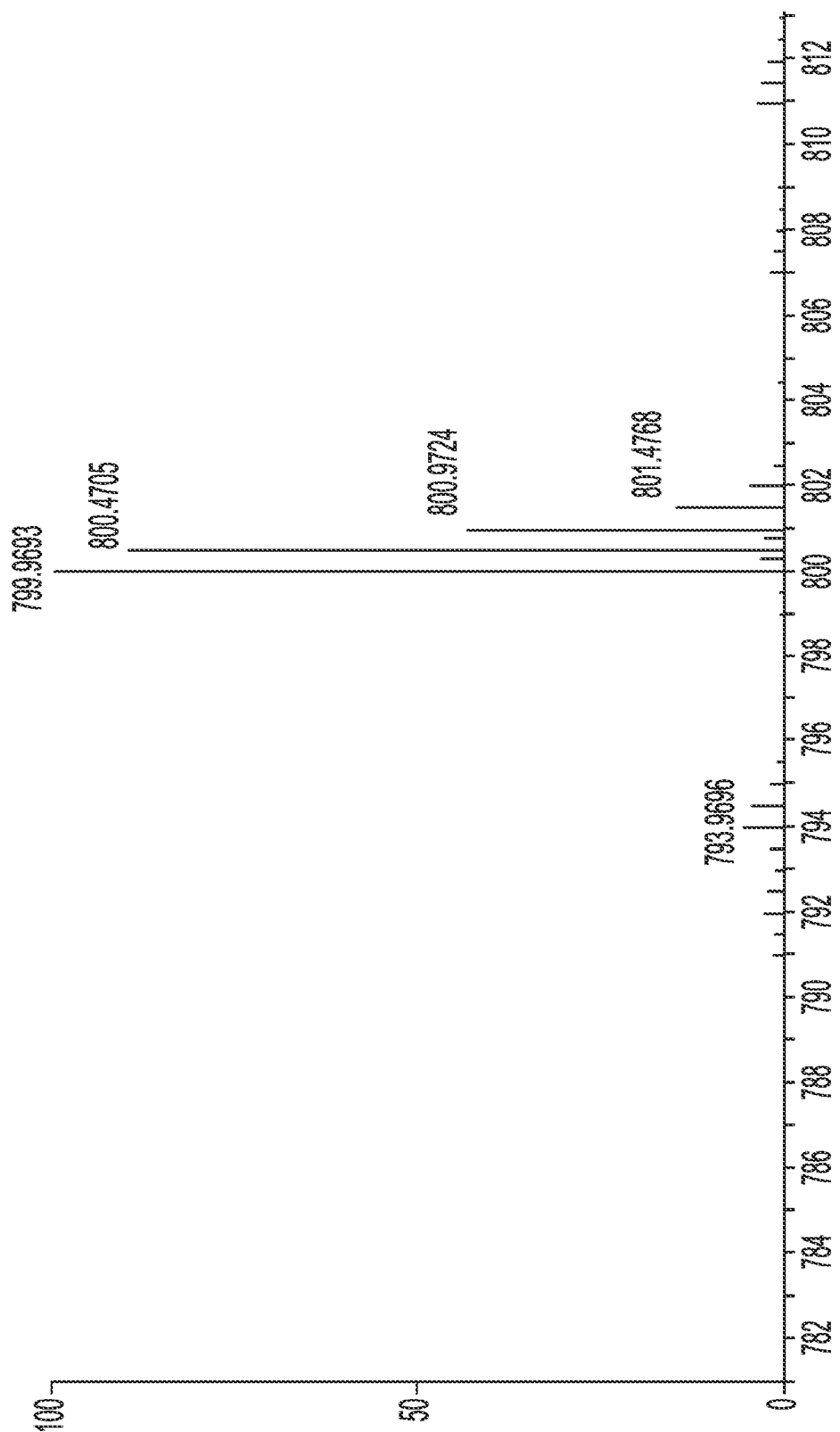
Figure 8E:
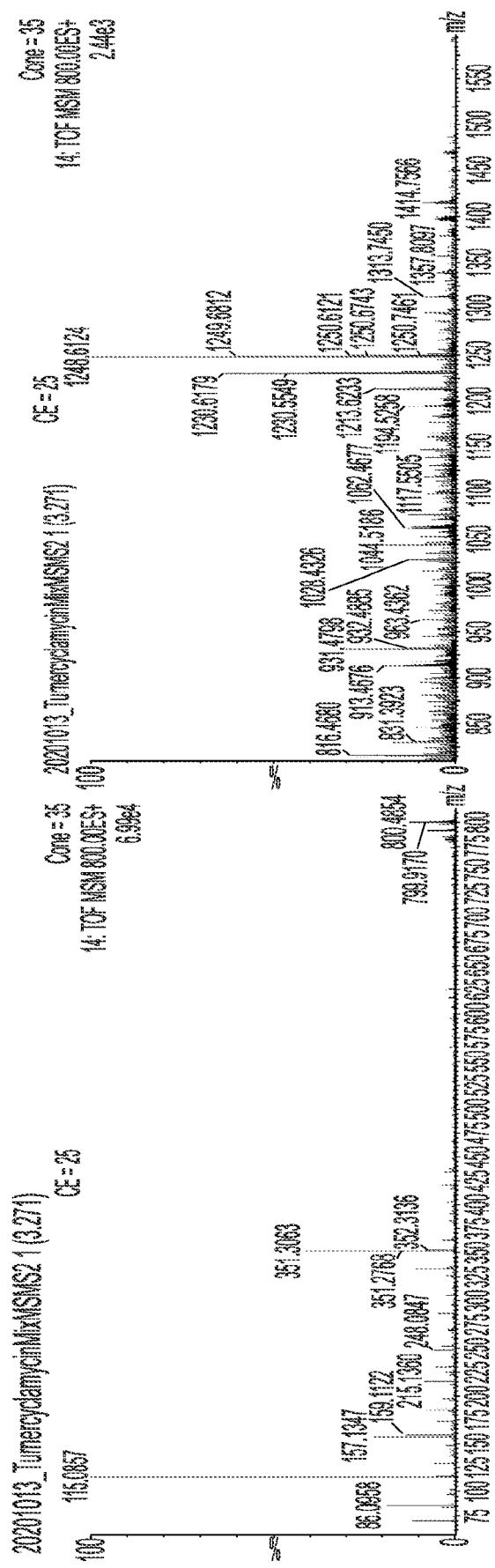
Figure 8F:
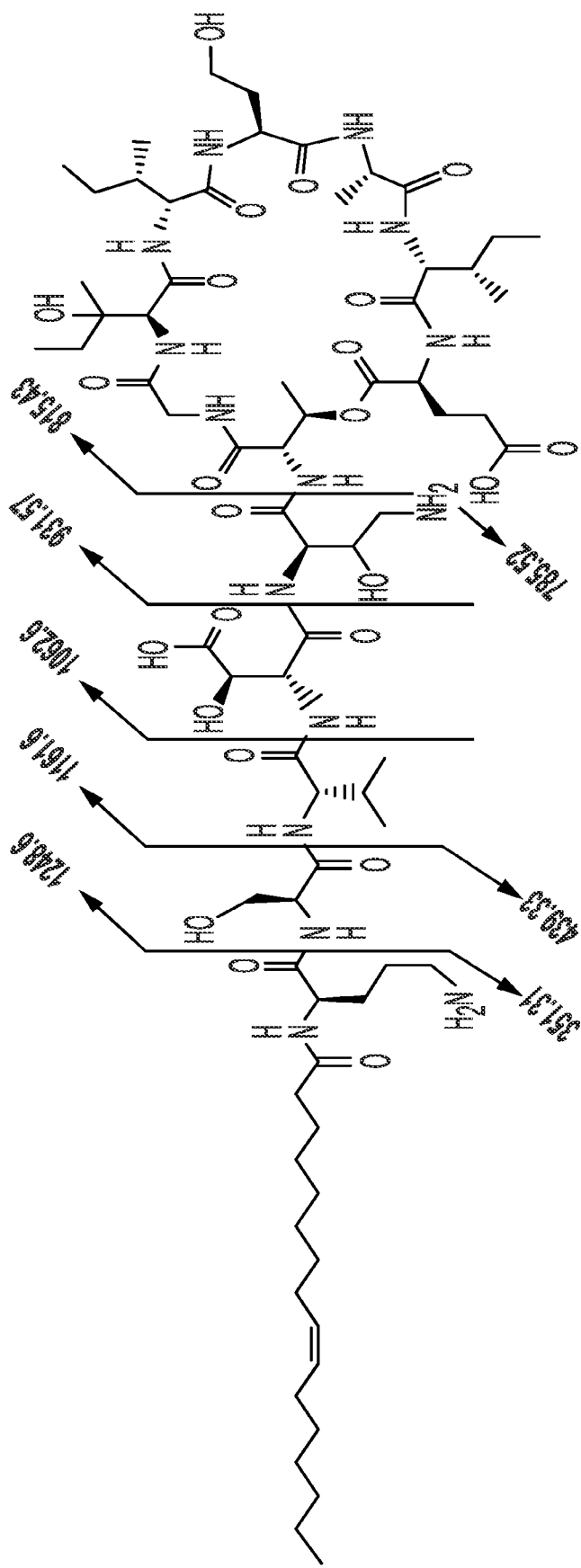
Figure 8G:
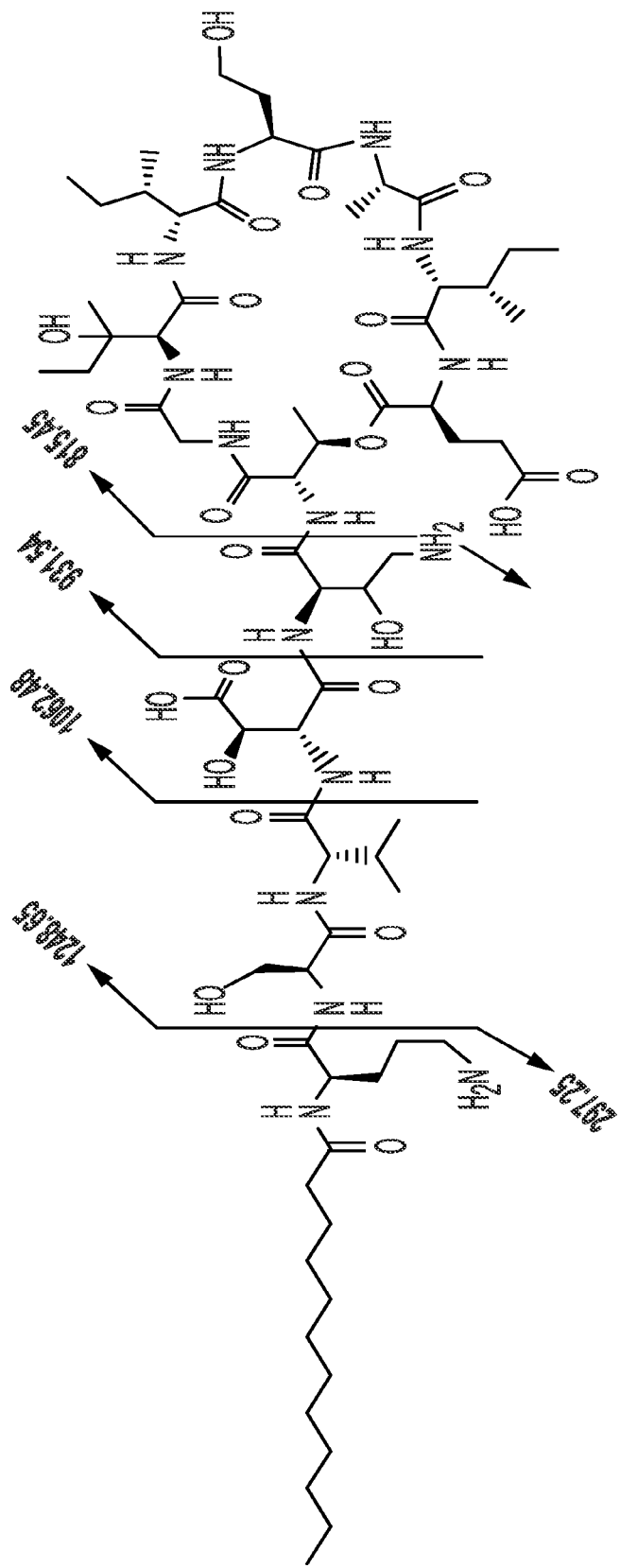
Figure 8H:
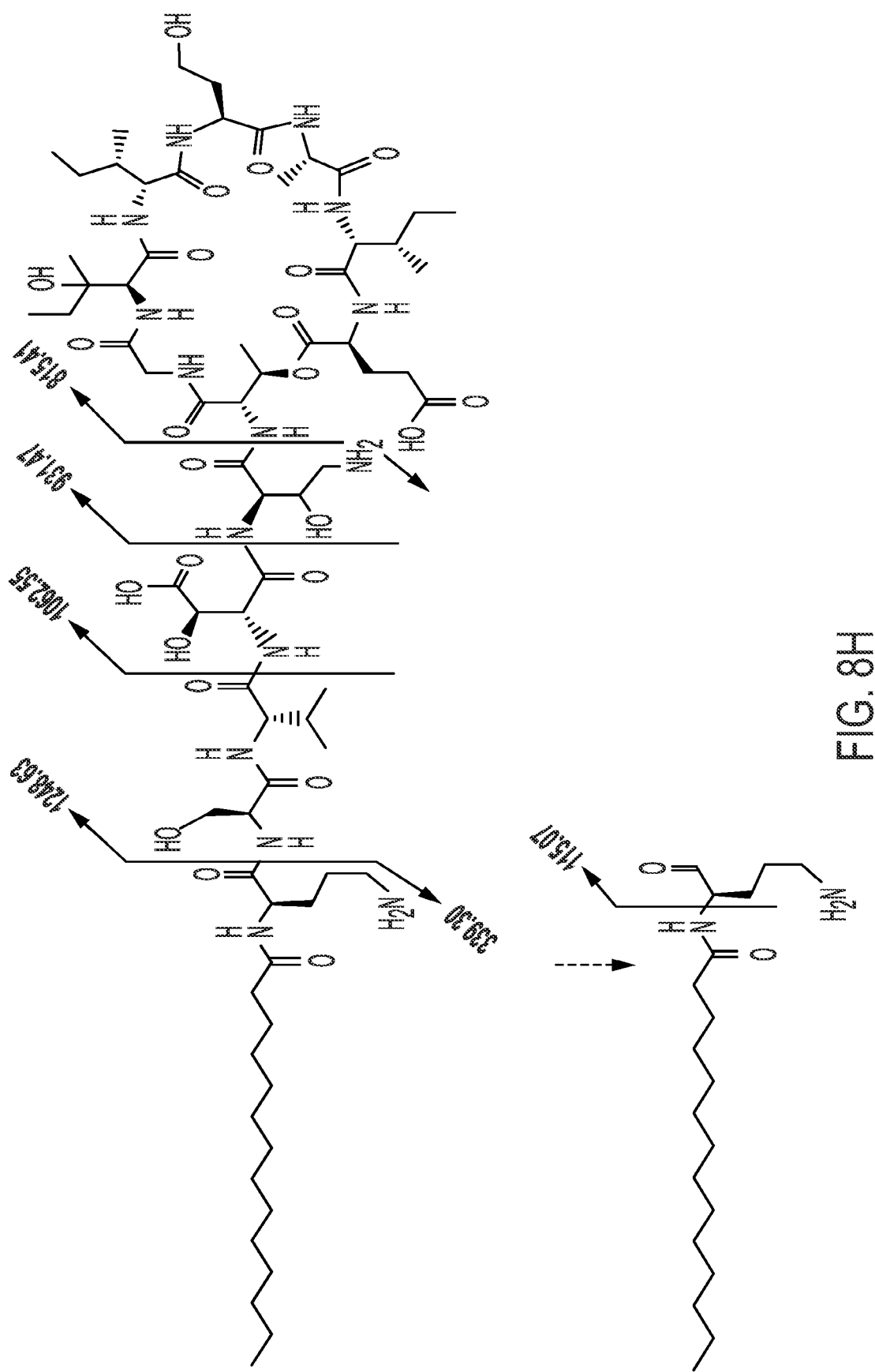
Figure 8I:
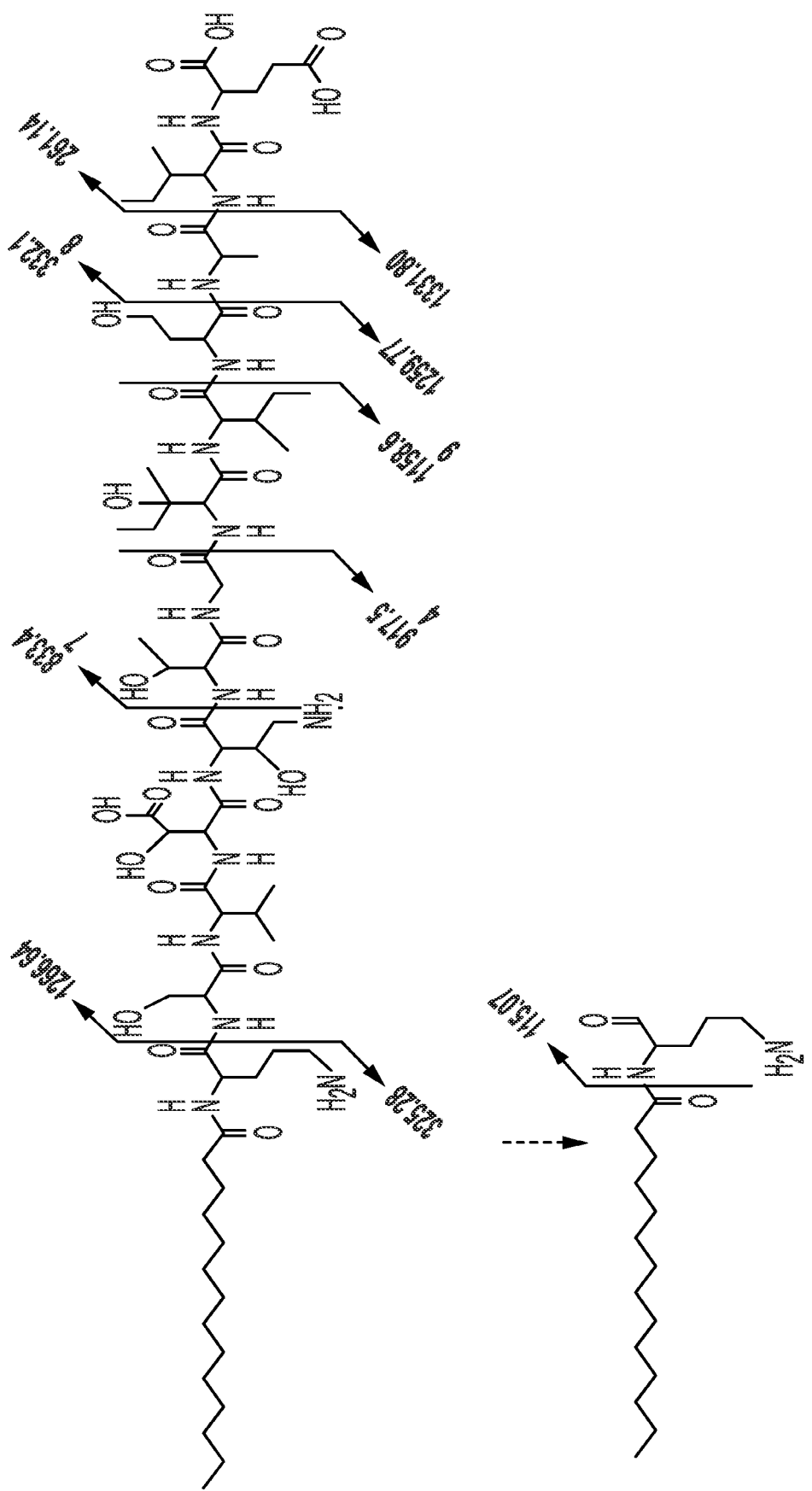
Figure 8J:
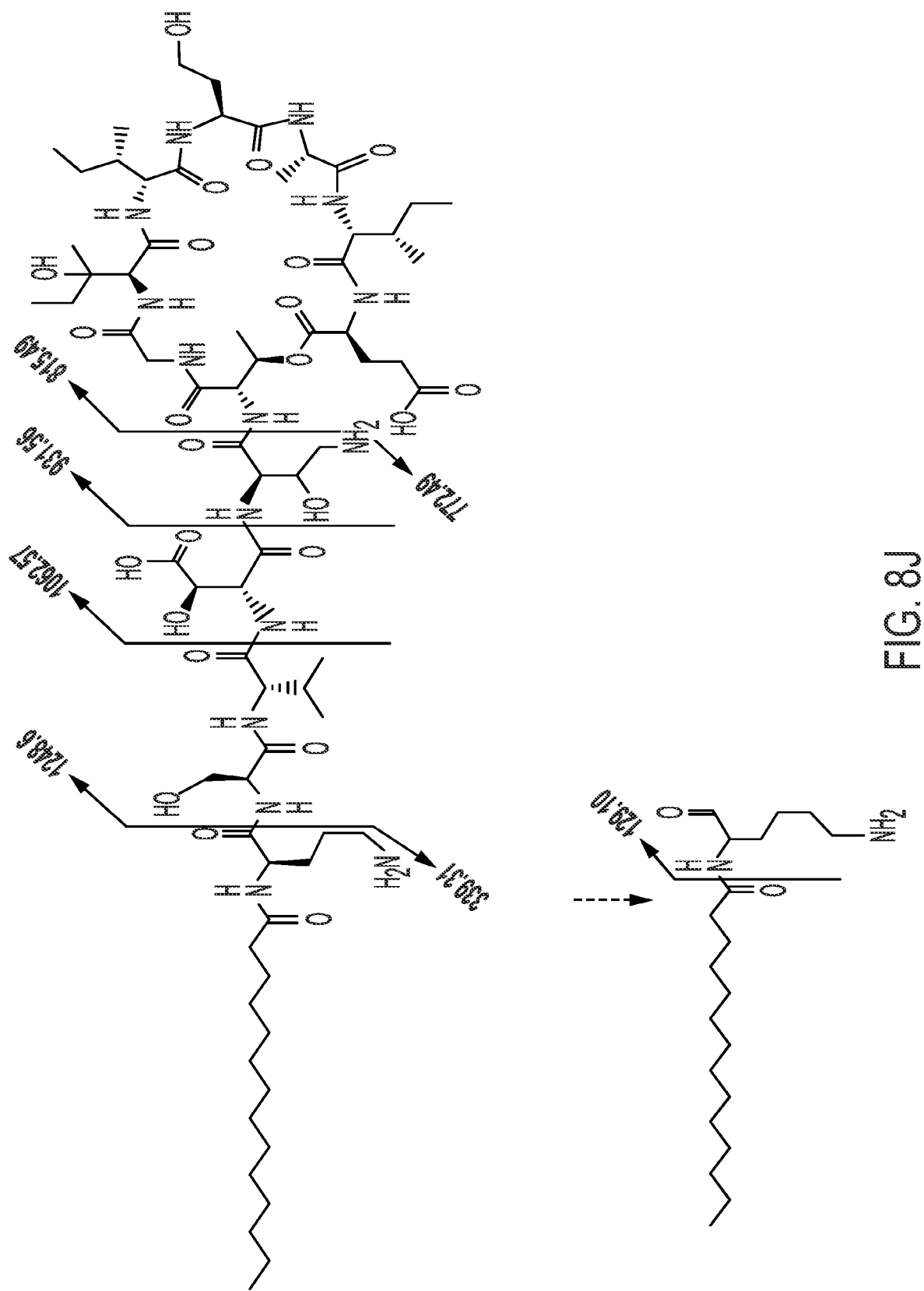

A number of other minor analogs were identifiable by LCMS analysis, but were inseparable by HPLC. MSMS fragmentation revealed the inclusion of a number of other lipid tails on the same peptide core, as well as two structural modifications to the peptide portion of the molecule. One appears to be an ornithine to lysine substitution, which is well supported by multiple fragment ions (FIG. 8D). The other is a loss of 14 amu that is localized to the cyclic portion of the peptide, but the fragmentation pattern did not clearly identify which amino acid was altered. The explanation most consistent with the data is that an isoleucine residue is substituted by valine.

Lastly, an assortment of analogs were detected by LCMS that represent ring-open linear peptides, methyl esters, and linear methyl esters. These represent hydrolysis artifacts and transesterification byproducts of the methanolic extraction and isolation work up (see Table 3, which shows MSMS fragmentation data of minor analogs).

TABLE 3

| Parent Mass $[M + 2H]^{2+}$ | $T_R$ (min) | Fatty Acid | Peptide Sequence Modifications |
| --- | --- | --- | --- |
| 779.96 | 3.01 | C13:0 | Same as 1 |
| 786.96 | 3.02 | C13:0 | Orn->Lys |
| 785.96 | 2.97 | C14:1 | Same as 1 |
| 795.96 | 3.11 | C14:0 | Ring Open |
| 779.96 | 3.05 | C14:0 | Loss of 14 amu in cyclic portion: Ile->Val |
| 802.96 | 3.13 | C14:0 | Ring Open + Methyl Ester (Glu) |
| 793.96 | 3.18 | C14:0 | Orn->Lys |
| 793.96 | 3.24 | C14:0 | +14 in cyclic portion, possible methyl ester of Glu |
| 808.99 | 3.21 | C16:1 | Ring Open |
| 800.96 | 3.46 | C16:0 | Same as 1 |
| 800.96 | 3.58 | C14:0 | Ring Open, Methyl Ester on Asp? |
| 813.97 | 3.7 | C16:1 | Ring Open, Methyl Ester on Asp? | c. Proposed Biogenesis

Bioinformatic analysis of the genome of *T. turnerae* T7901 using AntiSmash 5.0 led to the identification of a gene cluster containing five consecutive NRPS genes, encoding a total of 13 modules, which exactly matches the structure proposed for 1-4 and is the only gene cluster in the genome that potentially encodes the compound. The five genes include turA (3 modules, 11.2 kbp), turB (3 modules, 12.8 kbp), turC (2 modules, 6.6 kbp), turD (2 modules, 8.1 kbp), and turE (3 modules, 12.1 kbp). Each module contains a condensation (C), adenylation (A), and thiolation (T) domain, and 5 of the modules also contain epimerization domains. Together, these domains are responsible for selecting and activating amino acids, controlling their stereochemistry, and condensing them onto the growing peptide chain. The first domain begins with a so called C-starter domain, which are known to acylate the initial amino acid in a process known as lipoinitiation. (21) The final module terminates in a thioesterase domain, which is responsible for the macrocyclization and release of the final product. (22)

Figure 2:
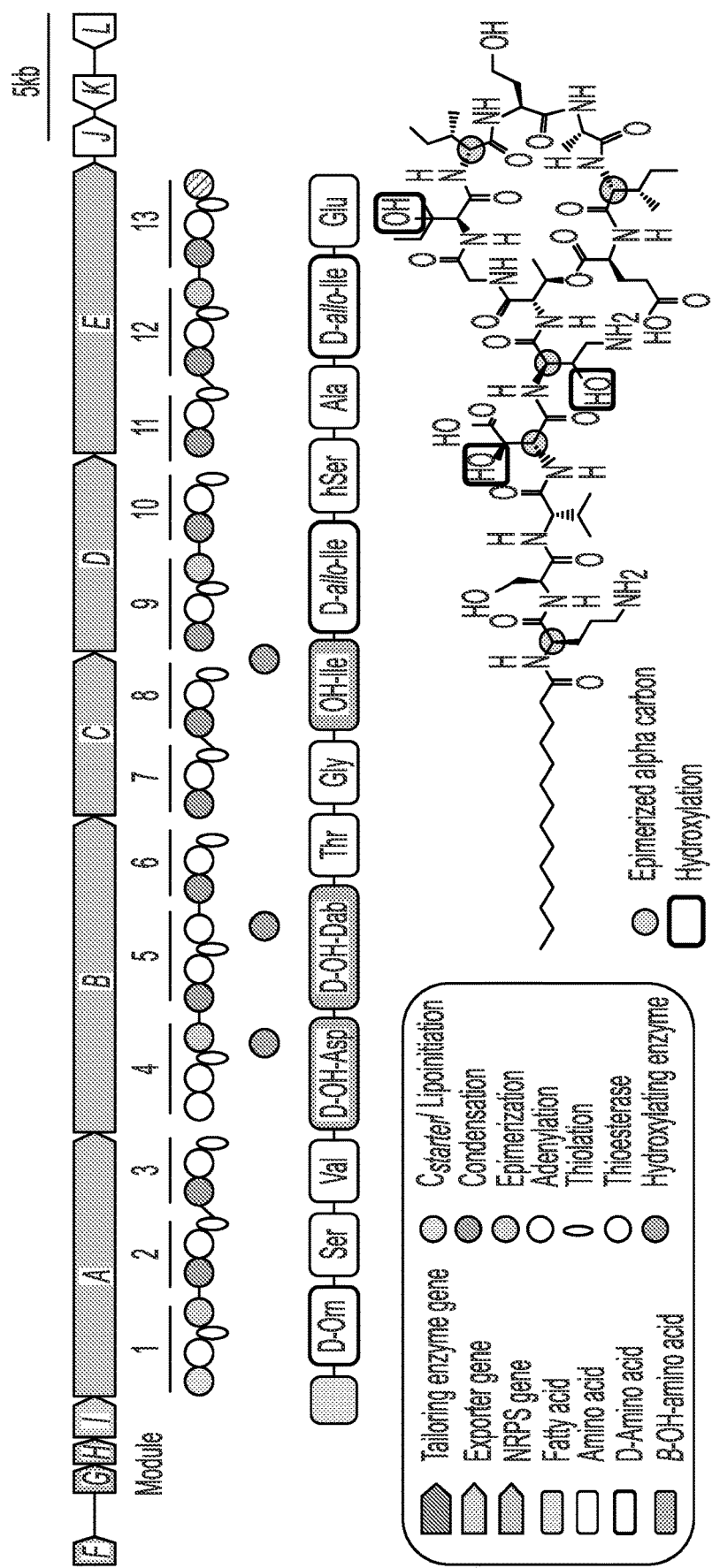
FIG. 2 shows a representative schematic illustrating the proposed biogenesis. Red amino acid labels indicate D-configuration, green indicates L-configuration, and blue hydroxyl groups are proposed to be installed by tailoring enzymes.

The adenylation domain substrate predictions of each NRPS module map very well to the NMR-elucidated structure. The only adenylation domains for which no substrate was predicted correspond to the incorporation of DAHB and homoserine, both unusual amino acids. The prediction for the modules incorporating b-OH-Asp and b-OH-Ile were aspartic acid and isoleucine, respectively. In addition, the presence or absence of epimerase domains perfectly matched the results of the Marfey's analysis, with E domains present in all D-configuration amino acid extensions for which standards were available (FIG. 2).

Upstream of the five NRPS megasynthase genes are four open reading frames that are predicted to be involved in the tailoring and export of the compound (see Table 4). Two, turF and turH, encode α-ketoglutarate-dependent dioxygenases (Fe/αKG), which are well characterized for performing hydroxylation reactions (Wu et al., 2016). Another, turG, encodes a cupin domain-containing protein with similarity to the protein JmjC. This class of enzyme also uses non-heme Fe and αKG to demethylate histones via hydroxylation, and related enzymes are responsible for the β-hydroxylation of lysine (Markolovic et al., 2018; Tsukada et al., 2006). Without wishing to be bound by theory, it is likely that these three enzymes are performing the three β-hydroxylation reactions for the final product (FIG. 2).

d. Stereochemical Assignment by Advanced Marfey's Analysis

Compound 1 was hydrolyzed, and the constituent amino acids were derivatized with L-FDLA then analyzed by RP-UPLC-HRESIMS. See FIG. 1B. The result was compared against derivatized standards, when available, and d-FDLA derivatized 1-configuration standards were used to confirm retention times for d-configuration amino acids. This analysis confirmed the serine, valine, threonine, homoserine, alanine, and glutamic acid residues are all 1-configuration. The omithine residue was determined to be in the d-configuration, and both isoleucine residues were confirmed to be d-allo-configured by comparison to d- and 1-FDLA derivatized standards of 1-Ile and 1-allo-Ile, which all separated by UPLC. These results were all in accordance with the presence or absence of an epimerase domain within their associated NRPS modules in the proposed biosynthetic gene cluster. See Table 4, which shows gene annotations and nearest homologs of the biosynthetic gene cluster.

TABLE 4

| Gene | Gene name | Protein Size | Annotation or Proposed Function | Homolog (Accession, organism) | Identity (%) |
|---|---|---|---|---|---|
| TERTU_RS1035 5 | turF | 332 | Fe/α(Kg dependent dioxygenase | WP_144695392.1, *Alteromonadaceae bacterium* 2753L.S.0a.02 | 71.9 |
| TERTU_RS1035 0 | turG | 290 | jmjC-like cupin domain containing protein | WP_044617703.1, *Gynuella sunshinyii* | 47.45 |
| TERTU_RS1034 5 | turH | 322 | Fe/α(Kg dependent dioxygenase | WP_044619903.1, *Gynuella sunshinyii* | 61.49 |
| TERTU_RS1034 0 | turI | 561 | Cyclic peptide export ABC transporter | WP_044616742.1, *Gynuella sunshinyii* | 68.86 |
| TERTU_RS1033 5 | turA | 3718 | NRPS | WP_044616743.1, *Gynuella sunshinyii* | 48.39 |
| TERTU_RS1033 0 | turB | 4249 | NRPS | WP_044616744.1, *Gynuella sunshinyii* | 54.07 |
| TERTU_RS1032 5 | turC | 2214 | NRPS | WP_044616745.1, *Gynuella sunshinyii* | 56.71 |
| TERTU_RS1032 0 | turD | 2685 | NRPS | WP_052830181.1, *Gynuella sunshinyii* | 62.56 |
| TERTU_RS2136 5 | turE | 4025 | NRPS | WP_052830181.1, *Gynuella sunshinyii* | 60.44 |
| TERTU_RS1031 0 | turJ | 531 | MBL fold metallo-hydrolase | WP_044616748.1, *Gynuella sunshinyii* | 72.69 |
| TERTU_RS1030 5 | turK | 542 | Family 43 glycosyl-hydrolase | WP_012488586.1, *Cellvibrio japonicus* | 67.34 |
| TERTU_RS1030 0 | turL | 417 | Lipolytic enzyme | NVK57725.1, *Alteromonadaceae bacterium* | 68.01 |

The β-hydroxyaspartic acid was resolved based on comparison of the elution order to the reported values in Fuji et al., 1997 and the elution pattern from the potashchalins (Li et al., 2020). The hyrolysate of 1 was derivatized with both L-FDLA and D-FDLA, and after considerable LC method development, a small but distinct change in retention time was observed. The L-FDLA derivatized peak elutes earlier, which corresponds to the D-configured alpha carbon. This is further supported by the presence of an epimerase domain within the module incorporating this residue into the growing peptide chain. The L- and D-FDLA derivatized hydrolysate peaks were then compared to the L-FDLA derivatized D/L-threo-β-hydroxyaspartic acid standard. The elution of the standard matches well with that of the hydrolysate, and thus the absolute configuration is deemed to be D-threo-β-hydroxyaspartic acid. EICs and retention times for the derivatized hydrolaste and amino acid standards are supplied in FIGS. 9A-G and Table 6.

As no standards are available for DAHB, the amino acid was synthesized following the methods employed in the total synthesis of odilorhabdin, in which the base hydrolysis and subsequent deacetylation of hydroxyectoine was reported to result in a 70:30 mixture of the 2S,3S and 2R,3S diastereomers, respectively (Sarciaux et al., 2018). The crude reaction mixture was derivatized with L- and D-FDLA, and the four diastereomers were clearly distinguishable based on retention time and peak height. The minor peak in the L-FDLA-derivatized reaction mixture, corresponding to 2R,3S DAHB, matched the L-FDLA-derivitized peak in the hydrolysate of 1.

e. Stereochemical Prediction by Biosynthetic Logic

The two remaining residues, f-hydroxyisoleucine and DAHB, both presented challenges due to the lack of any commercially available standards. β-hydroxyisoleucine is rarely found in natural products, and it was reported without stereochemical assignments in stalobactin (Matsui et al., 2020) and the C2 and C3 configurations of this residue were only resolved in phomopsin A through X-ray crystallography (Culvenor et al., 1989). Attempts to grow diffraction-quality crystals were unsuccessful, so investigation of the NRPS domain architecture for the proposed biosynthesis of the tumercyclamycins was used to predict the C2 stereochemistry. The L- or D-configuration of all ten residues that were assigned via Marfey's analysis perfectly correlated to the absence or presence of an epimerase domain. Thus, it is predicted that the β-hydroxyisoleucine is in the L-configuration due to the lack of an epimerase domain. The C3 position, however, remains ambiguous due to a lack of knowledge of the stereoselectivity of the hydroxylating enzyme for this position.

DAHB provides an additional challenge. This amino acid is found in several antibacterial lipopeptides, including odilorhabdins (Pantel et al., 2018) and ogipeptins (Kozuma et al., 2017), but its biosynthesis remains unknown. Due to the common incorporation of DAHB in numerous cycliclipopetides and the presence of three separate enzymes capable of hydroxylating amino acids upstream of the NRPS cluster, this moiety is being produced through the beta-hydroxylation of diaminobutyric acid (DAB). DAB is typically found in the L-configuration when an epimerase domain is not present in the NRPS module, so the presence of an epimerase domain in the module responsible for its incorporation indicates a D-configuration at position C2. DAHB is also found in peptidyl nucleic acid antibiotics, where it is made by a different biosynthetic route.

f. Antibiotic Activity of 1 and 2

Figures 11E, 11F:
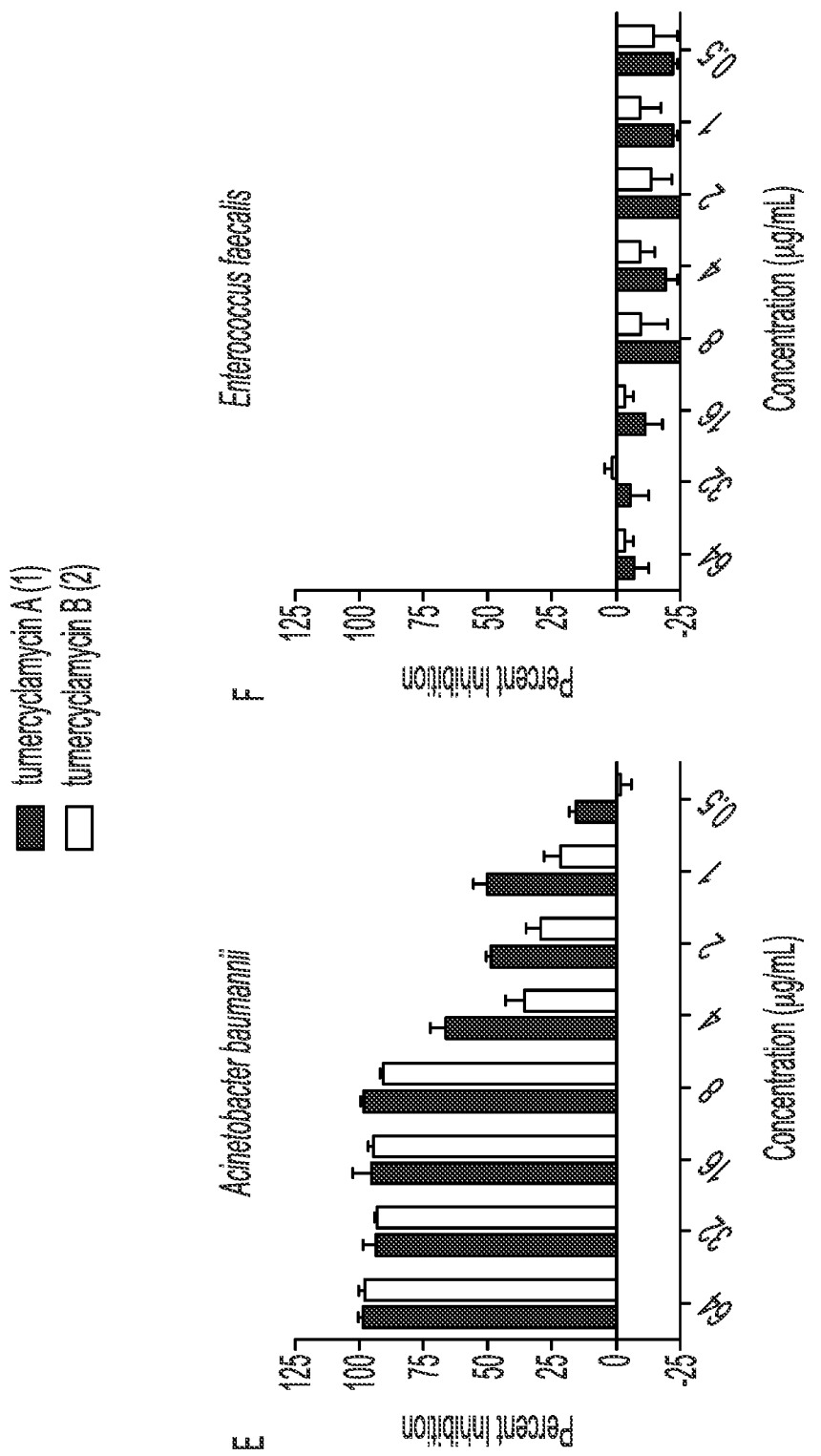
FIG. 11A-Q show representative data illustrating the results of broth microdilution assays for MIC determination.
Figure 11H:
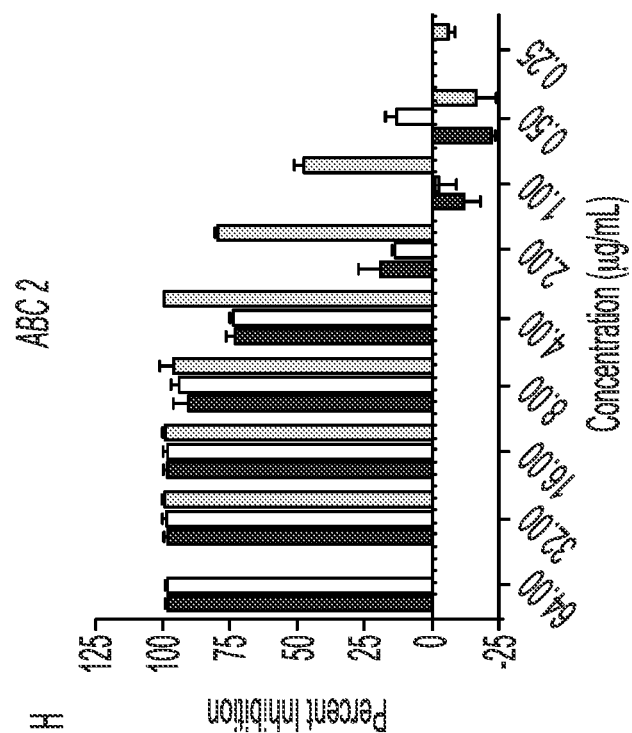
Figure 11G:
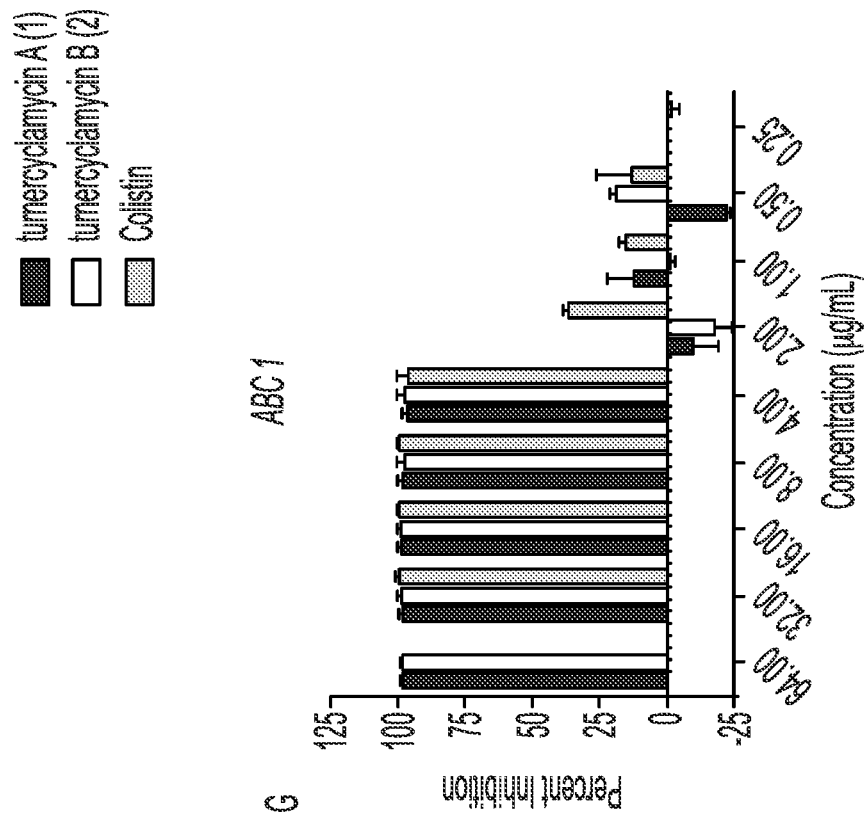
Figures 11I, 11J:
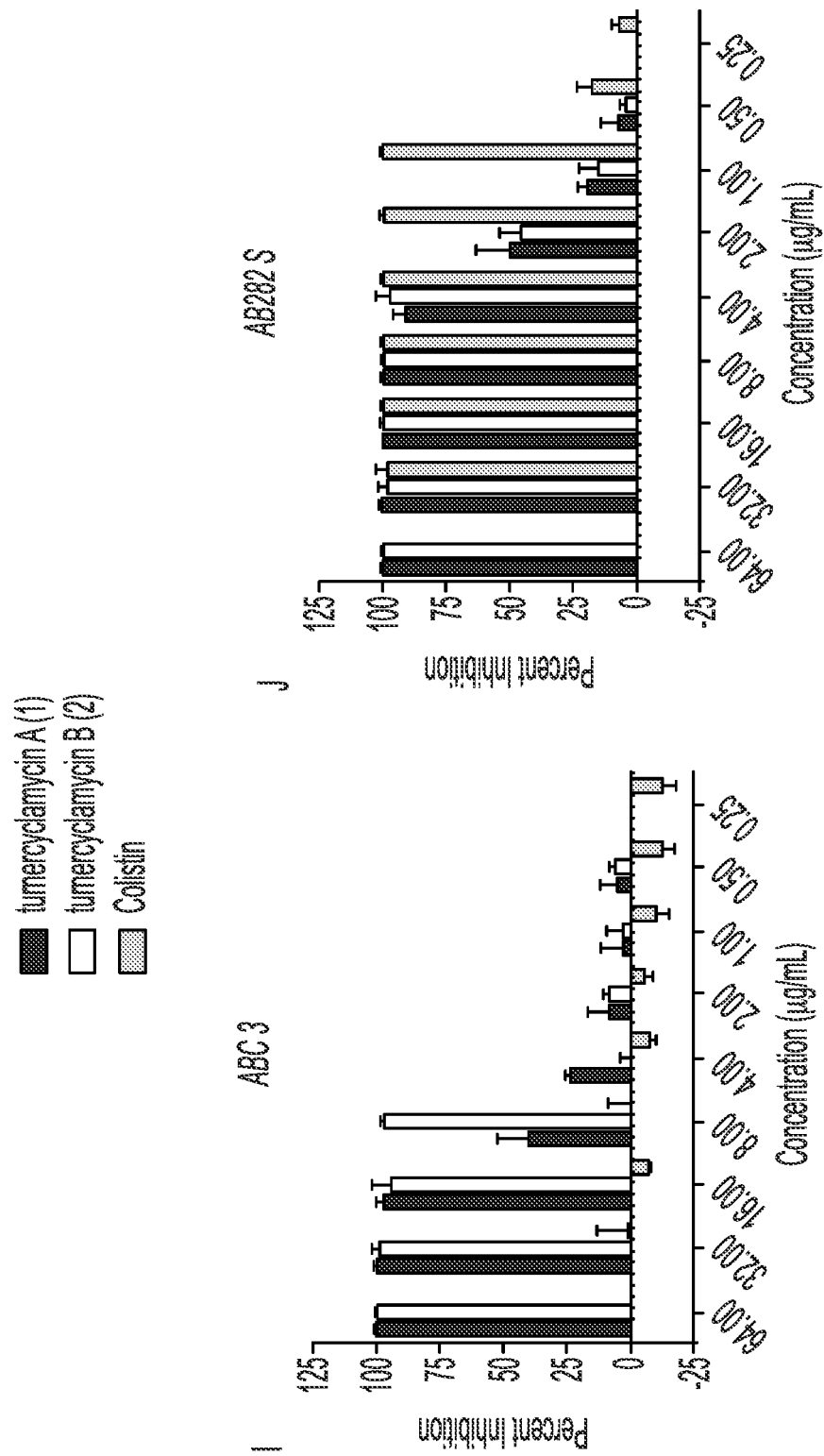
Figures 11K, 11L:
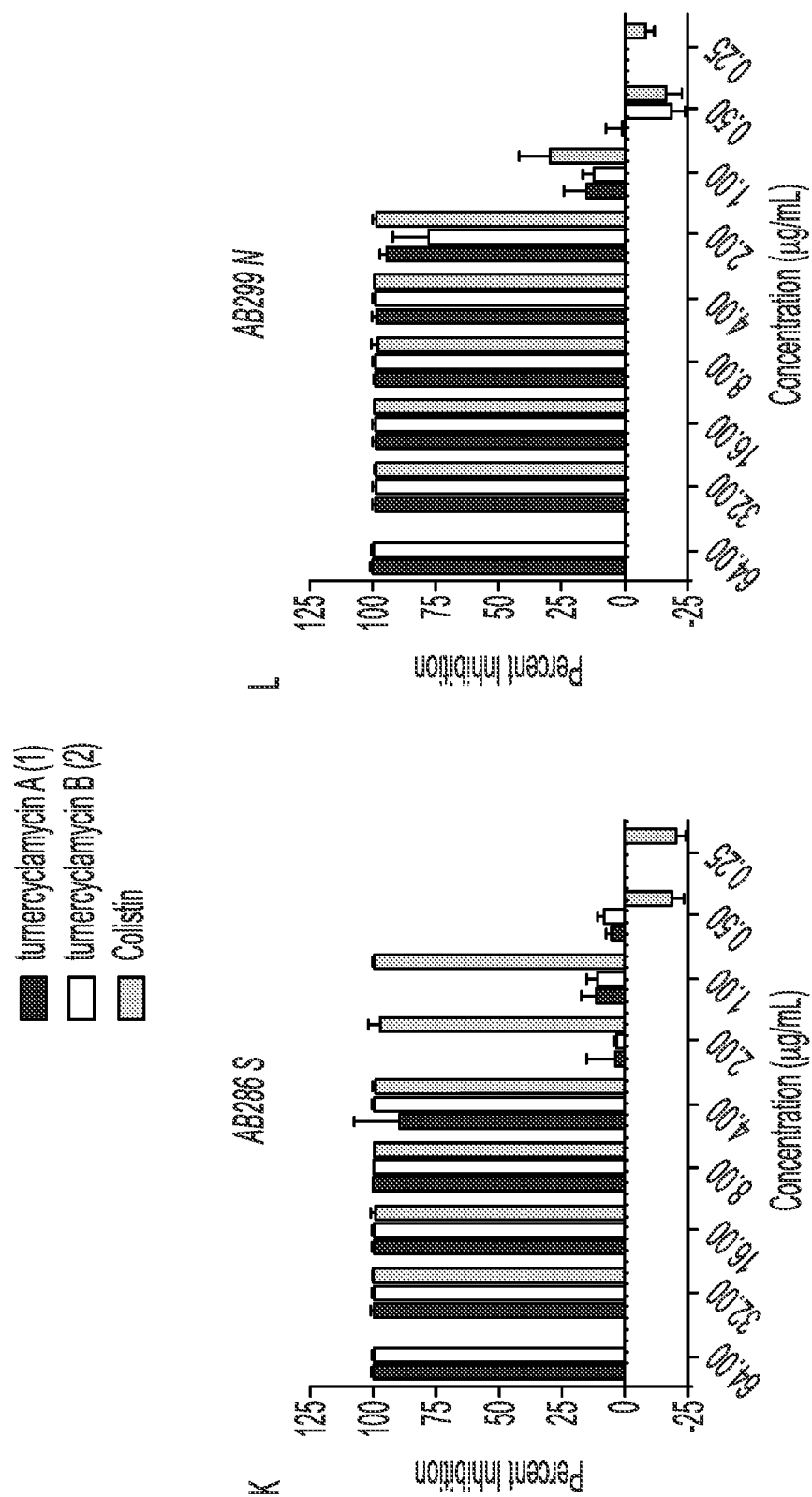
Figure 11O:
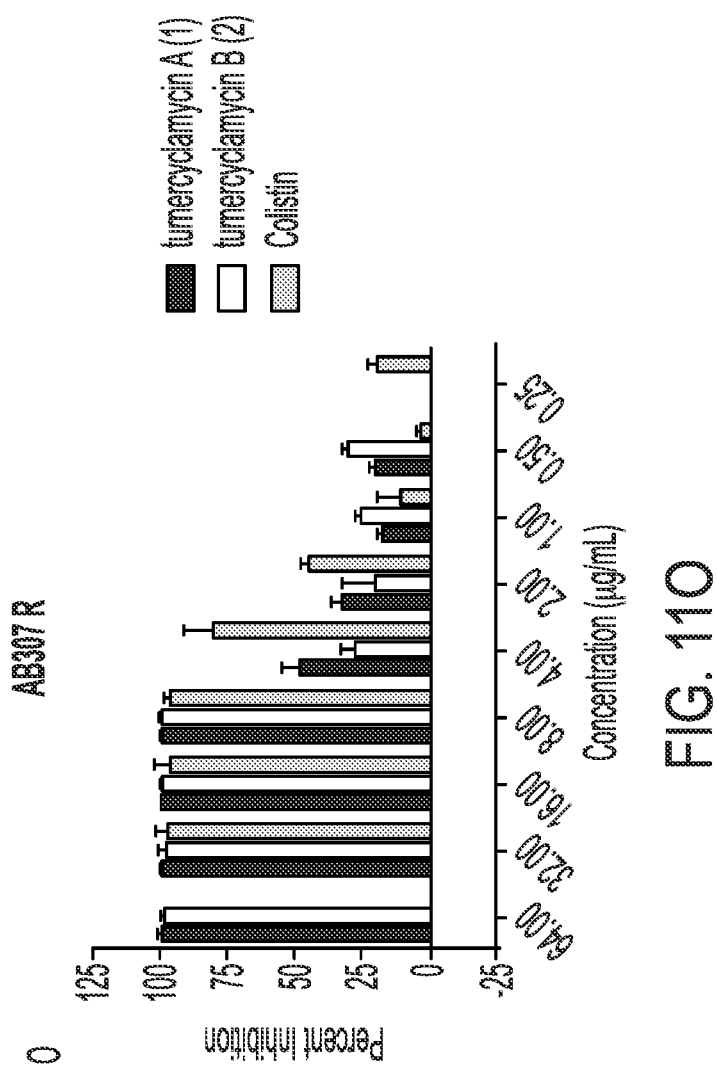
Figure 11Q:
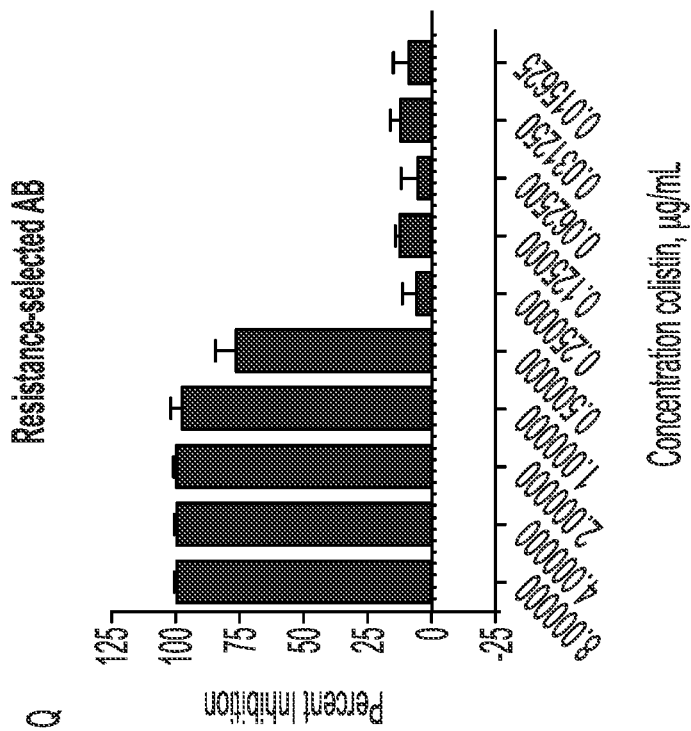
Figure 11P:
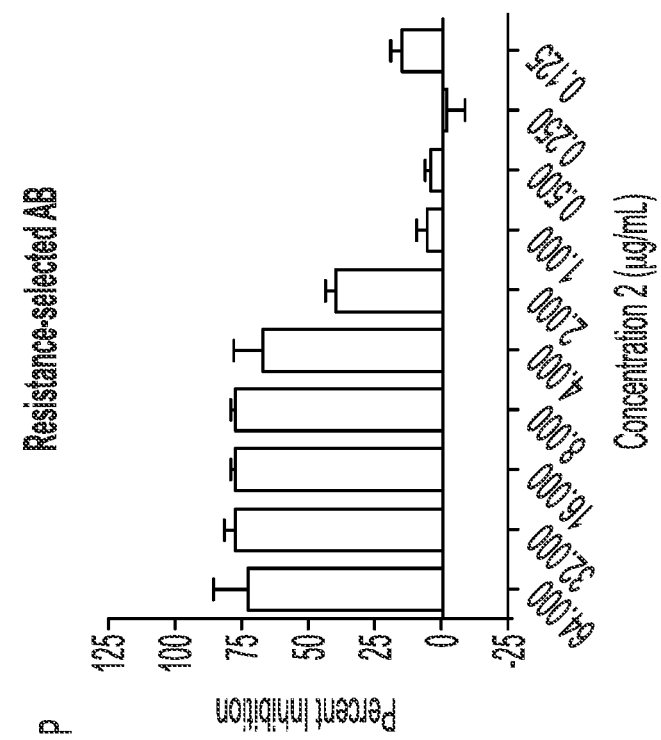

Compounds 1 and 2 were initially tested against a panel of Gram-positive and Gram-negative pathogens in liquid broth assays. See Table 5a below, which shows $MIC_{90}$'s of compounds 1 and 2 in bacterial and human (HEK-293) cells. Neither 1 nor 2 were bactericidal to *Staphylococcus aureus* at concentrations up to 64 mg/mL, but at 4 mg/mL and above they slowed growth, decreasing it by 50% during the period of the assay (FIG. 11A). In contrast, both compounds 1 and 2 were significantly active against *Escherichia coli* (MIC 1 μg/mL), *Acinetobacter baumannii* (MIC 8 μg/mL), and *Klebsiella pneumonia* (MIC 2 μg/mL), and neither compound showed activity against any of the Gram-positive pathogens up to 64 μg/mL. Since many antibiotics are relatively inactive against *A. baumannii*, substituting the nonpathogenic relative *A. baylyi* was performed for further experiments. Compounds 1 and 2 showed the same MIC against *A. baylyi*, with similar phenotypic effects on the organism, validating the use of the strain. Plating of inhibited wells from *A. baylyi* broth cultures determined that the growth inhibition was a result of bactericidal, not bacteriostatic activity (FIG. 10A-D).

TABLE 5A

| Pathogen or Cell Line | $MIC_{90}$ (μg/mL) | |
|---|---|---|
| | 1 | 2 |
| *Acinetobacter baumanii* | 8 | 8 |
| *Escherichia coli* | 1 | 1 |
| *Enterococcus faecalis* | >64 | >64 |
| *Klebsiella pneumoniae* | 2 | 2 |
| *Staphylococcus aureus* | >64 | >64 |
| HEK-293 | >64 | >64 |

Lipopeptide antibiotics often meet hurdles in development due to toxicity against mammalian cells and the lysing of erythrocytes owing to their amphipathic nature (Agner et al., 2000). Thus, 1 and 2 were tested for cytotoxicity against the human kidney-derived HEK-293 cell line and for hemolytic activity in freshly harvested murine erythrocytes. Both compounds showed no activity in either assay up to 64 μg/mL, in comparison to control compounds that behaved as expected.

Figure 4:
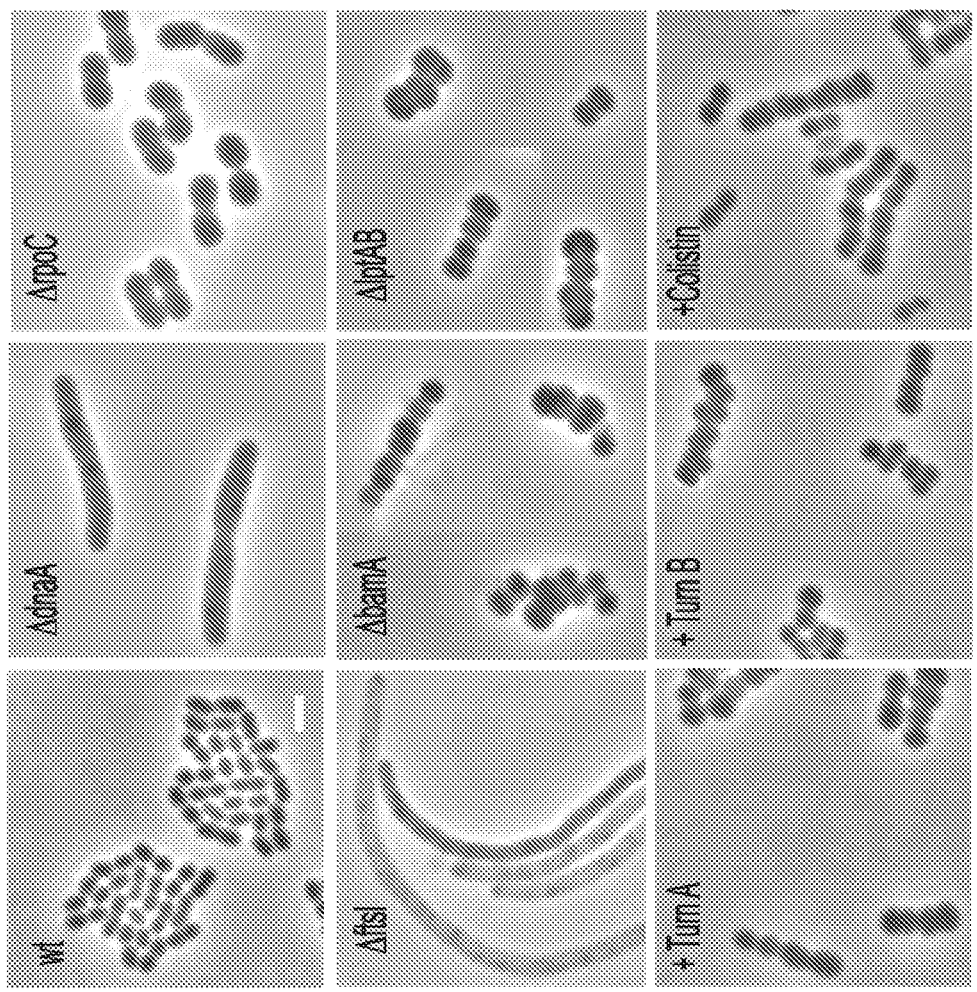
FIG. 4 shows representative images illustrating the terminal morphologies of mutant and antibiotic-treated A. baylyi. Each panel is a compilation of representative cells from the same condition. Cells are moved closer to each other than they appeared under the microscope so that they fit within each panel, but the overlaid images do not obscure other cells. The images show bacteria whose growth has been inhibited by essential gene deletion or treatment with antibiotics at approximately the MICs (tumercyclamycin A and B, 8 mg/mL; colistin, 0.5 mg/mL). The deletion mutations inactivate the following processes: dnaA, DNA replication; rpoC, transcription; ftsI, cell division; bamA, outer membrane protein localization; lptAB, LPS localization. Scale bar, 2 mm. wt, wild type; TurnA, tumercyclamycin A (1); Turn B, tumercyclamycin B (2).
Figure 5A:
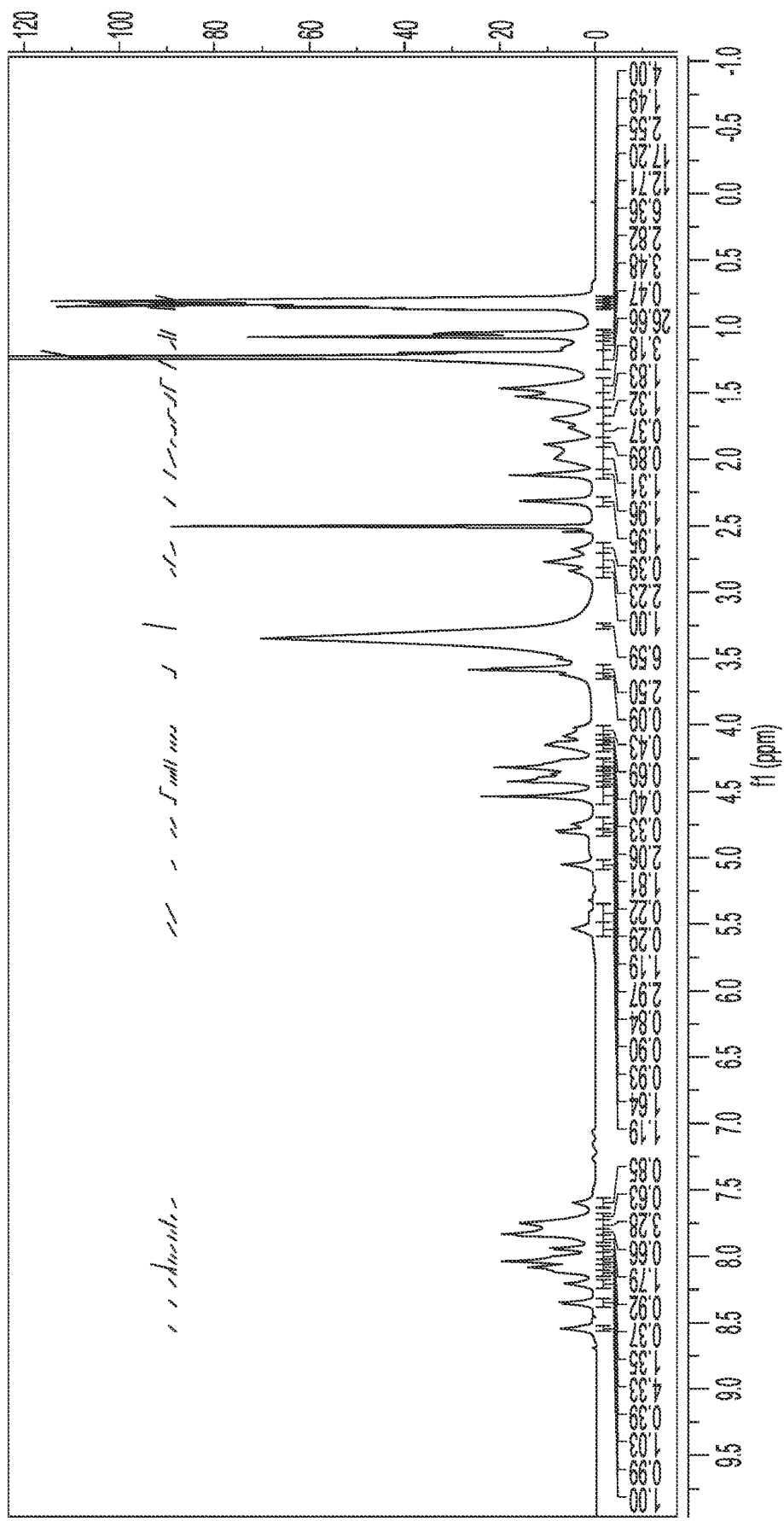
FIG. 5A-G show representative NMR spectra of compound 1.
Figure 5B:
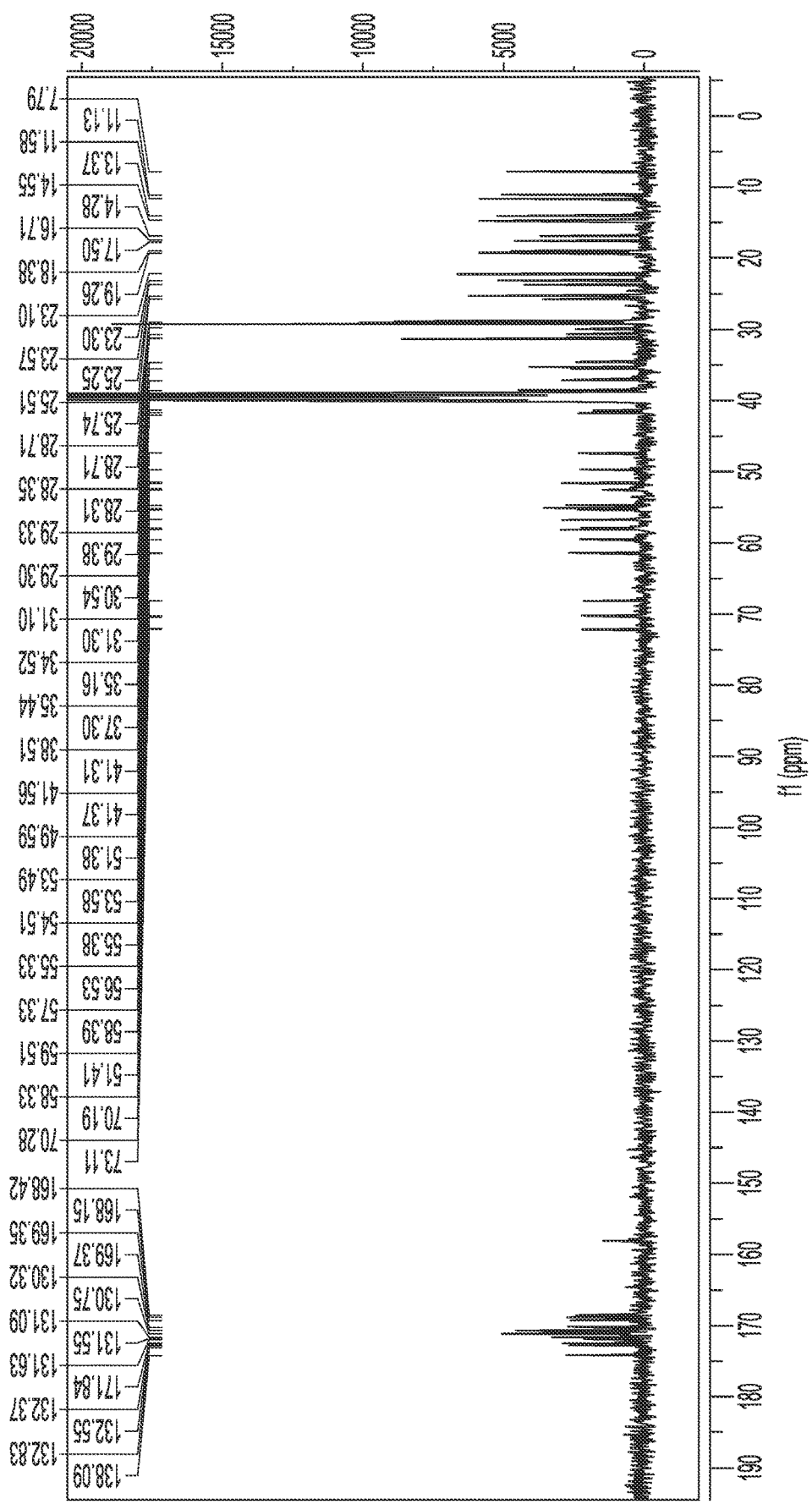
Figure 5C:
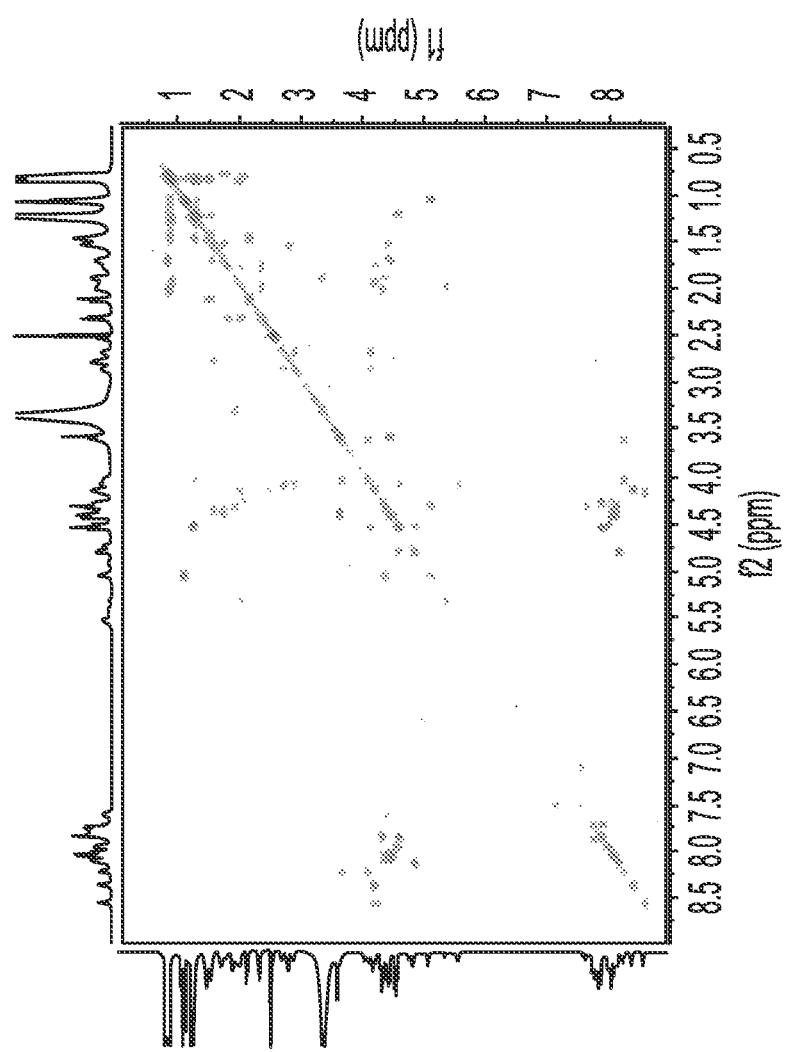
Figure 5D:
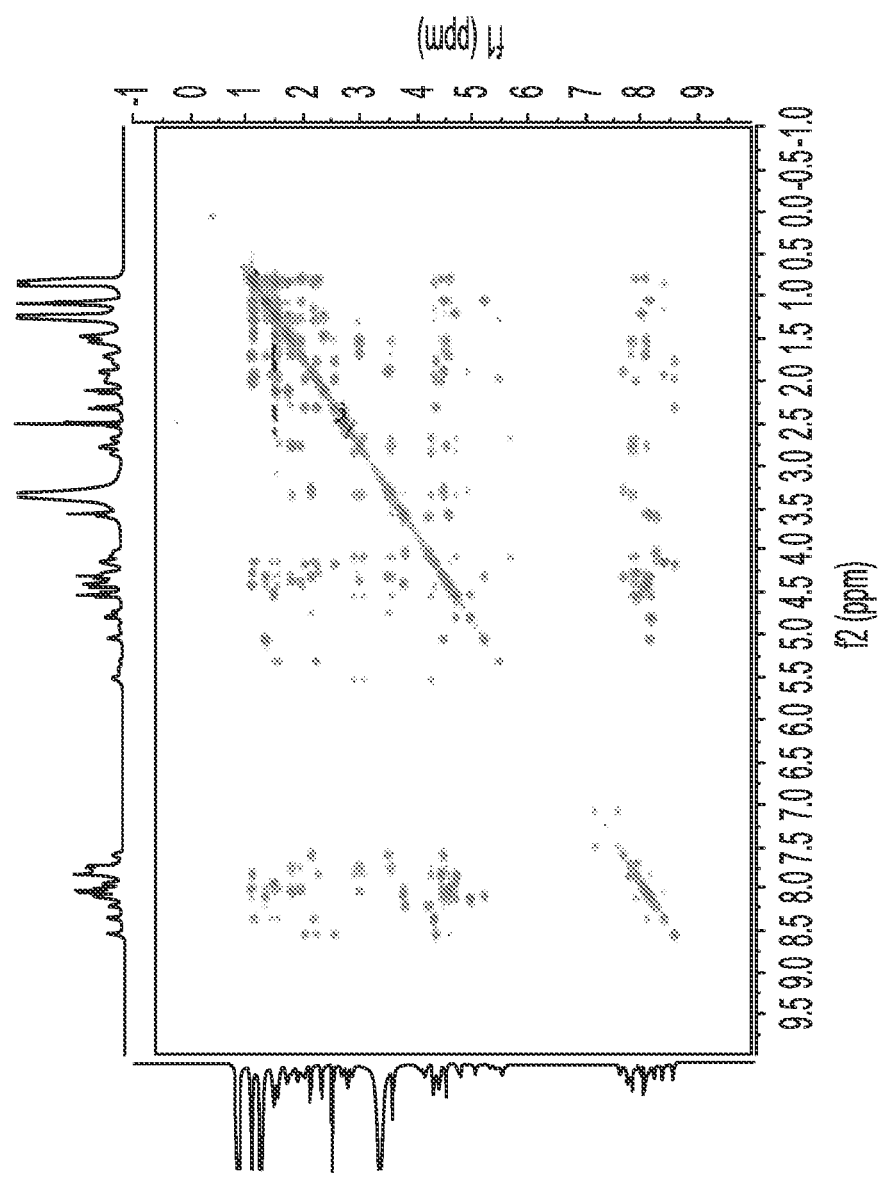
Figure 5E:
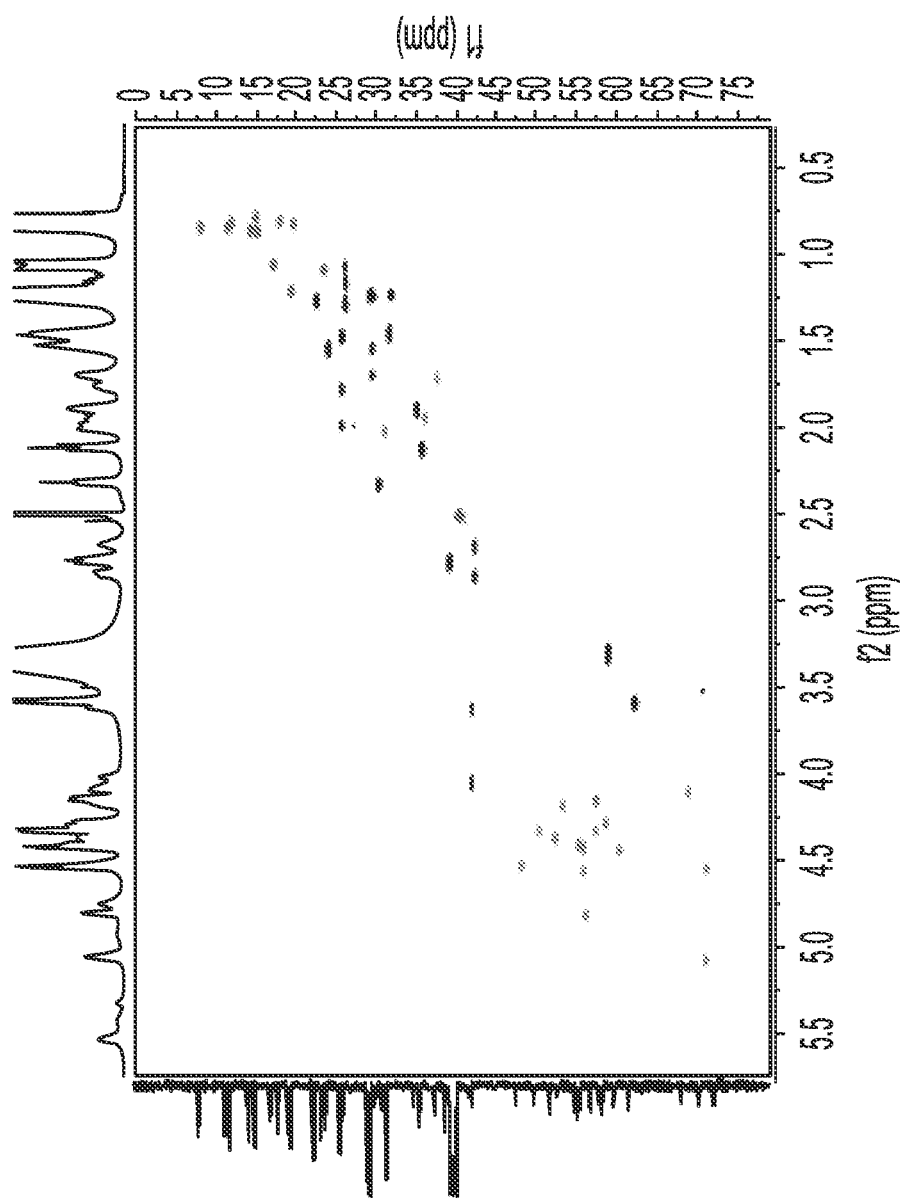
Figure 5F:
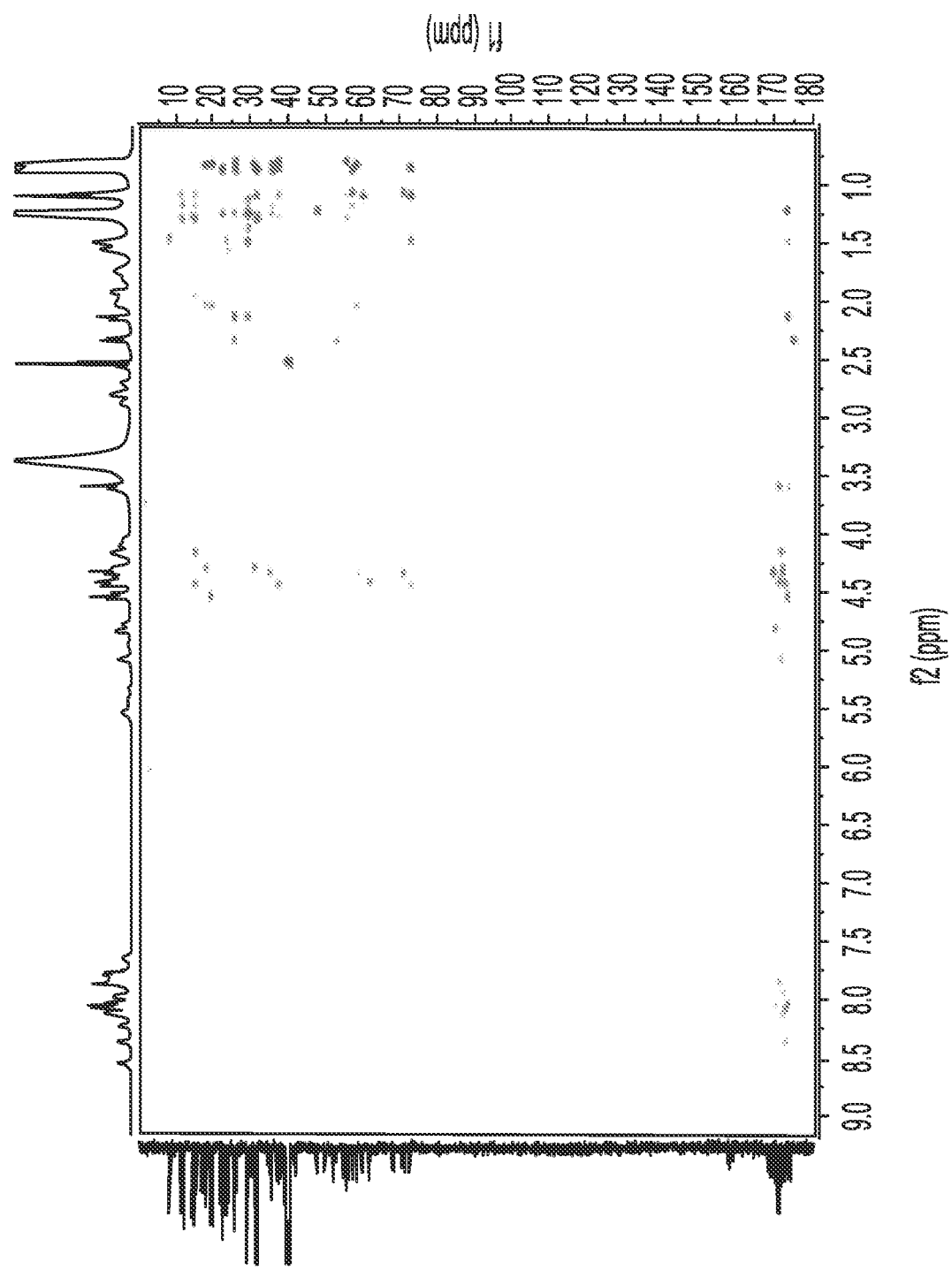
Figure 5G:
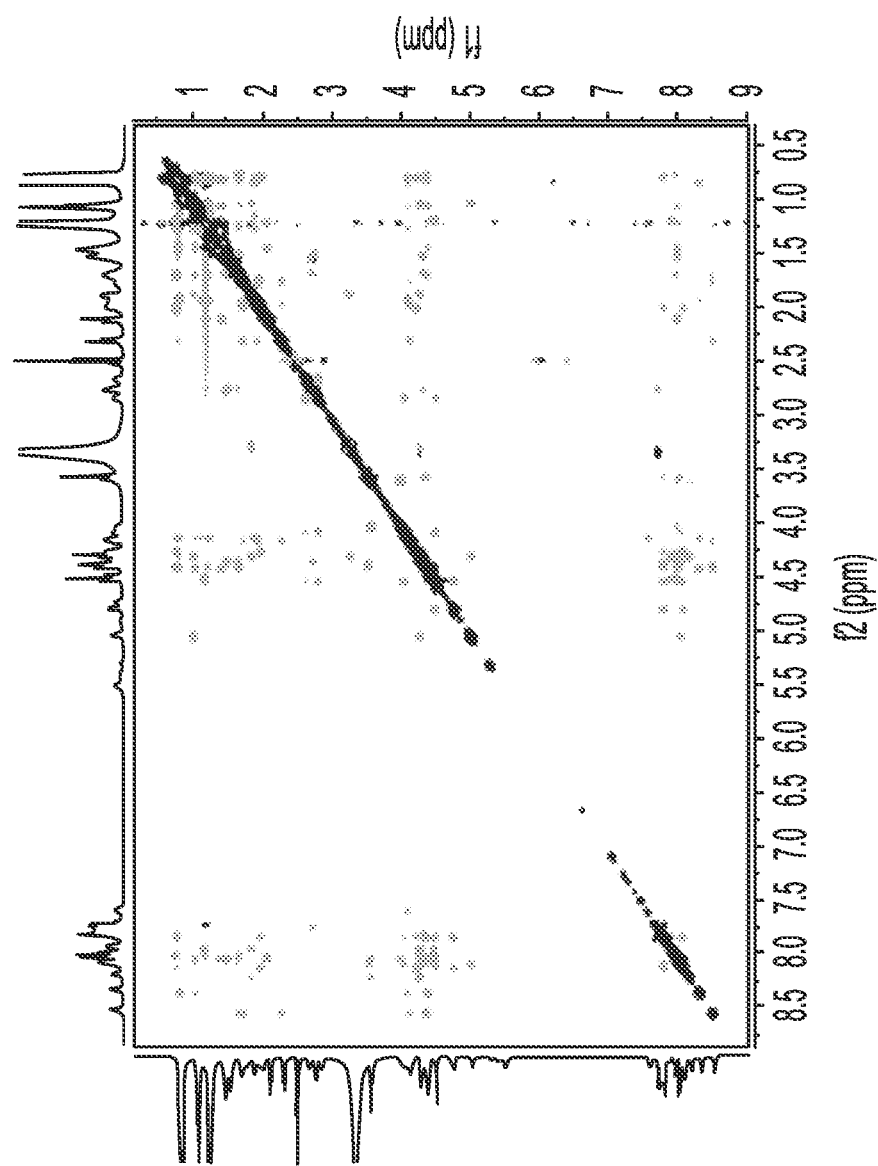
Figure 6A:
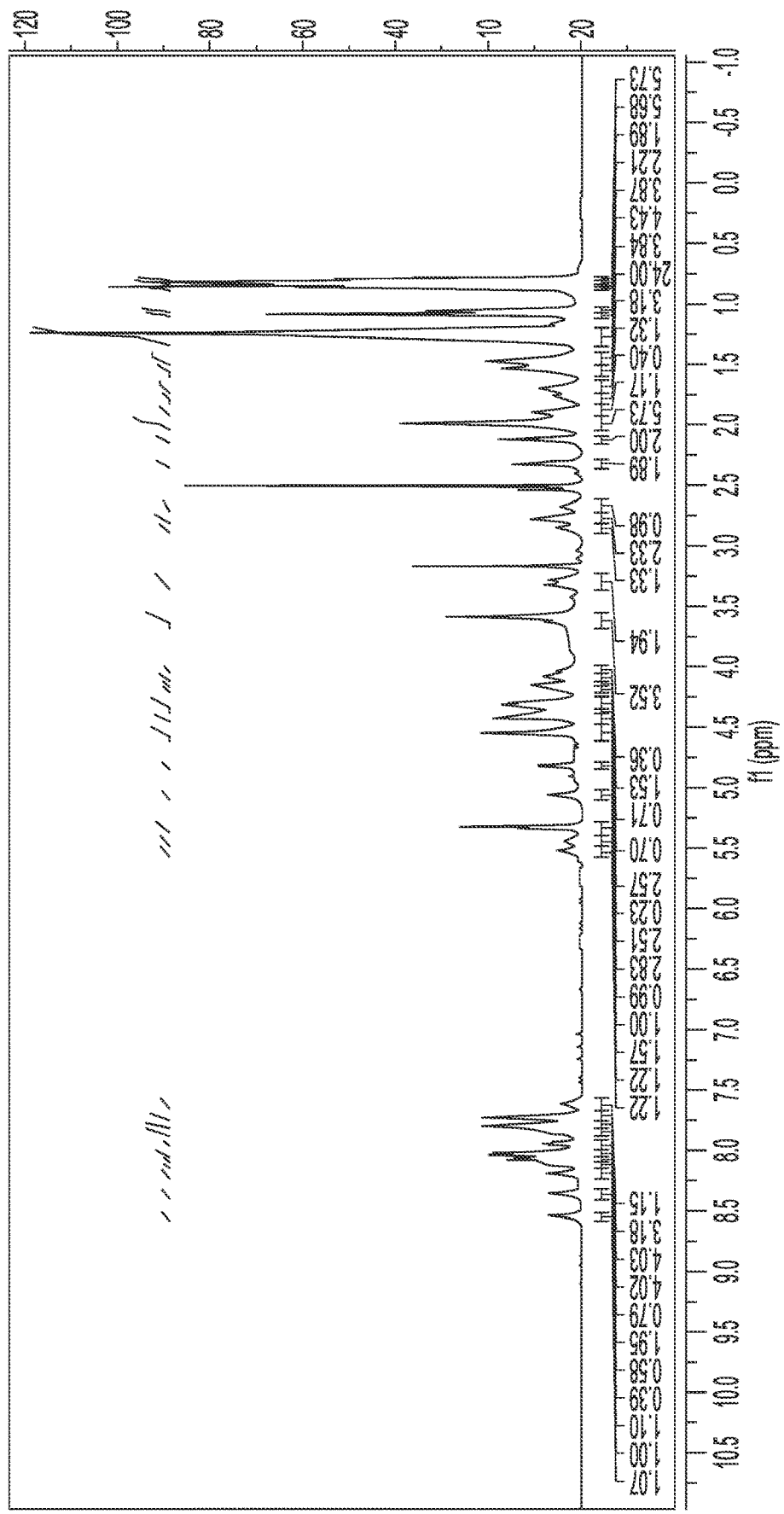
FIG. 6A-G show representative NMR spectra of compound 2.
Figure 6B:
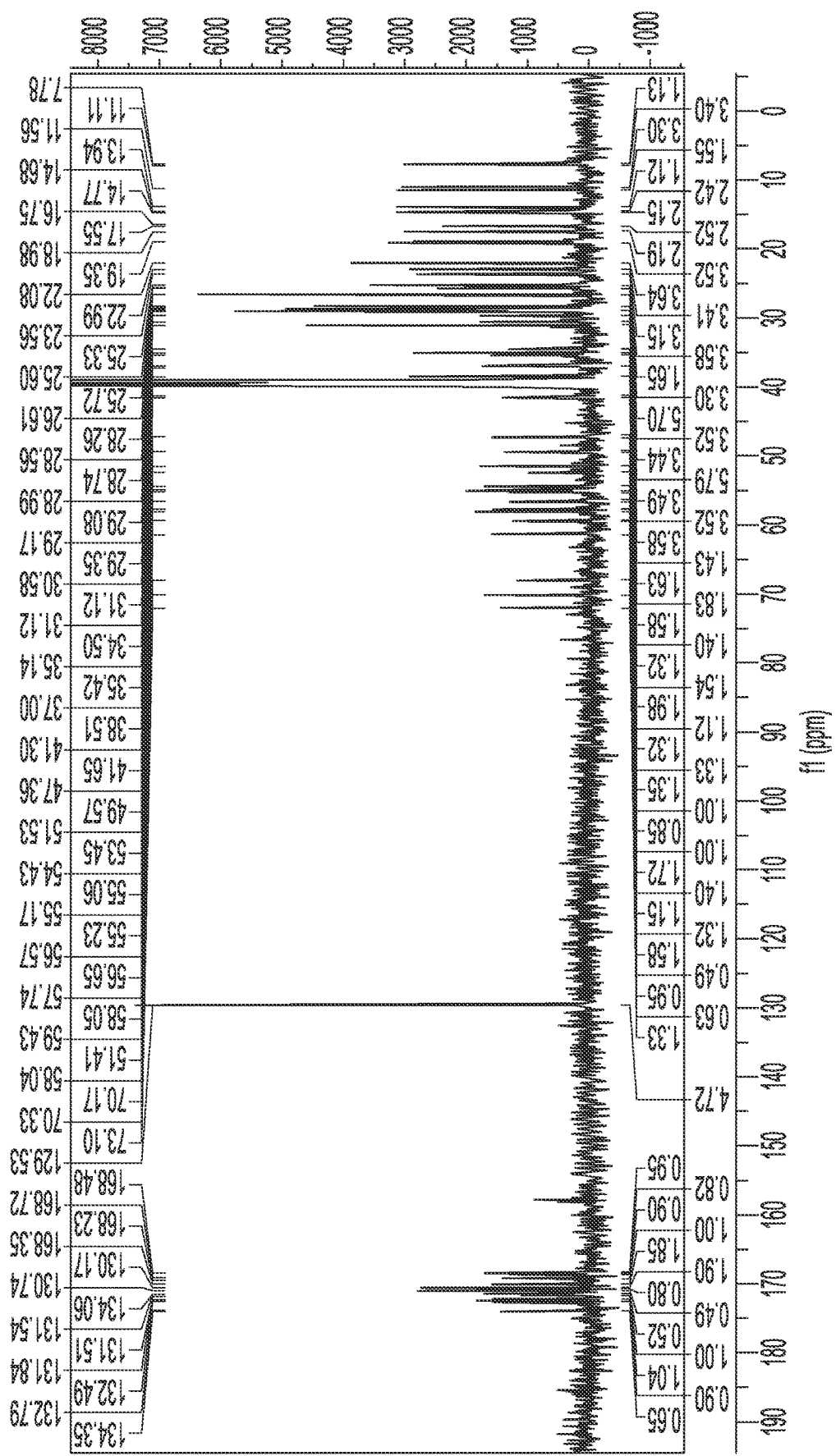
Figure 6C:
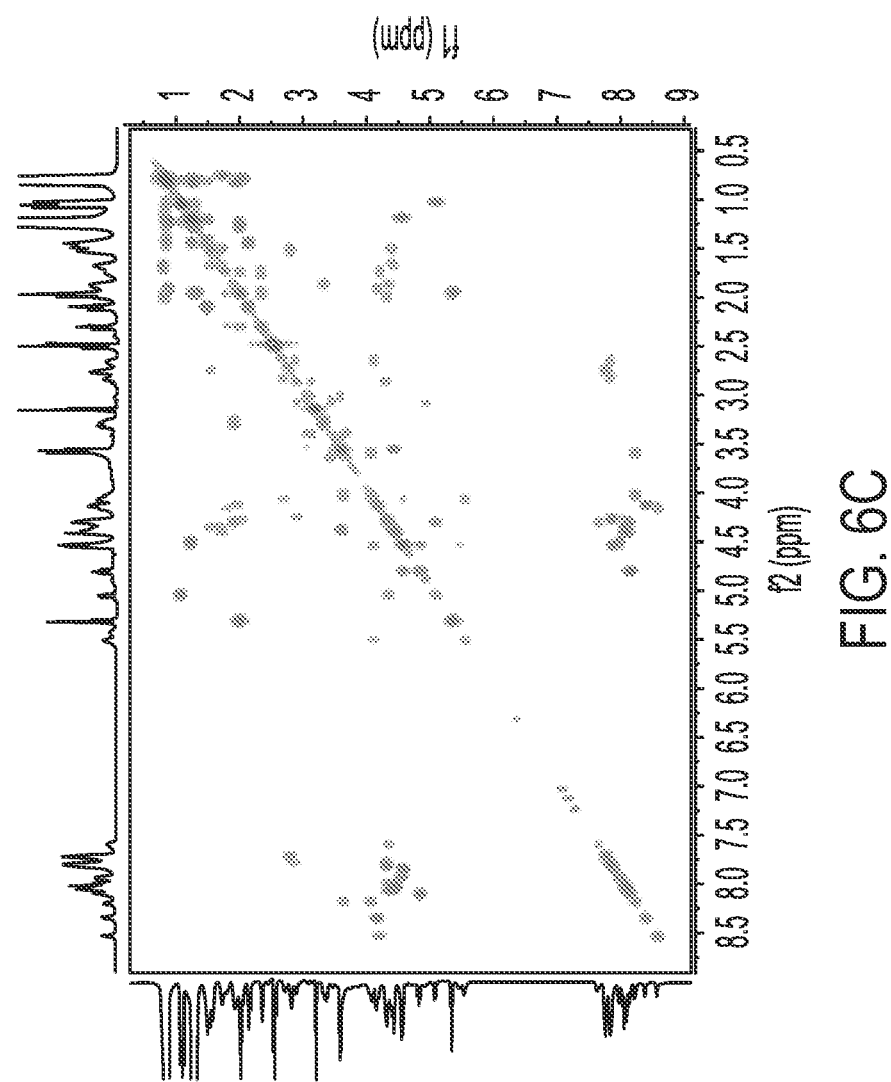
Figure 6D:
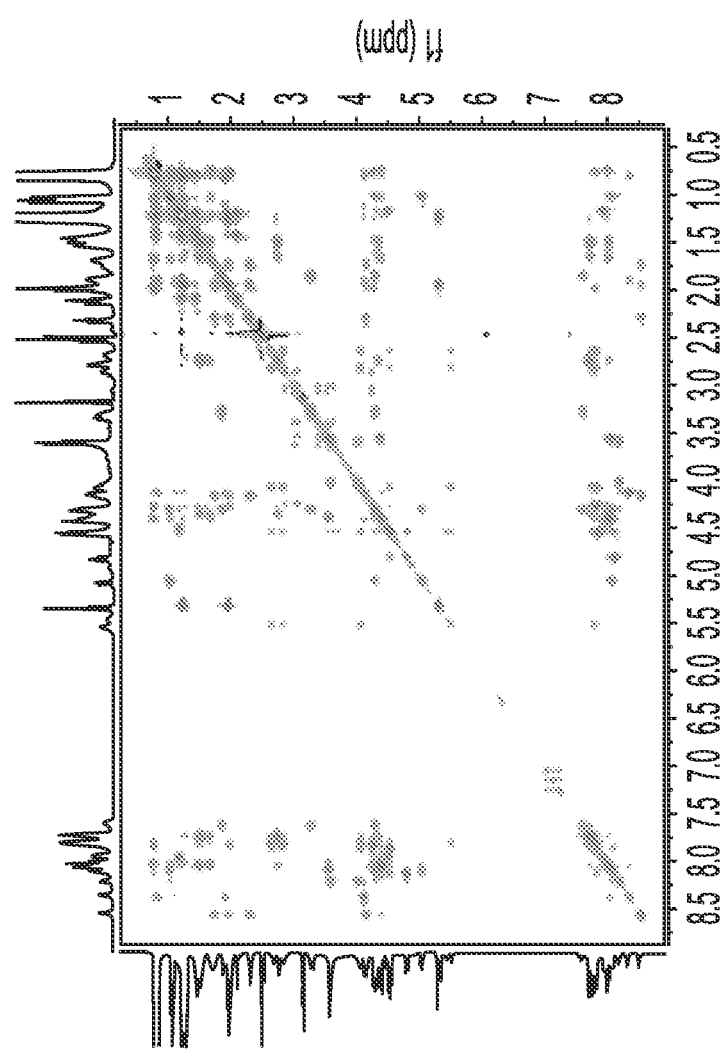
Figure 6E:
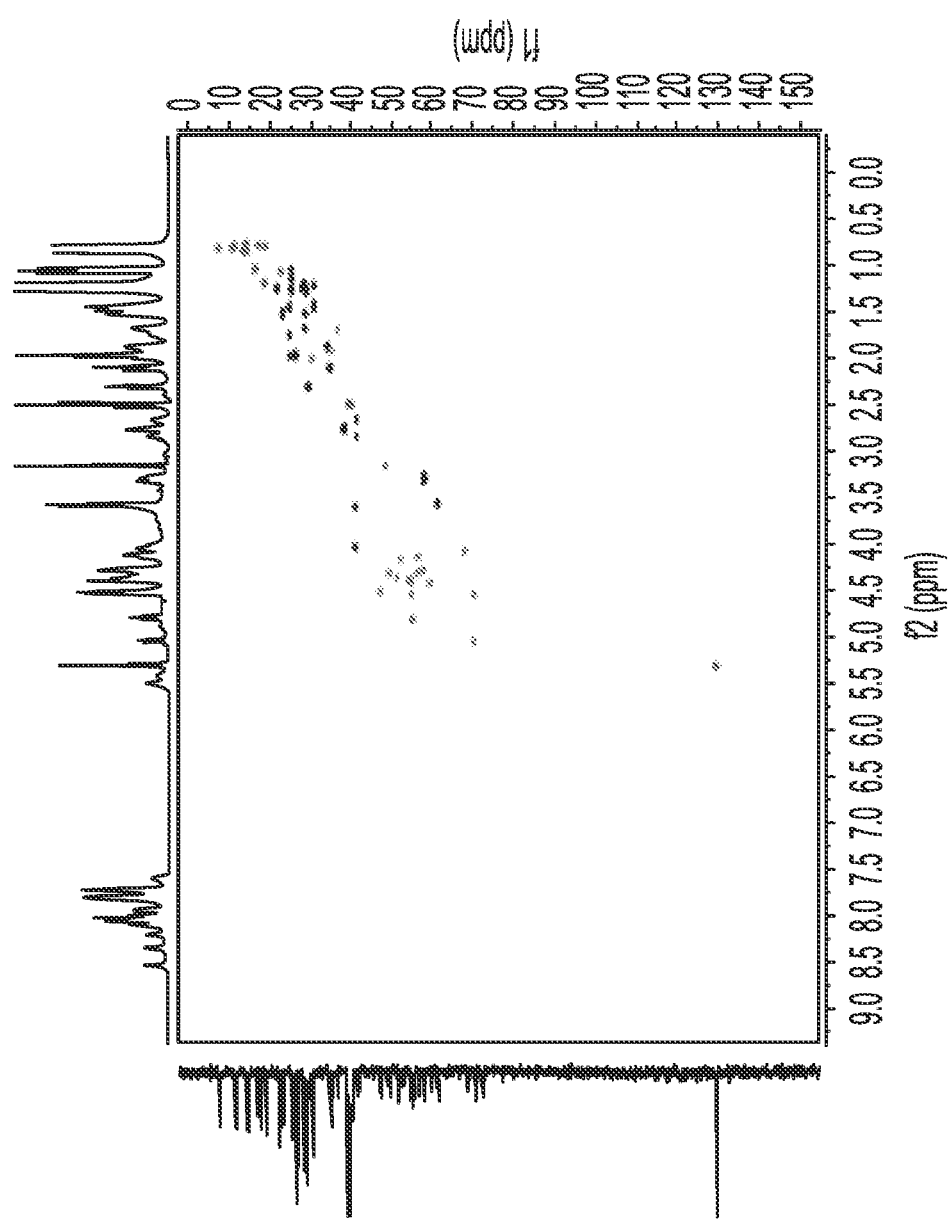
Figure 6F:
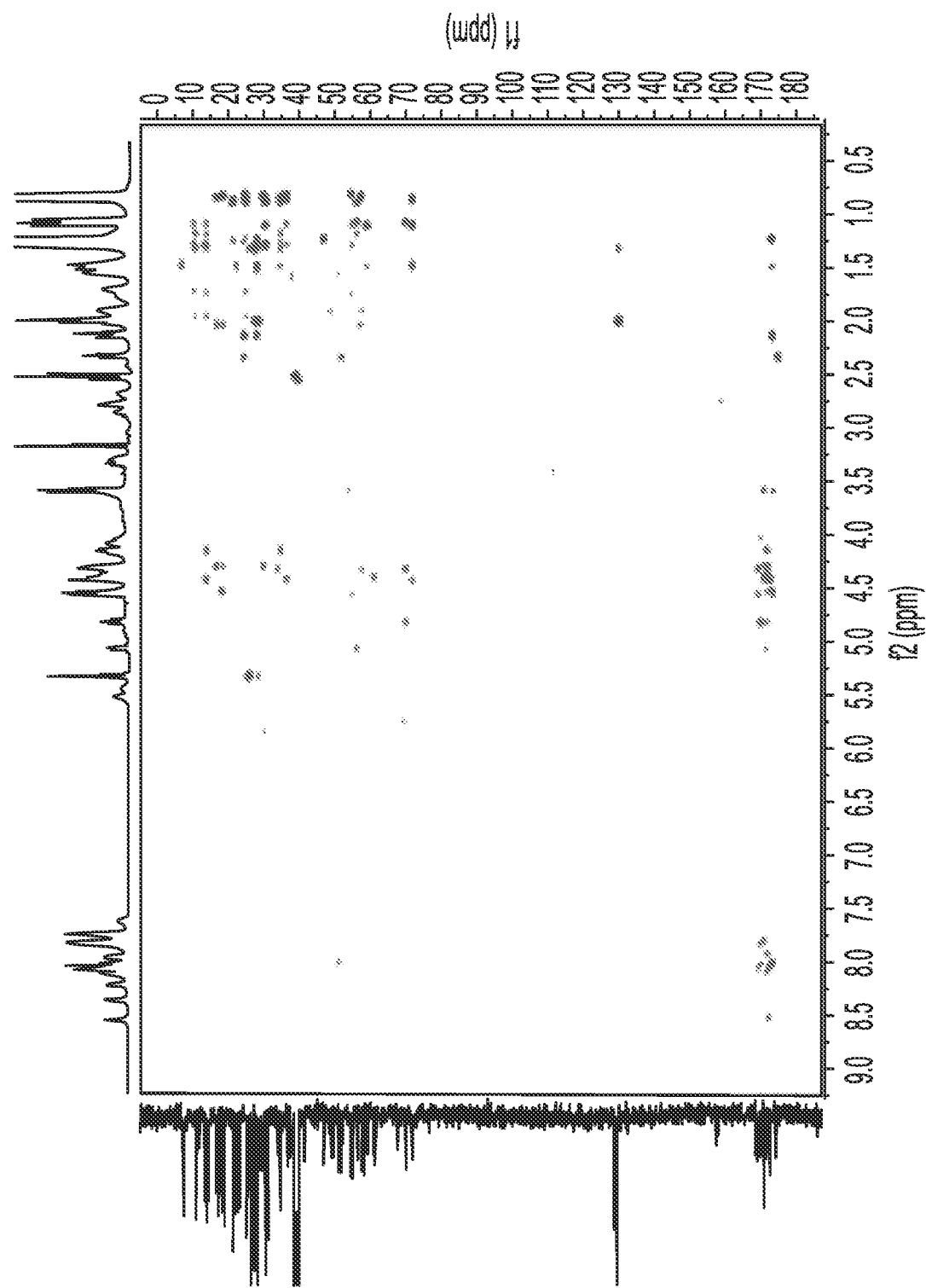
Figure 6G:
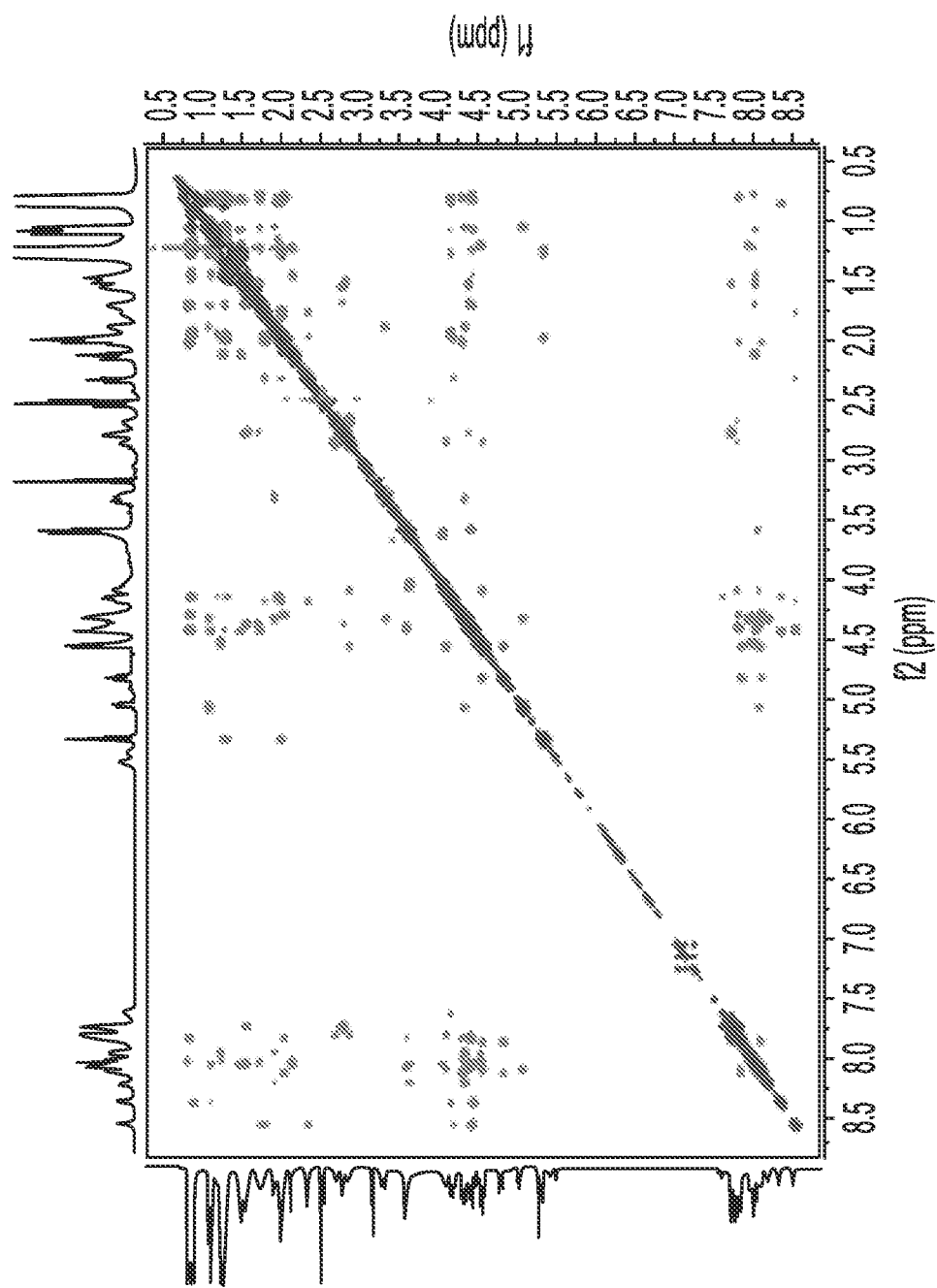
Figure 7A:
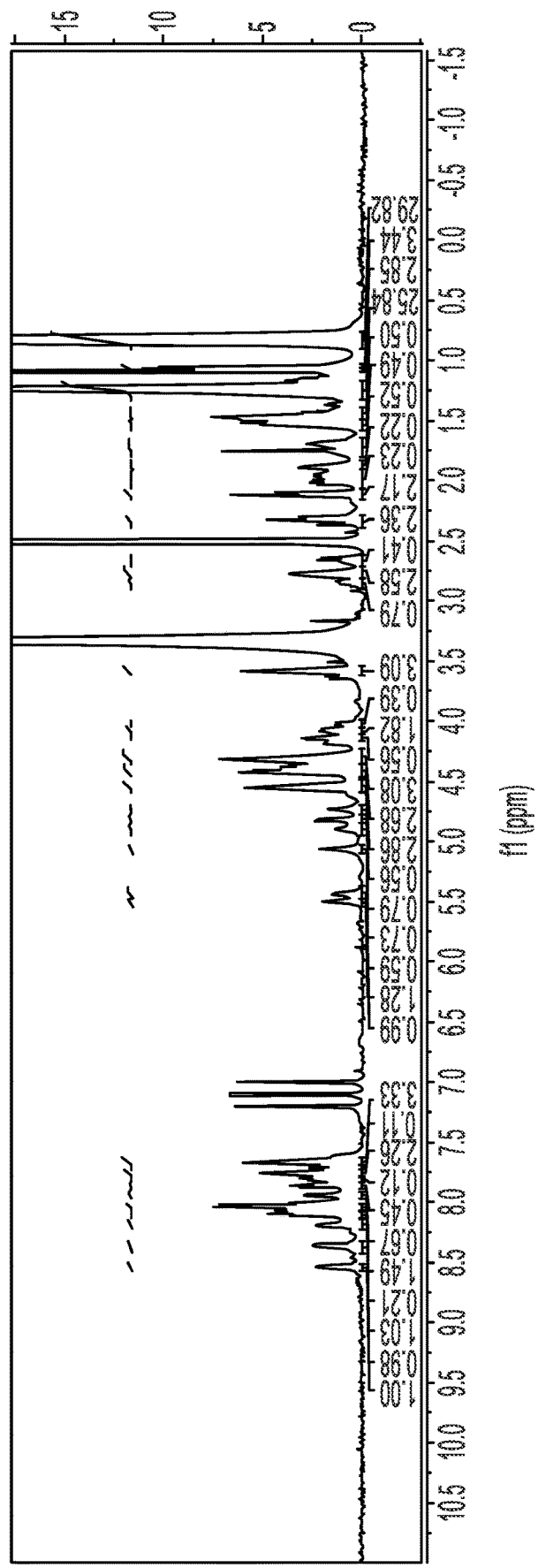
FIG. 7A-D show representative NMR spectra of compound 3 and 4.
Figure 7B:
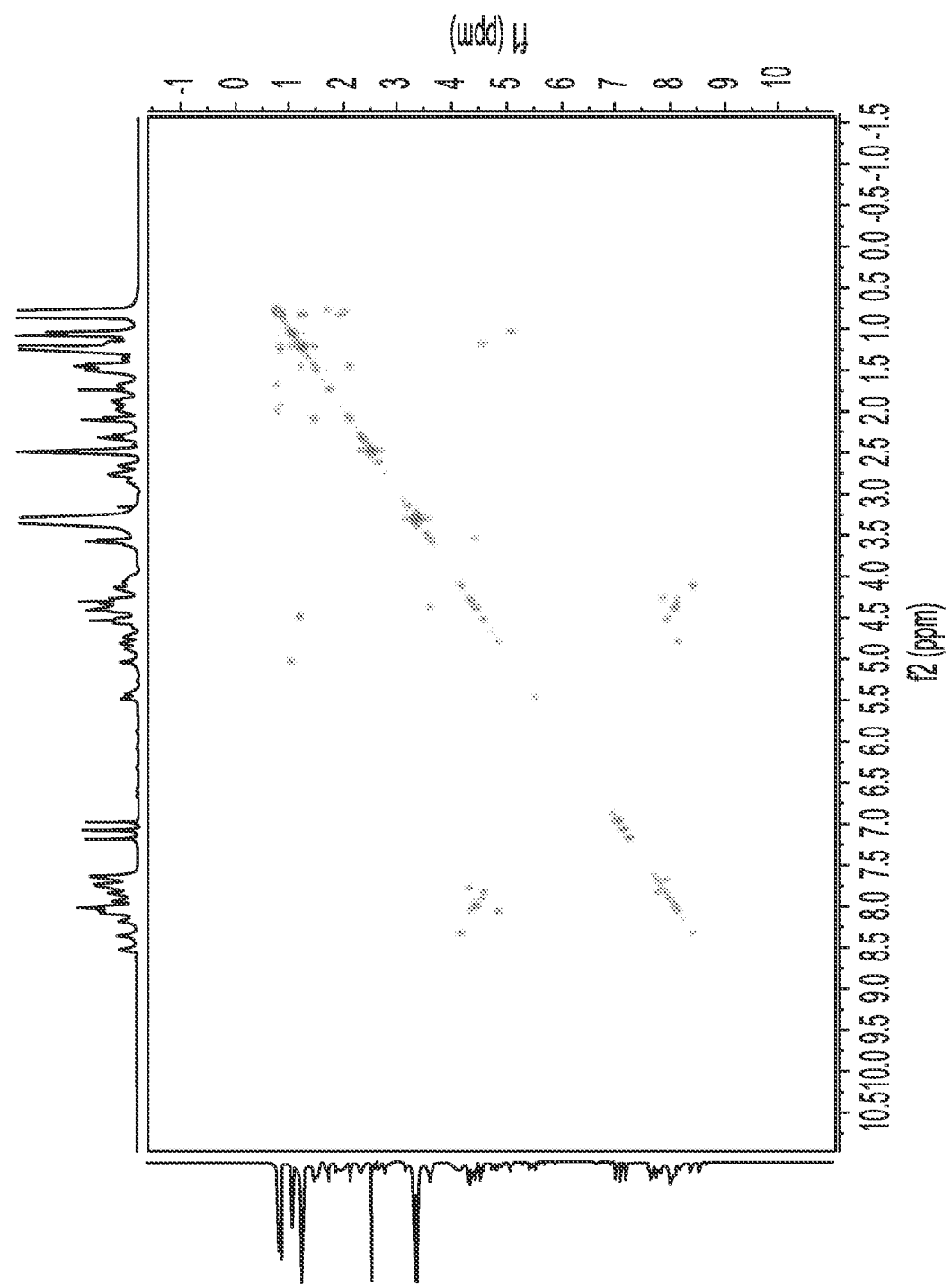
Figure 7C:
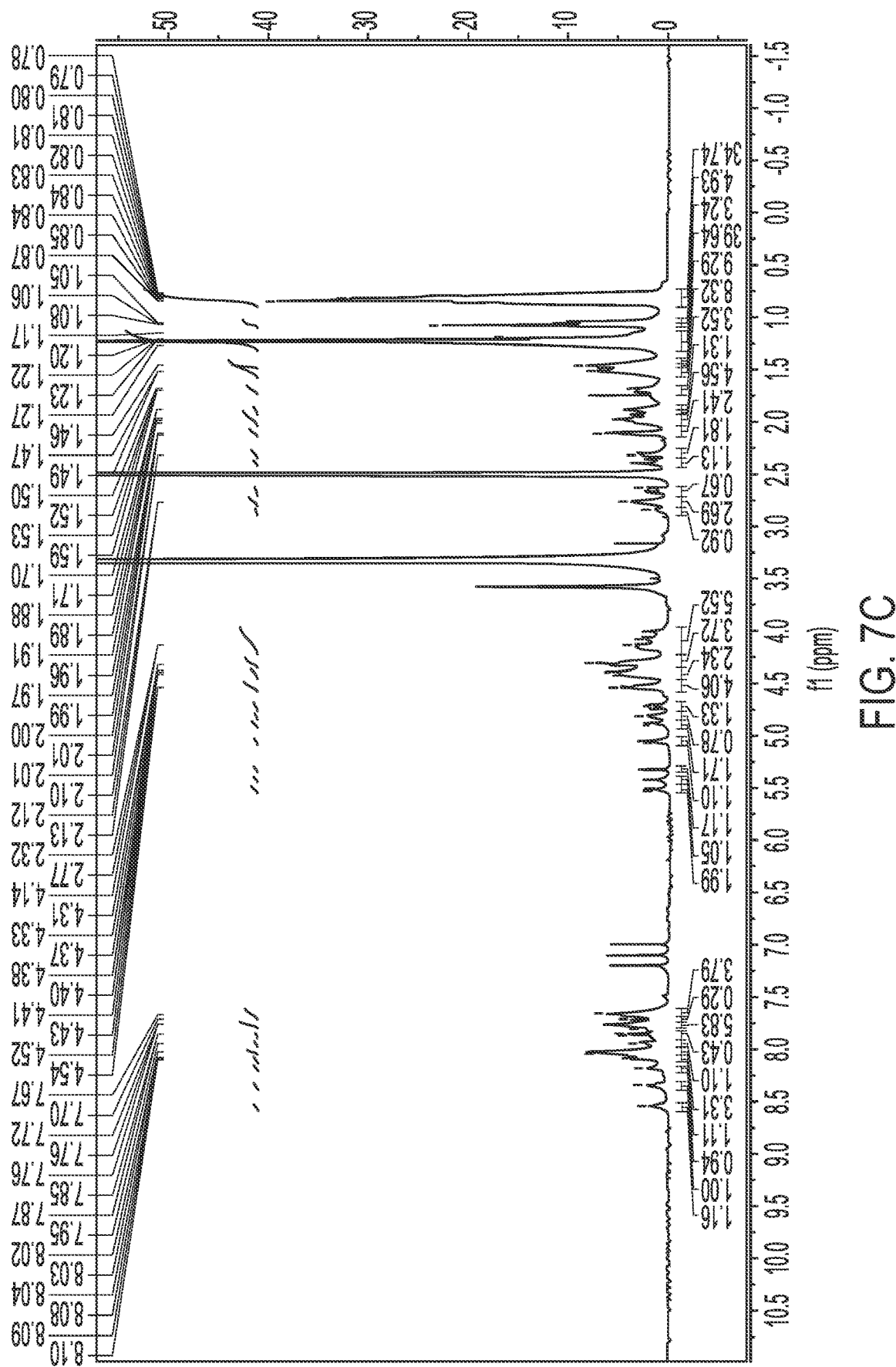
Figure 7D:
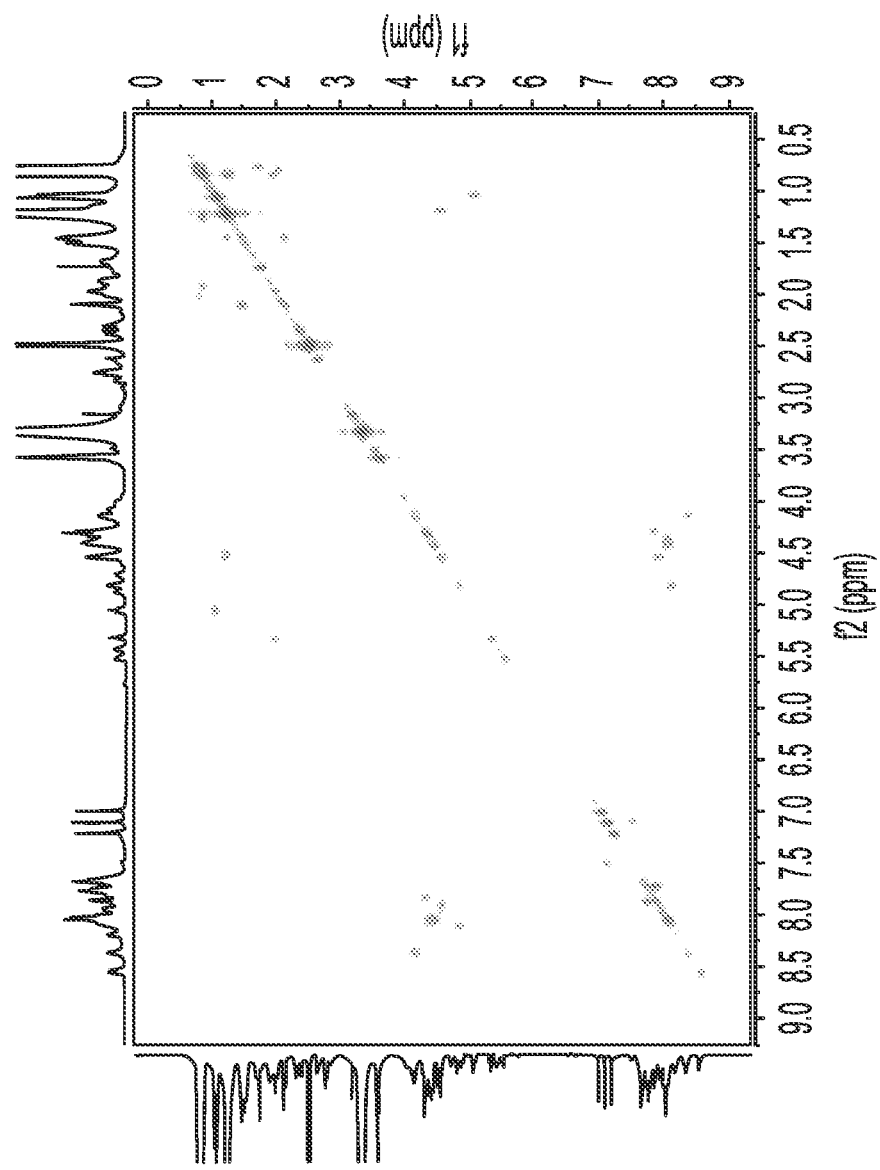

The combination of bactericidal activity against *Acinetobacter* and a lack of observed toxicity led to further investigations of the mechanism of action. A phenotypic assay was employed in which *A. baylyi* was cultivated in the presence or absence of drug, and the morphology and growth characteristics were compared to knockout mutants that are deficient in various proteins (Bailey et al., 2019; Gallagher et al., 2020). A total of 43 genes corresponding to 14 essential processes have been deleted, and the terminal morphologies of the mutant cells are distinct and depend on the process inactivated (FIG. 4). In the presence of either 1 or 2 at the MIC, cells would divide a few times, then their shape would change to be rounded and clumped. This death phenotype was strikingly similar to what is observed in the mutants deficient in outer membrane protein and LPS synthesis (lolCD, bamA, tamAB, and lptAB) (FIG. 4). Treatment with colistin, a clinically used lipopeptide targeting the outer membrane, also produced clumped, rounded cells. At concentrations 4 times the MIC, both 1 and 2 killed cells immediately and without the same morphological changes, potentially indicating a second mechanism at higher concentrations. Previous studies have shown that *Acinetobacter* sensitivity to colistin, an outer membrane targeting lipopeptide used in *Acinetobacter* infections, is greatly decreased by deletion of the 1ptE gene. However, a Δ1ptE *A. baylyi* strain was still sensitive to 1 and 2 at 8 μg/mL, indicating that the tumercyclimycins can act on the outer membrane through a different specific molecular target Overall, these findings imply that the tumercyclaymycins compromise the outer membrane integrity.

If colistin and tumercyclamycins have the same molecular mechanism, it might be expected that colistin-resistant strains would also evade tumercyclamycins. To test this, clinical *A. baumannii* complex isolates were obtained from the Associated Regional and University Pathologists (ARUP) laboratory and the *A. baumannii* panel from the Centers for Disease Control and Prevention (CDC). Six of the CDC strains were tested, including two each of strains susceptible, moderately resistant, and highly resistant to colistin. The three ARUP strains also showed a range of colistin resistance levels. Strikingly, tumercyclamycins retained their potency against these strains, including against highly colistin-resistant *Acinetobacter* strains (Table 5b). Without wishing to be bound by theory, this implies that the molecular mechanisms of these two lipopeptide classes may differ.

TABLE 5B

| Pathogen | MIC (μg/mL) | | |
|---|---|---|---|
| | 1 | 2 | Colistin |
| *Acinetobacter baumannii* | 8 | 8 | 2 |
| ARUP ABC 1 | 4 | 4 | 4 |
| ARUP ABC 2 | 8 | 8 | 4 |
| ARUP ABC 3 | 16 | 8 | >32 |
| CDC AB282 | 4 | 4 | 1 |
| CDC AB286 | 4 | 4 | 1 |
| CDC AB299 | 2 | 4 | 2 |
| CDC AB302 | 8 | 4 | 2 |
| CDC AB303 | 8 | 8 | >32 |
| CDC AB307 | 8 | 8 | 8 |

Since colistin/polymyxin resistance is increasingly important in diverse Gram-negative bacteria, the effectiveness of 1 and 2 against *Yersinia pestis* was also investigated. This belongs to a subset of bacteria in which the linkage of 4-aminoarabinose to the LPS confers polymyxin resistance (Aoyagi et al., 2015). *Y. pestis* susceptibility to 1 and 2 could be neatly correlated to a series of genetic mutants containing and lacking 4-aminoarabinose (Table 5c). Thus, while 1 and 2 are effective against bacteria such as *Acinetobacter*, which resist polymyxins by adding phosphoethanolamine to their LPS (Beceiro et al., 2011), among other mechanisms, they may not be as effective against bacteria that resist polymyxins primarily by adding 4-aminoarabinose.

TABLE 5B

| Pathogen | Ara-4N modification level[a] | MIC (μg/mL) 1 | 2 | Polymyxin B |
|---|---|---|---|---|
| Y. pestis KIM6+ | High | ≥256 | ≥256 | ≥256 |
| Y. pestis ΔarnB | Mid | 8 | 8 | 16 |
| Y. pestis ΔarnOP | Low | 4 | 8 | 0.0625 |
| Y. pestis ΔarOP-Comp | High | ≥256 | ≥256 | ≥256 |

[a]From Aoyagi et al., 2015.

To investigate the potential resistance of *A. baumannii* to tumercyclamiycins, dilutions of wild-type cells were incubated in the presence of 2 at 23 MIC (16 mg/mL) for 4 days. Cells were added in 10 concentrations from 86 to 1.6 3 108 colony-forming units (CFU) per mL, and growth was monitored daily. Wells starting at densities of 10,752 CFU/mL and above were visibly turbid after 24 h. At 96 h, a well containing 2,150 CFU/mL was slightly turbid in one replicate, but not in a second replicate. By contrast, colistin cleared cultures containing up to 1.3 3 106 CFU/mL. Broth was obtained from a well that turned turbid on the fourth day of incubation and plated on medium containing 2 at 23 MIC. Strikingly, only five colonies grew, when a lawn might be expected if cells in the well were resistant to the drug. A surviving colony was used for MIC determination, and interestingly the maximal activity of 2 was reached at the same concentration as the original wild-type strain (8 mg/mL), but only 70% inhibition was achieved, even up to 64 mg/mL (FIG. 11P). This same strain showed no changes in its MIC toward colistin (FIG. 11Q). This indicates an inoculum effect in Mueller Hinton broth for 2 starting at ~104 CFU/mL (Brook, 1989). To investigate this effect on solid medium, dense (108 CFU/mL) cultures of wild-type *A. baumannii* were inoculated and spread on Mueller Hinton Agar containing 43 MIC of 2. A distinct growth pattern was observed in which patches of lawn growth formed where the inoculum was first introduced to the plate, but no growth or colonies were observed where the cells had been spread. Taken together, these findings suggest that standard culture conditions are resulting in inoculum effects that complicate the determination of spontaneous resistance incidence.

2. Discussion

Antimicrobial compounds, particularly those with new structural scaffolds and potentially new mechanisms of action, are in high demand. Each year, at least 35,000 people die from antibiotic-resistant bacterial infections in the United States (Howard et al., 2012; Lee et al., 2017; Piperaki et al., 2019; Wong et al., 2017). This is a number that keeps increasing, as bacteria are increasingly resistant to available drugs. *Acinetobacter* is an especially daunting pathogen, with more than 60% of patient isolated strains showing resistance to standard treatments derived from beta-lactams or fluoroquinolones. An increasing number of strains is extremely drug-resistant, being untreatable even by the last-line lipopeptide agent, colistin (polymyxin E). Because there are very few *Acinetobacter* treatments in development, the US Centers for Disease Control considers carbapenem-resistant *Acinetobacter* to be an urgent threat (Centers for Disease Control and Prevention (U.S.), 2019). Here, a group of lipopeptides that are still effective against colistin-resistant *Acinetobacter* are described. Since clinical isolates resistant to colistin, as well as all other widely used anti-*Acinetobacter* drugs, were used, this provides a chemical entity that might guide development of treatments for multidrug-resistant *Acinetobacter.*

Symbiotic relationships represent unique environments that are promising for antimicrobial natural products discovery. These systems are typically described and understood based on the primary metabolic and nutritional interactions involved. However, exchanges of secondary metabolites also play important roles in these relationships. Microbes living within animal host tissues are of particular interest for antibiotic discovery because compounds made within these contexts must be non-toxic to the host cells and possess properties to facilitate distribution throughout the host tissues, which can translate to favorable pharmacokinetics. The shipworm-*Teredinibacter* symbiotic relationship was investigated as a particularly promising source of antibiotic compounds due to: (1) previous studies showing a nearly axenic cecum, despite this being the site of cellulose degradation, likely resulting in an abundance of free glucose; (2) the presence of bacterial cellulases in this same organ, suggesting a route of transport from symbiont-containing gills to the cecum; and (3) a number of highly conserved biosynthetic gene clusters shared throughout the *Teredinibacter* lineage that could be producing complex PKS and NRPS compounds.

Following the ecology-guided rationale, a new family of *Acinetobacter*-active cyclic lipodepsipeptides, the tumercyclamycins, was isolated and characterized. This family consists of a conserved, NRPS-derived 13 amino acid core sequence and a variable fatty alkyl tail. The peptide portion is cyclized through an ester linkage via the threonine hydroxyl group, resulting in an eight amino acid macrocycle and five amino acid linear portion. A number of features are unique to this structural family, most notably the inclusion of three β-hydroxy amino acid residues, two of which, β-hydroxyisoleucine and 2,4-diamino-3-hydroxy-buatnoic acid, are exceptionally rare. There is precedent for 1-hydroxyaspartic acid in the literature, as it is a common feature of microbial siderophores. Notably, in BGC_1-encoding tumercyclamycins, all of the needed proteins and protein domains are present, including those needed for β-hydroxylation (Reitz et al., 2019; Markolovic et al., 2018; Hibi et al., 2011).

Genes encoding three enzymes likely to perform these hydroxylation reactions are found upstream of the NRPS megasynthases. Two of these, turF and turH, encode non-heme Fe(II)/αKG dependent dioxygenases, while the third, turG, is a cupin domain-containing protein that has similarity to the JmjC family enzymes, which include hydroxylases and demethylases. While it is not currently known which enzyme is responsible for the hydroxylation of each residue, literature precedent and an examination of stereochemistry and domain architecture can give some clues. A recent genomic analysis of aspartyl β-hydroxylases identified two subtypes, one stand-alone Fe(II)/αKG enzyme and one encoded within the NRPS domain (Reitz et al., 2019). All of the known standalone hydroxylases act on the PCP-bound amino acid and produce either the D-threo or L-erythro stereoisomer. The presence of D-threo-o-hydroxyaspartic acid in the tumercyclamycins indicates that either turF or turH is acting in this capacity. While the same analysis identified 31 absolutely conserved residues in all previously described aspartyl hydroxylases, neither turF nor turH contains all 31. However, turH does contain 29/31 conserved residues, and aligns more closely with the sequences of the aspartyl hydroxylases, and is thus a good candidate for this particular tailoring reaction.

It is unclear how the other two hydroxylated amino acids are formed. Due to the high prevalence of DAB moieties in lipopeptides, it is feasible that DAB is first incorporated into the growing chain, then hydroxylated while bound to the thiolation domain, similar to the aspartic acid. However, there is precedent for post-translational β-hydroxylation of lysine residues on proteins by jmjC oxygenases (Markolovic et al., 2018). BLAST analysis of turG showed a conserved jmjC domain, so this possibility cannot be ruled out. Finally, there is literature precedent for the hydroxylation of free amino acids, including isoleucine, by Fe(II)/αKG dependent dioxygenases (Hibi et al., 2011). While the adenylation domains in the modules responsible for incorporating the two Ile residues are almost identical, they only share approximately 55% identity to the A domain of turC that incorporates OH-Ile. It is feasible that one of the dioxygenases is acting upon free Ile to produce a local pool of β-OH-Ile, which is then recognized as the substrate for the A domain and incorporated into the growing chain.

The chemical properties of the tumercyclamycins are also intriguing when considering their mechanism of action. One of the last line defenses for resistant *Acinetobacter* infections is colistin, which is a polycationic cyclic lipopeptide that acts through disruption of the outer membrane (Li et al., 2006). It is believed that the highly cationic peptide portion, which gains its positive charges through the side chains of five DAB moieties, displaces magnesium and calcium counter ions in the LPS, while the lipid tail works to solubilize the membrane through a detergent-like mechanism (Dixon and Chopra, 1986). The tumercyclamycins, on the other hand, are not rich in DAB residues or other cationic peptide side chains, and indeed maintain a neutral charge balance. This chemical property may be important in explaining how the tumercyclamycins retain activity against colistin-resistant strains, and likely points to a different molecular mechanism of action that accomplishes the same goal of outer membrane disruption. By contrast, some Gram-negative bacteria, including *Y. pestis*, incorporate 4-aminoarabinose into their LPS to evade polymyxins and other cationic antimicrobial peptides. This mode of resistance is clearly effective against tumercyclamycins, revealing that the compounds may exhibit therapeutic selectivity. In addition, the lack of toxicity or hemolytic activity of tumercyclamycins suggest that they may make useful therapeutics. Although we did not observe emergence of classic resistance mutations, the bacteria could evade inhibition by other means under certain conditions. An inoculum effect was observed, which warrants further study. This effect is similar to that reported for daptomycin, and further knowledge of the molecular mechanism of action and ion dependence of tumercyclamycin will be necessary to allow for more accurate resistance studies (Quinn et al., 2007; Silverman et al., 201). Further, in vivo evaluation is required to determine the potential clinical utility of the compounds.

It is clear that secondary metabolism plays a large role in the association between *T turnerae* and their shipworm hosts, albeit largely underexplored. Thus far, three compound families that are completely conserved among *T turnerae* have been described that play logical roles in symbiosis biology. The exquisite potency of tartrolon D/E against apicomplexan parasites is hypothesized to protect the mollusk from gregarines, which are known to be pathogens of mollusks (Elshahawi et al., 2013; O'Connor et al., 2020; Rueckert et al., 2019). Tumerbactin, the triscatecholate siderophore, may be important both for the acquisition of iron for the symbiont and host, as well as for the sequestration of iron to limit the growth of pathogenic or opportunistic bacteria (Han et al., 2013). This most recent discovery of the tumercyclamycins represents the addition of a potent bactericidal agent to the molecular arsenal of *T. turnerae*, capable of directly killing bacteria that pose threats to its shipworm host, their shared food supply, or the ecological niche of the symbiont itself. This finding underscores the importance of closely examining the chemical biology of symbiotic systems with a particular focus on ecological rationale and metagenomics in the pursuit of new pharmacological agents for improved human health.

3. Materials and Methods a. General Experimental Procedures

UV-vis spectra were obtained using a Molecular Devices SpectraMax M2 spectrophotometer. High resolution mass spectra were acquired using a Waters Xevo G2-XS QT of mass spectrometer equipped with a Zspray ESI source and fed by an Acquity H class UPLC system with a Waters Acquity CSH C18 column (2.1×50 mm, 1.8 µm). NMR data were collected using a Varian 500 MHz NMR spectrometer with 5 mm Varian HCN Oneprobe for proton detected experiments and a 3 mm Varian inverse probe for carbon detected experiments ($^1$H 500 MHz, $^{13}$C 125 MHz). Residual signals from solvents were used for referencing. ECD spectra were obtained on an AVIV Biomedical, Inc. CD Spec Model 410 (Lakewood, NJ, USA). Analytical and semi-preparative HPLC was performed on a Thermo Ulti-Mate 3000 system with a DAD detector.

b. Bacterial Strains and Culture Media

*T. turnerae* T7901 was grown in shipworm basal medium (SBM) (Waterbury et al., 1983). *Staphylococcus aureus* (*S. aureus* subsp *aureus* ATCC 1600), *Enterococcus faecalis* (ATCC 29212), *Klebsiella pneumoniae* (ATCC BAA-1705), *Acinetobacter baumannii* (ATCC 19606), and the CDC strains AB282, AB286, AB299, and AB302 were grown in Mueller Hinton Broth II (MHBII). *E. coli* was grown in Luria-Bertani broth. Each strain was grown from a single colony. *T. turnerae* was grown at 30° C. with 180 rpm shaking, while all other strains were grown at 37° C. with 220 rpm shaking.

c. Mammalian Cell Lines and Culture Methods

HEK-293 (ATCC CRL-1573) cells were cultured in RPMI 1640 medium supplemented with 10% fetal bovine serum, 100 units of penicillin, and 100 mg/mL of streptomycin under a humidified environment with 5% $CO_2$ at 37° C.

d. Chemical Extraction of *T. Turnerae* and Purification of Turnercyclamycins

A glycerol stock of *T turnerae* T7901 was revived by streaking 5 µL on a plate of Shipworm Basal Medium (SBM). (40) 5 mL liquid SBM cultures were inoculated with single colonies and incubated at 30° C. with shaking at 180 RPM for 4 days. These seed cultures were used to inoculate six liquid SBM (with phosphate f/c=15 µM) 1.1 L cultures in 2.8 L baffled Fembach flasks, which were incubated at 30° C. with shaking at 180 RPM for 7 days. Cells were removed from culture media by centrifugation at 7,068×g, 4° C., for 30 min. The supernatant was decanted, and the cell pellet was frozen and lyophilized to dryness.

The dry cell pellet was extracted three times with 400 mL each of 2:1 DCM:MeOH. The extracts were combined and concentrated in vacuo to remove DCM, and water was added to a composition of 5% v/v in MeOH, then partitioned 3 times with an equal volume of hexanes. The methanolic fraction was dried in vacuo, then partitioned 3 times between equal volumes of water and DCM. The aqueous layer was then subsequently partitioned 3 times with equal volumes of ethyl acetate. This step formed a particularly well-defined insoluble boundary layer, which was collected separately.

The boundary layer was dried in vacuo then re-suspended in MeOH. This was centrifuged to pellet insoluble material, then the supernatant was filtered (Nylon, 0.45 μm) and subjected to semipreparative RPHPLC (Phenomenex Luna Cis column, 250×10 mm, 5 μm, flow rate 4.0 mL/min). Isocratic conditions (20% ACN/80% $H_2O$/0.01% TFA) were held for 5 min followed by a linear gradient to 75% ACN/25% $H_2O$/0.01% TFA for 15 min to yield turnercyclamycins A-D (1, $t_R$=15.3 min, 5.6 mg; 2, $t_R$=15.8 min, 6.8 mg; 3, $t_R$=14.2 min, 0.9 mg; 4, $t_R$=16.8 min, 0.6 mg).

Turnercyclamycin A (1): Off-white amorphous solid; UV/vis: $\lambda_{max}$ 250, 270 nm; IR (neat) $v_{max}$ 32%, 3067, 2930, 1645, 1538, 1204, 1140 cm$^{-1}$; $^1$H and $^{13}$C NMR data in DMSO-$d_6$, Table 2; HRESIMS [M+2H]$^{2+}$ ion at m/z=786.9619 (calculated for $C_{71}H_{125}N_{15}O_{24}$: 786.9584).

Turnercyclamycin B (2): Off-white amorphous solid; UV/vis: $\lambda_{max}$ 250, 270 nm; IR (neat) $v_{max}$ 32%, 3065, 2921, 1645, 1540, 1204, 1139 cm$^{-1}$; $^1$H and $^{13}$C NMR data in DMSO-$d_6$, Table 2; HRESIMS [M+2H]$^{2+}$ ion at m/z=799.9693 (calculated $C_{73}H_{127}N_{15}O_{24}$=799.9662).

Turnercyclamycin C (3): Off-white amorphous solid; $^1$H NMR in DMSO-$d_6$, FIGS. 7A-D; HRESIMS [M+2H]$^{2+}$ ion at m/z=772.9473 (calculated for $C_{69}H_{121}N_{15}O_{24}$: 772.9427).

Turnercyclamycin D (4): Off-white amorphous solid; $^1$H NMR in DMSO-$d_6$, FIGS. 7A-D; HRESIMS [M+2H]$^{2+}$ ion at m/z=793.%21 (calculated for $C_{72}H_{127}N_{15}O_{24}$: 793.9662).

e. Synthesis of 2,4-Diamino-3-Hydroxy-Butanoic Acid

5-Hydroxyectoine (12.1 mg, 0.0765 mmol) was dissolved in water (2 mL). NaOH (2 equiv., 0.153 mmol, 6.12 mg) was added and the mixture was stirred at 50° C. for 6 h. The solvent was removed under a stream of $N_2$ gas, and the resulting residue was dissolved in aqueous HCl (6N, 2 mL), and the mixture was heated at 110° C. for 3 h. The solution was diluted with water (4 mL), frozen at −80° C., then lyophilized. The resulting residue was dissolved in water (1.53 mL) and analyzed by advanced Marfey's method, described below.

f. Determination of Amino Acid Stereochemistry 1 mL 6 N HCl was added separately to 1 mg of 1 and 1 mg of 2 and the reaction vessels were heated to 100° C. with stirring for 24 h. Solvent was evaporated under a stream of nitrogen gas and the resulting residues were dissolved in 250 μL of H2O. 50 μL of each hydrolysate solution was transferred to a clean glass vial, to which 20 μL aqueous 1 M NaHCO$_3$ and 100 μL Marfey's reagent (L-FDLA, 1% solution in acetone, TCI Chemicals) were added. The reactions were incubated for 1 h at 40° C., then quenched with 20 μL 1 N HCl. Ibis solution was filtered through a polypropylene filter (0.45 μm), then diluted into MeOH for UPLC-MS analysis. Analysis was performed on an analytical Waters Acquity® UPLC equipped with a Acquity® HSS T3 column (100×2.1 mm, 1.8 μm, Waters, flow rate =0.3 mL min-1, method: 0-2 min: 20% (v/v) ACN in water containing 0.1% formic acid; 2-30 min: linear gradient 20%-65% ACN in water containing 0.1% formic acid; 30-31 min: linear gradient 65%-100% ACN in water containing 0.1% formic acid). Amino acid standards were derivatized in the same manner for comparison, and D-FDLA was used to derivatize L-configured amino acid standards to obtain the retention times for D-amino acids. Retention times for amino acids derived from 1, 2, and amino acids standards are summarized in Table 6.

TABLE 6

| Amino Acid | $t_{rL-FDLA}$ (min) Analyte | $t_{rL}$ (min) Standard | $t_{rD}$ (min) Standard |
|---|---|---|---|
| Valine | 14.58 | 14.63 | 18.7 |
| Alanine | 12.54 | 12.61 | 15.15 |
| Serine | 10.36 | 10.41 | 11.01 |
| Threonine | 10.17 | 10.25 | 13.27 |
| allo-Threonine | N/A | 10.8/12.05 | 10.8/12.05 |
| Isoleucine | N/A | 16.11 | 20.6 |
| allo-Isoleucine | 20.49 | 15.95 | 20.49 |
| Glutamic acid | 11.51 | 11.51 | 12.4 |
| Homoserine | 10.36 | 10.47 | 11.44 |
| β-OH-Aspactic Acid | 8.66 | 8.73 | 8.66 |
| αN, δN-diFDLA Ornithine | 20.4 | 20.82 | 20.45 | g. Antimicrobial Microdilution Assay

Glycerol stocks of *Staphylococcus aureus* (*S. aureus* subsp *aureus* ATCC®16001), *Enterococcus faecalis* (ATCC® 29212™ *Klebsiella pneumoniae* (ATCC® BAA-1705™), and *Acinetobacter baumannii* (ATCC® 196061) were streaked on Mueller Hinton Agar (MHA). *Escherichia coli* (ATCC® 237241), on the other hand was streaked on Luria-Bertani agar (LBA) plates. Plates were incubated at 37° C. for 8-12 h. Single colonies from the plates were then transferred into Mueller Hinton Broth II (MHB II) (Luria-Bertani broth for *E. coli*) and incubated for 6-8 h at 30° C., 150 rpm. The turbidity of the broth culture was then adjusted to match 0.5 McFarland standard (1×10$^8$ cells/mL). The adjusted broth culture was diluted 200-fold and used as inoculum for the assay. 200 μL of each test organism was added to each well of a 96-well flat plate. Compounds were then added using a two-fold dilution scheme starting at 64 μg/mL with 8 dilutions each. Following 18-20 h incubation, ten microliters of MTT (5 mg/mL) were added to wells and incubated for 2 hours. One hundred microliters of DMSO was then added to wells and incubated for 1 hour. The $A_{570}$ was then measured using a Biotek-Synergy 2 Microplate Reader (Biotek, Winooski VT). For *Y. pestis*, testing was performed at 28° C. as previously described (Aoyagi et al., 2015) except cation-adjusted Mueller Hinton broth was used instead of HI broth.

h. Mammalian Antiproliferative Assay

HEK-293 (ATCC(@CRL-1573™) cells were cultured in RPMI 1640 medium supplemented with 10% fetal bovine serum, 100 units of penicillin, and 100 μg/mL of streptomycin under a humidified environment with 5% C02 at 37° C. The cells were seeded (10000 cells/well) in 96-well plates and treated after 24 h with varying concentrations of the compound. After 72 h, the media was removed and 15 μL of MTT (5 mg/mL) was added to each well. The plates were then incubated for 3 h at 37° C., 5% C02. After incubation, 100 μL of DMSO was added and absorbance was read at 570 nm using a Biotek-Synergy 2 Microplate Reader (Biotek, Winooski VT).

i. Hemolysis Assay

Hemolytic activity of the compounds was measured using freshly purified 0.25% Cgrp grp mouse red blood cell suspension in 1×phosphate buffered saline (PBS). Various concentrations of the compounds were then added to the red blood cell suspension in 2-fold serial dilutions, and incubated for 1 h at 37° C. The suspension was then centrifuged at 1000 g for 5 min and the supernatant was collected. 100 μL of the supernatant was then transferred to wells of a 96-well plate. Absorbance was then read at 540 nm using a Biotek-Synergy 2 Microplate Reader (Biotek, Winooski VT). Results are reported as concentration of compound resulting in 10% hemolysis with Triton X-100 as positive control.

j. Dilution Broth Inhibition Experiments

*A. baumannii* (ATCC 19606) was grown overnight, as described above. The correlation between OD600 and CFU/mL was determined by plating serial dilutions and counting colonies. Five plates at each concentration were used to count colonies. At the same time, this initial seed culture was used to initiate dilution experiments and was serially diluted 5-fold 10 times, for a final dilution series ($1.6 \times 10^8$, $3.36 \times 10^7$, $6.72 \times 10^6$, $1.34 \times 10^6$, 268,800, 53,760, 10,752, 2,150, 430, 86 CFU/mL). Each dilution (200 mL) was placed in 5 replicate wells, for a total of 50 wells, to which was added 2 at 2×MIC (16 mg/mL). In addition, each dilution (200 mL) was added to the plate in triplicate without antibiotic. Two biological replicates were performed, with 96-well plates at 37° C. for 96 h. Plates were monitored every 24 h by observing turbidity. At 96 h, plates were removed from incubation, and an MTT test was performed. One plate was used with colistin at 2×MIC in an identical manner. From one of the broth dilutions that was turbid at 2,150 CFU/mL, broth (100 mL) was plated on MHBII in the presence of 2×MIC, yielding 5 colonies. One of these was picked, and its MIC was determined in the same manner described above.

k. Microscopy of Growth-Inhibited Bacteria

*A. baylyi* strain ADP1 overnight cultures grown in M9 minimal-succinate medium were diluted 1:4 and grown with shaking for one additional hour at 30° C., followed by spotting on thin minimal-succinate agar pads containing different drugs [tumercyclamycin (8 mg/mL) or colistin (0.5 mg/mL)] (Bailey et al., 2019). Bacteria were imaged after 8 h incubation at 30° C. Terminal morphologies of essential gene deletion mutants were evaluated after transformation with kanamycin-resistance marked PCR fragments as described earlier (Bailey et al., 2019; Gallagher et al., 2020). Phase contrast imaging was performed using a Nikon Eclipse 90 microscope using a 100×oil objective.

l. Tur Gene Clusters Analysis in *T. Turnerae* Strains

A full or partial tur gene cluster was extracted from antiSMASH output of each *T. turnerae* genome assembly using multigeneblast with tur in 17901 as reference. Protein sequences of a full NRPS genes (according to "CDS" feature) or A-domains (according to "aSDomain" feature) were extracted from the antiSMASH output genbank file using a bash script (see below). The identity between NRPS genes or A-domains were calculated by BLASTp search (-outfmt "6 qseqid sseqid pident length evalue qcovs qlen slen"). An identity matrix table was made and plotted in R 3.5 using the pheatmap package.

```
#!/bin/bash
  rm temp3
  rm $2
  n1=$(grep -n "FEATURES" $1 | awk -F : '{print $1}')
  n2=$(grep -n "ORIGIN" $1 | awk -F : '{print $1}')
  sed -n "$n1, $n2 p" $1 > temp1
  cut -b 1-20 temp1 | nl -b a > temp2
  while read s1 s2; do
     if [ "$s2" != "" ]; then
        echo $s1 $s2 >> temp3
     fi
  done < temp2
  nl -b a temp3 > temp3_1
  while read line1 line2 line3; do
     if [ "$line3" = "unsure" ]; then # replace "unsure" with "CDS" if extract NRPS genes
        line_start=$line2
        line_next=$[$line1+1]
        line_end=$[$(sed -n "$line_next p" temp3_1 | awk '{print $2}')-1]
        sed -n "$line_start, $line_end p" temp1 | sed 's/^.\{21\}//' > temp4
        grep -n "\/" temp4 | awk -F : '{print $1,$2}' | nl -b a > temp5
        temp4_line=$(grep \' temp4 | wc -l)
        temp5_line=$(grep \' temp5 | wc -l)
        seq_head1=$(echo $1 | awk -F / '{print $NF}' | awk -F . '{print $1}')
        seq_head2=$(grep "/domain_id=" temp4 | awk -F '\"' '{print $2}' | sed 's/_/_/g')
              # seq_head2=$(grep "/locus_tag=" temp4 | sed 's/\/locus_tag=//'
  | sed 's/'"//g' | awk -F _ '{print $(NF-1)"_"$NF}') # enable this line if extract NRPS genes
        seq_head3=$(grep "/specificity=" temp4 | awk -F '\"' '{print $2}' | sed 's/_/_/g')
        aSDomain=$(grep "/aSDomain=" temp4 | awk -F '\"' '{print $2}' | sed 's/_/_/g')
        if [ "$aSDomain" = "AMP-binding" ]; then # remove this if loop if extract A-donmain only
              echo \>$seq_head1"_"$seq_head2"_"$seq_head3 >> $2
              read position seq_start <<< $(grep "translation=" temp5 | awk '{print $1,$2}')
              echo $seq_start
              if [ $position -eq $temp5_line ]; then
                 seq_end=$temp4_line
                 elif [ $position -lt $temp5_line ]; then
                    seq_end=$(sed -n "$[$position+1] p " temp5 | awk '{print $2}')
                    echo $seq_end
              fi
              sed -n "$seq_start, $[$seq_end-1] p" temp4 | sed 's/\/translation="//g' | sed 's/'"//g'>> $2
        fi # remove this if loop if extract A-donmain only
     fi
  done < temp3_1
``` m. Spectroscopy

UV-vis spectra were obtained using a Molecular Devices SpectraMax M2 spectrophotometer. IR spectra were obtained using a Nicolet iS50 FT-IR (Thermo Scientific). High resolution mass spectra were acquired using a Waters Xevo G2-XS QTof mass spectrometer equipped with a Zspray ESI source and fed by an Acquity H class UPLC system with a Waters Acquity CSH C18 column (2.1×50 mm, 1.8 um). NMR data were collected using a Varian 500 MHz NMR spectrometer with 5 mm Varian HCN Oneprobe for proton detected experiments and a 3 mm Varian inverse probe for carbon detected experiments ($^1$H 500 MHz, $^{13}$C 125 MHz). Residual signals from solvents were used for referencing. ECD spectra were obtained on an AVIV Biomedical, Inc. CD Spec Model 410 (Lakewood, NJ, USA). Analytical and semi-preparative HPLC was performed on a Thermo UltiMate 3000 system with a DAD detector.

n. Quantification and Statistical Analysis

All MIC data was graphed in GraphPad Prism 6.0 software. Error bars on MIC graphs were indicated as mean±SD of 3 replicate wells. The dose response curves for 1 and 2 against the HEK-293 cell line were plotted in GraphPad Prism 6.0 software, and non-linear regression failed to calculate an IC50 value due to a lack in inhibitory activity. Error bars were indicated as mean±SD of 3 replicate wells. Hemolysis data were graphed in GraphPad Prism 6.0 software. Error bars were indicated as mean±SD of 3 replicate wells.

4. Creating Oxidase Deficient Mutant in *Teredinibacter Turnerae* T7901 a. General Knockout Method

Figure 12A:
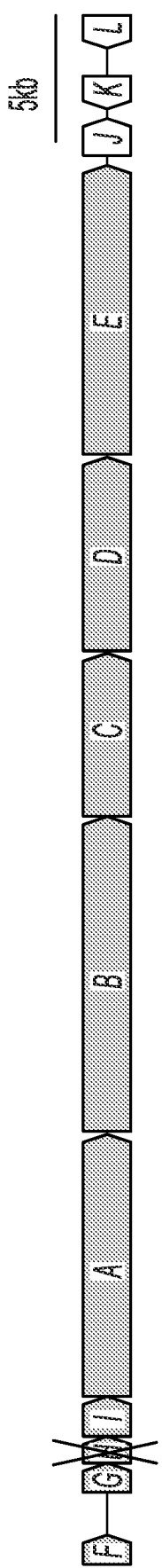
FIG. 12A-C show representative results for creating the oxidase deficient mutant in Teredinibacter turnerae 17901.

As shown in FIG. 12A, an in-frame, scarless deletion mutant of the turH gene was generated through recombinant engineering. The gene to be knocked out was amplified by two sets of primers, each of which were used to generate a DNA fragment that is ~800 bp in length (total: 1600 bp). The upstream region begins approximately 800 bp prior to the start site of the gene to be deleted, terminating at the start codon. The downstream gene begins with the seven terminal amino acids of the gene and continues for ~800 bp past the stop site. This design enabled the deletion to be in frame.

Genes were amplified by PCR with Phusion® High-Fidelity DNA Polymerase and combined using Gibson assembly into the pCM488_kanT vector, including kanamycin resistance and sacB genes. The assembly product was transformed into *E. coli* DH10B and verified by Sanger sequencing. The resulting plasmid was transformed into *E. coli* S17-1, a donor strain for conjugation. A single colony of *E. coli* S17-1 was inoculated into LB medium (5 ml), supplemented with 50 µg/ml kanamycin, and simultaneously a *T. turnerae* T7901 colony was inoculated into SBM+cellulose medium (10 ml). The strains were grown overnight at 30° C. with shaking at 200 rpm. *E. coli* S17-1 cells were pelleted by centrifugation at 5500 rpm for 10 minutes, and the supernatant was discarded. *T. turnerae* T7901 was also pelleted in the same way. The cells were resuspended with the residual medium after discarding the supernatant, and spotted together on an SBM+LB agar plate, enabling conjugation between *E. coli* S17-1 to *T. turnerae* T7901. Cells were maintained at 30° C. After two days, half of the spotted cells were scooped up in a loop, resuspended in 1 ml sterile SBM+cellulose medium, and spread on SBM+cellulose agar with 50 µg/ml kanamycin. The cells were grown at 30° C. for two weeks, selecting for recombinants that are kanamycin resistant. Each colony was transferred to SBM+cellulose+1% sucrose, which induces sacB-mediated homologous gene recombination in *T. turnerae* T7901. Colonies were then picked and streaked on two plates, one with SBM+1% sucrose with and without 50 µg/ml kanamycin. Colonies showing growth only on plates lacking kanamycin were assumed to be potential gene deletion mutants, which was further confirmed by PCR.

b. Production of New Compound

Figure 12B:
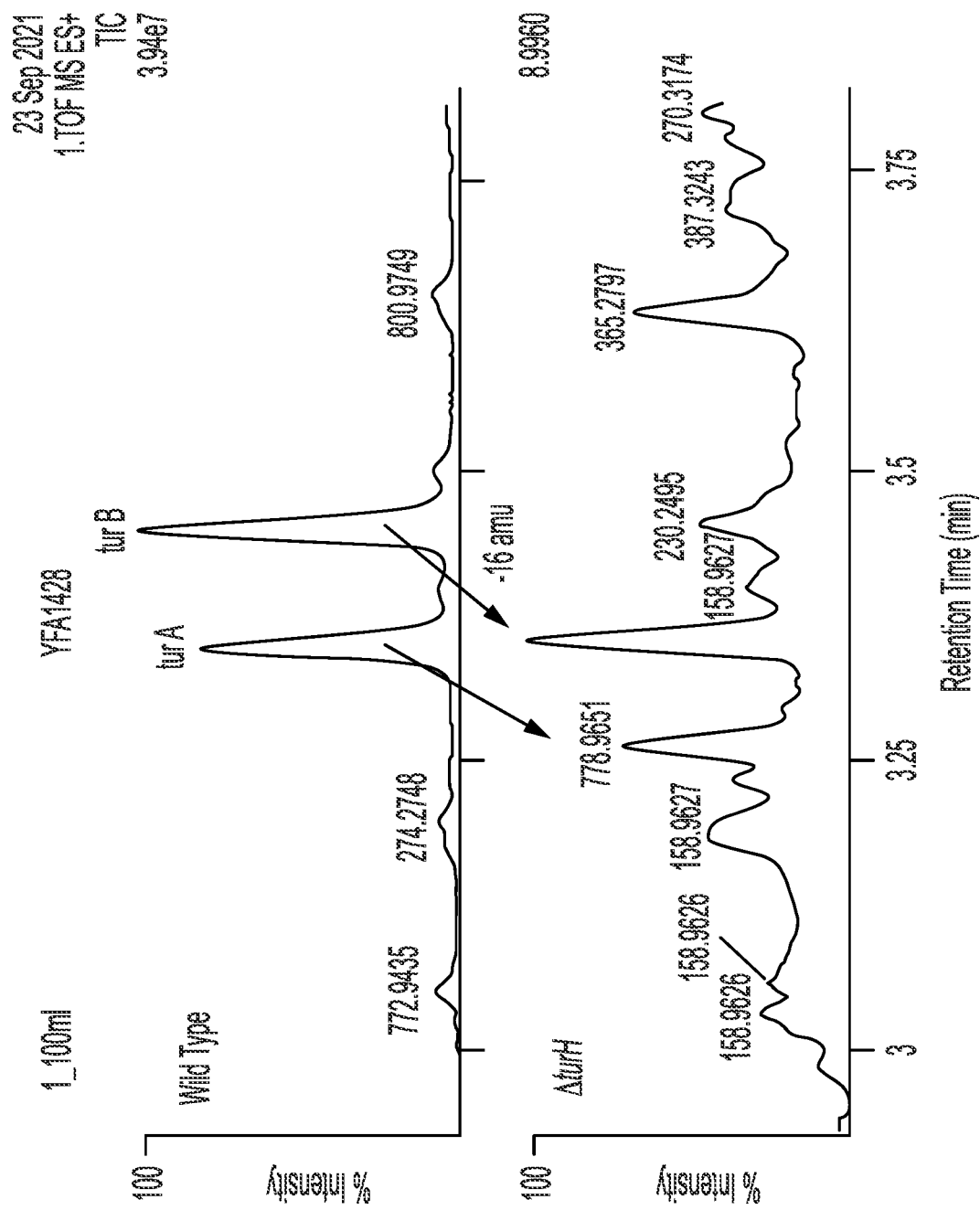
Figure 12C:
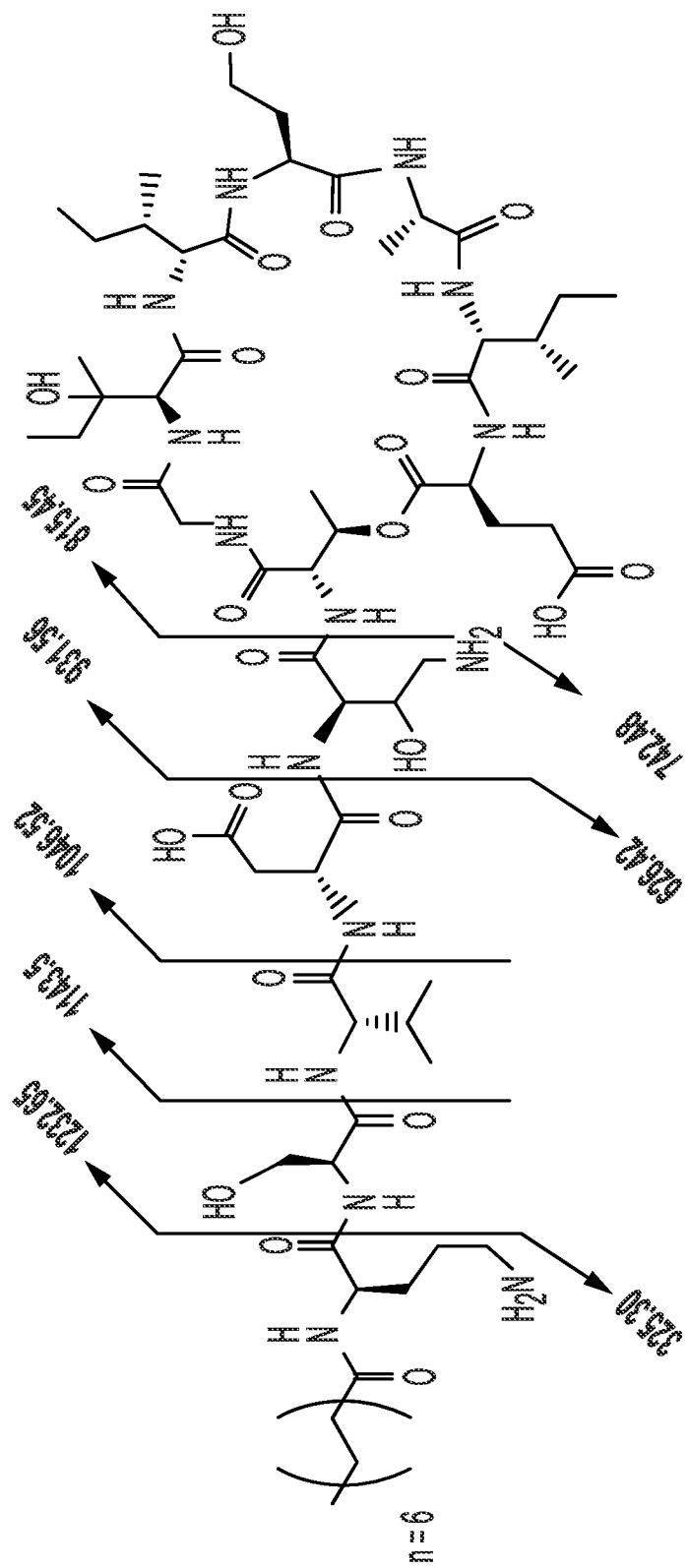

Oxidase turH was knocked out by the above method. The purified knockout mutant was cultivated, and compounds isolated as described in Miller et al., Cell Chem. Biol. 2021. As shown in FIGS. 12B-C, UPLC-MS and MS/MS led to the determination that TurH normally oxidizes aspartic acid in turnercyclamycins. New compounds lacking hydroxylation on aspartic acid were obtained after growing the knockout 5. Resistance and Mechanism of Action The major colistin resistance gene (mcr-1) was expressed in a laboratory strain of *Escherichia coli*. As shown in Table 7 below, while colistin susceptibility is greatly decreased by 16-fold in the presence of mcr-1 (MIC=0.5 µg/mL vs 8 µg/mL), the gene has no effect on tumercyclamycins (n=3 per condition in this experiment). In other conditions, modest changes were observed, inconsistent with increase. This provides molecular evidence supporting the usefulness of tumercyclamycin in treating colistin-resistant infections. Moreover, since mcr-1 refactors key cell membrane lipids that are essential to colistin activity, this demonstrates that tumercyclamycins have a different mechanism of action than colistin/polymyxins.

TABLE 7

| | MIC (µg/mL) | | | |
|---|---|---|---|---|
| Compound | DH5α | pGDP2-MCR-1 in DH5α | C600 | pGDP2-MCR-1 in C600 |
| Colistin | 0.5 | 8 | 0.5 | 8 |
| Turnercyclamycin A | 2 | 2 | 2 | 4 |
| Turnercyclamycin B | 2 | 4 | 4 | 4 |

6. Importance of the Lipid Tail

After growing 100+L of *Teredinibacter turnerae*, several milligrams of minor natural tumercyclamycin analogs with shorter lipid tails ($C_{12}$ and $C_{13}$) have been obtained. These derivatives will enable the testing of the SAR of the lipid side chain.

7. Materials and Equipment for In Vivo Studies a. Test Substance and Dosing Regimen For pharmacokinetic in-life and bioanalysis mouse studies, Tumercyclamycin A (C. factor: 1.010) was formulated in 3% ethanol/phosphate buffered saline (PBS) at the concentrations of 1 mg/mL for IV administration at a dosing volume of 5 mL/kg.

For maximum tolerated dose (MTD) mouse studies, Turnercyclamycin A (C. factor: 1.010) was formulated in 3% ethanol/PBS at the concentrations of 2.5, 5, and 10 mg/mL for IV administration twice daily with a 12-hour interval (q12h) at a dosing volume of 10 mL/kg.

b. Animals

BALB/c female mice, weighing 18 f 2 g, were provided by BioLasco Taiwan (under Charles River Laboratories Licensee). All animals were maintained in a well-controlled temperature (20-24° C.) and humidity (30%-70%) environment with 12 hours light/dark cycles. Free access to standard lab diet [MFG (Oriental Yeast Co., Ltd., Japan)] and autoclaved tap water were granted. All aspects of this work including housing, experimentation, and animal disposal were performed in general accordance with the "Guide for the Care and Use of Laboratory Animals: Eighth Edition" (National Academies Press, Washington, D.C., 2011) in an AAALAC-accredited laboratory animal facility. In addition, the animal care and use protocol was reviewed and approved by the IACUC at Pharmacology Discovery Services Taiwan, Ltd)

c. Chemicals

Acetonitrile (ACN; Fisher Scientific U.K. Ltd., England), Ammonium acetate ($CH_3COONH_4$; Sigma, USA), Dimethyl sulfoxide (DMSO) (Merck, Germany), Ethanol (Merck, Germany), Formic acid (FA; Merck, Germany), Methanol (MeOH, AENCORE, Australia), Oxybutynin (Sigma, USA), and PBS (Sigma, USA).

d. Equipment 0-1000 g Electronic scale (Tanita Corporation, Japan), Animal cage (Allentown, USA), Centrifuge 5810R (Eppendrof, Germany), Disposal syringe (1 mL, Terumo Corporation, Japan), Gilson Pipettes (#P200 Neo-P10N Micro Pipette; Gilson, France), Impromini™ EDTA-K2 tube (Improve Medical, China), LC-MS/MS Triple Quad™ 5500+ (SCIEX, USA), Microcentrifuge tubes 1.5 mL click-cap (Treff AG, Switzerland), Phenomenex Synergi™ 4 μm, Polar-RP 80A LC Column 50×2 mm (Phenomenex, USA), Polypropylene 96-well round U-bottom deepwell plates and silicone microplate lids (StorPlate-96 U and StorMat-96; PerkinElmer Inc., USA), RAININ Pipettes (E4 Multi E12-50XLS+, E12-300XLS, Refurbished Rainin E4TM XLS™ electronic 12 channel pipette, 30-300 μL, E4 Pipette Multi E12-1200XLS+, and EA6-300XLS; RAININ, USA), Pipette Tips (Costar, USA), and Stop watch (Casio, China).

8. Pharmacokinetic (Pk) In-Vivo Mouse Study a. Methods

A PK study was performed in female BALB/c mice (immune competent; uninfected) following intravenous (IV) administration of Turnercyclamycin A at 5 mg/kg. The plasma samples were collected and at 0.05, 0.167, 0.5, 1, 2, 4, 8, and 24 hour(s) after administration. The parameters for this study are summarized in Table 8.

TABLE 8

| Animal Use | |
|---|---|
| Animal Species/Strain | Mouse/Female BALB/c |
| Body Weight | 18 ± 2 g |
| Fasting Regimen | None |
| Pre-dose Observations | Body weight (gm) |
| Test Article Dosing and PK Sample Collection | |
| Test Article ID | Turnercyclamycin A |
| Route(s) of Administration | IV |
| Dose Levels (mg/kg) | 5 |
| Dose Volume (mL/kg) | 5 |
| Proposed Formulation/Vehicle | 3% ethanol/PBS |
| Number of Animals per Dosing Group | 24 |
| Total Number of Animals | 24 |
| Total Number of Samples | 24 plasma |
| PK Sample (Plasma) Collection Time | 0.05, 0.167, 0.5, 1, 2, 4, 8, and 24 hour(s) |
| Target Blood Sample Volume (mL) | 0.3 mL via cardiac puncture |
| Preferred Anticoagulation | $EDTA-K_2$ |
| Preferred Sample Storage | ≤−70° C. |

Blood aliquots were collected via cardiac puncture (0.3 mL). Blood aliquots were collected in tubes coated with EDTA-K2, mixed gently, then kept on ice and centrifuged at 2,500×g for 15 minutes at 4° C. within 1 hour of a collection. The plasma (supernatant) was then harvested and kept frozen at −70° C. until further processing.

The plasma samples were processed using acetonitrile precipitation and analyzed by LC-MS/MS. The detailed chromatographic conditions are summarized in Table 9 below.

TABLE 9

| | |
|---|---|
| Instrument control no. | LCM-MS-002 |
| Data processor | Analyst 1.7 |
| Ionization mode | Electrospray, Positive ions |
| Scan Mode | Multiple reaction monitoring (MRM) |
| Instrument response | Peak area ratio |
| Regression model | Weighted linear regression by $1/X^2$ |
| MRM of Analyte | 786.4/1248.5 (Turnercyclamycin A) |
| MRM of Internal standard (IS) | 358.3/142.3 (Oxybutynin) |
| Column | Agilent Poroshell 120 EC-C18 column 2.7 μm (3.0 × 50 mm) |
| Column Temperature (° C.) | 40 |
| Run Time (min) | 3.00 |
| Injection Volume (μL) | 5.0 |
| Mobile phase | Mobile Phase A: Water ($H_2O$)/FA= 100/0.2 (v/v) |
| | Mobile Phase B: ACN/MeOH/FA= 5/25/0.2 (v/v) |

| | Time (min) | Flow Rate (μL/min) | A (%) | B (%) |
|---|---|---|---|---|
| HPLC conditions | 0.00 | 300 | 70.0 | 30.0 |
| | 0.50 | 300 | 70.0 | 30.0 |
| | 1.00 | 300 | 10.0 | 90.0 |
| | 2.00 | 300 | 10.0 | 90.0 |
| | 2.50 | 300 | 70.0 | 30.0 |
| | 3.50 | 300 | 70.0 | 30.0 |

Mouse plasma samples were prepared for LC-MS/MS analysis in the standard range of 200-50000 ng/mL via protein precipitation by acetonitrile. 20 μL of sample were transferred to a well of a 96-wells plate. Next, 500 μL of 0.01 ng/μL IS in CAN were added to each well except for sample "00" and carryover. 500 μL of ACN were then added to each well, followed by vortexing for 1 m and centrifugation for 5 min at 4000 rpm. Lastly, 50 μL of the supernatant were added to 500 μL $H_2$ for LC-MS/MS analysis. The acceptance criteria for the bioanalysis are summarized in Table 10.

TABLE 10

| Sample type | Criteria for Sample Analysis |
|---|---|
| Calibration standards (STDs) | The calculated concentrations of the calibration STDs, including the lower limit of quantification (LLOQ) and upper limit of quantification (ULOQ), should not deviate more than 25% from the nominal value (75.0% < Accuracy < 125.0%). At least 75% of the non-zero calibration standards (e.g. 6 in 8 calibration standards) should meet the above criteria. |
| 00 (Double blank) and 0 (Blank) | 1. Analyte peak area (00 or 0) ≤ Analyte peak area (LLOQ in calibration curve) 2. IS peak area (00) ≤ IS peak area (LLOQ in calibration curve) |
| Quality control (QC) | The calculated of the QC samples should be within 25% of the nominal values (75.0% < Accuracy < 125.0%). At least ⅔ of the QC samples should be within the above limits. |

The exposure levels (ng/mL) of Tumnercyclamycin A in plasma samples were determined by LC-MS/MS. Plots of plasma concentrations (mean±SD) vs. time for Tumercyclamycin A were constructed. The PK parameters of the test compound after IV ($t_{1/2}$, $C_0$, $AUC_{last}$, $AUC_{Inf}$, $AUC_{Extr}$, MRT, $V_{ss}$, and CL) were obtained from the non-compartmental analysis (NCA) of the plasma data using WinNonlin.

b. Results

The body weight of each mouse before treatment is shown below in Table 11. The body weight for each animal was recorded before dosing.

TABLE 11

| Treatment | Dose | Route | Time point | No. | B.W. |
|---|---|---|---|---|---|
| Tumercyclamycin A PT# 1250365 UUM-1 | 5 mg/kg 5 mL/kg | IV | 0.05 hr | 1 | 18 |
| | | | | 2 | 18 |
| | | | | 3 | 18 |
| | | | | Mean | 18.0 |
| | | | | SEM | 0.0 |
| | | | 0.167 hr | 1 | 18 |
| | | | | 2 | 18 |
| | | | | 3 | 18 |
| | | | | Mean | 18.0 |
| | | | | SEM | 0.0 |
| | | | 0.5 hr | 1 | 19 |
| | | | | 2 | 18 |
| | | | | 3 | 18 |
| | | | | Mean | 18.3 |
| | | | | SEM | 0.3 |
| | | | 1 h | 1 | 18 |
| | | | | 2 | 19 |
| | | | | 3 | 19 |
| | | | | Mean | 18.7 |
| | | | | SEM | 0.3 |
| | | | 2 h | 1 | 18 |
| | | | | 2 | 18 |
| | | | | 3 | 18 |
| | | | | Mean | 18.0 |
| | | | | SEM | 0.0 |
| | | | 4 h | 1 | 18 |
| | | | | 2 | 18 |
| | | | | 3 | 18 |
| | | | | Mean | 18.0 |
| | | | | SEM | 0.0 |
| | | | 8 h | 1 | 18 |
| | | | | 2 | 18 |
| | | | | 3 | 18 |
| | | | | Mean | 18.0 |
| | | | | SEM | 0.0 |
| | | | 24 h | 1 | 18 |
| | | | | 2 | 18 |
| | | | | 3 | 18 |
| | | | | Mean | 18.0 |
| | | | | SEM | 0.0 |
| Blank | NA | NA | NA | 1 | 18 |
| | | | | 2 | 18 |
| | | | | 3 | 18 |
| | | | | Mean | 18.0 |
| | | | | SEM | 0.0 |

The exposure levels (ng/mL) of Tumnercyclamycin A in plasma samples were then determined by liquid chromatography-tandem mass spectrometry (LC-MS/MS). The results of the LC-MS/MS are shown in Table 12 below.

TABLE 12

| Time (h) | Sample concentration (ng/mL) | | | Mean | Standard Deviation |
|---|---|---|---|---|---|
| 0.05 | 52235 | 51887 | 55877 | 53333 | 2210 |
| 0.167 | 36107 | 38906 | 40924 | 38646 | 2419 |
| 0 | 34373 | 31954 | 34645 | 33657 | 1481 |
| 1 | 24635 | 33834 | 29337 | 29269 | 4600 |
| 2 | 26373 | 25446 | 26782 | 26200 | 685 |
| 4 | 22923 | 22209 | 22495 | 22542 | 359 |
| 8 | 11661 | 13130 | 11123 | 11971 | 1039 |
| 24 | 974 | 764 | 1054 | 931 | 150 |

Figure 13:
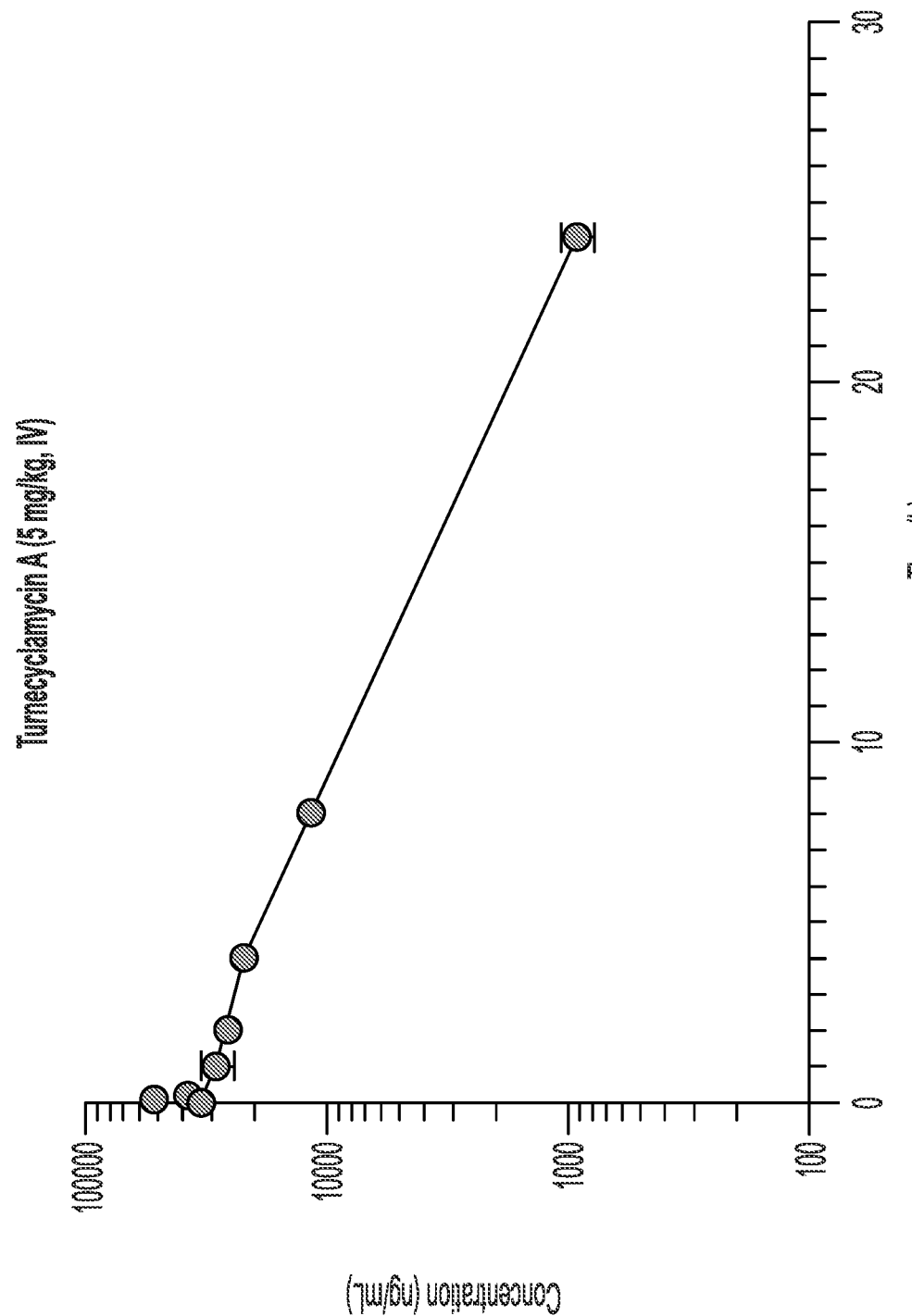
FIG. 13 shows a representative plot of plasma concentrations [mean±standard deviation (SD)] vs. time for tumercyclamycin A.

Plots of plasma concentrations [mean±standard deviation (SD)] vs. time for Tumercyclamycin A are shown in FIG. 13. The fundamental PK parameters of the Tumercyclamycin A after IV ($t_{1/2}$, Co, $AUC_{last}$, $AUC_{Inf}$, $AUC_{Extr}$, MRT, $V_{ss}$, and CL) were obtained from the non-compartmental analysis (NCA) of the plasma data using WinNonlin and are shown in Table 13.

TABLE 13

| $t_{1/2}$ (h) | C0 (ng/mL) | AUClast (h*ng/mL) | AUCInf (h*ng/mL) | AUC/D (h*kg*ng/ mL/mg) | AUC Extr (%) | MRT (h) | Vss (L/kg) | CL (mL/min/ kg) |
|---|---|---|---|---|---|---|---|---|
| 4.35 | 33657 | 284562 | 290402 | 58080 | 2.01 | 5.83 | 0.10 | 0.29 |

The analytical raw data for this study is shown in Table 14 and Table 15 below.

TABLE 14

|  | Sample name | Nominal conc. (ng/ml) | Area ratio | Calculated Conc. (ng/mL) | Accuracy (%) |
|---|---|---|---|---|---|
| Calibration curve | LLOQ | 200. | 0.0053725 | 203.637 | 101.82 |
|  | STD1 | 500. | 0.012201 | 485.578 | 97.12 |
|  | STD2 | 1000. | 0.023620 | 957.118 | 95.71 |
|  | STD3 | 2000. | 0.049625 | 2030.899 | 101.54 |
|  | STD4 | 5000. | 0.12282 | 5053.197 | 101.06 |
|  | STD5 | 10000. | 0.23852 | 9830.612 | 98.31 |
|  | STD6 | 30000. | 0.75927 | 31333.307 | 104.44 |
|  | ULOQ | 50000. | 1.2113 | 49997.290 | 99.99 |
| QCs | QH1 | 40000. | 1.0271 | 42390.762 | 105.98 |
|  | QM1 | 25000. | 0.54412 | 22449.375 | 89.80 |
|  | QL1 | 600. | 0.016661 | 669.762 | 111.63 |
|  | QH2 | 40000. | 1.0300 | 42513.167 | 106.28 |
|  | QM2 | 25000. | 0.65953 | 27214.841 | 108.86 |
|  | QL2 | 600. | 0.017746 | 714.558 | 119.09 |

TABLE 15

|  | Calculated Conc. (ng/ml) | Dilution factor | Sample Conc. (ng/mL) |
|---|---|---|---|
| Turnercyclamycin A 5 mg/kg, IV Mouse#1 0.05 h | 52235.245 | 1 | 52235 |
| Turnercyclamycin A 5 mg/kg, IV Mouse#2 0.05 h | 51887.441 | 1 | 51887 |
| Turnercyclamycin A 5 mg/kg, IV Mouse#3 0.05 h | 55876.749 | 1 | 55877 |
| Turnercyclamycin A 5 mg/kg, IV Mouse#1 0.167 h | 36106.528 | 1 | 36107 |
| Turnercyclamycin A 5 mg/kg, IV Mouse#2 0.167 h | 38905.696 | 1 | 38906 |
| Turnercyclamycin A 5 mg/kg, IV Mouse#3 0.167 h | 40923.642 | 1 | 40924 |
| Turnercyclamycin A 5 mg/kg, IV Mouse#1 0.5 h | 34372.523 | 1 | 34373 |
| Turnercyclamycin A 5 mg/kg, IV Mouse#2 0.5 h | 31953.705 | 1 | 31954 |
| Turnercyclamycin A 5 mg/kg, IV Mouse#3 0.5 h | 34645.464 | 1 | 34645 |
| Turnercyclamycin A 5 mg/kg, IV Mouse#1 1 h | 24634.969 | 1 | 24635 |
| Turnercyclamycin A 5 mg/kg, IV Mouse#2 1 h | 33834.174 | 1 | 33834 |
| Turnercyclamycin A 5 mg/kg, IV Mouse#3 1 h | 29337.146 | 1 | 29337 |
| Turnercyclamycin A 5 mg/kg, IV Mouse#1 2 h | 26372.977 | 1 | 26373 |
| Turnercyclamycin A 5 mg/kg, IV Mouse#2 2 h | 25445.875 | 1 | 25446 |
| Turnercyclamycin A 5 mg/kg, IV Mouse#3 2 h | 26781.788 | 1 | 26782 |
| Turnercyclamycin A 5 mg/kg, IV Mouse#1 4 h | 22922.951 | 1 | 22923 |
| Turnercyclamycin A 5 mg/kg, IV Mouse#2 4 h | 22209.036 | 1 | 22209 |
| Turnercyclamycin A 5 mg/kg, IV Mouse#3 4 h | 22495.261 | 1 | 22495 |
| Turnercyclamycin A 5 mg/kg, IV Mouse#1 8 h | 11660.778 | 1 | 11661 |
| Turnercyclamycin A 5 mg/kg, IV Mouse#2 8 h | 13129.991 | 1 | 13130 |
| Turnercyclamycin A 5 mg/kg, IV Mouse#3 8 h | 11122.976 | 1 | 11123 |
| Turnercyclamycin A 5 mg/kg, IV Mouse#1 24 h | 973.920 | 1 | 974 |
| Turnercyclamycin A 5 mg/kg, IV Mouse#2 24 h | 763.685 | 1 | 764 |
| Turnercyclamycin A 5 mg/kg, IV Mouse#3 24 h | 52235.245 | 1 | 1054 |

9. Maximum Tolerated Dose (MTD) In-Vivo Mouse Study a. Methods

Female BALB/c mice were employed to evaluate the Maximum Tolerated Dose (MTD) of Tumercyclamiycin A. Animals were rendered neutropenic by two intraperitoneal (IP) injections of cyclophosphamiide, the first at 150 mg/kg 4 days before infection (Day −4) and the second at 100 mg/kg 1 day before treatment (Day −1). Tumnercyclamiycin A (25, 50, and 100 mg/kg) was administered IV twice daily with a 12-hour interval (bid; q12h) on Day 0. All three doses were executed in parallel. Animals were humanely euthanized at 24 hours after the last treatment or at humane endpoints. The study design is summarized in Table 16 below.

TABLE 16

| Group | Test Substance | Dose Schedule | Dose Route | Conc. mg/mL | Dosage mL/kg | Dosage mg/kg/dose | Dosage mg/kg/24 h | Mouse BALB/c (female)[d] |
|---|---|---|---|---|---|---|---|---|
| 1 | Vehicle[a] | bid (q12h)[b] | IV[c] | NA | 10 | NA | NA | 3 |
| 2 | Turnercyclamycin A (C. factor: 1.010) | bid (q12h)[b] | IV[c] | 10 | 10 | 100 | 200 | 3 |
| 3 | Turnercyclamycin A (C. factor: 1.010) | bid (q12h)[b] | IV[c] | 5 | 10 | 50 | 100 | 3 |
| 4 | Turnercyclamycin A (C. factor: 1.010) | bid (q12h)[b] | IV[c] | 2.5 | 10 | 25 | 50 | 3 |

[a]Vehicle: 3% ethanol/PBS
[b]administered twice per day (BID) at 12 hour intervals (q12h) for 24 h
[c]IV bolus in slow injection at least for 10 secounds
[d]Neutropenic BALB/c mice were used for this study Animals were observed for the presence of acute toxic symptoms (mortality, convulsions, tremors, muscle relaxation, sedation, and etc.) and autonomic effects (diarrhea, salivation, lacrimation, vasodilation, piloerection, and etc.) during the first 5 minutes for each dose. Body weights were recorded at pre-dose and at 24 hours after the first treatment. Mortality was observed again at 24 hours after the first treatment. The clinical symptoms for observation are shown in Table 17 below.

TABLE 17

| Body Weight (B.W.) (g) | Decrease in Touch Response | Decrease in Spontaneous Activity | Low Limb Post | Body Temperature |
|---|---|---|---|---|
| Irritability | Increase in Exploration | Straub Tail | Skin Color | Piloerection |
| Hyperactivity | Decrease in Exploration | Reactivity | Respiration | Increase in Palpebral Size |
| Increase in Startle Response | Pinna | Righting | Salivation (Fluid and Viscosity) | Decrease in Palpebral Size |
| Increase Touch Response | Placing | Ataxia | Lacrimation | Death |
| Decrease Startle Response | Tremor | Convulsion (Chronic/Tonic) | Diarrhea | | a. Results

Turnercyclamycin A at 100 mg/kg was not tolerated as the mortality was induced in Mouse #1 in one minute of administration. Therefore, the rest two animals (Mouse #2 and Mouse #3) were not administered. And no second dose was treated. The mortality data is summarized in Table 18. Female BALB/c mice (18 f 2 g) were employed. Animals were rendered neutropenic by two IP injections of cyclophosphamide, the first at 150 mg/kg 4 days before infection (Day −4) and the second at 100 mg/kg 1 day before infection (Day −1). Turnercyclamycin A (25, 50, and 100 mg/kg) was administered via IV twice daily with a 12-hour interval (bid; q12h) on Day 0. All three doses were executed in parallel. Mortality was observed again at 24 hours after the first treatment

TABLE 18

| Compound | Route | Dose (mg/kg) | Gender | Mortality (death/test) Day 0 | Day 1 |
|---|---|---|---|---|---|
| Vehicle (3% ethanol/PBS) | IV | 10 mL/kg bid (q12 h) × 1 | Female | 0/3 | 0/3 |

TABLE 18-continued

| Compound | Route | Dose (mg/kg) | Gender | Mortality (death/test) Day 0 | Day 1 |
|---|---|---|---|---|---|
| PT# 1250365 (UUM-1) Turnercyclamycin A | IV | 100 a bid (q12 h) × 1 | Female | 1/1 | NA |
| | IV | 50 bid (q12 h) × 1 | Female | 0/3 | 0/3 |
| | IV | 25 bid (q12 h) × 1 | Female | 0/3 | 0/3 |

Turnercyclamycin A at 25 mg/kg IV (bid; q12h) was considered tolerated. Some adverse effects such as the decrease in adnominal tone, limb tone, and spontaneous activity, and tremor, piloerection, and increase in the respiration rate (fast) were noted after the two administrations. The adverse effects 5 minutes after the $1^{st}$ dose are presented in Table 19. The adverse effects 5 minutes after the $2^{nd}$ dose are shown in Table 20. More pronounced effects such as vocalization, ataxia, reactivity, and hunch back were elicited by Turnercyclamycin A at 50 mg/kg IV (bid; q12h).

TABLE 19

| Treatment | Vehicle (3% ethanol/PBS) | | | PT# 1250365 (UUM-1) Turnercyclamycin A | | | | | | | | |
|---|---|---|---|---|---|---|---|---|---|---|---|---|
| Route | IV, bid (q12h) × 1 | | | | | | | | | | | |
| Dosage | 10 mL/kg | | | 100 mg/kg $^a$ | | | 50 mg/kg | | | 25 mg/kg | | |
| Observation time | | | | 5 minutes after the $1^{st}$ dose | | | | | | | | |
| Gender | | | | Female | | | | | | | | |
| BEHAVIORAL | No. 1 | No. 2 | No. 3 | No. 1 | No. 2 | No. 3 | No. 1 | No. 2 | No. 3 | No. 1 | No. 2 | No. 3 |
| B.W. (g) | − | − | − | NA | NA | | − | − | − | − | − | − |
| Irritability | − | − | − | | | | − | − | − | − | − | − |
| Hyperactivity | − | − | − | | | | − | − | − | − | − | − |
| Inc. Startle | − | − | − | | | | − | − | − | − | − | − |
| Inc. Touch | − | − | − | | | | − | − | − | − | − | − |
| Dec. Startle Response | − | − | − | | | | − | − | − | − | − | − |
| Dec. Touch Response | − | − | − | | | | − | − | − | − | − | − |
| Inc. Exploration | − | − | − | | | | − | − | − | − | − | − |
| Dec. Exploration | − | − | − | | | | − | − | − | − | − | − |
| Pinna | − | − | − | | | | − | − | − | − | − | − |
| Placing | − | − | − | | | | − | − | − | − | − | − |
| NEUROLOGIC | | | | | | | | | | | | |
| Tremor | − | − | − | NA | NA | | − | − | ± | − | ± | − |
| Dec. Spont. Activity | − | − | − | | | | ± | − | − | − | − | − |
| Straub Tail | − | − | − | | | | − | − | − | − | − | − |
| Reactivity | − | − | − | | | | ± | − | ± | − | − | − |
| Righting | − | − | − | | | | − | − | − | − | − | − |
| Ataxia | − | − | − | | | | − | − | − | − | − | − |
| Convulsion | − | − | − | | | | − | − | − | − | − | − |
| C.T.C-T | | | | | | | | | | | | |
| Low Limb Post | + | ± | − | | | | ± | − | ± | − | ± | + |
| Abdominal Tone | + | + | + | | | | + | + | + | + | + | ± |
| Limb Tone | + | + | + | | | | + | + | + | + | + | + |
| Grip Strength | − | − | − | | | | − | − | − | − | − | − |
| AUTONOMIC | | | | | | | | | | | | |
| Skin Color | − | − | − | NA | NA | | − | − | − | − | − | − |
| Respiration | − | − | − | | | | Fast ± | Fast ± | − | − | − | − |
| Salivation F.V. | − | − | − | | | | − | − | − | − | − | − |
| Lacrimation | − | − | − | | | | − | − | − | − | − | − |
| Diarrhea | − | − | − | | | | − | − | − | − | − | − |
| Body Temperature | − | − | − | | | | − | − | − | − | − | − |

TABLE 19-continued

| Treatment | Vehicle (3% ethanol/ PBS) | | | PT# 1250365 (UUM-1) Turnercyclamycin A | | | | | |
|---|---|---|---|---|---|---|---|---|---|
| Piloerection | − | ± | ± | ± | ± | ± | ± | ± | ± |
| Inc. Palpebral Size | − | − | − | − | − | − | − | − | − |
| Dec. Palpebral Size | − | − | − | − | − | − | − | − | − |
| Others | − | − | − | − | − | − | − | − | − |
| Death | − | − | − | + | − | − | − | − | − |

−: no effects; ±: Slight to moderate effects; +: Severe effects; Inc.: Increased; Dec.: Decreased; Spont.: Spontaneous; C.: Chronic; T.: Tonic; C-T: Chronic-Tonic; F.: Fluid; V.: Viscosity; Voc: Vocalization; H.B.: Hunch back

TABLE 20

| Treatment | Vehicle (3% ethanol/ PBS) | | | | PT# 1250365 (UUM-1) Turnercyclamycin A | | | | | | | |
|---|---|---|---|---|---|---|---|---|---|---|---|---|
| Route | | | | | IV. bid (q12h) x 1 | | | | | | | |
| Dosage | 10 mL/kg | | | | 100 mg/kg a | | 50 mg/kg | | | 25 mg/kg | | |
| Observation time | | | | | 5 minutes after the 2$^{nd}$ dose | | | | | | | |
| Gender | | | | | Female | | | | | | | |
| BEHAVIORAL | No. | No. | No. | No. | No. | No. | No. | No. | No. | No. | No. | No. |
| B.W. (g) | − | − | − | | NA | | − | − | − | − | − | − |
| Irritability | − | − | − | | | | Voc | Voc | − | Voc | − | − |
| Hyperactivity | − | − | − | | | | − | − | − | − | − | − |
| Inc. Startle | − | − | − | | | | − | − | − | − | − | − |
| Inc. Touch | − | − | − | | | | ± | − | − | − | − | − |
| Dec. Startle | − | − | − | | | | − | − | − | − | − | − |
| Dec. Touch | − | − | − | | | | − | − | − | − | − | − |
| Inc. Exploration | − | − | − | | | | − | − | − | − | − | − |
| Dec. Exploration | − | − | − | | | | − | − | − | − | − | − |
| Pinna | − | − | − | | | | − | − | − | − | − | − |
| Placing | − | − | − | | | | − | − | − | − | − | − |
| NEUROLOGIC | | | | | | | | | | | | |
| Tremor | − | − | − | | NA | | − | − | − | − | − | − |
| Dec. Spont. | − | − | − | | | | ± | − | ± | − | − | ± |
| Straub Tail | − | − | − | | | | − | − | − | − | − | − |
| Reactivity | − | − | − | | | | − | − | ± | − | − | − |
| Righting | − | − | − | | | | − | − | − | − | − | − |
| Ataxia | − | − | − | | | | ± | − | ± | − | − | − |
| Convulsion | − | − | − | | | | − | − | − | − | − | − |
| Low Limb Post | + | − | − | | | | + | + | + | + | ± | ± |
| Abdominal Tone | + | + | + | | | | + | + | + | + | + | + |
| Limb Tone | + | + | + | | | | + | + | + | + | + | + |
| Grip Strength | − | − | − | | | | − | − | − | − | − | − |
| AUTONOMIC | | | | | | | | | | | | |
| Skin Color | − | − | − | | NA | | − | − | − | − | − | − |
| Respiration | − | Fast | Fast | | | | Fast | Fast | Fast | − | Fast | Fast |
| Salivation F.V. | − | − | − | | | | − | − | − | − | − | − |
| Lacrimation | − | − | − | | | | − | − | − | − | − | − |
| Diarrhea | − | − | − | | | | − | − | − | − | − | − |
| Body Temperature | − | − | − | | | | − | − | − | − | − | − |
| Piloerection | − | ± | ± | | | | ± | ± | ± | ± | ± | ± |
| Inc. Palpebral Size | − | − | − | | | | − | − | − | − | − | − |
| Dec. Palpebral | − | − | − | | | | − | − | − | − | − | − |
| Others | − | − | − | | | | H.B | H.B | H.B | − | − | − |
| Death | − | − | − | | | | − | − | − | − | − | − |

−: no effects; ±: Slight to moderate effects; +: Severe effects; Inc.: Increased; Dec.: Decreased; Spont.: Spontaneous; C.: Chronic; T.: Tonic; C-T: Chronic-Tonic; F.: Fluid; V.: Viscosity; Voc: Vocalization; H.B.: Hunch back Table 21 shows the results for body weight. No body weight drop and no mortalities were observed. No mortality was induced, but slight body weight losses were noted at 24 hours. The 50 mg/kg dose is therefore not recommended for administration to mice.

TABLE 21

| Compound | Route | Dose (mg/kg) | No. | Gender | Body Weight (g) | | | | |
|---|---|---|---|---|---|---|---|---|---|
| | | | | | Day −4 | Day −1 | Day 0 (first) | Day 0 (second) | Day 1 |
| Vehicle (3% ethanol/PBS) | IV | 10 mL/kg bid (q12h) x1 | 1 | Female | 16 | 16 | 16 | 15 | 16 |
| | | | 2 | | 16 | 17 | 17 | 16 | 16 |
| | | | 3 | | 16 | 16 | 17 | 16 | 16 |
| PT# 1250365 (UUM-1) Turnercyclamycin A | IV | 100 $^a$ bid (q12h) x1 | 1 | Female | 17 | 16 | 15 | NA | |
| | | | 2 | | 17 | 16 | 16 | | |
| | | | 3 | | 17 | 17 | 16 | | |
| | IV | 50 bid (q12h) x1 | 4 | Female | 17 | 16 | 16 | 15 | 15 |
| | | | 5 | | 17 | 16 | 15 | 15 | 14 |
| | | | 6 | | 16 | 17 | 16 | 16 | 16 |
| | IV | 25 bid (q12h) x1 | 7 | Female | 18 | 17 | 17 | 16 | 17 |
| | | | 8 | | 17 | 17 | 17 | 16 | 17 |
| | | | 9 | | 17 | 17 | 17 | 17 | 17 |

10. Efficacy Study

The pharmacokinetics analysis shows a similar PK profile to the clinically used lipopeptide antibiotic daptomycin. The profile includes a half-life of 4.35 hours, which was used to determine the twice/day dosing regimen in efficacy studies. Moreover, turnercyclamycin was well tolerated in mice up to 50 mg/kg. The PK parameters of turnercyclamycin A compared to the approved lipopeptide antibiotic daptomycin are shown in Table 22 below. The data from Daptomycin is referenced from Benvenuto et al, Antimicrobial Agents and Chemotherapy, 2006, 50(10): 3245. Although the Benvenuto et al. study is not strictly comparable, similar in vivo properties are indicated.

TABLE 22

| Compound | Model | Clearance (mL/hr/kg) | Vss (L/kg) | Half Life (h) |
|---|---|---|---|---|
| Turnercyclamycin A | Healthy Mice (n = 24) | 17.4 | 0.1 | 4.35 |
| Daptomycin* | Healthy People | ~9 | ~0.1 | ~8 |

Figure 14:
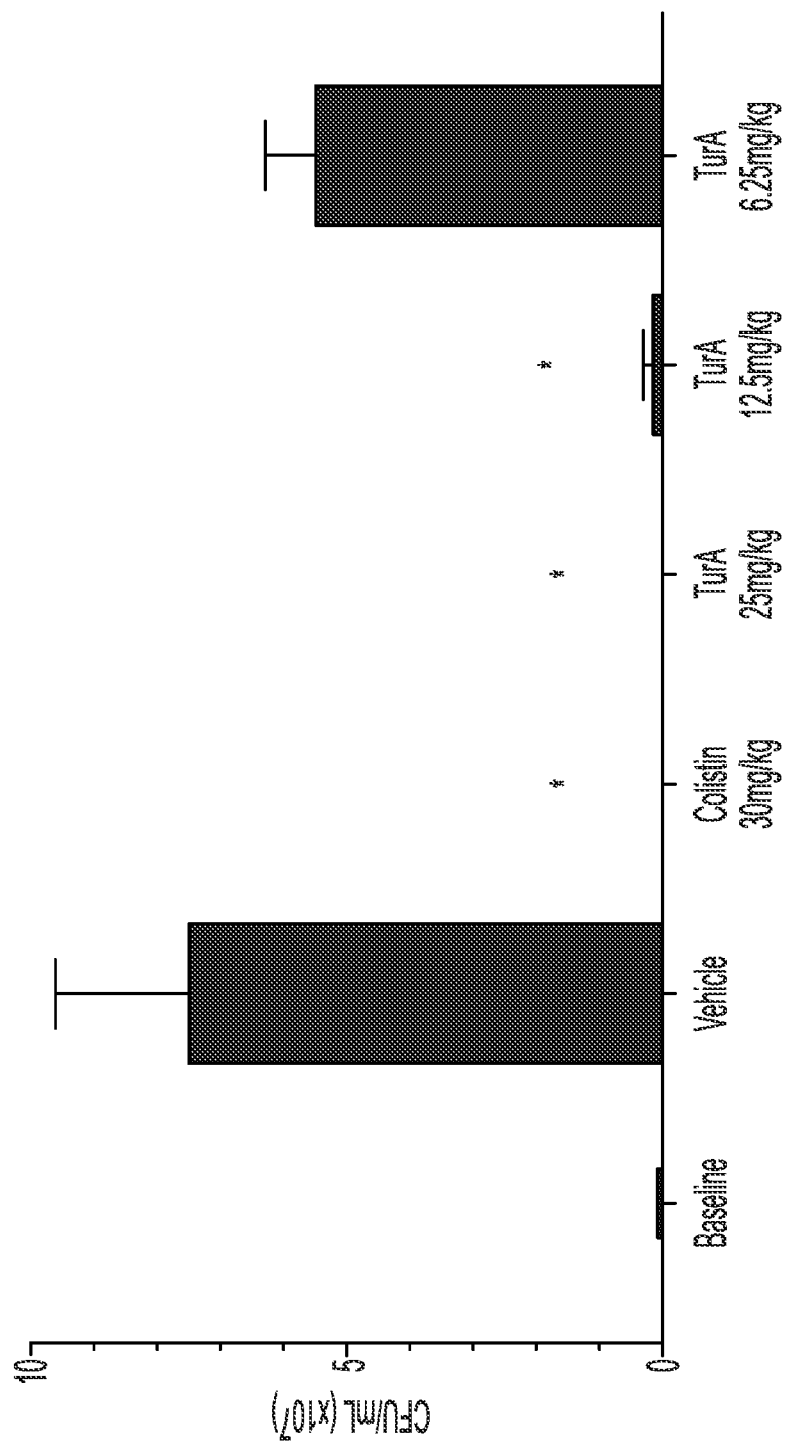
FIG. 14 shows a representative bar graph of the data for the efficacy analysis comparing tumercyclamycin A with the last-line standard colistin. Neutropenic mouse model of A. baumannii infection, with n=5 per condition.

In a thigh infection neutropenic mouse model with twice daily dosing of turnercyclamycin via IV administration, significant results (98% decrease in bacterial CFU/thigh, $p<0.05$) were obtained at 12.5 mg/kg, and 99.99% clearing was observed at 25 mg/kg. These results are shown in FIG. 14. The efficacy experiment was done by obtaining a baseline at 2 hours after injection, then at hours 2 and 14, the indicated dose of antibiotic was injected into the mouse IV. At 26 hours, the CFU were measured. The inoculation size was $1.9 \times 10^5$ CFU/mouse. The final results per mouse are shown in Table 23 below, and the raw data is shown in Table 24. The decrease (%) refers to the percentage decrease in counts (CFU/mouse) compared to the vehicle group control. A refers to the difference in the bacterial counts (CFU/mouse) relative to the baseline group (2 h initial counts). * Indicates a significant difference ($p<0.05$) compared to the corresponding vehicle control as determined by one-way ANOVA and Dunnett's test. # Indicates a significant difference ($p<0.05$) compared to the baseline count as determined by one-way ANOVA and Dunnett's test.

TABLE 23

| Group | Treatment | Dose Route/ Schedule | Animal No. | Thigh Weight (g) | CFU/thigh Time post inoculation 2, 26 h | Decrease (%) | Log (CFU/thigh) Time post inoculation 2, 26 h | Δ |
|---|---|---|---|---|---|---|---|---|
| 1 | Baseline, 2 h post infection | N/A | 1 | 0.741 | $4.20 \times 10^5$ | | 5.62 | |
| | | | 2 | 0.683 | $6.99 \times 10^5$ | | 5.84 | |
| | | | 3 | 0.766 | $4.14 \times 10^5$ | | 5.62 | |
| | | | 4 | 0.798 | $5.91 \times 10^5$ | | 5.77 | |
| | | | 5 | 0.748 | $2.64 \times 10^4$ | | 4.42 | |
| | | | Mean | 0.747 | $4.30 \times 10^5$ | — | 5.45 | — |
| | | | SEM | 0.019 | $1.14 \times 10^5$ | | 0.26 | |
| 2 | Vehicle (3% ethanol/ PBS) | 10 mL/kg IV, BID, q12h | 1 | 0.725 | $1.21 \times 10^8$ | | 8.08 | |
| | | | 2 | 0.738 | $2.96 \times 10^7$ | | 7.47 | |
| | | | 3 | 0.826 | $4.10 \times 10^7$ | | 7.61 | |
| | | | 4 | 0.813 | $1.30 \times 10^8$ | | 8.11 | |
| | | | 5 | 0.751 | $5.40 \times 10^7$ | | 7.73 | |
| | | | Mean | 0.771 | $7.51 \times 10^7$ | — | 7.80 | 2.35 |
| | | | SEM | 0.020 | $2.10 \times 10^7$ | | 0.13 | |
| 3 | Colistin | 30 mg/kg SC, BID, q12h | 1 | 0.718 | $1.77 \times 10^3$ | | 3.25 | |
| | | | 2 | 0.652 | $5.73 \times 10^3$ | | 3.76 | |
| | | | 3 | 0.648 | $5.64 \times 10^3$ | | 3.75 | |
| | | | 4 | 0.644 | $1.98 \times 10^3$ | | 3.30 | |
| | | | 5 | 0.739 | $3.57 \times 10^3$ | | 3.55 | |
| | | | Mean | 0.680 | $3.74 \times 10^3$ | 100 | 3.52* | −2.73[#] |
| | | | SEM | 0.020 | $8.54 \times 10^2$ | | 0.11 | |
| 4 | PT# 1251595 (UUM-2) (Turnercyclamycin A) | 25 mg/kg IV, BID, q12h | 1 | 0.644 | $5.91 \times 10^3$ | | 3.77 | |
| | | | 2 | 0.691 | $7.68 \times 10^3$ | | 3.89 | |
| | | | 3 | 0.602 | $8.76 \times 10^3$ | | 3.94 | |
| | | | 4 | 0.713 | $1.38 \times 10^4$ | | 4.14 | |
| | | | 5 | 0.709 | $1.89 \times 10^3$ | | 3.28 | |
| | | | Mean | 0.672 | $7.61 \times 10^3$ | 100 | 3.80* | −1.65[#] |
| | | | SEM | 0.021 | $1.94 \times 10^3$ | | 0.14 | |
| 5 | PT# 1251595 (UUM-2) (Turnercyclamycin A) | 12.5 mg/kg IV, BID, q12h | 1 | 0.783 | $5.67 \times 10^5$ | | 5.75 | |
| | | | 2 | 0.803 | $7.02 \times 10^6$ | | 6.85 | |
| | | | 3 | 0.771 | $7.89 \times 10^5$ | | 5.90 | |
| | | | 4 | 0.766 | $1.32 \times 10^5$ | | 5.12 | |
| | | | 5 | 0.752 | $1.35 \times 10^4$ | | 4.13 | |
| | | | Mean | 0.775 | $1.70 \times 10^6$ | 98 | 5.55* | 0.10 |
| | | | SEM | 0.009 | $1.34 \times 10^6$ | | 0.45 | |
| 6 | PT# 1251595 (UUM-2) (Turnercyclamycin A) | 6.25 mg/kg IV, BID, q12h | 1 | 0.782 | $4.59 \times 10^7$ | | 7.66 | |
| | | | 2 | 0.821 | $3.63 \times 10^7$ | | 7.56 | |
| | | | 3 | 0.788 | $4.62 \times 10^7$ | | 7.66 | |
| | | | 4 | 0.753 | $6.93 \times 10^7$ | | 7.84 | |
| | | | 5 | 0.000 | $7.71 \times 10^7$ | | 7.89 | |
| | | | Mean | 0.629 | $5.50 \times 10^7$ | 27 | 7.72 | 2.27 |
| | | | SEM | 0.158 | $7.76 \times 10^6$ | | 0.06 | |

TABLE 24

| Group | Treatment | Dose Route/ Schedule | Animal No. | Thigh Weight (g) | Dilution (CFU/plate) | | | | | | |
|---|---|---|---|---|---|---|---|---|---|---|---|
| | | | | | 0 | $10^1$ | $10^2$ | $10^3$ | $10^4$ | $10^5$ | $10^6$ |
| 1 | Baseline, 2 h post infection | N/A | 1 | 0.741 | | >300 | 140 | 7 | 0 | | |
| | | | 2 | 0.683 | | >300 | 233 | 20 | 1 | | |
| | | | 3 | 0.766 | | >300 | 138 | 9 | 1 | | |
| | | | 4 | 0.798 | | >300 | 197 | 22 | 1 | | |
| | | | 5 | 0.748 | | 88 | 7 | 0 | 0 | | |
| 2 | Vehicle (3% ethanol/PBS) | 10 mL/kg IV, BID, q12h | 1 | 0.725 | | | | >300 | >300 | 121 | 8 |
| | | | 2 | 0.738 | | | | >300 | 296 | 28 | 1 |
| | | | 3 | 0.826 | | | | >300 | >300 | 41 | 3 |
| | | | 4 | 0.813 | | | | >300 | >300 | 130 | 7 |
| | | | 5 | 0.751 | | | | >300 | >300 | 54 | 4 |
| 3 | Colistin | 30 mg/kg SC, BID, q12h | 1 | 0.718 | 59 | 3 | 0 | 0 | | | |
| | | | 2 | 0.652 | 191 | 20 | 1 | 0 | | | |
| | | | 3 | 0.648 | 188 | 21 | 1 | 0 | | | |
| | | | 4 | 0.644 | 66 | 8 | 0 | 0 | | | |
| | | | 5 | 0.739 | 119 | 13 | 0 | 0 | | | |
| 4 | PT# 1251595 (UUM-2) (Turnercyclamycin A) | 25 mg/kg IV, BID, q12h | 1 | 0.644 | 197 | 26 | 3 | 0 | 0 | 0 | 0 |
| | | | 2 | 0.691 | 256 | 32 | 3 | 0 | 0 | 0 | 0 |
| | | | 3 | 0.602 | 292 | 29 | 1 | 0 | 0 | 0 | 0 |
| | | | 4 | 0.713 | >300 | 46 | 4 | 0 | 0 | 0 | 0 |
| | | | 5 | 0.709 | 63 | 8 | 1 | 0 | 0 | 0 | 0 |

TABLE 24-continued

| Group | Treatment | Dose Route/ Schedule | Animal No. | Thigh Weight (g) | 0 | $10^1$ | $10^2$ | $10^3$ | $10^4$ | $10^5$ | $10^6$ |
|---|---|---|---|---|---|---|---|---|---|---|---|
| 5 | PT# 1251595 (UUM-2) (Tumercyclamycin A) | 12.5 mg/kg IV, BID, q12h | 1 | 0.783 | >300 | >300 | 189 | 12 | 0 | 0 | 0 |
|   |   |   | 2 | 0.803 | >300 | >300 | >300 | 234 | 1 | 0 | 0 |
|   |   |   | 3 | 0.771 | >300 | >300 | 263 | 24 | 28 | 1 | 0 |
|   |   |   | 4 | 0.766 | >300 | >300 | 44 | 2 | 2 | 0 | 0 |
|   |   |   | 5 | 0.752 | >300 | 45 | 4 | 0 | 0 | 0 | 0 |
| 6 | PT# 1251595 (UUM-2) (Tumercyclamycin A) | 6.25 mg/kg IV, BID, q12h | 1 | 0.811 | >300 | >300 | >300 | >300 | 153 | 21 | 3 |
|   |   |   | 2 | 0.782 | >300 | >300 | >300 | >300 | 121 | 9 | 1 |
|   |   |   | 3 | 0.821 | >300 | >300 | >300 | >300 | 154 | 16 | 0 |
|   |   |   | 4 | 0.788 | >300 | >300 | >300 | >300 | 231 | 24 | 2 |
|   |   |   | 5 | 0.753 | >300 | >300 | >300 | >300 | 257 | 26 | 3 |

Figure 15B:
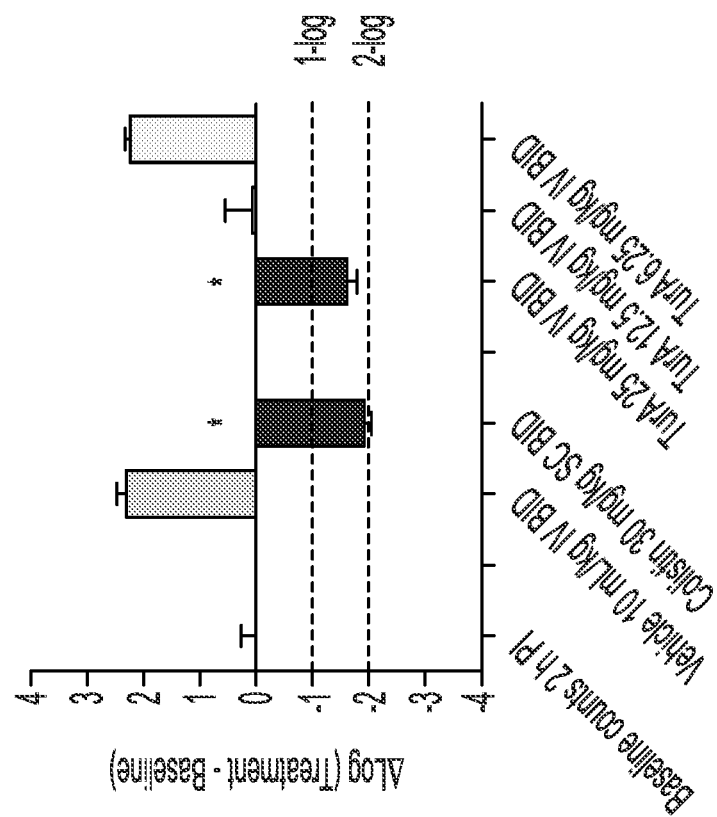
FIG. 15A and FIG. 15B show representative data illustrating the relative change in bacterial counts/thigh relative to the baseline control.
Figure 15A:
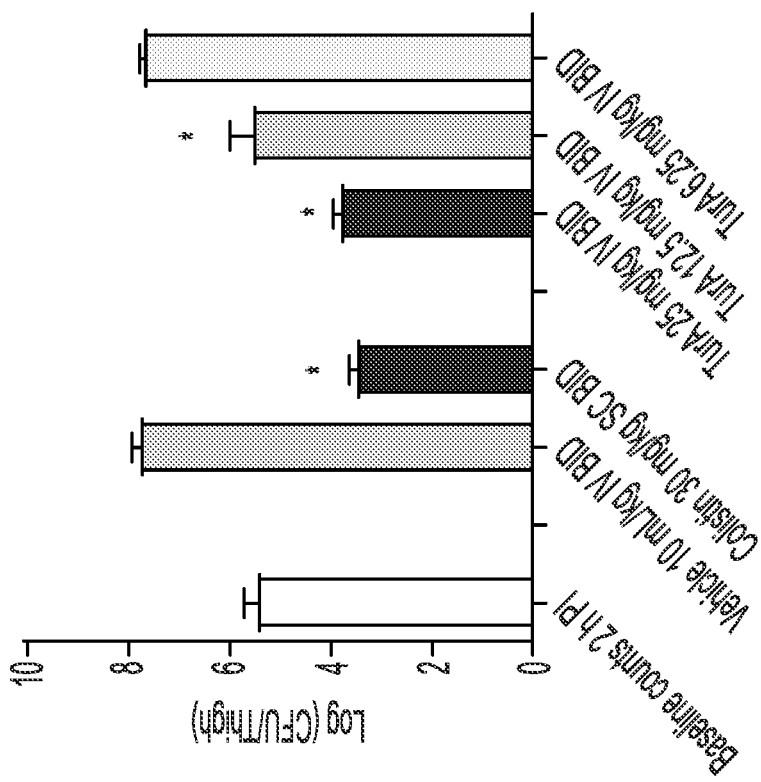

Referring to FIG. 15A and FIG. 15B, the effects of Tumercyclamiycin A and colistin in the *A. baumannii* ATCC 17978 thigh infection model with neutropenic BALB/c female mice is shown. Specifically, FIG. 15A shows the bacterial counts from excised thigh tissue for each treatment group. (*) indicates significant difference (p<0.05) compared to the respective vehicle control was determined by one-way ANOVA followed by Dunnett's test FIG. 15B shows the change in bacterial counts in thigh tissue at the 26 h sacrifice time point relative to the initial 2 h counts at the time of dosing. (*) indicates greater than 1-$\log_{10}$ reduction in counts relative to the baseline at the time of the first dose administration, 2 h after infection, with a significant difference (p<0.05) based on one-way ANOVA followed by Dunnett's test.

H. REFERENCES

1. D. L. Distel, D. J. Beaudoin, W. Morrill, Coexistence of Multiple Proteobacterial Endosymbionts in the Gills of the Wood-Boring Bivalve Lyrodus pedicellatus (Bivalvia: Teredinidae). Appl. Environ. Microbiol. 68, 6292-6299 (2002).
2. N. A. Ekborg, W. Morrill, A. M. Burgoyne, L. Li, D. L. Distel, CelAB, a Multifunctional Cellulase Encoded by Teredinibacter tumerae T7902T, a Culturable Symbiont Isolated from the Wood-Boring Marine Bivalve Lyrodus pedicellatus. Appl. Environ. Microbiol. 73, 7785-7788 (2007).
3. C. P. Lechene, Y. Luyten, G. McMahon, D. L. Distel, Quantitative Imaging of Nitrogen Fixation by Individual Bacteria Within Animal Cells. Science 317, 1563-1566 (2007).
4. R. M. O'Connor, et al., Gill bacteria enable a novel digestive strategy in a wood-feeding mollusk. PNAS 111, E5096-E5104 (2014).
5. M. A. Betcher, et al., Microbial Distribution and Abundance in the Digestive System of Five Shipworm Species (Bivalvia: Teredinidae). PLOS ONE 7, e45309 (2012).
6. S. I. Elshahawi, et al., Boronated tartrolon antibiotic produced by symbiotic cellulose-degrading bacteria in shipworm gills. PNAS 110, E295-E304 (2013).
7. J. C. Yang, et al., The Complete Genome of *Teredinibacter* tumerae T7901: An Intracellular Endosymbiont of Marine Wood-Boring Bivalves (Shipworms). PLOS ONE 4, e6085 (2009).
8. M. A. Altamia, et al., Secondary Metabolism in the Gill Microbiota of Shipworms (Teredinidae) as Revealed by Comparison of Metagenomes and Nearly Complete Symbiont Genomes. mSystems 5 (2020).
9. E. Tacconelli, et al., Discovery, research, and development of new antibiotics: the WHO priority list of antibiotic-resistant bacteria and tuberculosis. The Lancet Infectious Diseases 18, 318-327 (2018).
10. L. L. Silver, Challenges of Antibacterial Discovery. Clinical Microbiology Reviews 24, 71-109 (2011).
11. A. W. Han, et al., Tumerbactin, a Novel Triscatecholate Siderophore from the Shipworm Endosymbiont *Teredinibacter turnerae* T7901. PLOS ONE 8, e76151 (2013).
12. J. M. Raaijmakers, et al., Utilization of heterologous siderophores and rhizosphere competence of fluorescent Pseudomonas spp. Can. J. Microbiol. 41, 126-135 (1995).
13. R. M. O'Connor, et al., A symbiotic bacterium of shipworms produces a compound with broad spectrum anti-apicomplexan activity. PLOS Pathogens 16, e1008600 (2020).
14. H. W. Boucher, et al., Bad Bugs, No Drugs: No ESKAPE! An Update from the Infectious Diseases Society of America. Clin Infect Dis 48, 1-12 (2009).
15. K. Fujii, et al., A Nonempirical Method Using LC/MS for Determination of the Absolute Configuration of Constituent Amino Acids in a Peptide: Elucidation of Limitations of Marfey's Method and of Its Separation Mechanism. Anal. Chem. 69, 3346-3352 (1997).
16. Y. Li, et al., Potashchelins, a Suite of Lipid Siderophores Bearing Both L-threo and L-erythro Beta-Hydroxyaspartic Acids, Acquired From the Potash-Salt-Ore-Derived Extremophile Halomonas sp. MG34. Front Chem 8, 197 (2020).
17. K. Matsui, et al., Stalobacin: Discovery of Novel Lipopeptide Antibiotics with Potent Antibacterial Activity against Multidrug-Resistant Bacteria. J. Med. Chem. 63, 6090-6095 (2020).
18. C. C. J. Culvenor, et al., Structure elucidation and absolute configuration of phomopsin a, a hexapeptide mycotoxin produced by phomopsis leptostromiformis. Tetrahedron 45, 2351-2372 (1989).
19. L. Pantel, et al., Odilorhabdins, Antibacterial Agents that Cause Miscoding by Binding at a New Ribosomal Site. Molecular Cell 70, 83-94.e7 (2018).
20. S. Kozuma, et al., Identification and biological activity of ogipeptins, novel LPS inhibitors produced by marine bacterium. The Journal of Antibiotics 70, 79-83 (2017).
21. C. Rausch, I. Hoof, T. Weber, W. Wohlleben, D. H. Huson, Phylogenetic analysis of condensation domains in NRPS sheds light on their functional evolution. BMC Evol Biol 7, 78 (2007).
22. T. A. Keating, et al., Chain Termination Steps in Nonribosomal Peptide Synthetase Assembly Lines: Directed Acyl-S-Enzyme Breakdown in Antibiotic and Siderophore Biosynthesis. ChemBioChem 2, 99-107 (2001).
23. L.-F. Wu, S. Meng, G.-L. Tang, Ferrous iron and α-ketoglutarate-dependent dioxygenases in the biosynthesis of microbial natural products. Biochimica et Biophysica Acta (BBA)—Proteins and Proteomics 1864, 453-470 (2016).
24. Y. Tsukada, et al., Histone demethylation by a family of JmjC domain-containing proteins. Nature 439, 811-816 (2006).
25. S. Markolovic, et al., The Jumonji-C oxygenase JMJD7 catalyzes (3S)-lysyl hydroxylation of TRAFAC GTPases. Nat. Chem. Biol. 14, 688-695 (2018).
26. J. Zan, et al., A microbial factory for defensive kahalalides in a tripartite marine symbiosis. Science 364 (2019).
27. G. Agner, et al., Membrane-permeabilizing activities of cyclic lipodepsipeptides, syringopeptin 22A and syringomycin E from Pseudomonas syringae pv. syringae in human red blood cells and in bilayer lipid membranes. Bioelectrochemistry 52, 161-167 (2000).
28. L. A. Gallagher, J. Bailey, C. Manoil, Ranking essential bacterial processes by speed of mutant death. PNAS 117, 18010-18017 (2020).
29. J. Bailey, et al., Essential gene deletions producing gigantic bacteria. PLOS Genetics 15, e1008195 (2019).
30. E.-T. Piperaki, L. S. Tzouvelekis, V. Miriagou, G. L. Daikos, Carbapenem-resistant Acinetobacter baumannii: in pursuit of an effective treatment. Clinical Microbiology and Infection 25, 951-957 (2019).
31. C.-R. Lee, et al., Biology of Acinetobacter baumannii: Pathogenesis, Antibiotic Resistance Mechanisms, and Prospective Treatment Options. Front. Cell. Infect. Microbiol. 7 (2017).
32. D. Wong, et al., Clinical and Pathophysiological Overview of Acinetobacter Infections: a Century of Challenges. Clinical Microbiology Reviews 30, 409-447 (2017).
33. A. Howard, M. O'Donoghue, A. Feeney, R. D. Sleator, Acinetobacter baumannii: an emerging opportunistic pathogen. Virulence 3, 243-250 (2012).
34. Centers for Disease Control and Prevention (U.S.), "Antibiotic resistance threats in the United States, 2019" (Centers for Disease Control and Prevention (U.S.), 2019) https:/doi.org/10.15620/cdc:82532 (Oct. 21, 2020).
35. Z. L. Reitz, C. D. Hardy, J. Suk, J. Bouvet, A. Butler, Genomic analysis of siderophore β-hydroxylases reveals divergent stereocontrol and expands the condensation domain family. PNAS 116, 19805-19814 (2019).
36. M. Hibi, et al., Characterization of Bacillus thuringiensis 1-Isoleucine Dioxygenase for Production of Useful Amino Acids. Appl. Environ. Microbiol. 77, 6926-6930 (2011).
37. J. Li, et al., Colistin: the re-emerging antibiotic for multidrug-resistant Gram-negative bacterial infections. Lancet Infect Dis 6, 589-601 (2006).
38. R. A. Dixon, I. Chopra, Leakage of periplasmic proteins from *Escherichia coli* mediated by polymyxin B nonapeptide. Antimicrob Agents Chemother 29, 781-788 (1986).
39. S. Rueckert, E. L. Betts, A. D. Tsaousis, The Symbiotic Spectrum: Where Do the Gregarines Fit? Trends in Parasitology 35, 687-694 (2019).
40. J. B. Waterbury, C. B. Calloway, R. D. Turner, A Cellulolytic Nitrogen-Fixing Bacterium Cultured from the Gland of Deshayes in Shipworms (Bivalvia: Teredinidae). Science 221, 1401-1403 (1983).

Those skilled in the art will recognize, or be able to ascertain using no more than routine experimentation, many equivalents to the specific embodiments of the method and compositions described herein. Such equivalents are intended to be encompassed by the following claims.

What is claimed is:

1. A compound having a structure represented by a formula:

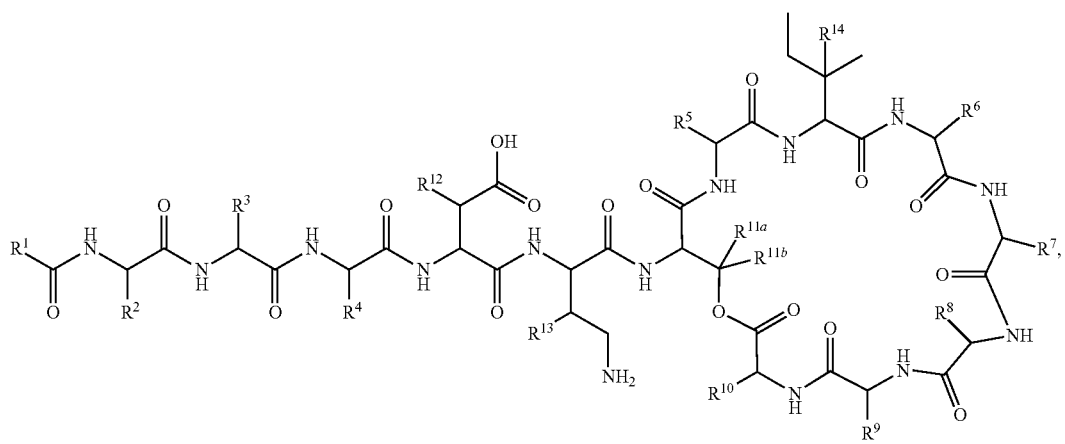

wherein R¹ is selected from C1-C24 alkyl and C2-C24 alkenyl wherein each of $R^2$, $R^6$, and $R^9$ is independently a side chain of a D-amino acid residue;

wherein $R^3$ is a polar uncharged side chain of an amino acid residue;

wherein $R^4$ is a hydrophobic side chain of an amino acid residue;

wherein $R^5$ is a side chain of an amino acid residue selected from cysteine, selenocysteine, glycine, and proline;

wherein $R^7$ is a side chain of a homo-amino acid residue selected from homoserine, homothreonine, homoasparagine, and homoglutamine;

wherein $R^8$ is a hydrophobic side chain of an amino acid residue;

wherein $R^{10}$ is an electrically charged side chain of an amino acid residue;

wherein each of $R^{11a}$ and $R^{11b}$ is independently selected from hydrogen and C1-C4 alkyl; and wherein each of $R^{12}$, $R^{13}$, and $R^{14}$ is independently selected from —OH, —SH, and —NH₂, or a pharmaceutically acceptable salt thereof, provided that the compound does not have a structure represented by a formula:

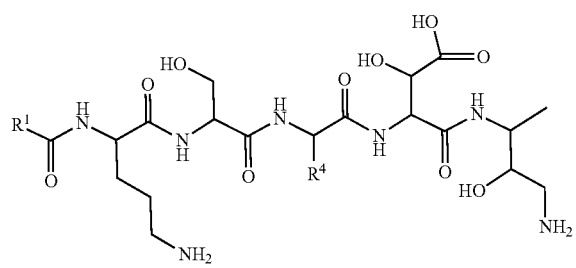

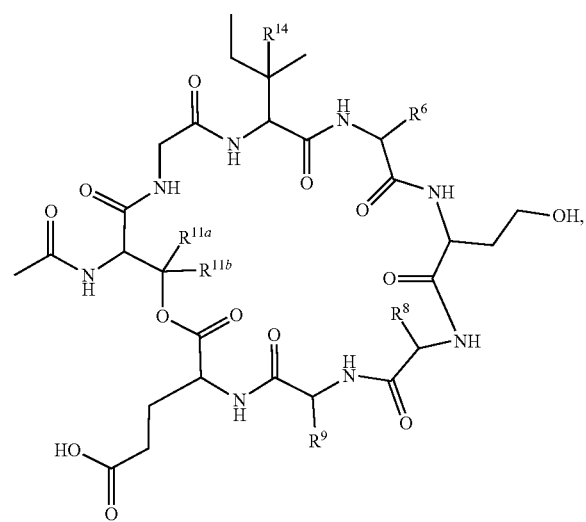

wherein $R^4$ is valine, $R^6$ is D-alloisoleucine, $R^8$ is alanine, $R^{11a}$ is methyl, $R^{11b}$ is hydrogen, and $R^{14}$ is —OH.

2. The compound of claim 1, wherein R¹ is selected from:

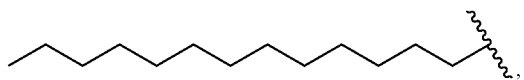

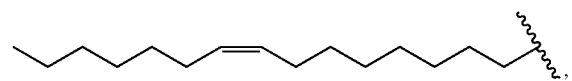

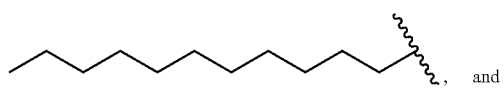

, and

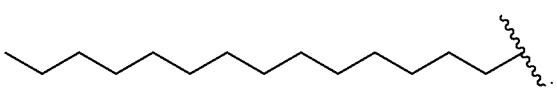

.

3. The compound of claim 1, wherein each of $R^2$, $R^6$, and $R^9$ is independently a side chain of a D-amino acid residue selected from D-lysine, D-threonine, D-phenylalanine, D-methionine, D-histidine, D-tryptophan, D-glutamine, D-aspartate, D-glutamate, D-arginine, D-alanine, D-proline, D-cysteine, D-asparagine, D-serine, D-tyrosine, D-ornithine, D-hydroxybutanoic acid, and D-alloisoleucine.

4. The compound of claim 1, wherein $R^3$ is a polar uncharged side chain of an amino acid residue selected from serine, threonine, asparagine, and glutamine.

5. The compound of claim 1, wherein $R^4$ is a hydrophobic side chain of an amino acid residue selected from alanine, isoleucine, leucine, methionine, phenylalanine, tryptophan, tyrosine, and valine.

6. The compound of claim 1, wherein $R^8$ is a hydrophobic side chain of an amino acid residue selected from alanine, isoleucine, leucine, methionine, phenylalanine, tryptophan, tyrosine, and valine.

7. The compound of claim 1, wherein $R^9$ is a side chain of an amino acid residue selected from D-alloisoleucine residue and D-valine.

8. The compound of claim 1, wherein $R^{10}$ is an electrically charged side chain of an amino acid residue selected from arginine, histidine, lysine, aspartic acid, and glutamic acid.

9. The compound of claim 1, wherein $R^{11a}$ is C1-C4 alkyl and $R^{11b}$ is hydrogen.

10. The compound of claim 1, wherein each of $R^{12}$, $R^{13}$, and $R^{14}$ is —OH.

11. The compound of claim 1, wherein the compound has a structure represented by a formula:

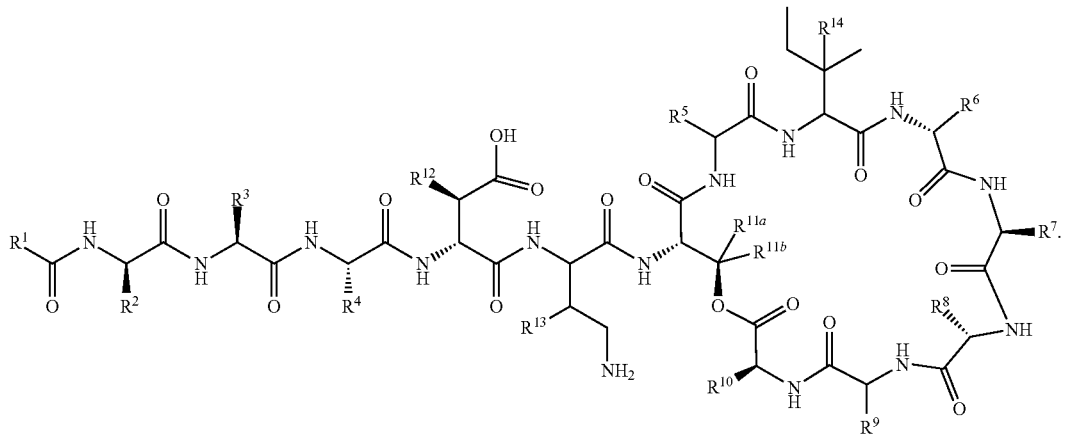

12. The compound of claim 1, wherein the compound has a structure represented by a formula:

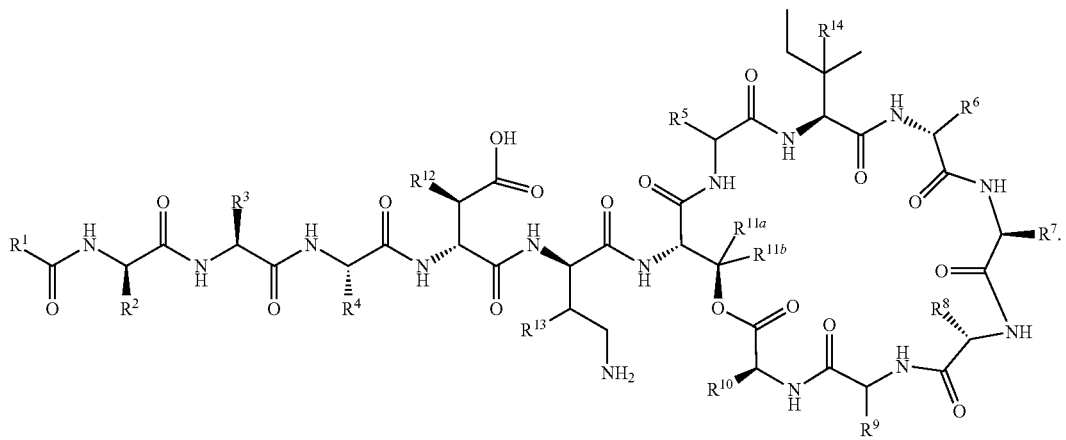

13. A pharmaceutical composition comprising a therapeutically effective amount of the compound of claim 1, and a pharmaceutically acceptable carrier.

14. The compound of claim 1, wherein $R^1$ is selected from C8-C18 alkyl and C8-C18 alkenyl.

15. The compound of claim 1, wherein $R^2$ is D-ornithine.

16. The compound of claim 1, wherein $R^3$ is serine, $R^4$ is valine, and $R^5$ is glycine.

17. The compound of claim 1, wherein $R^6$ is D-alloisoleucine.

18. The compound of claim 1, wherein $R^7$ is homoserine.

19. The compound of claim 1, wherein $R^8$ is alanine.

20. The compound of claim 1, wherein $R^{10}$ is glutamic acid.

* * * * *